(12) United States Patent
Sehgal et al.

(10) Patent No.: US 7,713,522 B2
(45) Date of Patent: *May 11, 2010

(54) EX VIVO AND IN VIVO EXPRESSION OF THE THROMBOMODULIN GENE FOR THE TREATMENT OF CARDIOVASCULAR AND PERIPHERAL VASCULAR DISEASES

(75) Inventors: Lakshman R. Sehgal, Monarch Beach, CA (US); Jonathan Wong, Palo Alto, CA (US)

(73) Assignee: BioVec, LLC, Chicago, IL (US)

( * ) Notice: Subject to any disclaimer, the term of this patent is extended or adjusted under 35 U.S.C. 154(b) by 4 days.

This patent is subject to a terminal disclaimer.

(21) Appl. No.: 12/219,714

(22) Filed: Jul. 28, 2008

(65) Prior Publication Data

US 2009/0123440 A1    May 14, 2009

Related U.S. Application Data

(63) Continuation of application No. 11/650,479, filed on Jan. 8, 2007, now Pat. No. 7,481,998, which is a continuation-in-part of application No. 10/725,013, filed on Dec. 2, 2003, now Pat. No. 7,179,459.

(60) Provisional application No. 60/430,099, filed on Dec. 2, 2002.

(51) Int. Cl.
| | |
|---|---|
| *A01N 63/00* | (2006.01) |
| *A61K 39/325* | (2006.01) |
| *A61K 31/715* | (2006.01) |
| *C12H 15/86* | (2006.01) |
| *C07H 21/04* | (2006.01) |

(52) U.S. Cl. .................. 424/93.6; 424/233.1; 514/44; 435/456; 536/23.5; 536/24.1; 536/24.2

(58) Field of Classification Search ........................ None
See application file for complete search history.

(56) References Cited

U.S. PATENT DOCUMENTS

| | | | |
|---|---|---|---|
| 4,826,811 A | 5/1989 | Sehgal et al. | |
| 5,981,225 A | 11/1999 | Kochanek et al. | |
| 6,290,949 B1 | 9/2001 | French et al. | |
| 7,179,459 B2 | 7/2007 | Sehgal et al. | |
| 7,481,998 B2* | 1/2009 | Sehgal et al. | 424/93.6 |
| 7,501,114 B2* | 3/2009 | Sehgal et al. | 424/93.6 |

OTHER PUBLICATIONS

Zuckerbraun, Brian S., et al., "Vascular Gene Therapy, A Reality of the 21st Century," Arch. Surg., vol. 137, pp. 854-61 (2002).
Kibbe, Melina R., et al., "Gene Therapy for Restenosis," Circ. Res., vol. 86, pp. 829-33 (2000).
Shears, Larry L., et al., "Efficient Inhibition of Intimal Hyperplasia by Adenovirus-Mediated Inducible Nitric Oxide Synthase Gene Transfer to Rats and Pigs In Vivo," J. Am. Coll. Surg., vol. 187, No. 3, pp. 295-306 (1998).
Ross, Russell, "The pathogenesis of atherosclerosis: a perspective for the 1990s," Nature, vol. 362, pp. 801-809 (1993).
Sadler, J. Evan, "Thrombomodulin Structure and Function," Tehomb Haemost., vol. 78, pp. 392-395 (1997).
Esmon, Charles T., "Thrombomodulin as a model of molecular mechanisms that modulate protease specificity and function at the vessel surface," Faseb J., vol. 9; pp. 946-955 (1995).
Salomaa, Veikko, et al., "Soluble thrombomodulin as a predicctor of incident coronary heart disease and symptomless carotid artery atherosclerosis in the Atherosclerosis Risk in Communities (ARIC) Study: a case-cohort study," Lancet, vol. 353, pp. 1729-1734 (1999).
Palmer, R.M.J., et al., "Nitric oxide release accounts for the biological activity of endothelium-derived relaxing factor," Nature, vol. 327, pp. 524-526 (1987).
Kubes, P., et al., "Nitric oxide: An endogenous modulator of leukocyte adhesion," Proc. Natl. Acad. Sci. USA, vol. 88, pp. 4651-4655 (1991).
Steg, P. Gabriel, M.D., et al., "Reduction of Restenosis After Angioplasty in an Atheromatous Rabbit Model by Suicide Gene Therapy," Circulation, vol. 96, pp. 408-411 (1997).
Van Belle, Eric, et al., "Accelerated Endothelialization by Local Delivery of Recombinant Human Vascular Endothelial Growth Factor Reduces In-Stent Intimal Formation," Biochem. and Biophs. Res. Communications, vol. 235, pp. 311-316 (1997).
Salyapongse, A. Neil, M.D., et al., "Gene Therapy and Tissue Engineering," Tissue Engineering, vol. 26, No. 4, pp. 663-676 (1999).
Kon, T., et al., "Bone Morphogenetic Protein-2-Stimulates Differentiation of Cultured Spinal Ligament Cells from Patients with Ossification of the Posterior Longitudinal Ligament," Calcif. Tissue Int., vol. 60; pp. 291-296 (1997).
Kibbe, Melina R., MD, et al., "Adenovirus-mediated gene transfer of human inducible nitric oxide synthase in porcine vein grafts inhibits intimal hyperplasia," J. Vasc. Surg., vol. 34, pp. 156-165 (2001).
He, Tong-Chuan, et al., "A simplified system for generating recombinant adenoviruses," Proc. Natl. Acad. Sci. USA, vol. 95, pp. 2509-2514 (1998).
Marmur, J., et al., "Strand Separation and Specific Recombination in Deoxyribonucleic Acids: Biological Studies," Proc. Natl. Acad. Sci. USA, vol. 46, pp. 453-461 (1960).
Doty, P., et al., "Strand Separation and Specific Recombination in Deoxyribonucleic Acids: Physical Chemical Studies," PNAS USA, vol. 46, pp. 461-476 (1960).

(Continued)

*Primary Examiner*—Richard Schnizer
(74) *Attorney, Agent, or Firm*—Ping Wang; Morris, Manning & Martin, LLP

(57) ABSTRACT

The present invention relates to methods and compositions for treatment of cardiovascular and peripheral vascular diseases using ex vivo and in vivo gene delivery technologies. One aspect of the present invention relates to a method for treating a vascular disease by introducing a DNA sequence encoding a TM protein or its variant into a segment of a blood vessel ex vivo using a gutless adenovirus vector. Another aspect of the present invention is to provide a gutless adenovirus vector carrying a transgene, such as a gene encoding TM protein or its variant.

11 Claims, 7 Drawing Sheets
(6 of 7 Drawing Sheet(s) Filed in Color)

OTHER PUBLICATIONS

Sambrook, J. Fritsch, et al., "Analysis of Genomic DNA by Southern Hybridization," Molecular Cloning: A Laboratory Manual (Cold Spring Harbor Lab. Press, Plainview, NY), vol. II, pp. 9.31-9.62 (1989).

Curiel, David T., "Strategies to Adapt Adenoviral Vectors for Targeted Delivery," Ann NY Acad Sci 886, pp. 158-171 (1991).

Haj-Ahmand, Yousef, et al., "Development of a Helper-Independent Human Adenovirus Vector and Its Use in the Transfer of the Herpes Simplex Virus Thymidine Kinase Gene," J. Virol. vol. 57, No. 1, 267-274 (1986).

Ragot, Thierry, et al., "Efficient adenivirus-mediated transfer of a human minidystrophin gene to skeletal muscle of mdx mice," Nature, vol. 361, pp. 647-650 (1993).

Howell, John McC., et al., "High-Level Dystrophin Expression after Adenovirus-Mediated Dystrophin Minigene Transfer to Skeletal Muscle of Dystrophic Dogs: Prolongation of Expression with Immunosuppression," Hum Gene Ther., vol. 9, pp. 629-634 (1998).

Parks, Robin J., et al., "A helper-dependent adenovirus vector system: Removal of helper virus by Cre-mediated excision of the viral packaging signal," Proc. Natl. Acad. Sci. USA, vol. 93, pp. 13565-13570 (1996).

Lieber, André, et al., "Recombinant Adenoviruses with Large Deletions Generated by Cre-Mediated Excision Exhibit Different Biological Properties Compared with First-Generation Vectors In Vitro and In Vivo," J. Virol, vol. 70, pp. 8944-8960 (1996).

Gossen, Manfred, et al., "Tight control of gene expression in mammalian cells by tetracycline-responsive promoters," Proc. Natl. Acad. Sci. USA, vol. 89, pp. 5547-5551 (1992).

Gossen, Manfred, et al., "Transcriptional Activation by Tetracyclines in Mammalian Cells," Science, vol. 268, pp. 1766-1769 (1995).

Kistner, Andreas, et al., "Doxycycline-mediated quantitative and tissue-specific control of gene expression in transgenic mice," Proc. Natl. Acad. Sci. USA, vol. 93, pp. 10933-10938 (1996).

No, David, et al., "Ecdysone-inducible gene expression in mammalian cells and transgenic mice," Proc. Natl. Acad. Sci. USA, vol. 93, pp. 3346-3351 (1996).

Wang, Yaolin, et al., "A regulatory system for use in gene transfer," PNAS USA, vol. 91, pp. 8180-8184 (1994).

Wang, Yaolin, et al., "Ligand-inducible and liver-specific target gene expression in transgenic mice," Nat. Biotech., vol. 15, pp. 239-243 (1997).

Magari, Shannon R., et al., "Pharmacologic Control of a Humanized Gene Therapy System Implanted into Nude Mice," J. Clin. Invest., vol. 100, No. 11, pp. 2865-2872 (1997).

Ye, Xuehai, et al., "Regulated Delivery of Therapeutic Proteins After in Vivo Somatic Cell Gene Transfer," Science, vol. 283, pp. 88-91 (1999).

Suzuki, Koji, et al., "Structure and expression of human thrombomodulin, a thrombin receptor on endothelium acting as a cofactor for protein C activation," EMBO J., vol. 6, No. 7, pp. 1891-1897 (1987).

Wen, Duanzhi, et al., "Human Thrombomodulin: Complete cDNA Sequence and Chromosome Localization of the Gene," Biochemistry, vol. 26, pp. 4350-4357 (1987).

Ng, Philip, et al., "Development of a FLP/frt Syste for Generating Helper-Dependent Adenoviral Vectors," Molecular Therapy, vol. 3, No. 5, pp. 809-815 (2001).

Umana, Pablo, et al., "Efficient FLPe recombinase enables scalable production of helper-dependent adenoviral vectors with negligible helper-virus contamination," Nature Biotechnology, vol. 19, pp. 582-585 (2001).

* cited by examiner

EX VIVO AND IN VIVO EXPRESSION OF THE THROMBOMODULIN GENE FOR THE TREATMENT OF CARDIOVASCULAR AND PERIPHERAL VASCULAR DISEASES

This application is a continuation of U.S. application of Ser. No. 11/650,479, filed Jan. 8, 2007, now U.S. Pat. No. 7,481,998, which is a continuation-in-part application of U.S. Ser. No. 10/725,013, filed Dec. 2, 2003, now U.S. Pat. No. 7,179,459, which claims priority from U.S. Provisional Application Ser. No. 60/430,099 filed Dec. 2, 2002. The entirety of all of the aforementioned applications is incorporated herein by reference.

FIELD

The present invention is directed to methods and compositions for the treatment of cardiovascular and peripheral vascular diseases, and in particular, is directed to methods and compositions for ex vivo and in vivo expression of the thrombomodulin gene using gutless adenovirus vector.

BACKGROUND

Atherosclerosis is one of the chief causes of morbidity and mortality in the United States and many other countries of the world. (Zuckerbraun et al., *Arch Surg.* 137:854-861 [2002]; Kibbe et al., *Circ Res.* 86:829-33 [2000]). This process can result in limiting the flow of blood to the heart, kidneys and the peripheral vessels, to name a few. Current approaches to the treatment of lesions in the arteries include coronary artery by-pass graft (CABG) surgery and angioplasty with or without the placement of a stent. The latter may serve as a vehicle for drug delivery, as is currently being tested in clinical trials. A number of pharmacological agents that affect platelet function or provide anticoagulant properties have so far failed to reduce re-occlusion or intimal hyperplasia. (Kibbe et al., *Circ Res.* 86:829-33 [2000]).

Cardiovascular diseases, however, are the result of complex pathophysiologic processes that involve the expression of many proteins and molecules that can adversely affect the grafted vessel (Shears et al., *J. Am Coll Surg.*, 187(3):295-306 [1998]; Ross et al., *Nature,* 362:801-9 [1993]). Approximately 15-30% of patients receiving vein grafts for coronary or peripheral vascular disease require follow-up treatment, either in the form of angioplasty or new grafts.

Thrombomodulin (TM) is an integral membrane glycoprotein expressed on the surface of endothelial cells (Sadler et al., *Trhomb Haemost.,* 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., *Faseb J.,* 9:946-55 [1995]). The latter two proteins are essential for the function of two of the coagulation proteases, namely factors IXa and Xa. TM thus plays an active role in blood clot formation in vivo and can function as a direct or indirect anticoagulant.

There are several other proteins or enzymes that have shown to reduce the process of intimal hyperplasia, whose evolution is the cause of late graft failure. For instance, Nitric oxide synthase, an enzyme expressed by endothelial cells has been shown in animal models to inhibit intimal hyperplasia, especially the inducible enzyme (iNOS) (Salmaa et al., *Lancet,* 353:1729-34 [1999]; Palmer et al., *Nature,* 327:524-26 [1987]; Kubes et al., *PNAS USA.,* 88:4651-5 [1991]).

Animal studies shown that cytoxic gene transfection utilizing the Herpes Simplex Virus thymidine kinase gene delivered via an adenoviral vector was able to inhibit intimal hyperplasia (Steg et al., *Circulation,* 96:408-11 [1997]). Vascular endothelial growth factor (VEGF), basic fibroblast growth factor (bFGF) and platelet derived growth factor (PDGF) have all been shown to promote reendothelization and enhance the healing of vascular injury and help limit intimal hyperplasia. (Ban Belle et al., *Biochem Biophs Res Commun.,* 235:311-16 [1997]; Salyapongse et al., *Tissue Engineering* 26(4):663-76 [1999]).

A gene therapy approach is currently under clinical investigation. It involves the injection, directly into heart muscles, of an adenoviral vector delivery system containing the gene for the expression of vascular endothelial growth factor (VEGF). This is being tested in patients whose coronary vessels are not amenable to standard grafting procedures. However, some recent adverse clinical events demonstrated that injection of large quantities of adenovirus vectors is associated with significant risks. Accordingly, there still exists a need for a method to effectively introduce therapeutic genes, such as TM, into vascular tissues.

SUMMARY

One aspect of the present invention relates to methods for treating a vascular disease in a mammal. In one embodiment, the method comprises the steps of: infecting a segment of blood vessel in vitro using a gutless adenoviral vector comprising a polynucleotide encoding a thrombomodulin protein or its variant, and grafting the virus-treated blood vessel in the mammal, wherein the thrombomodulin protein or its variant is expressed in a amount sufficient to reduce re-occlusion or intimal hyperplasia in the grafted blood vessel, and wherein the gutless adenoviral vector comprises the nucleotide sequence of SEQ ID NO:13 or SEQ ID NO:15.

In another embodiment, the method comprises the steps of: evacuating a clot from a blood vessel in the mammal, isolating a segment of the blood vessel around the evacuation site, and infecting the segment of blood vessel in vivo using a gutless adenoviral vector comprising a polynucleotide encoding a thrombomodulin protein or its variant, wherein the thrombomodulin protein or its variant is expressed in a amount sufficient to reduce re-occlusion or intimal hyperplasia in the infected blood vessel, and wherein said gutless adenoviral vector comprises the nucleotide sequence of SEQ ID NO:13 or SEQ ID NO:15.

In another embodiment, the method comprises the step of administering a therapeutically effective amount of a gutless adenovirus vector into a segment of a blood vessel in vivo using a stent, wherein the gutless adenovirus vector comprises the nucleotide sequence of SEQ ID NO:13 or SEQ ID NO:15, and is capable of expressing a thrombomodulin protein or a variant of the thrombomodulin protein.

In another embodiment, the method comprises the step of administering intravenously an effective amount of a gutless adenoviral vector comprising a polynucleotide encoding a thrombomodulin protein or its variant, wherein the gutless adenoviral vector comprises the nucleotide sequence of SEQ ID NO:13 or SEQ ID NO:15.

Another aspect of the present invention pertains to a gutless adenovirus vector comprising the nucleotide sequence of SEQ ID NO:13 or SEQ ID NO:15.

Another aspect of the present invention pertains to a gutless adenovirus vector comprising a polynucleotide encoding a thrombomodulin protein having the amino acid sequence of SEQ ID NO:2, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a vascular disease, comprising the gutless adenovirus vector described above and a pharmaceutically acceptable carrier.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
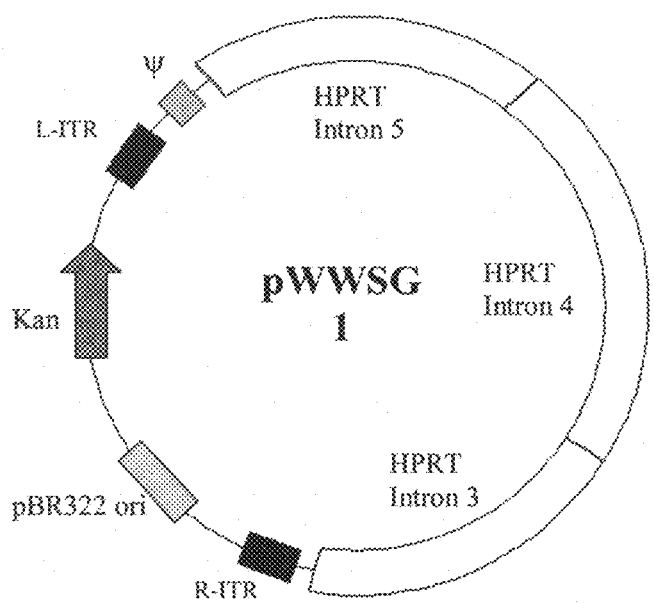
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating vascular diseases using gene delivery technologies. One aspect of the present invention relates to a method for treating a vascular disease by introducing a DNA sequence encoding a TM protein or its variant into a segment of a blood vessel in vitro using a gutless adenovirus vector and grafting the virus-treated vessel in a patient affected by a vascular disease. The virus-mediated TM expression reduces re-occlusion and intimal hyperplasia in the grafted vessel. This ex vivo approach eliminates the need to inject a large quantity of virus into a patient and hence significantly reduces the viral-related toxicity.

In one embodiment, the method is used for a coronary artery bypass. In another embodiment, the method is used for the treatment of peripheral vascular diseases. In yet another embodiment, the method is used for the maintenance of vein access in renal dialysis patients.

Another object of the present invention is to provide a method to deliver a gutless adenovirus vector carrying a DNA sequence encoding a TM protein or its variant using a stent. The viral vector is embedded in the stent and is released only at a treatment site. Since the viral infection is restricted at the treatment site and the surrounding area, only a small amount of the virus is needed and the virus-related toxicity is reduced.

Yet another object of the present invention pertains to a gutless adenovirus carrying a TM gene. In one embodiment, the gutless adenovirus, which contains a regulatory element operably linked to a DNA sequence encoding a TM protein or its variant and a polyA sequence, is produced using a novel shuttle vector containing a pBR322 replication origin, a selection marker, an adenovirus left inverted terminal repeat, an adenovirus encapsidation signal, a stuffer sequence, and an adenovirus left inverted terminal repeat.

In one embodiment, the regulatory element is a constitutive promoter such a CMV promoter and RSV promoter. In another embodiment, the regulatory element is an inducible promoter.

The forth object of the present invention is to provide a pharmaceutical composition which comprises an effective amount of gutless adenovirus carrying a TM gene of the present invention and a pharmaceutically acceptable carrier. Such compositions may be liquids or lyophilized or otherwise dried formulations and may further include diluents of various buffer content, (e.g., Tris-HCl, acetate, phosphate) pH and ionic strength, additives such as albumin and gelatin to prevent absorption to surfaces, detergents (e.g., Tween 20, Tween 80, Pluronic F68, bile acid salts), solubilizing agents (e.g., glycerol, polyethylene glycerol); anti-oxidants (e.g., ascorbic acid, sodium metabisulfite), and preservatives (e.g. Thimerosal, benzyl alcohol, parabens).

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles including "naked" expression vectors, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a, DNA regulatory sequence that is sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, muscle creatine kinase (MCK) promoter, myosin promoter, (α-actin promoter) and the like.

The term "transduction" denotes the delivery of a DNA molecule to a recipient cell either in vivo or in vitro, via a replication-defective viral vector, such as via a recombinant adenovirus.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *PNAS USA* 46:453 (1960) and Doty et al., *PNAS USA* 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "Tm." The Tm. of a particular nucleic acid duplex under specified conditions is the temperature at which on average half of the base pairs have disassociated. The equation for calculating the Tm. of nucleic acids is well known in the art.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data bands, or in a Southern hybridization experiment under, for example, stringent conditions as defined for that particular system. Suitable conditions include those characterized by a hybridization buffer comprising 0.9M sodium citrate ("SSC") buffer at a temperature of about 37° C. and washing in SSC buffer at a temperature of about 37° C.; and preferably in a hybridization buffer comprising 20% formamide in 0.9M SSC buffer at a temperature of about 42° C. and washing in 0.2×SSC buffer at about 42° C. Stringency conditions can be further varied by modifying the temperature and/or salt content of the buffer, or by modifying the length of the hybridization probe as is known to those of skill in the art. Defining appropriate hybridization conditions is within the skill of the art. See e.g., Sambrook, J. Fritsch, E. J., & Maniatis, T. (1989) *Molecular Cloning: A Laboratory Manual* (Cold Spring Harbor Lab. Press, Plainview, N.Y.).

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

The term "thrombomodulin variant" is a polypeptide that differs from a native thrombomodulin polypeptide in one or more substitutions, deletions, additions and/or insertions, such that the bioactivity of the native thrombomodulin polypeptide is not substantially diminished or enhanced. In other words, the bioactivity of a thrombomodulin variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a thrombomodulin variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

Thrombomodulin variants preferably exhibit at least about 70%, more preferably at least about 90% and most preferably at least about 95% sequence homology to the original thrombomodulin polypeptide.

A thrombomodulin variant also includes a thrombomodulin polypeptides that is modified from the original thrombomodulin polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Adenovirus Vectors:

The genome of an adenovirus can be manipulated such that it encodes and expresses a gene product of interest but is inactivated in terms of its ability to replicate in a normal lyric viral life cycle (Curie D T, *Ann N Y Acad Sci* 886, 158-171 [1991]). Suitable adenoidal vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells and muscle cells. Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoidal genome for foreign DNA is large (up to 8 kilobases) relative to other gene delivery vectors (Haj-Ahmand et al. *J. Virol.* 57, 267-273 [1986]). Most replication-defective adenoidal vectors currently in use are deleted for all or parts of the viral E1 and E3 genes but retain as much as 80% of the adenoidal genetic material. Adenoidal vectors deleted for all viral coding regions are also described by Kochanek et al. and Chamberlain et al. (U.S. Pat. No. 5,985,846 and U.S. Pat. No. 6,083,750).

Adenovirus vectors have been successfully tested in a number of animal models (Ragot et al. *Nature* 361, 647-650 [1993]; Howell et al. *Hum Gene Ther* 9, 629-634 [1998]). Nonetheless, the toxicity and immunogenicity remain major hurdles to overcome before the adenovirus vectors can be safely used in humans.

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The so-called "gutless" rAd vectors contain a minimal amount of adenovirus DNA and are incapable of expressing any adenovirus antigens (hence the term "gutless"). The gutless rAd vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., *J. Virol.* 70:8944-8960 (1996).

The "inverted terminal repeats (ITRs) of adenovirus" are short elements located at the 5' and 3' termini of the linear adenoviral genome, respectively and are required for replication of the viral DNA. The left ITR is located between 1-130 bp in the Ad genome (also referred to as 0-0.5 mu). The right ITR is located from about 3,7500 bp to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward.

The "encapsidation signal of adenovirus" or "adenovirus packaging sequence" refers to the ψ sequence which comprises five (AI-AV) packaging signals and is required for encapsidation of the mature linear genome; the packaging signals are located from about 194 to 358 bp in the Ad genome (about 0.5-1.0 mμ).

One aspect of the present invention relates to a viral backbone shuttle vector for the construction of gutless rAd vectors. In one embodiment, the viral backbone shuttle vector of the present invention contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb. (SEQ ID NO: 1).

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may encode protein, or contain regulatory sites, including but not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human, etc., origin. Specific examples of promoters are the promoters of the genes PGK, TK, GH, α-EF1, APO, CMV, RSV etc. or artificial promoters, such as those for p53, E2F or cAMP.

In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1.

One aspect of the present invention relates to a gutless adenoviral vector that carries a DNA sequence encoding a native TM protein or a variant of a TM protein. In one embodiment, the native TM protein is a human TM protein having the amino acid sequence recited in SEQ ID NO:2. Another aspect of the present invention also relates to a gutless adenoviral vector that carries other transgenes. These transgenes may include, but are not limited to, those coding for cytokines such as IL-1, IL-2, IL-3, IL-4, IL-5, IL-6, IL-7, IL-8, IL-9, IL-10, IL-11, IL-12, IL-13, IL-14, IL-15, IL-16, IL-17 and other interleukins; hematopoetic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2; KGF, myotrophin, NGF, OSM, PDGF, somatotrophin, TGF-β, TGF-α and VEGF; antiviral cytokines such as interferons, antiviral proteins induced by interferons, TNF-α, and TNF-β; amyloid protein and amyloid precursor protein; anti-angiogenic proteins such as angiostatin, endostatin, METH-1 and METH-2; clotting factors such as Factor IX, Factor VIII, and others in the clotting cascade; collagens; cyclins and cyclin inhibitors, such as cyclin dependent kinases, cyclin D1, cyclin E, WAF1, cdk4 inhibitor, and MTS1; cystic fibrosis transmembrane conductance regulator gene (CFTR); enzymes such as cathepsin K, cytochrome p-450 and other cytochromes, farnesyl transferase, glutathione-s transferases, heparanase, HMG CoA synthetase, n-acetyltransferase, phenylalanine hydroxylase, phosphodiesterase, ras carboxyl-terminal protease, telomerase and TNF converting enzyme; glycoproteins such as cadherins, e.g., N-cadherin and E-cadherin; cell adhesion molecules; selectins; transmembrane glycoproteins such as CD40; heat shock proteins; hormones such as 5-α reductase, atrial natriuretic factor, calcitonin, corticotrophin releasing factor, diuretic hormones, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, and thyroid stimulating hormone; proteins involved in immune responses, including antibodies, CTLA4, hemagglutinin, MHC proteins, VLA-4, and kallikrein-kininogen-kinin system; ligands such as CD4; oncogene products such as sis, hst, protein tyrosine kinase receptors, ras, abl, mos, myc, fos, jun, H-ras, ki-ras, c-fns, bcl-2, L-myc, c-myc, gip, gsp, and HER-2; receptors such as bombesin receptor, GABA receptors, estrogen receptor, growth factor receptors including EGFR, PDGFR, FGFR, and NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb.

In one embodiment, the DNA sequence is controlled by a regulatory element. In on embodiment, the regulatory element is a constitutive promoter such as the CMV promoter or RSV promoter. In another embodiment, the DNA sequence is controlled by a regulatable expression system. Systems to regulate expression of therapeutic genes have been developed and incorporated into the current viral gene delivery vectors. These systems are briefly described below:

Tet-onloff system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP 16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

Ex Vivo and In Vivo Thrombomodulin Gene Transfer

The instant invention uses a gutless adenovirus vector to express a native thrombomodulin protein or a variant of the thrombomodulin protein at a vessel graft or angioplasty site to prevent or reduce re-occlusion and intimal hyperplasia. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]).

In one embodiment, the in vivo expression of thrombomodulin or a thrombomodulin variant is used for the treatment of atherosclerotic cardiovascular disease (CVD). Though venous grafts can be used for bypass surgeries, the veins eventually, become occluded by thrombosis resulting the recurrence of the diseases. In this embodiment, TM gene delivery is used in coronary artery bypass grafting, and vascular graft prostheses to block thrombosis. Specifically, TM gene is introduced into a segment of blood vessel in vitro using a gene transfer vector.

TM gene delivery can be also used for the reduction of no-intima formation, for the prevention of atherosclerosis; for the prevention of myocardial infarction and for the inhibition of fibrinolysis in hemophilic plasma. TM gene transfer at the site of thrombus formation is potent approach to reverse these vascular diseases.

In another embodiment, in vivo TM expression is achieved by embedding a gene transfer vector in a stent which is placed at the treatment site following percutaneous transluminal coronary angioplasty, peripheral artery angioplasty, thrombectomy, or an intravascular stenting procedure.

In another embodiment, the in vivo expression of thrombomodulin, or a thrombomodulin variant is used for the treatment of end stage renal failure (ESRD). ESRD patients often exhibit decreased antithrombotic activity due to low TM levels. In such patients, enhanced in vivo TM gene expression can be potentially very useful.

In another embodiment, the in vivo TM expression is achieved by administering a gene transfer vector to a mammal intravenously (i.v.), intramuscularly (i.m.), intraperitoneally (i.p.) or subcutaneously. For adenoviral and AAV vectors, intravenous administration often lead to viral infection of hepatocytes and transgene expression in the liver.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At bp 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRI/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence. The new plasmid is designated as pShuttle-ITR-HPRT (SEQ ID NO:1)

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette. The intermediate vector used was pCDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV. pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The human TM cDNA (SEQ ID NO:5) was obtained from Dr. Sadler (Dittman et al., *Biochemistry*, 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at bp 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                              (SEQ ID NO: 8)
    5'-gtaacactgg cccaggaggc ctttctggtg acccc-3'

(SEQ ID NO: 9)
    3'-tgacc gggtcctccg gaaagaccac tggggatt-5'
```

Creation of pTMadap-Stuffer1

Based on the published sequence HSU71148 of the human X chromosome region q28 the following PCR primers were synthesized:

```
                                             (SEQ ID NO: 10)
    Forward: 5' TAGTTCCTTCTGCCTGGAATAC 3'

(SEQ ID NO: 11)
    Reverse: 5' CAAGTCACAAGGATGGACTACA 3'
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 bp was inserted into the BstEII and SfiI sites of pTMadap, resulting in pTMadap-stuffer1.

2(a)-4 Creation of pTMadap-Stuffer1-Short

To reduce the size of the stuffer1 fragment in pTMadap-stuffer1, pTMadap-stuffer1 was digested with SanDI and BstEII and the resulting DNA ends were modified by a fill-in reaction with Klenow. Re-ligation resulted in the 25207 bp vector pTMadap-stuffer1-short. The sequence of stuffer1-short fragment is shown in SEQ ID NO:13.

2(a)-5 Creation of pTMadap-Stuffer1-Short-Stuffer2

The plasmid p2-2 (SEQ ID NO: 14, obtained from GenBank) was cut with NotI and the resulting fragment of approximately 5954 bp (stuffer 2, SEQ ID NO: 15) was inserted into the NotI site of pTMadap-stuffer1 short, resulting in pTMadap-stuffer1-short-stuffer2.

2(a)-6 Removal of PacI Site from pTMadap-Stuffer1Short-Stuffer2

Figure 2:
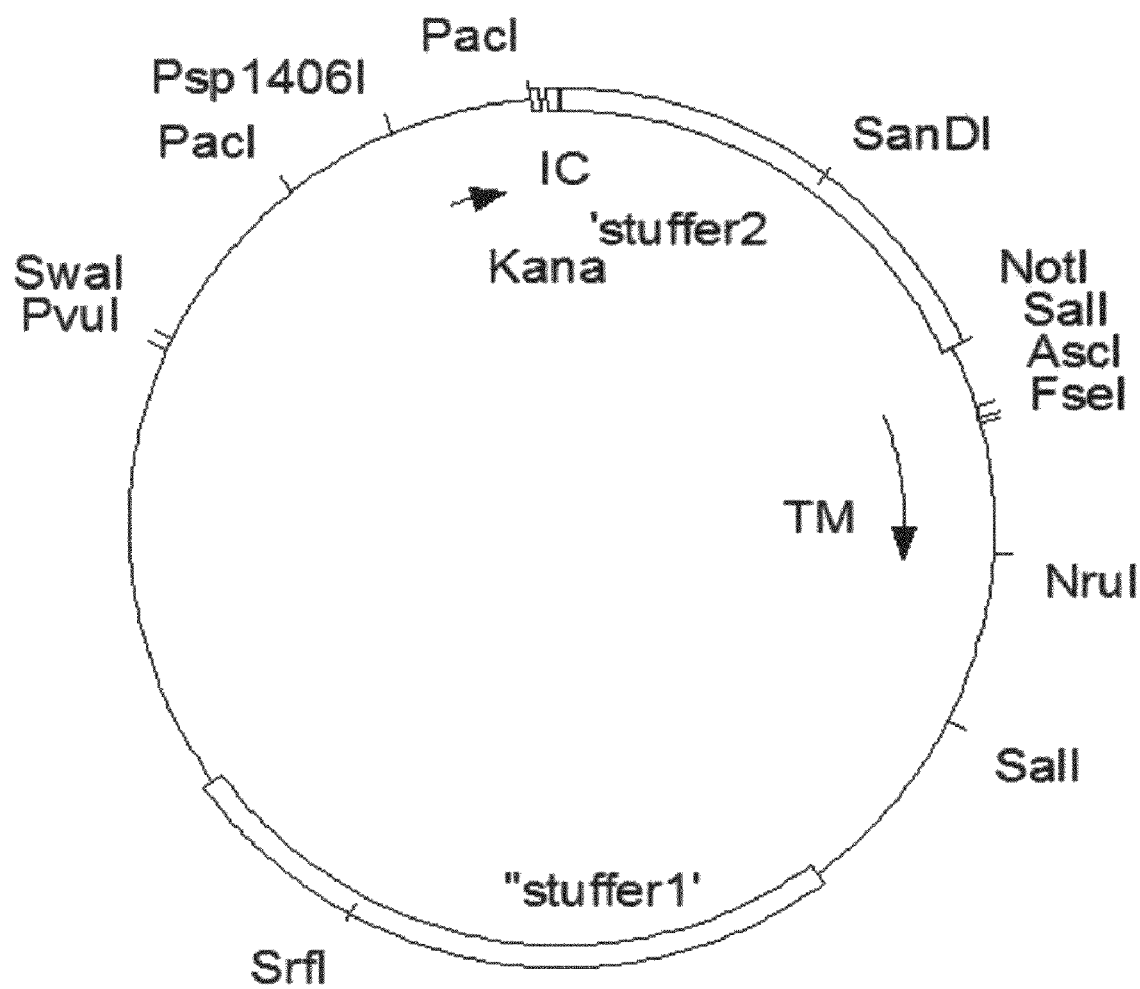
FIG. 2 is a schematic drawing of an embodiment of the full length backbone vector pTM-final.

Plasmid pTMadap-stuffer1-short-stuffer2 was cut with AclI and BsiW1. The resulting 28790 bp fragment was isolated from gel. pShuttle-ITR-HPRT (SEQ ID NO:1) was cut with AclI and Acc65I. The resulting 1966 bp fragment was ligated into the isolated 28790 bp fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

EXAMPLE 3

Preparation of Gutless Adenovirus Carrying Human Thrombomodulin Gene (gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 µg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy*, 3(5):809-815 [2001]; Umana et al., *Nature Biotechnology*, 19:582-585 [2001]).

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETOH. Cotton swabs (one swab for each tube) were used to completely dry out the tube, and two tubes were used per sample.

14. Preparation of the first gradient: 2.5 mL CsCl-Density 1.25, and 2.5 mL CsCl-Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/ml. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris-pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5 10, and 15 µg/ml. (BSA is fine). Sample cuvettes were prepared using 1-10 µl of sample, depending on estimate of titer. (Sample OD must be within the linear range of the standard line.) OD was taken at 595λ and formula of the line was calculated from standards. The protein concentration of the samples was calculated using this formula. The following formula was used to convert protein concentration to titer: $[12.956+224.15 (\mu g/ml)] \times 10^8$.

EXAMPLE 4

Figure 3:
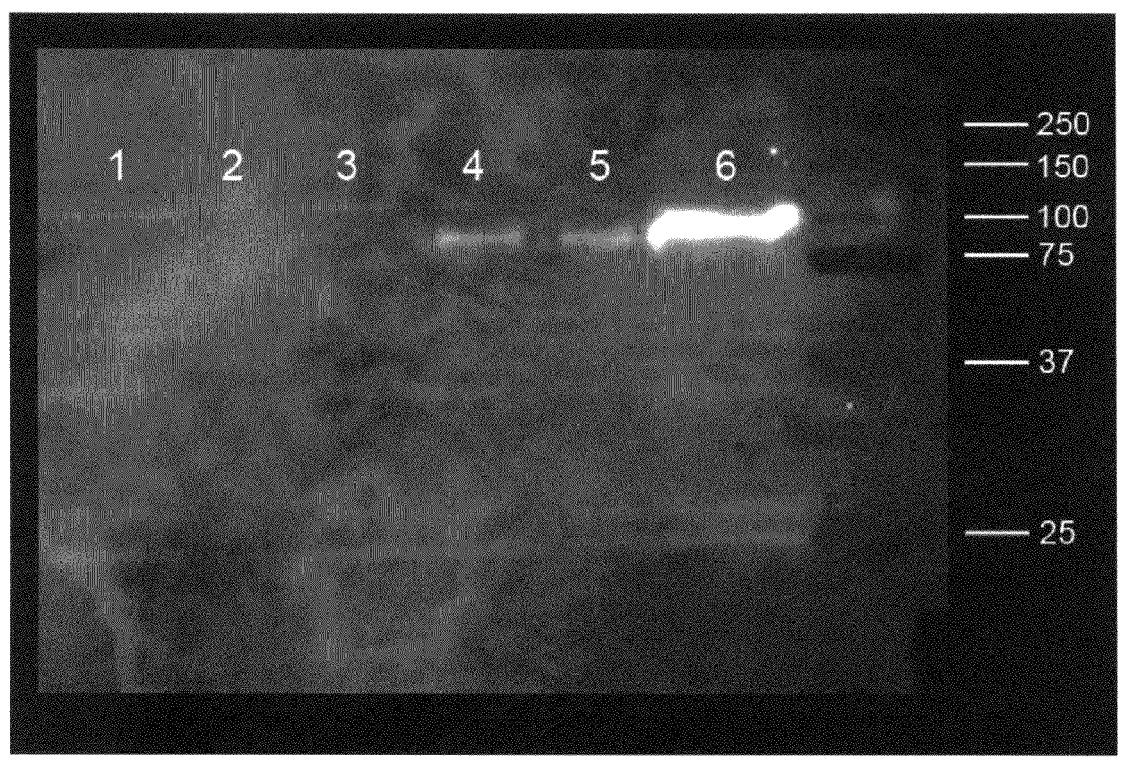
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-Final HEK 293 cells were cultured in a 6 well cluster and transfected with 1 µg of pTM-final. After 24 hours, the cells were washed with PBS and lysed in 125 µl RIPA buffer with protease inhibitors Protein samples (16 µl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 µl Igepal ca-630, 50 mg sodium deoxycholate, 500 µl 20% SDS, 10 mM β-mercapto ethanol, and 1 ml 10× PBS, and add water to a final volume of 10 ml at room temperature. A cocktail of protease inhibitors containing 11.5 µl PMSF (from 34.8 mg/ml in isopropanol, 64 µl Benzamidine (from 15.6 mg/ml stock), 100 µl sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(B) Expression of hTM in P2 Lysate of 293FLP Cells

Figure 4:
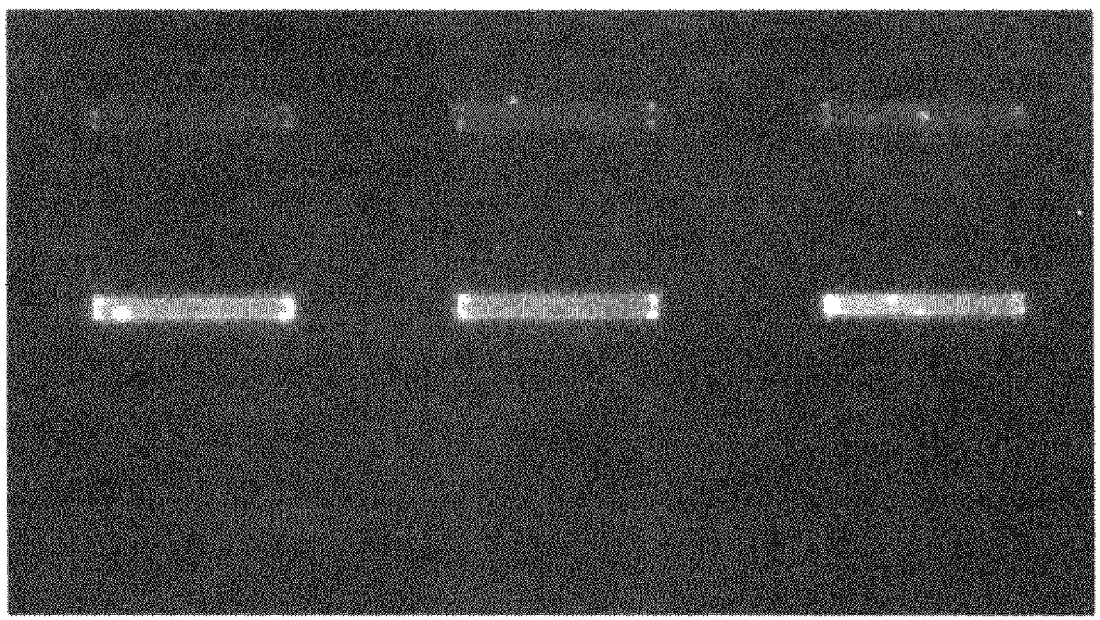
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250µl RIPA buffer. 7 ul of 5× loading buffer was added to 35 µl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11.5 µl PMSF (from 34.8 mg/ml in isopropanol, 64 µl Benzamidine (from 15.6 mg/ml stock), 100 µl sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
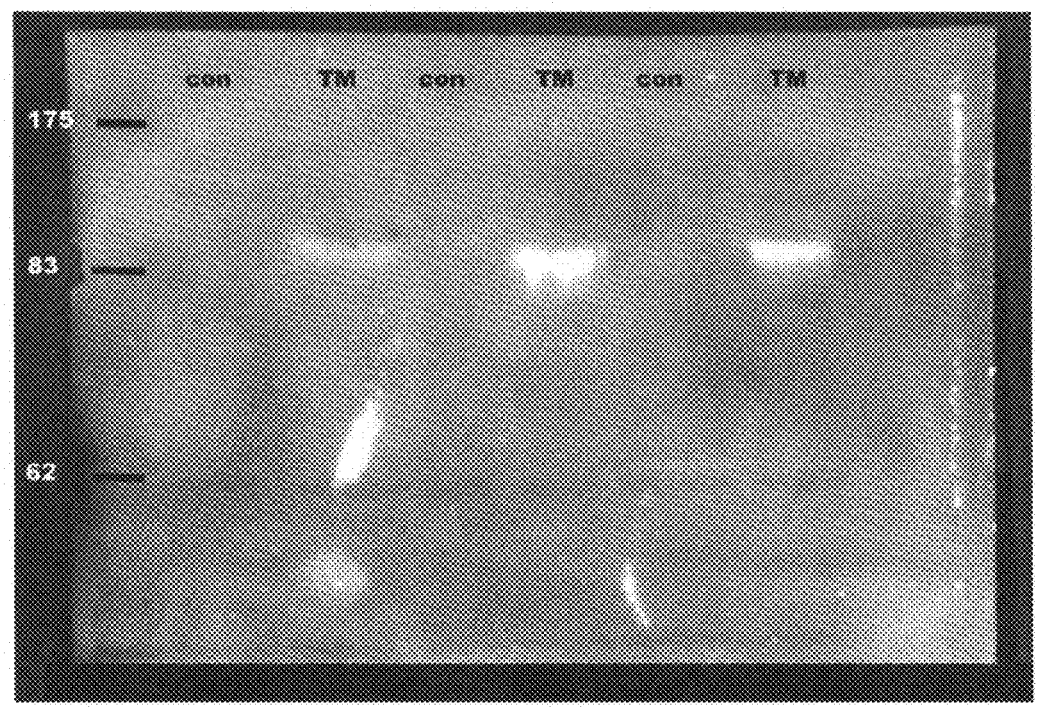
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 µg of PacI digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
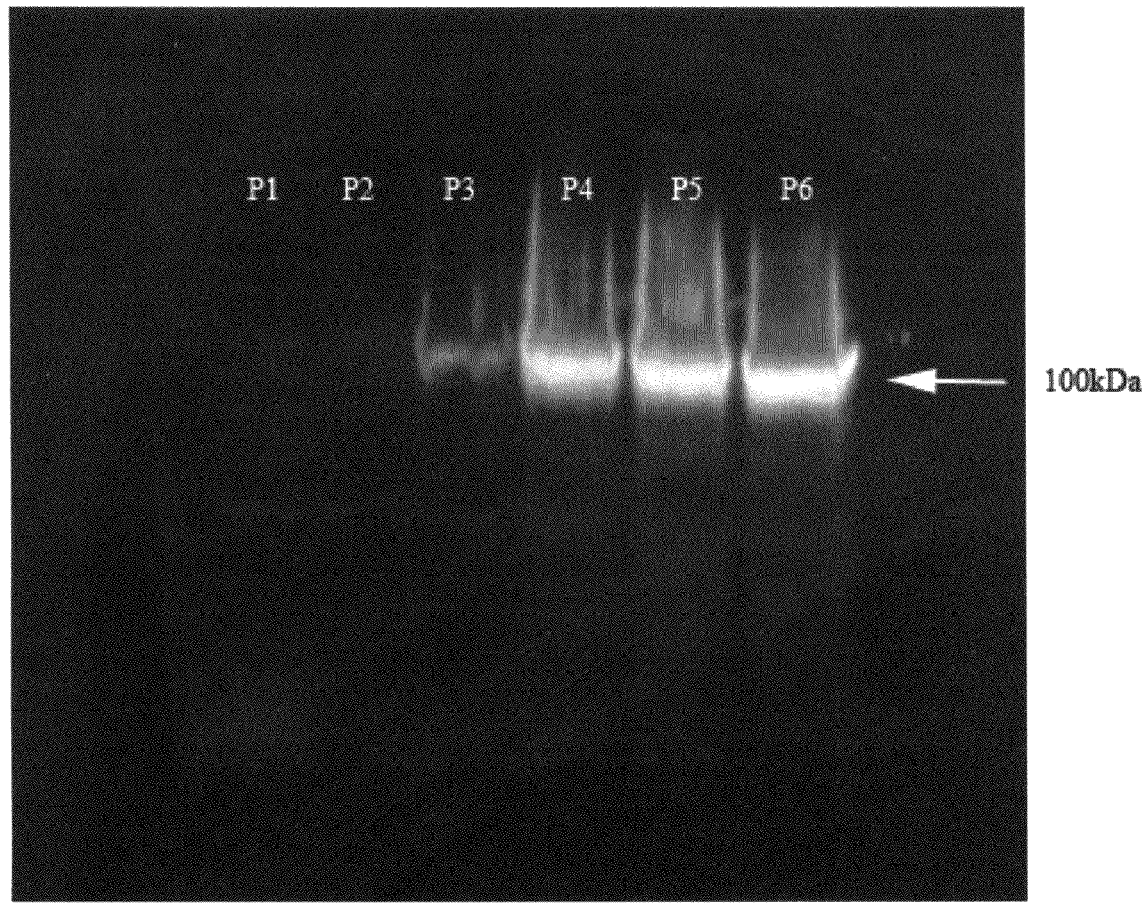
FIG. 6 is a picture of a Western bolt showing TM expression in CRE cells at passage number 1-6 (P1-P6).

HEK 293 cells were cultured in a 6 well cluster and transfected with 200 µl of TM gutless virus of passage 1-6. After 24 hours, the cells were washed with PBS and lysed in 125 µl RIPA buffer. Protein samples (16 µl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293 CRE cells.

The RIPA buffer (10 ml) was prepared as follows: 100 µl Igepal ca-630, 50 mg sodium deoxycholate, 500 µl 20% SDS, 10 mM β-mercapto ethanol, 1 ml 10×PBS, add water to make up 10 ml. Immediately before use, the following protease inhibitors were added to the RIPA buffer: 115 µl PMSF (from 34.8 mg/ml in isopropanol), 64 µl Benzamidine (from 15.6 mg/ml stock), 100 µl sodium orthovanadate (100 mM), 5 µl pepstatin (from 1 mg/ml stock), 1 µl leupeptin (from 5 mg/ml stock), 1 µl aprotin (from 5 mg/ml stock).

EXAMPLE 5

Composition of The Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Treatment for Renal Disease

In this application, the vein in the kidney is treated following evacuation of the clot. A catheter is inserted in the kidney vein and both the proximal and distal balloons are inflated to isolate the vein segment to be transfected. The segment is evacuated of all blood, rinsed with physiologic saline; it is then filled with the CVDS described above, under pressure. The isolated vein segment is exposed to the CVDS for a period of 10 to 45 minutes, depending upon the desired transfection efficiency.

EXAMPLE 9

In Vivo Treatment with Virus Containing Stent

In this application, a virus-coated stent is placed at a treatment site after angioplasty. The virus is a gutless adenovirus carrying a polynucleotide encoding a thrombomodulin protein or a variant of a thrombomodulin protein. Alternatively, the virus may be embedded in the stent and is releases gradually through a time-releasing mechanism well-known to one skilled in the art.

EXAMPLE 10

In Vivo Expression of Transgene by Intravenous Infusion of Viral Vectors

Figure 7:
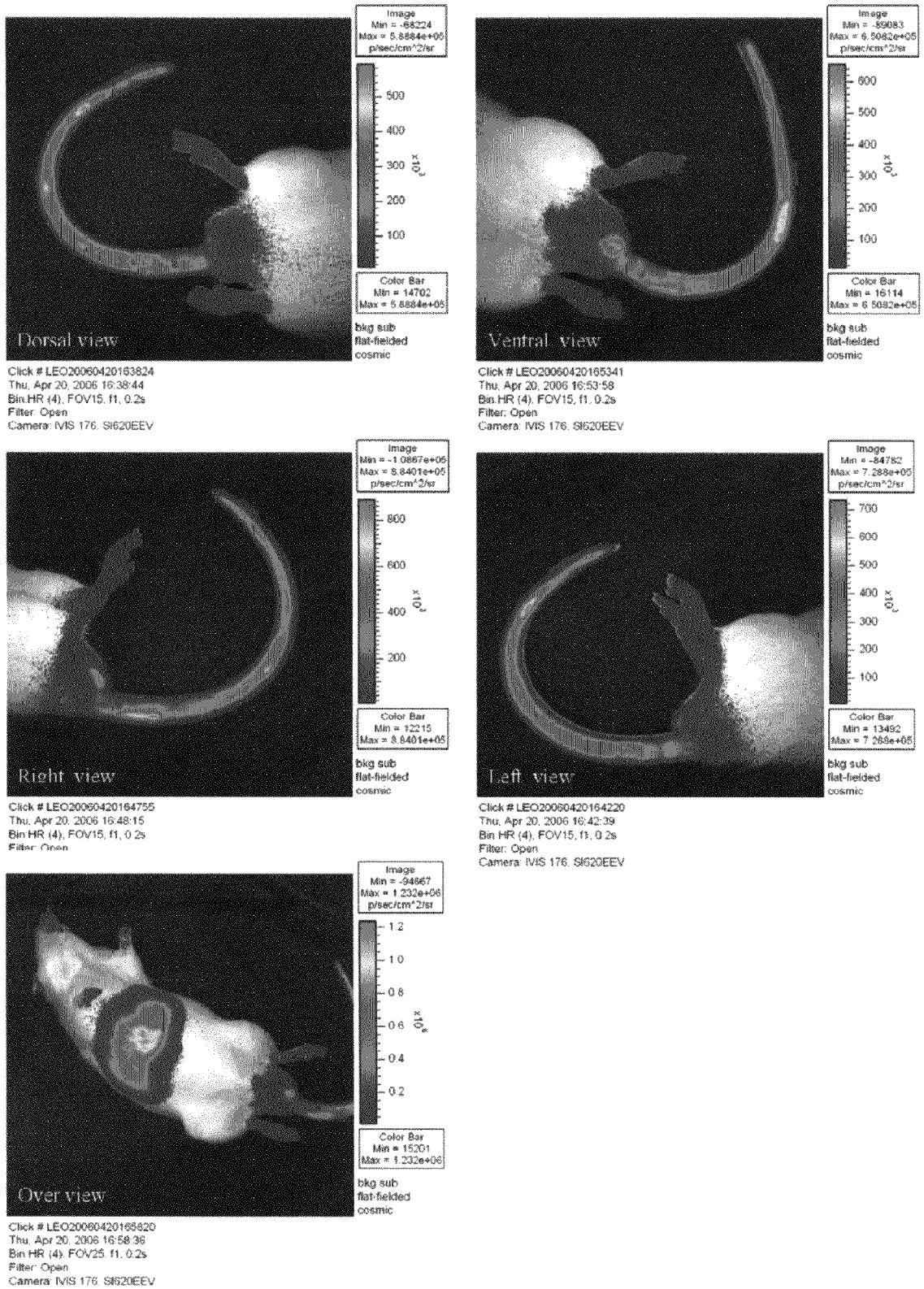
FIG. 7 is a composite of images showing gutless adenovirus-mediated luciferase expression in rat tail vein.

In one experiment, the tail vein of experimental rats was flushed with a solution containing a gutless adenoviral vector carrying a luciferase transgene. As shown in FIG. 7, the expression of luciferase was still very strong in the tail vein eight days after viral infection.

In another experiment, experimental rats were injected intravenously with the gutless TM viruses at doses ranging from $1 \times 10^8$ to $3 \times 10^{11}$ particles/rat. TM expression in liver will be analyzed by the rate of blood coagulation (APTT) and by Western blot of liver biopsy samples.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

```
SEQ ID NO: 1 (pShuttle-ITR/HPRT)
CATCATCAATAATATACCTTATTTTGGATTGAAGCCAATATGATAATGAG

GGGGTGGAGTTTGTGACGTGGCGCGGGGCGTGGGAACGGGGCGGGTGACG

TAGTAGTGTGGCGGAAGTGTGATGTTGCAAGTGTGGCGGAACACATGTAA

GCGACGGATGTGGCAAAAGTGACGTTTTTGGTGTGCGCCGGTGTACACAG

GAAGTGACAATTTTCGCGCGGTTTTAGGCGGATGTTGTAGTAAATTTGGG

CGTAACCGAGTAAGATTTGGCCATTTTCGCGGGAAAACTGAATAAGAGGA

AGTGAAATCTGAATAATTTTGTGTTACTCATAGCGCGTAATACTGGTACC

GCGGCCGCCTCGAGTCTAGAACTAGTGGATCCCCCGGGCTGCAGGAATTC

TGATGGCTCTCAAAATTCCTGCCTCCTTTAGGGATAAAAGACTTTAAGAC

TTTTTAACAAAAAAGAAAAAGAAAAAAAAAATTCCTGCCTCCTGGTGTAC

ACACACAGAAGGGTTCCCTCCCCTTGAATGTGACCAGGATCTGTGAAAAT

AACGGGATAGCCGCTCCTGTGATTAGGTTATGTGGTAGACTAGAGCAAGA

TTCTCCTGCTGGTTTTGAAGAAGTCAGCTGCCATGTTGTGAGACTGTCAT

GGGCTAGGGCATGAGCCTTTAAATATCTGGGAGCAACCCCTGGCCAGCAG

CCAGTGAGAAAACGGGCCCTCAGTCCTACAATCACAAGGAACTAAATTCT

GCCAACAACCTGAAGGAACTTTGAAGAGGATCATGAGTCCCTTGATTCAG

CTTGATGAGCCCCTGAGCAGAGGATACAGCTAACTTGTACTAGGGAAGTA

TAAAAACATGCATGGGAATGATATATATCAACTTTAAGGATAATTGTCA

TACTTCTGGGAATGAAGGGAAAGAAATGGGGCTTTAGTTGTATTATGATC

TTTAATTTCTCAAAAAAAATAAGATCAGAAGCAAATATGGCAAAATGTTA

ATACTTTTGTGGGTACGTAGGTATTCAGCATACCCTTTTTTCTGAGTTCA

AAATATTTTATAATTAAAATGAAATGCAGGCCAGGCACAGTGGCTCATGC

CTATAATACCAGCACTTTGCGAGGCCGAGGTGGGAGGATGGCTTGAGGCC

AGACCAGCCTGGCCAACATGGCAAAACCCCATCTCTACTTAAAAAAAAAA

AAACTATATATATATATATGTGTGTGTGTGTATATATATATATGTATA

TATATTTATATATGTGTGTATATATATATATGTATATATATTTATATATG

TGTGTGTATATATATATACACACACACATATATACATACATACATA

CACACACACACACACAATTAGCCAGGCATGGTGGCGCACACCTGTAGT

CCCAGCTACTTGGGAGGCTGAGACATGAGAATTGCTTGAACCTGGGAGGC

AGAGTAGTTAGTGAGCTGAGATCATACCACTGCACTCCAGCCTGGTGACA

GAGTGAGACTCTGTCTTAAAAAAAATAAAAATTAAAATTAAATGCAAAAG

GTCCAAGTGAATTGAAGAGGAAAGGGGTATCAAGGAAGGTTTTGTGGAGG

TGACGTTTGAGCTGGGTCTTAAATGACTTAAACATGGGATAAGAAGGGAG

GGAATAAGGACATTTCAGGTACGAGAAATAAGGAGCAAACAGTGGAAACA

ACCTAACGTCTGTCAACCAGTGAATGGATAACAAAAATGTAATTCAGATG

GTATCCAACTTACGATGGTTCAACATGAGATTTTTCTGACTTTAGGATAG

ATTTATCAAAGTAGTAAATCCATTTTCAACTTATGATATTTTCAACTTCA

GATGGGTTTATCAGGACACAGTTGAGGAACACCTGTCTATCCATACAATT

TGGCAATAAAAAGGAAATGAGTGCAGATATACTCCACAACATGAATGAAC

CTTGAAAACATTAAGTGAGAGAAGCCAGATACAAAAGGCCACATATTGTA
```

```
TGATTCTATTTATACAAAATGTCCAGAATAGGCAAATCTTATAGACAGCA
AGTAGGTAGATGATCAGTTTGCTAGGTGCTGGGGGAAGGGGAAATGGGGA
GTGATGGCTAAGGGGATTGGGTTTCTTTGTGGGGCAATGAAAATGTTTTA
AAATTGAGCGTGATAATGATTGCACAATGCTGCATATATATATAATCTAT
AGATTATATATATAAAGAGAGGCTGTTAGACAGTGATAAGTGATATAT
ATATATATATACATAGAGAGAGAGAGAGAGAGAGAGGCTGTTAGTG
ATAAGTGATCAGGAAAATAAAAGTATTGAGGAGGAATACGAAGTTGACGG
TGTGAAAACATGAGATTTTATATAGGATGGCCAGGGAAGGCCTTAATGAG
AAAGTGACTTATGAGTAAAAACAAGGGATCCTAAACCTTAGCATGCATCA
GAATCACTCGGAAACTTGTTAAAGCATAGCTTGCTGGGCCTCATCACAGA
TATTTTGATTCGGTAGGTTCTTGTCTGATATTAATACTTTTGGTCTAGGG
AACCACATTTTGAGAACCACTGAGCTAAAGGAAGTAAAGGTTTCCCTTAG
TTTACTAGCTGGTAACCCTAGGAAACTGCTTAGCCTCTCGGTGCTAAGAT
ACAAAATACTTTAGCACATAATAACACATGGAAAATAGTCTATAAATTAT
AAATATTATTTTTTATGTACCAAATATTACATAAGACAAAATCTAAGCAA
GATATATATATATACATAAAATATAAGATATATATGTATATATTTAT
ATAGATAAATAGAGAGAGAGAGTTATGTTTAGAAAGAAAATACTTCAAAC
TAAAAAAAGAGAGGTAGGAAGTATACCATTCCATTATTGGTAAAAACAAA
TTACTAAGTAGTCTTTACAAAAAACCAATCTCACTCCTTTAGAACACAAG
CCCACCATTAAAACTGATGCAGAGGAATTTCTCTCCCTGGCTTACCTTTA
GGATGGTGCATACTAAGTTAGAAAAGTCATAAATGTTATATTAAAAGTAA
ATGTGAACTTACTTCCACAATCAAGACATTCTAGAAGAAAAAGAGAAATG
AAAATCAGTACAATGAATAAAACGGTATTTCCAATTATAAGTCAAATCAC
ATCATAACAACCCTAAGGAATTATCCAAACTCTTGTTTTTAGATGCTTTA
TTATATCAAACTCTCCTTTAAACAAGTGGCCCATCTGCTGGGATTTGGAA
GCCTGTAATACTGAAATTTTCATCATAATGGAAATTTTAAAAACAGAATT
TGACCCACCTGTTTTTAAAACACTTTCATTACTTAACAAGAGGTCTAATC
TTGGGCAAGTCTTGAAATTTCTCTGGCCTTAGTTTCCCATGTGTTAAATG
AAACTTGAAGCAGTTGGTCTCTTATAGTCTCCTGACTCTAACATTCTAAG
AATTATATTTGTACAATAACTCAAAAATCACATAATTTAATTTACCATAT
GGACTCCAAAATATATTTTCTCATTAGGCTAAACTTGATCTGCATTTTCT
GGATGTGTCCATATTCTTGGACTACACTAAAACATGATACCAATGCTTCC
TCTCACCATAAACCCTCACTTCGCTTTCTACATTTAAGAATTTTATAGCT
GGAAGAGTCCTTAACAGAAAATACCATCTAATAATTACCCCTCAAAATCG
AGAAAGTCCTATCTGTTCTTATGCTAGTTATAAGAATGAGGCAGCATTTC
ACATAATGGTTATAAACACTGCCACAAGAAGATTCATGATGTGTTGTTTA
TCTGTAGCTCTCATCATACTCTGTCATATAACTATAGCATTAAGATTTTA
ATGTTCTATATATTCTTCTAAGACAGTGTTTACCAGAGTAAGGCACAAAA
GATCCACTGGTTTGCAAGAAAGATTAGAACTTTTAAATTTTTTACCTCAC
CTTGTTTAATCTATATTTTTGTATGTATTTTGTAACATATATATTATTAT
TACCATAAATCATATATAATTTAAAATGCATATATTAGGGGTAAATGCTC
AGGAAACTTTTTATAAATTGGGCATGCAAATACAAGTTTGAAGACTCACT
GTTCTAGGTATTAAAAGTAAAGTTATAACCAAGTAAAGCTTCCACCTTTT
CATGTCTCAAAGCAGTTTATTGTTGGAGGTAAGATCTCTTAGAAGCCTAA
ACAGGTCCAAGTACAGAATGAAGTAAGGCTAGCCCATAACTTGTGGCAAG
CAATTCATACTATTTCTCTCATGCTGAGCTCTCCTCAGTGAAGCAGCTAC
TATACACAACTGCAGCCTATTGGTAGCCTATTTTACAGGCAGGAAAAAAA
TTACTTTTTATTCAAAGTGGAACTCAGGACATGGGGAGAAAATGAATACA
AAAAATAGGGTCAATCCAAAGGCACACAGCAAATGAGTAACACAGTTATG
TTTTTTTCCCATTTGTATGAGGTCCCAGTAAATTCTAAGTAAACTGCAAA
TTTAATAATACACTAAAAAAGCCATGCAATTGTTCAAATGAATCCCAGCA
TGGTACAAGGAGTACAGACACTAGAGTCTAAAAAACAAAAGAATGCCATT
ATTGAGTTTTTGAATTATATCAAGTAGTTACATCTCTACTTAATAAATGA
GAAAAACGAGGATAAGAGGGCATTTGATAAAATGAAAATAGCCAAGAAGT
GGTATTAGAGACTTGAATACAGGTATTCGGGTCCAAAGTTCATCTGCTCA
AATACTAACTGGGGAAAAGAGGGAAAAATATTTATATACATATATATCTG
CACACAAAAATACCCCCAAAAGACAAAATGAGGCCAGGCAGGGTGGCTCA
CACCCGTAATCCCGGTACTTTGGGAGGCTGAGGCAGGTGGATCCTGAGA
TCAGGAGTTGGAGATCAGCCTGGTCAACATGGTGAAACCCTGTCTCTACT
AAAGATAAAAAATTAGCCAGGCATGGTGGCGTGCGCCTGTAATCCCAGC
TACTTGGGAGTCTGAGGCAGGAGAATCACTTGAACTGGGAAGGGGAGGTT
GCAGTGAGCCAAGATCGTACTACTGCACTCCAGCCTGGGCAGCAGAGTGA
GACTCCATCACAAAAATAAATAAATAAAATACAATGAAACAGAAAG
TTCAAATAATCCCATAATCTTACCACCAAGAAATAACTTTCACTCGTTAT
ACTTATTGATTTTCCATAATAAATGTACTTTACTGTGACTATCATGAAA
AGAAAGTTATTTTAGAAACAGAGAACTGTTTCAGATCAAATCTATGTAGT
AGAACAGAGCCATTAGGTGGGAAAGACGAGATCAAACTAAATCTCAGAAG
GCCTAAAAGGCTAGGTCCATTCCAGCACTAAAAACTGACCAGACAAGTAA
TGGCTTCAACAGCTTCTAAATATGGACAAAGCATGCTGAAAGGGAAGGAC
AGGTCTAACAGTGGTATATGAAATGAACAGGAGGGGCAAAGCTCATTTCT
CCTCTGAAGTTTTCCAAAGATGCTGAGGAGGACATTAGTTTGACATGACC
CTGATATGGGACAAGATAATTTCACAGAAGTTTTACATGTTAAAGTTTTC
TTATAGATACTCATTCAAGTAAGCAATGAACACTAAAATCTAAAGAAAGA
AAAGAGCTTTAGAGTCAGGTCTGTATTCAAATTCAAGCTCTACCACTTAC
TGGTTCTGTGACTTTGGGCAAGTCTTTTAACCTTATTAAGTCTTAATTTC
CTGATTTGTAAAATGGGGATATCGTCTCCCTCACAGGATTGTTGTGAAAC
TTTTATGAGATTAATGCCTTTATATTTGGCATAGTGTAAGTAAACAATAA
CTGGCAGCTTCAAAAAAAAAAAGCAGTAGCATTCCATCATTTATTATTGG
TTACTCTCAAAAAGTTTTTCAATGTACTAGAAGATAAATATTCAAATACC
TTAATATCTCCATTATTTTTCAGGTAAACAGCATGCTCCTGAACAACCAAT
```

-continued

```
GGGTCAACAAATAAATTAAAAGGGAAATCTAAAAACATCTTGATATTAAA
CTACATGGAAGCACAATATACCAAAACCAATGGTTCACACTAGGAGAATT
TTAAGGTACAAGAAAACTCTTTGAGATTTCTTAAAATAATAGTATGTCTG
AATTTATTGAGTGATTTACCAGAAACTGTTGTAAGAGCTCTACTTGCATT
ATAGCACTTAATCCTCTTAACTCTATGGCTGCTATTATCAACCTCACCCT
AATCACATATGGGACACAGAGAGGTTAAGTAACTTGCCCAAGGTCAGAGT
TAGGAAGTACTAAGCCATGCTTTGAATCAGTTGTCAGGCTCCGGAACTCA
CACTTTCAGCCACTACATAATACTGCTTTGCTATCTTTTAGGAAACTATG
TGAGTCTACCTCACATAGACTCACATAGGTTTGTTTTTTTTTTTTTTTA
AAGGCTATCTTTTCCCCCATCAATGTTTTTGAAGGATCCCAAATTAGAG
TCCCACAGAGGCAGACAGCAGTACTTGACAATATGGACATTTAAGGTTAA
TGTTGGATTCTACTGTCTTTTACTACATGACCTAGGGAACGATAATTAA
CCTAGACTGCTTCCAAGGGTTAAATAACCCATTTAGTTATACTATGTAAA
TTATCTCTTAGTGATTGATTGAAAGCACACTGTTACTAATTGACTCGGTA
TGAAGTGCTTTTTTTTCTTCCCTTTCAAGATACATACCTTTCCAGTTAAA
GTTGAGAGATCATCTCCACCAATTACTTTTATGTCCCCTGTTGACTGGTC
ATTCTAGTTAAAAAAAAAAAAACTATATATATATATATCTACACACACA
TATGTATATGTATATCCTTATGTACACACACAAACTTCAAATTAAATGAG
AACTAGAAGATTTGAGAAGTTAGCTAGCTAATATCCATAGCATTATGATA
TTCTAAATGATATGAATTATAAGAATTAGGTTTCCTGAAATGAATGACTA
GAAAACTTTCAAGTAGAGATTAGTAAAAATTAAAAAGTCCTAATCGGCCA
TTACTGATTTGATGTTTTTAAGAGTCCTAAAAAATGGGTTACATCCATTT
TTAAGTGGGTAGTATTATAACAGCCACCCATCTTCAATCACAGTGATTTC
TGAATTGTGAGGGAAGTTATTAGCATGACAGGTGTCTGGTTCTGGCCCTG
TACGATTCCCATGAGTCAAGCAAATTGTAAGGGCTGGTCTATATCACACC
CAACCCCAAGGATATGTCCCTCAAAAGTCTAGCCCAGGCCCCGTCATCTT
CAGCATCATCTGGGAAACCAGGTCTGATTAGTAGTCCTTTAAGGAATACC
TCTTAGGCTCCCATTTTACTGCTATCACAGAATCCAATAAAACCCTTACA
GGAGATTCAATGGGAAATGCTCAACACCCACTGTAGTTGGTGGTGACAAT
GACCATAATTTGGCTGTGCTGGATTCAGGACAGAAAATTTGGGTGAAAGA
GCAGGTGAACAAAAGAGCTTCGACTTGCCCTAGCAGAGAGCAAGCCATAC
CATACCACAAAGCCACAGCAATTACAACGGTGCAGTACCAGCACAGTAAA
TGAACAAAGTAGAGCCCAGAAACAGACCCAGAACTATATGAGGATTTAGT
ATACAATAAAGATGGTATTTCGAGTCAGTAGGGAAAAGATGAATTATTCA
ATAAATGATGTTTGGCCAACTAGTAACCCATTTGGGAAAAAATAAAAGTA
TGGTCCCTACCTCACAGCATACACAAAATAAATTCCAGACGGATTAAAA
TCTAAATGTAAAAAATAAAGCCATAAGTGGACTGGAAGAAAATAGAGAAT
TTTTTTTAACATCCGTAGAAAGGGTAAAAACCCAGGCATGACATGAACCA
AAACTGAAGAGGTTCTGTAACAAATACCCCCTTTTATATATTGGGCTCCA
ACAATAAGAACCCATAGGAAAATGGAGAATGAACACAAATAGACAATTTA
TAGAAGAGAAGGTTATAAGGTGTAAAATTATATCTATCTGAGAAACAAAC
ACTAAAACAATGTGATTCTACTGTTCTCCCACCCATACTGGCAAAACTTA
AGCCTGATAATATGCTGAGGGGAAATAAGCACTCTTGTTGGTGAGAGTAT
TAATTGGCATAGCTTCTTTTGAAAATGACATAGCAATACCTGTTAAAATT
GCAAACATGCATGTCACTTAATCCAGTAATCCCACTTCTGGGAATCAATG
CTACAAAAACACTGACAAGTATACAAAGATACATTCAAGAGTGTTCACTG
GGCCGGGTGCGGTGGCTTCATGCCTGTAATCCCAGGGAGGCAGAGGCAAG
ACGATCGCTTGACCCCAGGAGTTCAAGGCCAGCCCGAGAAACACAGCAAG
ACCCTGTCTCTCTTTTTTTATTTAAAAAATAAATGTTCACTGTATCAGT
TGTTCACAAAAACAAACCAACATGTCCATTAACAGGGAACCATTTAAATT
AATCAAGTTCATCTACACAATGTAATACCATGCAACTATTAAAAAGCACC
TGATAATCCAAAGCACACTGAGACAGAATAATGCTATTAAAAACACCAAG
TAGTGGAACACTGTGTTGCCTATGACACCATTTTTATTCAACATTTAAAC
AAATTTGTAACAGCAATTACATGAGTAGTGACAATGGCGTTTATGAGACT
TTTCACTTTTATGTGCTTCTATTTTTGTTATGGTTCTATATATACATCCA
TTTATTATGGAGTGTTACTTTCAAAAATCACAAATGGGCCAGTATTATTT
GGTGTTGCAAGGTGAGCATATGACTTCTGATATCAACCTTTGCATATTAC
TTCTCAATTTAGGGAAATTACAGACATCCCTTATTCTAACTAACTTAAAA
CCCAGCATTTCAAACATACAGAATTGATGGGAAAAAAAAGAAAGAAGAA
AGAAAGAAAAGGCAACAAGCTTCAGATGACAGTGACTCACATCAAATTAT
TTATAAAATCTGTTAAATAGTGCCATCTTCTGGAGATACCTGGTATTACA
GTCCAACTCCAGTTGATGTCTTTACAGAGACAAGAGGAATAAAGGAAAAA
ATATTCAAGAACTGAAAAGTATGGAGTCATGGAAAAATTGCTGTGATCCA
AAGGCTACGGTGATAGGACAAGAAACAAGAGAACTCCAAGCAGTAAGACA
CTGCTGTTCTATTAGCATCCAAACCTCCATACTGCTGTTTGCCCCAAGGC
TTTTTTAAAAAATAGAGACAGGATCTCACTATTTTGCTCAGGCTGGTCTT
GAACTCCTGGACTCAAGCTATCCTCCTGCCTCGGCCTCCTAAAGTGCCGA
GATTACAGGCTTGAGTCACCATACCTGGCTATTTATTTTTTCTTAACTCT
CTTGCCTGGCCTATAGCCACCATGGAAGCTAATAAAGAATATTAATTTAA
GAGTAATGGTATAGTTCACTACATTGGAATACAGGTATAAGTGCCTACAT
TGTACATGAATGGCATACATGGATCAATTACCCCACCTGGGTGGCCAAAG
GAACTGCGCGAACCTCCCTCCTTGGCTGTCTGGAACAAGCTTCCCACTAG
ATCCCTTTACTGAGTGCCTCCCTCATCTTTAATTATGGTTAAGTCTAGGA
TAACAGGACTGGCAAAGGTGAGGGGAAAGCTTCCTCCAGAGTTGCTCTAC
CCTCTCCTCTACCGTCCTATCTCCTCACTCCTCTCAGCCAAGGAGTCCAA
TCTGTCCTGAACTCAGAGCGTCACTGTCAACTACATAAAATTGCCAGAGA
AGCTCTTTGGGACTACAAACACATACCCTTAATGTCTTTATTTCTATTTT
GTCTACCTCTTCAGTCTAGGTGAAAAAATAGGAAGGATAATAGGGAAGAA
CTTTGTTTATGCCTACTTATCCGCCCCTAGGAATTTTGAAAACCTCTAGG
TAGCAATAAGAACTGCAGCATGGTATAGAAAAAGAGGAGGAAAGCTGTAT
```

```
AGAAATGCATAATAAATGGGCAGGAAAAGAACTGCTTGGAACAAACAGGG
AGGTTGAACTATAAGGAGAGAAAGCAGAGAGGCTAATCAACAAGGCTGGG
TTCCCAAGAGGGCATGATGAGACTATTACTAAGGTAGGAATTACTAAGGG
CTCCATGTCCCCTTAGTGGCTTAGTACTATGTAGCTTGCTTTCTGCAGTG
AACTTCAGACCCTTCTTTTAGGATCCTAGAATGGACTTTTTTTTTTTATC
GGAAAACAGTCATTCTCTCAACATTCAAGCAGGCCCCAAGTCTACCACAC
TCAATCACATTTTCTCTTCATATCATAATCTCTCAACCATTCTCTGTCCT
TTTAACTGTTTTTCTATACCCTGATCAAATGCCAACAAAAGTGAGAATGT
TAGAATCATGTAATTTTAGAGGTAGACTGTATCTCAGATAAAAAAAAAGG
GCAGATATTCCATTTTCCAAAATATGTATGCAGAAAAAATAAGTATGAAA
GGACATATGCTCAGGTAACAAGTTAATTTGTTTACTTGTATTTTATGAAT
TCCCTAAAACCTACGTCACCCGCCCCGTTCCCACGCCCCGCCACGTCA
CAAACTCCACCCCCTCATTATCATATTGGCTTCAATCCAAAATAAGGTAT
ATTATTGATGATGTTAATTAACATGCATGGATCCATATGCGGTGTGAAAT
ACCGCACAGATGCGTAAGGAGAAAATACCGCATCAGGCGCTCTTCCGCTT
CCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAA
CGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGA
CACGACTTATCGCCACTGGCAGCAGCCACTGGTAACAGGATTAGCAGAGC
GAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTT
ACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAG
TGGAACGAAAACTCACGTTAAGGGATTTTGGTCATGAGATTATCAAAAG
GATCTTCACCTAGATCCTTTTAAATTAAAAATGAAGTTTTAAATCAATCT
AAAGTATATATGAGTAAACTTGGTCTGACAGTTACCAATGCTTAATCAGT
GAGGCACCTATCTCAGCGATCTGTCTATTTCGTTCATCCATAGTTGCCTG
ACTCCCCGTCGTGTAGATAACTACGATACGGGAGGGCTTACCATCTGGCC
CCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAG
TAAGTAGTTCGCCAGTTAATAGTTTGCGCAACGTTGTTGCCATTGCTGCA
```

```
GCCATGAGATTATCAAAAGGATCTTCACCTAGATCCTTTTCACGTAGAA
AGCCAGTCCGCAGAAACGGTGCTGACCCCGGATGAATGTCAGCTACTGGG
CTATCTGGACAAGGGAAAACGCAAGCGCAAAGAGAAAGCAGGTAGCTTGC
AGTGGGCTTACATGGCGATAGCTAGACTGGGCGGTTTTATGGACAGCAAG
CGAACCGGAATTGCCAGCTGGGGCGCCCTCTGGTAAGGTTGGGAAGCCCT
GCAAAGTAAACTGGATGGCTTTCTTGCCGCCAAGGATCTGATGGCGCAGG
GGATCAAGCTCTGATCAAGAGACAGGATGAGGATCGTTTCGCATGATTGA
ACAAGATGGATTGCACGCAGGTTCTCCGGCCGCTTGGGTGGAGAGGCTAT
TCGGCTATGACTGGGCACAACAGACAATCGGCTGCTCTGATGCCCCCGTG
TTCCGGCTGTCAGCGCAGGGGCGCCCGGTTCTTTTTGTCAAGACCGACCT
GTCCGGTGCCCTGAATGAACTGCAAGACGAGGCAGCGCGGCTATCGTGGC
TGGCCACGACGGGCGTTCCTTGCGCAGCTGTGCTCGACGTTGTCACTGAA
GCGGGAAGGGACTGGCTGCTATTGGGCGAAGTGCCGGGGCAGGATCTCCT
GTCATCTCACCTTGCTCCTGCCGAGAAAGTATCCATCATGGCTGATGCAA
TGCGGCGGCTGCATACGCTTGATCCGGCTACCTGCCCATTCGACCACCAA
GCGAAACATCGCATCGAGCGAGCACGTACTCGGATGGAAGCCGGTCTTGT
CGATCAGGATGATCTGGACGAAGAGCATCAGGGGCTCGCGCCAGCCGAAC
TGTTCGCCAGGCTCAAGGCGAGCATGCCCGACGGCGAGGATCTCGTCGTG
ACCCATGGCGATGCCTGCTTGCCGAATATCATGGTGGAAAATGGCCGCTT
TTCTGGATTCATCGACTGTGGCCGGCTGGGTGTGGCGGACCGCTATCAGG
ACATAGCGTTGGCTACCCGTGATATTGCTGAAGAGCTTGGCGGCGAATGG
GCTGACCGCTTCCTCGTGCTTTACGGTATCGCCGCTCCCGATTCGCAGCG
CATCGCCTTCTATCGCCTTCTTGACGAGTTCTTCTGAATTTTGTTAAAAT
TTTTGTTAAATCAGCTCATTTTTTAACCAATAGGCCGAAATCGGCAAAAT
CCCTTATAAATCAAAAGAATAGACCGAGATAGGGTTGAGTGTTGTTCCAG
TTTGGAACAAGAGTCCACTATTAAAGAACGTGGACTCCAACGTCAAAGGG
CGAAAAACCGTCTATCAGGGCGATGGCCCACTACGTGAACCATCACCCTA
ATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCG
AGAAAGGAAGGGAAGAAAGCGAAAGGAGCGGGCGCTAGGGCGCTGGCAAG
TGTAGCGGTCACGCTGCGCGTAAGCACCACACCCGCCGGGCTTAATGCGC
CGCTACAGGGCGCGTCCATTCGCCATTCAGGATCGAATTAATTCTTAATT
AA
```

SEQ ID NO: 2 (human TM amino acid sequence)
MLGVLVLGALALAGLGFPAPAEPQPGGSQCVEHDCFALYPGPATFLNASQ
ICDGLRGHLMTVRSSVAADVISLLLNGDGGVGRRRLWIGLQLPPGCGDPK
RLGPLRGPQWVTGDNNTSYSRWARLDLNGAPLCGPLCVAVSAAEATVPSE
PIWEEQQCEVKADGFLCEFHFPATCRPLAVEPGAAAAAVSITYGTPFAAR
GADFQALPVGSSAAVAPLGLQLMCTAPPGAVQGHWAREAPGAWDCSVENG
GCEHACNAIPGAPRCQCPAGAALQADGRSCTASATQSCNDLCEHFCVPNP DQPGSYSCMCETGYRLAADQHRCEDVDDCILEPSPCPQRCVNTQGGFECH
CYPNYDLVDGECVEPVDPCFRANCEYQCPLNQTSYLCVCAEGFAPIPHE
PHRCQMFCNQTACPADCDPNTQASCECPEGYILDDGFICTDIDECENGGF
CSGVCHNLPGTFECICGPDSALARHIGTDCDSGKVDGGDSGSGEPPPSPT
PGSTLTPPAVGLVHSGLLIGISIASLCLVVALLALLCHLRKKQGAARAKM
EYKCAAPSKEVVLQHV RTERTPQRL SEQ ID NO: 3 (human TM nucleotide sequence)
atgcttggg gtcctggtcc ttggcgcgct ggccctggcc
ggcctggggt tccccgcacc cgcagagccg cagccgggtg
gcagccagtg cgtcgagcac gactgcttcg cgctctaccc
gggccccgcg accttcctca atgccagtca gatctgcgac
ggactgcggg ccacctaat gacagtgcgc tcctcggtgg
ctgccgatgt catttccttg ctactgaacg cgacggcgg
cgttggccgc cggcgcctct ggatcggcct gcagctgcca
cccggctgcg cgaccccaa cgcctcggg cccctgcgcg
gcttccagtg ggttacggga gacaacaaca ccagctatag
caggtgggca cggctcgacc tcaatgggc tcccctctgc
ggcccgttgt gcgtcgctgt ctccgctgct gaggccactg
tgcccagcga gccgatctgg gaggagcagc agtgcgaagt
gaaggccgat ggcttcctct gcgagttcca cttcccagcc
acctgcaggc cactggctgt ggagcccggc gccgcgctg
ccgccgtctc gatcacctac ggcaccccgt tcgcggcccg
cggagcggac ttccaggcgc tgccggtggg cagctccgcc
gcggtggctc ccctcggctt acagctaatg tgcaccgcgc
cgccccggagc ggtccagggg cactgggcca gggaggcgcc
gggcgcttgg gactgcagcg tggagaacgg cggctgcgag
cacgcgtgca atgcgatccc tggggctccc cgctgccagt
gcccagccgg cgccgccctg caggcagacg ggcgctcctg
caccgcatcc gcgacgcagt cctgcaacga cctctgcgag
cacttctgcg ttccaaccc cgaccagccg ggctcctact
cgtgcatgtg cgagaccggc taccggctgg cggccgacca
acaccggtgc gaggacgtgg atgactgcat actggagccc
agtccgtgtc cgcagcgctg tgtcaacaca cagggtggct
tcgagtgcca ctgctaccct aactacgacc tggtggacgg
cgagtgtgtg agcccgtgg accgtgctt cagagccaac
tgcgagtacc agtgccagcc cctgaaccaa actagctacc
tctgcgtctg cgccgagggc ttcgcgccca ttccccacga
gccgcacagg tgccagatgt tttgcaacca gactgcctgt
ccagccgact gcgacccaa cacccaggct agctgtgagt
gcctgaagg ctacatcctg gacgacggtt tcatctgcac
ggacatcgac gagtgcgaaa acggcggctt ctgctccggg gtgtgccaca acctccccgg taccttcgag tgcatctgcg
ggcccgactc ggccccttgcc cgccacattg caccgactg
tgactccggc aaggtggacg gtggcgacag cggctctggc
gagcccccgc ccagcccgac gcccggctcc accttgactc
ctccggccgt ggggctcgtg cattcgggct tgctcatagg
catctccatc gcgagcctgt gcctggtggt ggcgcttttg
gcgctcctct gccacctgcg caagaagcag ggcgccgcca
gggccaagat ggagtacaag tgcgcggccc cttccaagga
ggtagtgctg cagcacgtgc ggaccgagcg gacgccgcag
agactc SEQ ID NO: 4 (CMV promoter)
TCTAGACGCGTTGACATTGATTATTGACTAGTTATTAATAGTAATCAATT
ACGGGGTCATTAGTTCATAGCCCATGATATCATATGGAGTTCCGCGTTAC
ATAACTTACGGTAAATGGCCCGCCTGGCTGACCGCCCAACGACCCCCGCC
CATTGACGTCAATAATGACGTATGTTCCCATAGTAACGCCAATAGGGACT
TTCCATTGACGTCAATGGGTGGAGTATTTACGGTAAACTGCCCACTTGGC
AGTACATCAAGTGTATCATATGCCAAGTACGCCCCCTATTGACGTCAAT
GACGGTAAATGGCCCGCCTGGCATTATGCCCAGTNCATGACCTTATGGGA
CTTTCCTACTTGGCAGACATCTACGTATTAGTCATCGCTATTACCATGGT
GATGCGGTTTTGGCAGTACATCAATGGGCGTGGATAGCGGTTTGACTCAC
GGGGATTTTCCAAGTCTCCACCCCATTGACGTCAATGGGAGTTTGTTTTG
GCACCAAAATCAACGGGACTTTCCAAAATGTCGTAACAACTCCGCCCCAT
TGACGCAAATGGGCGGTAGGCGTGTACGGTGGGAGGTCTATATAAGCAGA
GCTCTCTGGCTAACTAGAGAACCCCTGCTTACTGGCTTATCGAGATATC SEQ ID NO: 5 (hTM cDNA)
GGCAGCGCGCAGCGGCAAGAAGTGTCTGGGCTGGGACGGACAGGAGAGGC
TGTCGCCATCGGCGTCCTGTGCCCCTCTGCTCCGGCACGGCCCTGTCGCA
GTGCCCGCGCTTTCCCCGGCGCCTGCACGCGGCGCGCCTGGGTAACATGC
TTGGGGTCCTGGTCCTTGGCGCGCTGGCCCTGGCCGGCCTGGGGTTCCCC
GCACCCGCAGAGCCGCAGCCGGGTGGCAGCCAGTGCGTCGAGCACGACTG
CTTCGCGCTCTACCCGGGCCCCGCGACCTTCCTCAATGCCAGTCAGATCT
GCGACGGACTGCGGGGCCACCTAATGACAGTGCGCTCCTCGGTGGCTGCC
GATGTCATTTCCTTGCTACTGAACGCGACGGCGGCGTTGGCCGCCGGCG
CCTCTGGATCGGCCTGCAGCTGCCACCCGGCTGCGGCGACCCCAAGCGCC
TCGGGCCCCTGCGCGGCTTCCAGTGGGTTACGGGAGACAACAACACCAGC
TATAGCAGGTGGGCACGGCTCGACCTCAATGGGCTCCCCTCTGCGGCCC
GTTGTGCGTCGCTGTCTCCGCTGCTGAGGCCACTGTGCCCAGCGAGCCGA
TCTGGGAGGAGCAGCAGTGCGAAGTGAAGGCCGATGGCTTCCTCTGCGAG
TTCCACTTCCCAGCCACCTGCAGGCCACTGGCTGTGGAGCCCGGCGCCGC
GGCTGCCGCCGTCTCGATCACCTACGGCACCCCGTTCGCGGCCCGCGGAG
CGGACTTCCAGGCGCTGCCGGTGGGCAGCTCCGCCGCGGTGGCTCCCCTC

```
GGCTTACAGCTAATGTGCACCGCGCCGCCCGGAGCGGTCCAGGGGCACTG
GGCCAGGGAGGCGCCGGGCGCTTGGGACTGCAGCGTGGAGAACGGCGGCT
GCGAGCACGCGTGCAATGCGATCCCTGGGGCTCCCCGCTGCCAGTGCCCA
GCCGGCGCCGCCCTGCAGGCAGACGGGCGCTCCTGCACCGCATCCGCGAC
GCAGTCCTGCAACGACCTCTGCGAGCACTTCTGCGTTCCCAACCCCGACC
AGCCGGGCTCCTACTCGTGCATGTGCGAGACCGGCTACCGGCTGGCGGCC
GACCAACACCGGTGCGAGGACGTGGATGACTGCATACTGGAGCCCAGTCC
GTGTCCGCAGCGCTGTGTCAACACACAGGGTGGCTTCGAGTGCCACTGCT
ACCCTAACTACGACCTGGTGGACGGCGAGTGTGTGGAGCCCGTGGACCCG
TGCTTCAGAGCCAACTGCGAGTACCAGTGCCAGCCCCTGAACCAAACTAG
CTACCTCTGCGTCTGCGCCGAGGGCTTCCCGCCCATTCCCCACGAGCCGC
ACAGGTGCCAGATGTTTTGCAACCAGACTGCCTGTCCAGCCGACTGCGAC
CCCAACACCCAGGCTAGCTGTGAGTGCCCTGAAGGCTACATCCTGGACGA
CGGTTTCATCTGCACGGACATCGACGAGTGCGAAAACGGCGGCTTCTGCT
CCGGGGTGTGCCACAACCTCCCCGGTACCTTCGAGTGCATCTGCGGGCCC
GACTCGGCCCTTGCCCGCCACATTGGCACCGACTGTGACTCCGGCAAGGT
GGACGGTGGCGACAGCGGCTCTGGCGAGCCCCGCCCAGCCCGACGCCCG
GCTCCACCTTGACTCCTCCGGCCGTGGGGCTCGTGCATTCGGGCTTGCTC
ATAGGCATCTCCATCGCGAGCCTGTGCCTGGTGGTGGCGCTTTTGGCGCT
CCTCTGCCACCTGCGCAAGAAGCAGGGCGCCGCCAGGGCCAAGATGGAGT
ACAAGTGCGCGGCCCCTTCCAAGGAGGTAGTGCTGCAGCACGTGCGGACC
GAGCGGACGCCGCAGAGACTCTGAGCGGCCTCCGTCCAGGAGCCTGGCTC
CGTCCAGGAGCCTGTGCCTCCTCACCCCCAGCTTTGCTACCAAAGCACCT
TAGCTGGCATTACAGCTGGAGAAGACCCTCCCCGCACCCCCCAAGCTGTT
TTCTTCTATTCCATGGCTAACTGGCGAGGGGGTGATTAGAGGGAGGAGAA
TGAGCCTCGGCCTCTTCCGTGACGTCACTGGACCACTGGGCAATGATGGC
AATTTTGTAACGAAGACACAGACTGCGATTTGTCCCAGGTCCTCACTACC
GGGCGCAGGAGGGTGAGCGTTATTGGTCGGCAGCCTTCTGGGCAGACCTT
GACCTCGTGGGCTAGGGATGACTAAAATATTTATTTTTTTTAAGTATTTA
GGTTTTTGTTTGTTTCCTTTGTTCTTACCTGTATGTCTCCAGTATCCACT
TTGCACAGCTCTCCGGTCTCTCTCTCTCTACAAACTCCCACTTGTCATGT
GACAGGTAAACTATCTTGGTGAATTTTTTTTCCTAGCCCTCTCACATTT
ATGAAGCAAGCCCCACTTATTCCCCATTCTTCCTAGTTTTCTCCTCCCAG
GAACTGGGCCAACTCACCTGAGTCACCCTACCTGTGCCTGACCCTACTTC
TTTTGCTCTTAGCTGTCTGCTCAGACAGAACCCCTACATGAAACAGAAAC
AAAAACACTAAAAATAAAAATGGCCATTTGCTTTTTCACCAGATTTGCTA
ATTTATCCTGAAATTTCAGATTCCCAGAGCAAAATAATTTTAAACAAAGG
TTGAGATGTAAAAGGTATTAAATTGATGTTGCTGGACTGTCATAGAAATT
ACACCCAAAGAGGTATTTATCTTTACTTTTAAACAGTGAGCCTGATATTT
TGTTGCTGTTTTGATTTGTACTGAAAATGGTAATTGTTGCTAATCTTCTT
ATGCAATTTCCTTTTTTGTTATTATTACTTATTTTTGACAGTGTTGAAAA
TGTTCAGAAGGTTGCTCTAGATTGAGAGAAGAGACAAACACCTCCCAGGA
GACAGTTCAAGAAAGCTTCAAACTGCATGATTCATGCCAATTAGCAATTG
ACTGTCACTGTTCCTTGTCACTGGTAGACCAAAATAAAACCAGCTCTACT
GGTCTTGTGGAATTGGGAGCTTGGGAATGGATCCTGGAGGATGCCCAATT
AGGGCGTAGCCTTAATCAGGTCCTCAGAGAATTTCTACCATTTCAGAGAG
GCCTTTTGGAATGTGGCCCCTGAACAAGAATTGGAAGCTGCCCTGCCCAT
GGGAGCTGGTTAGAAATGCAGAATCCTAGGCTCCACGCCATCCAGTTCAT
GAGAATCTATATTTAACAAGATCTGCAGGGGGTGTGTCTGCTCAGTAATT
TGAGGACAACCATTCCAGACTGCTTCCAATTTTCTGGAATACATGAAATA
TAGATCAGTTATAAGTAGCAGGCCAAGTCAGGCCCTTATTTTCAAGAAAC
TGAGGAATTTTCTTTGTGTAGCTTTGCTCTTTGGTAGAAAAGGCTAGGTA
CACAGCTCTAGACACTGCCACACAGGGTCTGCAAGGTCTTTGGTTCAGCT
AAGCTAGGAATGAAATCCTGCTTCAGTGTATGGAAATAAATGTATCATAG
AAATGTAACTTTTGTAAGACAAAGGTTTTCCTCTTCTATTTTGTAAACTC
AAAAATATTTGTACATAGTTATTTATTTATTGGAGATAATCTAGAACACAG
GCAAAATCCTTGCTTATGACATCACTTGTACAAAATAAACAAATAACAAT
GTGAAAAAAAAAAAAAAAAAAAAAAAAAAAAAAAAAAAAAA
```

SEQ ID NO: 6 (CMV-hTM expression cassette)
```
GTTTAAACGGGCCCTCTAGACGCGTTGACATTGATTATTGACTAGTTATT
AATAGTAATCAATTACGGGGTCATTAGTTCATAGCCCATGATATCATATG
GAGTTCCGCGTTACATAACTTACGGTAAATGGCCCGCCTGGCTGACCGCC
CAACGACCCCCGCCCATTGACGTCAATAATGACGTATGTTCCCATAGTAA
CGCCAATAGGGACTTTCCATTGACGTCAATGGGTGGAGTATTTACGGTAA
ACTGCCCACTTGGCAGTACATCAAGTGTATCATATGCCAAGTACGCCCCC
CTATTGACGTCAATGACGGTAAATGGCCCGCCTGGCATTATGCCCAGTNC
ATGACCTTATGGGACTTTCCTACTTGGCAGACATCTACGTATTAGTCATC
GCTATTACCATCGTGATGCGGTTTTGGCAGTACATCAATGGGCGTGGATA
GCGGTTTGACTCACGGGGATTTCCAAGTCTCCACCCCATTGACGTCAAT
GGGAGTTTGTTTTGGCACCAAAATCAACGGGACTTTCCAAAATGTCGTAA
CAACTCCGCCCCATTGACGCAAATGGGCGGTAGGCGTGTACGGTGGGAGG
TCTATATAAGCAGAGCTCTCTGGCTAACTAGAGAACCCCTGCTTACTGGC
TTATCGAGATATCTGCAGAATTCATCTGTCGACTGCTACCGGCAGCGCGC
AGCGGCAAGAAGTGTCTGGGCTGGACGGACAGGAGAGGCTGTCGCCATC
GGCGTCCTGTGCCCCTCTGCTCCGGCACGGCCCTGTCGCAGTGCCCGCGC
TTTCCCCGGCGCCTGCACGCGGCGCGCCTGGGTAACATGCTTGGGGTCCT
GGTCCTTGGCGCGCTGGCCCTGGCCGGCCTGGGGTTCCCCGCACCCGCAG
AGCCGCAGCCGGGTGGCAGCCAGTGCGTCGAGCACGACTGCTTCGCGCTC
TACCCGGGCCCCGCGACCTTCCTCAATGCCAGTCAGATCTGCGACGGACT
GCGGGGCCACCTAATGACAGTGCGCTCCTCGGTGGCTGCCGATGTCATTT
```

-continued

CCTTGCTACTGAACGGCGACGGCGGCGTTGGCCGCCGGCGCCTCTGGATC
GGCCTGCAGCTGCCACCCGGCTGCGGCGACCCCAAGCGCCTCGGGCCCCT
GCGCGGCTTCCAGTGGGTTACGGGAGACAACAACACCAGCTATAGCAGGT
GGGCACGGCTCGACCTCAATGGGGCTCCCCTCTGCGGCCCGTTGTGCGTC
GCTGTCTCCGCTGCTGAGGCCACTGTGCCCAGCGAGCCGATCTGGGAGGA
GCAGCAGTGCGAAGTGAAGGCCGATGGCTTCCTCTGCGAGTTCCACTTCC
CAGCCACCTGCAGGCCACTGGCTGTGGAGCCCGGCGCCGCGGCTGCCGCC
GTCTCGATCACCTACGGCACCCCGTTCGCGGCCCGCGGAGCGGACTTCCA
GGCGCTGCCGGTGGGCAGCTCCGCCGCGGTGGCTCCCCTCGGCTTACAGC
TAATGTGCACCGCGCCGCCCGGAGCGGTCCAGGGGCACTGGGCCAGGGAG
GCGCCGGGCGCTTGGGACTGCAGCGTGGAGAACGGCGGCTGCGAGCACGC
GTGCAATGCGATCCCTGGGGCTCCCCGCTGCCAGTGCCCAGCCGGCGCCG
CCCTGCAGGCAGACGGGCGCTCCTGCACCGCATCCGCGACGCAGTCCTGC
AACGACCTCTGCGAGCACTTCTGCGTTCCCAACCCCGACCAGCCGGGCTC
CTACTCGTGCATGTGCGAGACCGGCTACCGGCTGGCGGCCGACCAACACC
GGTGCGAGGACGTGGATGACTGCATACTGGAGCCCAGTCCGTGTCCGCAG
CGCTGTGTCAACACACAGGGTGGCTTCGAGTGCCACTGCTACCCTAACTA
CGACCTGGTGGACGGCGAGTGTGTGGAGCCCGTGGACCCGTGCTTCAGAG
CCAACTGCGAGTACCAGTGCCAGCCCCTGAACCAAACTAGCTACCTCTGC
GTCTGCGCCGAGGGCTTCGCGCCCATTCCCCACGAGCCGCACAGGTGCCA
GATGTTTTGCAACCAGACTGCCTGTCCAGCCGACTGCGACCCCAACACCC
AGGCTAGCTGTGAGTGCCCTGAAGGCTACATCCTGGACGACGGTTTCATC
TGCACGGACATCGACGAGTGCGAAAACGGCGGCTTCTGCTCCGGGGTGTG
CCACAACCTCCCCGGTACCTTCGAGTGCATCTGCGGGCCCGACTCGGCCC
TTGCCCGCCACATTGGCACCGACTGTGACTCCGGCAAGGTGGACGGTGGC
GACAGCGGCTCTGGCGAGCCCCCGCCCAGCCCGACGCCCGGCTCCACCTT
GACTCCTCCGGCCGTGGGGCTCGTGCATTCGGGCTTGCTCATAGGCATCT
CCATCGCGAGCCTGTGCCTGGTGGTGGCGCTTTTGGCGCTCCTCTGCCAC
CTGCGCAAGAAGCAGGGCGCCGCCAGGGCCAAGATGGAGTACAAGTGCGC
GGCCCCTTCCAAGGAGGTAGTGCTGCAGCACGTGCGGACCGAGCGGACGC
CGCAGAGACTCTGAGCGGCCTCCGTCCAGGAGCCTGGCTCCGTCCAGGAG
CCTGTGCCTCCTCACCCCAGCTTTGCTACCAAAGCACCTTAGCTGGCAT
TACAGCTGGAGAAGACCCTCCCCGCACCCCCCAAGCTGTTTTCTTCTATT
CCATGGCTAACTGGCGAGGGGTGATTAGAGGGAGGAGAATGAGCCTCGG
CCTCTTCCGTGACGTCACTGGACCACTGGGCAATGATGGCAATTTTGTAA
CGAAGACACAGACTGCGATTTGTCCCAGGTCCTCACTACCGGGCGCAGGA
GGGTGAGCGTTATTGGTCGGCAGCCTTCTGGGCAGACCTTGACCTCGTGG
GCTAGGGATGACTAAAATATTTATTTTTTTAAGTATTTAGGTTTTGTT
TGTTTCCTTTGTTCTTACCTGTATGTCTCCAGTATCCACTTTGCACAGCT
CTCCGGTCTCTCTCTCTCTACAAACTCCCACTTGTCATGTGACAGGTAAA

-continued

CTATCTTGGTGAATTTTTTTTTCCTAGCCCTCTCACATTTATGAAGCAAG
CCCCACTTATTCCCCATTCTTCCTAGTTTTCTCCTCCCAGGAACTGGGCC
AACTCACCTGAGTCACCCTACCTGTGCCTGACCCTACTTCTTTTGCTCTT
AGCTGTCTGCTCAGACAGAACCCCTACATGAAACAGAAACAAAAACACTA
AAAATAAAAATGGCCATTTGCTTTTTCACCAGATTTGCTAATTTATCCTG
AAATTTCAGATTCCCAGAGCAAAATAATTTTAAACAAAGGTTGAGATGTA
AAAGGTATTAAATTGATGTTGCTGGACTGTCATAGAAATTACACCCAAAG
AGGTATTTATCTTTACTTTTAAACAGTGAGCCTGAATTTTGTTGCTGTTT
TGATTTGTACTGAAAAATGGTAATTGTTGCTAATCTTCTTATGCAATTTC
CTTTTTTGTTATTATTACTTATTTTTGACAGTGTTGAAAATGTTCAGAAG
GTTGCTCTAGATTGAGAGAAGAGACAAACACCTCCCAGGAGACAGTTCAA
GAAAGCTTCAAACTGCATGATTCATGGCAATTAGCAATTGACTGTCACTG
TTCCTTGTCACTGGTAGACCAAAATAAAACCAGCTCTACTGGTCTTGTGG
AATTGGGAGCTTGGGAATGGATCCTGGAGGATGCCCAATTAGGGCCTAGC
CTTAATCAGGTCCTCAGAGAATTTCTACCATTTCAGAGAGGCCTTTTGGA
ATGTGGCCCCTGAACAAGAATTGGAAGCTGCCCTGCCCATGGGAGCTGGT
TAGAAATGCAGAATCCTAGGCTCCACCCCATCCAGTTCATGAGAATCTAT
ATTTAACAAGATCTGCAGGGGGTGTGTCTGCTCAGTAATTTGAGGACAAC
CATTCCAGACTGCTTCCAATTTTCTGGAATACATGAAATATAGATCAGTT
ATAAGTAGCAGGCAAGTCAGGCCCTTATTTTCAAGAAACTGAGGAATTT
TCTTTGTGTAGCTTTGCTCTTTGGTAGAAAAGGCTAGGTACACAGCTCTA
GACACTGCCACACAGGGTCTGCAAGGTCTTTGGTTCAGCTAAGCTAGGAA
TGAAATCCTGCTTCAGTGTATGGAAATAAATGTATCATAGAAATGTAACT
TTTGTAAGACAAAGGTTTTCCTCTTCTATTTTGTAAACTCAAAATATTTG
TACATAGTTATTTATTTATTGGAGATAATCTAGAACACAGGCAAAATCCT
TGCTTATGACATCACTTGTACAAAATAAACAAATAACAATGTGAAAAAAA
AAAAAAAAAAAAAAAAAAAAAAAAAAAAAAGGTAGCAGTCGACAGAT
GAATTCCACCACACTGGACTAGTGGATCCGAGCTCGGTACCAAGCTTAAG
TTTAAAC

SEQ ID NO: 7 (pTMadap)
CATCATCAATAATATACCTTATTTTGGATTGAAGCCAATATGATAATGAG
GGGGTGGAGTTTGTGACGTGGCGCGGGGCGTGGGAACGGGGCGGGTGACG
TAGTAGTGTGGCGGAAGTGTGATGTTGCAAGTGTGGCGGAACACATGTAA
GCGACGGATGTGGCAAAAGTGACGTTTTTGGTGTGCGCCGGTGTACACAG
GAAGTGACAATTTTCGCGCGGTTTTAGGCGGATGTTGTAGTAAATTTGGG
CGTAACCGAGTAAGATTTGGCCATTTTCGCGGGAAAACTGAATAAGAGGA
AGTGAAATCTGAATAATTTTGTGTTACTCATAGCGCGTAATACTGGTACC
GCGGCCGCCTCGAGTCTAGAACTAGTGGATCCCCCAAACGGGCCCTCTAG
ACGCGTTGACATTGATTATTGACTAGTTATTAATAGTAATCAATTACGGG
GTCATTAGTTCATAGCCCATGATATCATATGGAGTTCCGCGTTACATAAC
TTACGGTAAATGGCCCGCCTGGCTGACCGCCCAACGACCCCCGCCCATTG ACGTCAATAATGACGTATGTTCCCATAGTAACGCCAATAGGGACTTTCCA
TTGACGTCAATGGGTGGAGTATTTACGGTAAACTGCCCACTTGGCAGTAC
ATCAAGTGTATCATATGCCAAGTACGCCCCCCTATTGACGTCAATGACGG
TAAATGGCCCGCCTGGCATTATGCCCAGTNCATGACCTTATGGGACTTTC
CTACTTGGCAGACATCTACGTATTAGTCATCGCTATTACCATGGTGATGC
GGTTTTGGCAGTACATCAATGGGCGTGGATAGCGGTTTGACTCACGGGGA
TTTTCCAAGTCTCCACCCCATTGACGTCAATGGGAGTTTGTTTTGGCACC
AAAATCAACGGGACTTTCCAAAATGTCGTAACAACTCCGCCCCATTGACG
CAAATGGGCGGTAGGCGTGTACGGTGGGAGGTCTATATAAGCAGAGCTCT
CTGGCTAACTAGAGAACCCCTGCTTACTGGCTTATCGAGATATCTGCAGA
ATTCATCTGTCGACTGCTACCGGCAGCGCGCAGCGGCAAGAAGTGTCTGG
GCTGGGACGGACAGGAGAGGCTGTCGCCATCGGCGTCCTGTGCCCCTCTG
CTCCGGCACGGCCCTGTCGCAGTGCCCGCGCTTTCCCCGGCGCCTGCACG
CGGCGCGCCTGGGTAACATGCTTGGGGTCCTGGTCCTTGGCGCGCTGGCC
CTGGCCGGCCTGGGGTTCCCCGCACCCGCAGAGCCGCAGCCGGGTGGCAG
CCAGTGCGTCGAGCACGACTGCTTCGCGCTCTACCCGGGCCCCGCGACCT
TCCTCAATGCCAGTCAGATCTGCGACGGACTGCGGGCCACCTAATGACA
GTGCGCTCCTCGGTGGCTGCCGATGTCATTTCCTTGCTACTGAACGGCGA
CGGCGGCGTTGGCCGCCGGCGCCTCTGGATCGGCCTGCAGCTGCCACCCG
GCTGCGGCGACCCCAAGCGCCTCGGGCCCCTGCGCGGCTTCCAGTGGGTT
ACGGGAGACAACAACACCAGCTATAGCAGGTGGGCACGGCTCGACCTCAA
TGGGGCTCCCCTCTGCGGCCCGTTGTGCGTCGCTGTCTCCGCTGCTGAGG
CCACTGTGCCCAGCGAGCCGATCTGGGAGGAGCAGCAGTGCGAAGTGAAG
GCCGATGGCTTCCTCTGCGAGTTCCACTTCCCAGCCACCTGCAGGCCACT
GGCTGTGGAGCCCGGCGCCGCGGCTGCCGCCGTCTCGATCACCTACGGCA
CCCCGTTCGCGGCCCCGCGGAGCGGACTTCCAGGCGCTGCCGGTGGGCAGC
TCCGCCGCGGTGGCTCCCCTCGGCTTACAGCTAATGTGCACCGCGCCGCC
CGGAGCGGTCCAGGGGCACTGGGCCAGGGAGGCGCCGGGCGCTTGGGACT
GCAGCGTGGAGAACGGCGGCTGCGAGCACGCGTGCAATGCGATCCCTGGG
GCTCCCCGCTGCCAGTGCCCAGCCGGCGCCGCCCTGCAGGCAGACGGGCG
CTCCTGCACCGCATCCGCGACGCAGTCCTGCAACGACCTCTGCGAGCACT
TCTGCGTTCCCAACCCCGACCAGCCGGGCTCCTACTCGTGCATGTGCGAG
ACCGGCTACCGGCTGGCGGCCGACCAACACCGGTGCGAGGACGTGGATGA
CTGCATACTGGAGCCCAGTCCGTGTCCGCAGCGCTGTGTCAACACACAGG
GTGGCTTCGAGTGCCACTGCTACCCTAACTACGACCTGGTGGACGGCGAG
TGTGTGGAGCCCGTGGACCCGTGCTTCAGAGCCAACTGCGAGTACCAGTG
CCAGCCCCTGAACCAAACTAGCTACCTCTGCGTCTGCGCCGAGGGCTTCG
CGCCCATTCCCCACGAGCCGCACAGGTGCCAGATGTTTTGCAACCAGACT
GCCTGTCCAGCCGACTGCGACCCCAACACCCAGGCTAGCTGTGAGTGCCC
TGAAGGCTACATCCTGGACGACGGTTTCATCTGCACGGACATCGACGAGT GCGAAAACGGCGGCTTCTGCTCCGGGGTGTGCCACAACCTCCCCGGTACC
TTCGAGTGCATCTGCGGGCCCGACTCGGCCCTTGCCCGCCACATTGGCAC
CGACTGTGACTCCGGCAAGGTGGACGGTGGCGACAGCGGCTCTGGCGAGC
CCCCGCCCAGCCCGACGCCCGGCTCCACCTTGACTCCTCCGGCCGTGGGG
CTCGTGCATTCGGGCTTGCTCATAGGCATCTCCATCGCGAGCCTGTGCCT
GGTGGTGGCGCTTTTGGCGCTCCTCTGCCACCTGCGCAAGAAGCAGGGCG
CCGCCAGGGCCAAGATGGAGTACAAGTGCGCGGCCCCTTCCAAGGAGGTA
GTGCTGCAGCACGTGCGGACCGAGCGGACGCCGCAGAGACTCTGAGCGGC
CTCCGTCCAGGAGCCTGGCTCCGTCCAGGAGCCTGTGCCTCCTCACCCCC
AGCTTTGCTACCAAAGCACCTTAGCTGGCATTACAGCTGGGAAGACCCT
CCCCGCACCCCCCAAGCTGTTTTCTTCTATTCCATGGCTAACTGGCGAGG
GGGTGATTAGAGGGGAGGAGAATGAGCCTCGGCCTCTTCCGTGACGTCACT
GGACCACTGGGCAATGATGGCAATTTTGTAACGAAGACACAGACTGCGAT
TTGTCCCAGGTCCTCACTACCGGGCGCAGGAGGGTGAGCGTTATTGGTCG
GCAGCCTTCTGGGCAGACCTTGACCTCGTGGGCTAGGGATGACTAAAATA
TTTATTTTTTTAAGTATTTAGGTTTTTGTTTGTTTCCTTTGTTCTTACC
TGTATGTCTCCAGTATCCACTTTGCACAGCTCTCCGGTCTCTCTCTCT
ACAAACTCCCACTTGTCATGTGACAGGTAAACTATCTTGGTGAATTTTTT
TTTCCTAGCCCTCTCACATTTATGAAGCAAGCCCCACTTATTCCCCATTC
TTCCTAGTTTTCTCCTCCCAGGAACTGGGCCAACTCACCTGAGTGACCCT
ACCTGTGCCTGACCCTACTTCTTTTGCTCTTAGCTGTCTGCTCAGACAGA
ACCCCTACATGAAACAGAAACAAAAACACTAAAAATAAAAATGGCCATTT
GCTTTTTCACCAGATTTGCTAATTTATCCTGAAATTTCAGATTCCCAGAG
CAAAATAATTTTAAACAAAGGTTGAGATGTAAAAGGTATTAAATTGATGT
TGCTGGACTGTCATAGAAATTACACCCAAAGAGGTATTTATCTTTACTTT
TAAACAGTGAGCCTGAATTTTGTTGCTGTTTTGATTTGTACTGAAAAATG
GTAATTGTTGCTAATCTTCTTATGCAATTTCCTTTTTTGTTATTATTACT
TATTTTTGAGAGTGTTGAAAATGTTCAGAAGGTTGCTCTAGATTGAGAGA
AGAGACAAACACCTCCCAGGAGACAGTTCAAGAAAGCTTCAAAGTGCATG
ATTCATGCCAATTAGCAATTGACTGTGACTGTTCCTTGTCACTGGTAGAC
CAAAATAAAAGCAGCTCTACTGGTCTTGTGGAATTGGGAGCTTGGGAATG
GATCCTGGAGGATGCCCAATTAGGGCCTAGCCTTAATCAGGTCCTCAGAG
AATTTCTACCATTTCAGAGAGGCCTTTTGGAATGTGGCCCCTGAACAAGA
ATTGGAAGCTGCCCTGCCCATGGGAGCTGGTTAGAAATGCAGAATCCTAG
GCTCCACCCCATCCAGTTCATGAGAATCTATATTTAACAAGATCTGCAGG
GGGTGTGTCTGCTCAGTAATTTGAGGACAACCATTCCAGACTGCTTCCAA
TTTTTCTGGAATACATGAAATATGATCAGTTATAAGTAGCAGGCCAAGTC
AGGCCCTTATTTTCAAGAAACTGAGGAATTTTCTTTGTGTAGCTTTGCTC
TTTGGTAGAAAAGGCTAGGTACACAGCTCTAGACACTGCCACACAGGGTC
TGCAAGGTCTTTGGTTCAGCTAAGCTAGGAATGAAATCCTGCTTCAGTGT -continued

```
ATGGAAATAAATGTATCATAGAAATGTAACTTTTGTAAGACAAAGGTTTT
CCTCTTCTATTTTGTAAACTCAAAATATTTGTACATAGTTATTTATTTAT
TGGAGATAATCTAGAACACAGGCAAAATCCTTGCTTATGACATCACTTGT
ACAAAATAAACAAATAACAATGTGAAAAAAAAAAAAAAAAAAAAAAAAA
AAAAAAAAAAAAAAGGTAGCAGTCGACAGATGAATTCCACCACACTGGAC
TAGTGGATCCGAGCTCGGTACCAAGCTTAAGTTTGGGCTGCAGGAATTCT
GATGGCTCTCAAAATTCCTGCCTCCTTTAGGGATAAAAGACTTTAAGACT
TTTTAACAAAAAAGAAAAAGAAAAAAAAAATTCCTGCCTCCTGGTGTACA
CACACAGAAGGGTTCCCTCCCCTTGAATGTGACCAGGATCTGTGAAAATA
ACGGGATAGCCGCTCCTGTGATTAGGTTATGTGGTAGACTAGAGCAAGAT
TCTCCTGCTGGTTTTGAAGAAGTCAGCTGCCATGTTGTGAGACTGTCATG
GGCTAGGGCATGAGCCTTTAAATATCTGGGAGCAACCCCTGGCCAGCAGC
CAGTGAGAAAACGGGCCCTCAGTCCTACAATCACAAGGAACTAAATTCTG
CCAACAACCTGAAGGAACTTTGAAGAGGATCATGAGTCCCTTGATTCAGC
TTGATGAGCCCCTGAGCAGAGGATACAGCTAACTTGTACTAGGGAAGTAT
AAAAAACATGCATGGGAATGATATATATCAACTTTAAGGATAATTGTCAT
ACTTCTGGGAATGAAGGGAAAGAAATGGGGCTTTAGTTGTATTATGATCT
TTAATTTCTCAAAAAAATAAGATCAGAAGCAAATATGGCAAATGTTAA
TACTTTTGTGGGTACGTAGGTATTCAGCATACCCTTTTTTCTGAGTTCAA
AATATTTTATAATTAAAATGAAATGCAGGCCAGGCACAGTGGCTCATGCC
TATAATACCAGCACTTTGCGAGGCCGAGGTGGGAGGATGGCTTGAGGCCA
GACCAGCCTGGCCAACATGGCAAAACCCCATCTCTACTTAAAAAAAAAA
AACTATATATATATATGTGTGTGTGTGTATATATATATGTATAT
ATATTTATATGTGTGTATATATATATGTATATATATTTATATGT
GTGTGTATATATATACACACACACATATACATACATACATAC
ACACACACACACAATTAGCCAGGCATGGTGGCGCACACCTGTAGTC
CCAGCTACTTGGGAGGCTGAGACATGAGAATTGCTTGAACCTGGGAGGCA
GAGTAGTTAGTGAGCTGAGATCATACCACTGCACTCCAGCCTGGTGACAG
AGTGAGACTCTGTCTTAAAAAAATAAAATTAAAATTAAATGCAAAAGG
TCCAAGTGAATTGAAGAGGAAAGGGGTATCAAGGAAGGTTTTGTGGAGGT
GACGTTTGAGCTGGGTCTTAAATGACTTAAACATGGGATAAGAAGGGAGG
GAATAAGGACATTTCAGGTACGAGAAATAAGGAGCAAACAGTGGAAACAA
CCTAACGTCTGTCAACCAGTGAATGGATAACAAAAATGTAATTCAGATGG
TATCCAACTTACGATGGTTCAACATGAGATTTTTCTGACTTTAGGATAGA
TTTATCAAAGTAGTAAATCCATTTTCAACTTATGATATTTTCAACTTCAG
ATGGGTTTATCAGGACACAGTTGAGGAACACCTGTCTATCCATACAATTT
GGCAATAAAAAGGAAATGAGTGCAGATATACTCCACAACATGAATGAACC
TTGAAAACATTAAGTGAGAGAAGCCAGATACAAAAGGCCACATATTGTAT
GATTCTATTTATACAAAATGTCCAGAATAGGCAAATCTTATAGACAGCAA
GTAGGTAGATGATCAGTTTGCTAGGTGCTGGGGGAAGGGGAAATGGGGAG
TGATGGCTAAGGGGATTGGGTTTCTTTGTGGGGCAATGAAAATGTTTTAA
AATTGAGCGTGATAATGATTGCACAATGCTGCATATATATATAATCTATA
GATTATATATATATAAAGAGAGGCTGTTAGACAGTGATAAGTGATATATA
TATATATATACATAGAGAGAGAGAGAGAGAGAGAGAGGCTGTTAGTGA
TAAGTGATCAGGAAAATAAAAGTATTGAGGAGGAATACGAAGTTGACGGT
GTGAAAACATGAGATTTTATATAGGATGGCCAGGGAAGGCCTTAATGAGA
AAGTGACTTATGAGTAAAAACAAGGGATCCTAAACCTTAGCATGCATCAG
AATCACTCGGAAACTTGTTAAAGCATAGCTTGCTGGGCCTCATCACAGAT
ATTTTGATTCGGTAGGTTCTTGTCTGATATTAATACTTTTGGTCTAGGGA
ACCACATTTTGAGAACCACTGAGCTAAAGGAAGTAAAGGTTTCCCTTAGT
TTACTAGCTGGTAACACTGGCCCAGGAGGCCTTTCTGGTGACCCCTAAGG
AATTATCCAAACTCTTGTTTTTAGATGCTTTATTATATCAAACTCTCCTT
TAAACAAGTGGCCCATCTGCTGGGATTTGGAAGCCTGTAATACTGAAATT
TTCATCATAATGGAAATTTTAAAAACAGAATTTGACCCACCTGTTTTTAA
AACACTTTCATTACTTAACAAGAGGTCTAATCTTGGGCAAGTCTTGAAAT
TTCTCTGGCCTTAGTTTCCCATGTGTTAAATGAAACTTGAAGCAGTTGGT
CTCTTATAGTCTCCTGACTCTAACATTCTAAGAATTATATTTGTACAATA
ACTCAAAAATCACATAATTTAATTTACCATATGGACTCCAAAATATATTT
TCTCATTAGGCTAAACTTGATCTGCATTTTCTGGATGTGTCCATATTCTT
GGACTACACTAAAACATGATACCAATGCTTCCTCTCACCATAAACCCTCA
CTTCGCTTTCTACATTTAAGAATTTTATAGCTGGAAGAGTCCTTAACAGA
AAATACCATCTAATAATTACCCCTCAAAATCGAGAAAGTCCTATCTGTTC
TTATGCTAGTTATAAGAATGAGGCAGCATTTCACATAATGGTTATAAACA
CTGCCACAAGAAGATTCATGATGTGTTGTTTATCTGTAGCTCTCATCATA
CTCTGTCATATAACTATAGCATTAAGATTTTAATGTTCTATATATTCTTC
TAAGACAGTGTTTACCAGAGTAAGGCACAAAAGATCCACTGGTTTGCAAG
AAAGATTAGAACTTTTAAATTTTTTACCTCACCTTGTTTAATCTATATTT
TTGTATGTATTTTGTAACATATATATTATTATTACCATAAATCATATATA
ATTTAAAATGCATATATTAGGGGTAAATGCTCAGGAAACTTTTTATAAAT
TGGGCATGCAAATACAAGTTTGAAGACTCACTGTTCTAGGTATTAAAAGT
AAAGTTATAACCAAGTAAAGCTTCCACCTTTTCATGTCTCAAAGCAGTTT
ATTGTTGGAGGTAAGATCTCTTAGAAGCCTAAACAGGTCCAAGTACAGAA
TGAAGTAAGGCTAGCCCATAACTTGTGGCAAGCAATTCATACTATTTCTC
TCATGCTGAGCTCTCCTCAGTGAAGCAGCTAGTATAGACAACTGCAGCCT
ATTGGTAGCCTATTTTACAGGCAGGAAAAAAATTACTTTTTATTCAAAGT
GGAACTCAGGACATGGGAGAAAATGAATACAAAAAATAGGGTCAATCGA
AAGGCACACAGCAAATGAGTAACACAGTTATGTTTTTTTCCCATTTGTAT
GAGGTCCCAGTAAATTCTAAGTAAACTGGAAATTTAATAATACACTAAAA
AAGCCATGCAATTGTTCAAATGAATCCCAGCATGGTACAAGGAGTACAGA
CACTAGAGTCTAAAAAACAAAAGAATGCCATTATTGAGTTTTTGAATTAT
```

```
ATCAAGTAGTTACATCTCTACTTAATAAATGAGAAAAACGAGGATAAGAG
GCCATTTGATAAAATGAAAATAGCCAAGAAGTGGTATTAGAGACTTGAAT
ACAGGTATTCGGGTCCAAAGTTCATCTGCTCAAATACTAACTGGGGAAAA
GAGGGAAAAATATTTATATACATATATATCTGCACACAAAAATACCCCCA
AAAGACAAAATGAGGCCAGGCAGGGTGGCTCACACCCGTAATGCCGGTAC
TTTGGGAGGCTGAGGCAGGTGGATACCTGAGATCAGGAGTTGGAGATCAG
CCTGGTCAACATGGTGAAACCCTGTCTCTACTAAAGATAAAAAAATTAGC
CAGGCATGGTGGCGTGCGCCTGTAATCCCAGCTACTTGGGAGTCTGAGGC
AGGAGAATCACTTGAACTGGGAAGGGGAGGTTGCAGTGAGCCAAGATCGT
ACTACTGCACTCCAGCCTGGGCAGCAGAGTGAGACTCCATCACAAAAATA
AATAAATAAATAAAATACAATGAAACAGAAAGTTCAAATAATCCCATAAT
CTTACCACCAAGAAATAACTTTCACTCGTTATACTTATTGATTTTTCCAT
AATAAATGTACTTTACTGTGACTATCATGAAAAGAAAGTTATTTTAGAAA
CAGAGAACTGTTTCAGATCAAATCTATGTAGTAGAACAGAGCCATTAGGT
GGGAAAGACGAGATCAAACTAAATCTCAGAAGGCCTAAAAGGCTAGGTCC
ATTCCAGCACTAAAAACTGACCAGACAAGTAATGGCTTCAACAGCTTCTA
AATATGGACAAAGCATGCTGAAAGGGAAGGACAGGTCTAACAGTGGTATA
TGAAATGAACAGGAGGGGCAAAGCTCATTTCTCCTCTGAAGTTTTCCAAA
GATGCTGAGGAGGACATTAGTTTGACATGACCCTGATATGGGACAAGATA
ATTTCACAGAAGTTTTACATGTTAAAGTTTTCTTATAGATACTCATTCAA
GTAAGCAATGAACACTAAAATCTAAAGAAAGAAAAGAGCTTTAGAGTCAG
GTCTGTATTCAAATTCAAGCTCTACCACTTACTGGTTCTGTGACTTTGGG
CAAGTCTTTTAACCTTATTAAGTCTTAATTTCCTGATTTGTAAAATGGGG
ATATCGTCTCCCTCACAGGATTGTTGTGAAACTTTTATGAGATTAATGCC
TTTATATTTGGCATAGTGTAAGTAAACAATAACTGGCAGCTTCAAAAAAA
AAAAGCAGTAGCATTCCATCATTTATTATTGGTTACTCTCAAAAAGTTTT
TCAATGTACTAGAAGATAAATATTCAAATACCTTAATATCTCCATTATTT
TCAGGTAAACAGCATGCTCCTGAACAACCAATGGGTCAACAAATAAATTA
AAAGGGAAATCTAAAAACATCTTGATATTAAACTACATGGAAGCACAATA
TACCAAAACCAATGGTTCACACTAGGAGAATTTTAAGGTACAAGAAAACT
CTTTGAGATTTCTTAAAATAATAGTATGTCTGAATTTATTGAGTGATTTA
CCAGAAACTGTTGTAAGAGCTCTACTTGCATTATAGCACTTAATCCTCTT
AACTCTATGGCTGCTATTATCAACCTCACCCTAATCACATATGGGACACA
GAGAGGTTAAGTAACTTGCCCAAGGTCAGAGTTAGGAAGTACTAAGCCAT
GCTTTGAATCAGTTGTCAGGCTCCGGAACTCACACTTTCAGCCACTACAT
AATACTGCTTTGCTATCTTTTAGGAAACTATGTGAGTCTACCTCACATAG
ACTCACATAGGTTTGTTTTTTTTTTTTTTAAAGGCTATCTTTTCCCCC
ATCAATGTTTTTTGAAGGATCCCAAATTAGAGTCCCACAGAGGCAGACAG
CAGTACTTGACAATATGGACATTTAAGGTTAATGTTGGATTCTACTGTCT
TTTTACTACATGACCTAGGGAACGATAATTAACCTAGACTGCTTCCAAGG
GTTAAATAACCCATTTAGTTATACTATGTAAATTATCTCTTAGTGATTGA
TTGAAAGCACACTGTTACTAATTGACTCGGTATGAAGTGCTTTTTTTTCT
TCCCTTTCAAGATACATACCTTTCCAGTTAAAGTTGAGAGATCATCTCCA
CCAATTACTTTTATGTCCCCTGTTGACTGGTCATTCTAGTTAAAAAAAAA
AAAACTATATATATATATATCTACACACACATATGTATATGTATATCCT
TATGTACACACAAACTTCAAATTAAATGAGAACTAGAAGATTTGAGAA
GTTAGCTAGCTAATATCCATAGCATTATGATATTCTAAATGATATGAATT
ATAAGAATTAGGTTTCCTGAAATGAATGACTAGAAAACTTTCAAGTAGAG
ATTAGTAAAAATTAAAAAGTCCTAATCGGCCATTACTGATTTGATGTTTT
TAAGAGTCCTAAAAAATGGGTTACATCCATTTTTAAGTGGGTAGTATTAT
AACAGCCACCCATCTTCAATCACAGTGATTTCTGAATTGTGAGGGAAGTT
ATTAGCATGACAGGTGTCTGGTTCTGGCCCTGTACGATTCCCATGAGTCA
AGCAAATTGTAAGGGCTGGTCTATATCACACCCAACCCCAAGGATATGTC
CCTCAAAAGTCTAGCCCAGGCCCCGTCATCTTCAGCATCATCTGGGAAAC
CAGGTCTGATTAGTAGTCCTTTAAGGAATACCTCTTAGGCTCCCATTTTA
CTGCTATCACAGAATCCAATAAAACCCTTACAGGAGATTCAATGGGAAAT
GCTCAACACCCACTGTAGTTGGTGGTGACAATGACCATAATTTGGCTGTG
CTGGATTCAGGACAGAAAATTTGGGTGAAAGAGCAGGTGAACAAAAGAGC
TTCGACTTGCCCTAGCAGAGAGCAAGCCATACCATACCACAAAGCCACAG
CAATTACAACGGTGCAGTACCAGCACAGTAAATGAACAAAGTAGAGCCCA
GAAACAGACCCAGAACTATATGAGGATTTAGTATACAATAAAGATGGTAT
TTCGAGTCAGTAGGGAAAAGATGAATTATTCAATAAATGATGTTTGGCCA
ACTAGTAACCCATTTGGGAAAAAATAAAAGTATGGTCCCTACCTCACAGC
ATACACAAAAATAAATTCCAGACGGATTAAAATCTAAATGTAAAAAATAA
AGCCATAAGTGGACTGAAAGAAAATAGAGAATTTTTTTTAACATCCGTAG
AAAGGGTAAAAACCCAGGCATGACATGAACCAAAACTGAAGAGGTTCTGT
AACAAATACCCCCTTTTATATATTGGGCTCCAACAATAAGAACCCATAGG
AAAATGGAGAATGAACACAAATAGACAATTTATAGAAGAGAAGGTTATAA
GGTGTAAAATTATATCTATCTGAGAAACAAACACTAAAACAATGTGATTC
TACTGTTCTCCCACCCATACTGGCAAAACTTAAGCCTGATAATATGCTGA
GGGGAAATAAGCACTCTTGTTGGTGAGAGTATTAATTGGCATAGCTTCTT
TTGAAAATGACATAGCAATACCTGTTAAAATTGCAAACATGCATGTCACT
TAATCCAGTAATCCCACTTCTGGGAATCAATGCTACAAAAACACTGACAA
GTATACAAAGATACATTCAAGAGTGTTCACTGGGCCGGGTGCGGTGGCTT
CATGCCTGTAATCCCAGGGAGGCAGAGGCAAGACGATCGCTTGACCCCAG
GAGTTCAAGGCCAGCCCGAGAAACACAGCAAGACCCTGTCTCTCTTTTTT
TTATTTAAAAAATAAATGTTCACTGTATCAGTTGTTCACAAAAACAAACC
AACATGTCCATTAACAGGGAACCATTTAAATTAATCAAGTTCATCTACAC
AATGTAATACCATGCAACTATTAAAAAGCACCTGATAATCCAAAGCACAC
TGAGACAGAATAATGCTATTAAAAACACCAAGTAGTGGAACACTGTGTTG
```

-continued

```
CCTATGACACCATTTTTATTCAACATTTAAACAAATTTGTAACAGCAATT
ACATGAGTAGTGACAATGGCGTTTATGAGACTTTTCACTTTTATGTGCTT
CTATTTTGTTATGCTTCTATATATACATCCATTTATTATGGAGTGTTAC
TTTCAAAAATCACAAATGGGCCAGTATTATTTGGTGTTGCAAGGTGAGCA
TATGACTTCTGATATCAACCTTTGCATATTACTTCTCAATTTAGGGAAAT
TACAGACATCCCTTATTCTAACTAACTTAAAACCCAGCATTTCAAACATA
CAGAATTGATGGGAAAAAAAGAAAGAAGAAAGAAAGAAAAGGCAACAA
GCTTCAGATGACAGTGACTCACATCAAATTATTTATAAAATCTGTTAAAT
AGTGCCATCTTCTGGAGATACCTGGTATTACAGTCCAACTCCAGTTGATG
TCTTTACAGAGACAAGAGGAATAAAGGAAAAAATATTCAAGAACTGAAAA
GTATGGAGTCATGGAAAAATTGCTGTGATGCAAAGGCTACGGTGATAGGA
CAAGAAAGAAGAGAACTCCAAGCAGTAAGAGACTGCTGTTCTATTAGCAT
CCAAACCTCCATACTCCTGTTTGCCCCAAGGCTTTTTTAAAAAATAGAGA
CAGGATCTCACTATTTTGCTCAGGCTGGTCTTGAACTCCTGGACTCAAGC
TATCCTCCTGCCTCGGCCTCCTAAAGTGCCGAGATTACAGGCTTGAGTCA
CCATACCTGGCTATTTATTTTTCTTAACTCTCTTGCCTGGCCTATAGCC
ACCATGGAAGCTAATAAAGAATATTAATTTAAGAGTAATGGTATAGTTCA
CTACATTGGAATACAGGTATAAGTGCCTACATTGTACATGAATGGCATAC
ATGGATCAATTACCCCACCTGGGTGGCCAAAGGAACTGCGGGAACCTCCC
TCCTTGGCTGTCTGGAACAAGCTTCCCACTAGATCCCTTTACTGAGTGCC
TCCCTCATCTTTAATTATGGTTAAGTCTAGGATAACAGGACTGGCAAAGG
TGAGGGGAAAGCTTCCTCCAGAGTTGCTCTAGCCTCTCCTCTACCGTCCT
ATCTCCTCACTCCTCTCAGCCAAGGAGTCCAATCTGTCCTGAACTCAGAG
CGTCACTGTCAACTACATAAAATTGCCAGAGAAGCTCTTTGGGACTACAA
ACACATACCCTTAATGTCTTTATTTCTATTTTGTCTACCTCTTCAGTCTA
GGTGAAAAAATAGGAAGGATAATAGGGAAGAACTTTGTTTATGCCTACTT
ATCCGCCCCTAGGAATTTTGAAAACCTCTAGGTAGCAATAAGAACTGCAG
CATGGTATAGAAAAGAGGAGGAAAGCTGTATAGAAATGCATAATAAATG
GGCAGGAAAAGAACTGCTTGGAACAAACAGGGAGGTTGAACTATAAGGAG
AGAAAGCAGAGAGGCTAATCAACAAGGCTGGGTTCCAAGAGGGCATGAT
GAGACTATTACTAAGGTAGGAATTACTAAGGGCTCCATGTCCCCTTAGTG
GCTTAGTACTATGTAGCTTGCTTTCTGCAGTGAACTTCAGACCCTTCTTT
TAGGATCCTAGAATGGACTTTTTTTTTTATCGGAAAACAGTCATTCTCT
CAACATTCAAGCAGGCCCCAAGTCTACCACACTCAATCACATTTTCTCTT
CATATCATAATCTCTCAACCATTCTCTGTCCTTTTAACTGTTTTCTATA
CCCTGATCAAATGCCAACAAAAGTGAGAATGTTAGAATCATGTATTTTA
GAGGTAGACTGTATCTCAGATAAAAAAAAGGGCAGATATTCCATTTTCC
AAAATATGTATGCAGAAAAAATAAGTATGAAAGGACATATGCTCAGGTAA
CAAGTTAATTTGTTTACTTGTATTTTATGAATTCCCTAAAACCTACGTCA
CCCGCCCCGTTCCCACGCCCCGCGCCACGTCACAAACTCCACCCCCTCAT
```

-continued

```
TATCATATTGGCTTCAATCCAAAATAAGGTATATTATTGATGATGTTAAT
TAACATGCATGGATCCATATGCGGTGTGAAATACCGCACAGATGCGTAAG
GAGAAAATACCGCATCAGGCGCTCTTCCGCTTCCTCGCTCACTGACTCGC
TGCGCTCGGTCGTTCGGCTGCGGCGAGCGGTATCAGCTCACTCAAAGGCG
GTAATACGGTTATCCACAGAATCAGGGGATAACGCAGGAAAGAACATGTG
AGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGC
TCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCG
GTAACTATCGTCTTGAGTCCAACCCGGTAAGACACGACTTATCGCCACTG
GCAGCAGCCACTGGTAACAGGATTAGCAGAGCGAGGTATGTAGGCGGTGC
TACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATC
CTTTGATCTTTTCTACGGGGTCTGACGCTCAGTGGAACGAAAACTCACGT
TAAGGGATTTTGGTCATGAGATTATCAAAAGGATCTTCACCTAGATCCT
TTTAAATTAAAAATGAAGTTTTAAATCAATCTAAAGTATATATGAGTAAA
CTTGGTCTGACAGTTACCAATGCTTAATCAGTGAGGCACCTATCTCAGCG
ATCTGTCTATTTCGTTCATCCATAGTTGCCTGACTCCCCGTCGTGTAGAT
AACTACGATACGGGAGGGCTTACCATCTGGCCCCAGTGCTGCAATGATAC
CGCGAGACCCACGCTCACCGGCTCCAGATTTATCAGCAATAAACCAGCCA
GCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTA
ATAGTTTGCGCAACGTTGTTGCCATTGCTGCAGCCATGAGATTATCAAAA
AGGATCTTCACCTAGATCCTTTTCACGTAGAAAGCCAGTCCGCAGAAACG
GTGCTGACCCCGGATGAATGTCAGCTACTGGGCTATCTGGACAAGGGAAA
ACGCAAGCGCAAAGAGAAAGCAGGTAGCTTGCAGTGGGCTTACATGGCGA
TAGCTAGACTGGGCGGTTTTATGGACAGCAAGCGAACCGGAATTGCCAGC
TGGGGCGCCCTCTGGTAAGGTTGGGAAGCCCTGCAAAGTAAACTGGATGG
CTTTCTTGCCGCCAAGGATCTGATGGCGCAGGGGATCAAGCTCTGATCAA
GAGACAGGATGAGGATCGTTTCGCATGATTGAACAAGATGGATTGCACGC
AGGTTCTCCGGCCGCTTGGGTGGAGAGGCTATTCGGCTATGACTGGGCAC
AACAGACAATCGGCTGCTCTGATGCCGCCGTGTTCCGGCTGTCAGCGCAG
GGGCGCCCGGTTCTTTTTGTCAAGACCGACCTGTCCGGTGCCCTGAATGA
ACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTG
```

-continued

CTATTGGGCGAAGTGCCGGGGCAGGATCTCCTGTCATCTCACCTTGCTCC
TGCCGAGAAAGTATCCATCATGGCTGATGCAATGCGGCGGCTGCATACGC
TTGATCCGGCTACCTGCCCATTCGACCACCAAGCGAAACATCGCATCGAG
CGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGG
CGAGCATGCCCGACGGCGAGGATCTCGTCGTGACCCATGGCGATGCCTGC
TTGCCGAATATCATGGTGGAAAATGGCCGCTTTTCTGGATTCATCGACTG
TGGCCGGCTGGGTGTGGCGGACCGCTATCAGGACATAGCGTTGGCTACCC
GTGATATTGCTGAAGAGCTTGGCGGCGAATGGGCTGACCGCTTCCTCGTG
CTTTACGGTATCGCCGCTCCCGATTCGCAGCGCATCGCCTTCTATCGCCT
TCTTGACGAGTTCTTCTGAATTTTGTTAAAATTTTTGTTAAATCAGCTCA
TTTTTTAACCAATAGGCCGAAATCGGCAAAATCCCTTATAAATCAAAAGA
ATAGACCGAGATAGGGTTGAGTGTTGTTCCAGTTTGGAACAAGAGTCCAC
TATTAAAGAACGTGGACTCCAACGTCAAAGGGCGAAAAACCGTCTATCAG
GGCGATGGCCCACTACGTGAACCATCACCCTAATCAAGTTTTTTGGGGTC
GAGGTGCCGTAAAGCACTAAATCGGAACCCTAAAGGGAGCCCCCGATTTA
GAGCTTGACGGGGAAAGCCGGCGAACGTGGCGAGAAAGGAAGGGAAGAAA
GCGAAAGGAGCGGGCGCTAGGGCGCTGGCAAGTGTAGCGGTCACGCTGCG
CGTAAGCACCACACCCGCCGCGCTTAATGCGCCGCTACAGGGCGCGTCCA
TTCGCCATTGAGGATCGAATTAATTCTTAATTAA

SEQ ID NO: 8 (BstII linker)
5'-gtaacactgg cccaggaggc ctttctggtg acccc-3'

SEQ ID NO: 9 (SfiI linker)
3'-tgacc gggtcctccg gaaagaccac tggggatt-5'

SEQ ID NO: 10 (Forward PCR primer)
5' TAGTTCCTTCTGCCTGGAATAC 3'

SEQ ID NO: 11 (Reverse PCR primer)
5' CAAGTCACAAGGATGGACTACA 3'

SEQ ID NO: 12 (Stuffer1)
TAGTTCCTTCTGCCTGGAATACTTCCTCATCTCACTTGCTTTCCTGCCTG
GCAGCTTCCTACTTGCCCTCTGGAACCAGCTCTAGGGTCACCACATCTCT
GCTTCTGAGTGCCTCCTCAGACACAGTCTGTATTTCCTCTTCCAAGCTCT
CATCACAAACATTGTGCTGTATTATATGTTTCTGTGTGGTCTTCCTTCTA
TGAGGAAGCCTTGGAAAGCAGGAGACTTATTTTAGTCTTCTTTATGTTTC
TTTTATTCCCAACACATTATGTCTGCCCCATAGACCTTTTCAATAAATGA
TTATTGAGTTAGTGACTCCTTTTACATGCTGACAAATGTGGCTCTTATTA
CTCCCCATTTCAGTATCACATATTTGTAAAAGTGAATCCTTCTTAATCGT
TTTACTTTTCTCCTAGTAAATTCCTCATCTATGCCTGTCTGCTGCTGTTC
TCTGTGCTGCTGGCCCTTCGTTTGGATGGCATCATACAGTGGAGTTACTG
GGCTGTCTTTGCTCCAATATGGCTGTGGAAGTTAATGGTCATTGTTGGAG
CCTCAGTTGGAACTGGAGTCTGGGCACGAAATCCTCAATATCGGTAATAC
TGCTTTATACAACCCATTGGTCTCTAGCATGAGGGAGCAATATCTTGACT -continued TTTCTCACTTTTGATGAAGTAAGGACCATTTTATTTTCTACCTATCTGGG
GTCTTAGAACTATAGTATAAGCTAACAGATCTCTTCTGTGTTTTTGAAAA
TTTAGTCTTTGGTATGTATTTTCTTACAAAAGCAGTGCCATTTGGGGGTA
AGTTGCCAGCCAGCTCACAGATGCCTATATAATCCAAAATGCACCCAAAA
TACAGAACTGGTATGCCATACTAGACTAAGCAGCATGAAACCACCCTGTT
TTTAGGAAAAGACACTCATATTATGTTTGGTCATGAAAGATCTTTCTCCA
ATACAGTTTTGGAACTGGGGCTCCCCTTGTCCCACCCTCCTAGTCCCAGA
GCTTTAGGACTATTAGCAGTGTAGGGGAGGTGGCTTGACCAGGAGACCAT
GAGTCCCTGAGACAGCAGCTGGGGAATGAGGAAAGTCAAAGATTGGATGC
CGAGAAGGAAAGCAGAGCCTTTGGGGGCAGGGGAGAGGGGTACCCTTTAC
CGTTTCCAACTCTTGCCCTCCCTGCTCTTGGATGCCTCCGCTGGCCCAAA
TTCCTGGGAGTTGCTCACGCCAGCATGCAACCTGCTTGTTGCTGGGACCT
GCGAGAGTCTTTCCCTTCTCTGCCACAGAGACTGTAACTACATAAAGGGA
AAAAGGGGGACTTAAGACTGGGAGGCTATTATGAACCTCCACTGGGAAAA
TGAGGAGTACAGGAATTCCCAGAAGGCAGCTGCTCATGTGGGAAAAGTGT
AAAGTTGAAACTACCGCACCTTTTTTTTTTTTTTTTTTTTTTTTTT
TTGAGACAGAGTTTCGCTCTTGTTGCCCAGGCTGGAGTGCAATGGTGTGA
TCTCGGCCCACTGCAGCCTCCACATCCCGGGTTCAAGTGATTCTCCTGCC
TCGGCCTCCTGAGTAGCTGGGATTACAGGCACCTGCCACCATGCCCAGCT
AATTTTTTGTATTTTTAGTAGAGATAGGGTTTCACCATGCCAGGCTAGTT
TTGAACTCCTGACATCAGGTGATCCACCCGCCTTGGCCTCCTGAAGTGCT
GGGATTACAGGTGTGAGCCACCACGTCCGGCCACTACATCAACTTTTTAA
ATTTTTGTTTACTAAATATGAAAATGATTCAGATTGTGTAAATTACATAT
CACATACATGTCTAAGAACTGTAAAACAGTTACACAGAGAGCCTTGGCAG
GTGAGGGACATTCATGTATAGCTGTTTCAGAGTTCTTAGATTTTTTTTGA
AAGATTGATGACCTGTGTGGCTGTATGTGTTTATTTTTTATGAGATAT
TTTCAGATATCTAATATTAATTGCTTCTCAAAGAATGCAAAGTTAAATAA
ACATTTAGGTTCTACTAATTGATATTTAGAATATATTCAAACTTCTCTTT
GTTGGTCTTATTTAAGATGTTTTGAGCAAGGAAAGGAATTGTGTATGTGG
GGTTGAATGTAAGGAATGTACAGGCGTGGTCATTCTCATGTTAACATTAA
CCAGTGGAACATGGTTGGGTCCTACAGGAATAACCTCTGATAGCATTTTC
TCTATGATCTAACTTCCGGTGTATTTGTCACCCACAATACATGTATATCA
TAAATGTTCATCTGTATTTTGAATAAACATTGTAGGCCTTTCAGATGCAT
TATAGAGCCTTTTCCTGATTAGCGGCCTTACCATTGCTCAATTGTAGATG
TGTTAAGGTTATTGTGCATGACTTAGCTAATTAAACTGATTTTGTTTG
AGAACAGTTTTAACTCTTGTTCTTCTTTCTCTTTCATGTGCAGGTGTTAA
TTTATCTTAATGGAATAGAAAGGAAAATGAAAATCATTTATACGTTTTAT
TTGCATTTAAAAATAGCACCTAACAATAGTTACTACTATCTTGAAATATA
AGTGGCACTTGTTCATAGAACTAGAGTTATTTTTATAATATTGTGTGAAG
GGTGGTTTACATGGTTTCTTGAAAAATGAGGATCATGAGACTTAAGGGGT -continued

```
ATTTGCCTGGTTTTAGCAGGAGAAGCAAATCAGCTTGAATAATCTTGGAA
GTAACTCTTGTTGTTGAATTTAAAGATGTGAACAGAAGTGTTTATGTACA
TTGTCAGGGAAATAAGAACTGGCTATTACTTTTGAGAATATCCTTATACG
GTTAAAACATTAAATTCTGGTTTGGTTGTAATGTTCATTTTGTATTATGT
AGTAGTTCTTCGATGTTTCAGAGATTGCCTACCAAAGCTTAGGTTTAAGT
TAGCTTTCTACCTGATTTCCCTTTGCTTTTGTCAAATTTTCAAGTAAAAT
TCAAAGTATAAATATAAGTTGGTATTTGCCCTGAACTGCTTGCTTATAGT
GGAGATTCTGAACTGAGGGTGTTTTCTTCTTCTCCCTTTTTTAGAGCA
GAAGGAGAAACGTGTGTGGAGTTTAAAGCCATGTTGATTGCAGTGGGCAT
CCACTTGCTCTTGTTGATGTTTGAAGTTCTGGTCTGTGACAGAATCGAGA
GAGGAAGCCATTTCTGGCTCCTGGTCTTCATGCCGCTGTTCTTTGTTTCC
CCGGTGTCTGTTGCAGCTTGCGTTTGGGGCTTTCGACATGACAGGTCACT
AGAGGTGAGATTTCATATATTTAAGAATGTTTTCCACTTTGGGAGGTCAA
GGCAGGTGGATCACTTGAGGTCAGGAGTTTGAGACCAGCCTGGCCAACAT
GGTGAAACCCCATCTCTACTAATAATACAAAAATTAGCCGGGTGTGGTGG
CATGCGCCAGTAATCCCAGCTTCTCCGGAGGCTGAGGCGGGAGAATCTCT
TGAACCCAGGAGGCGGAGGTTGCAGTGAGCCAAGATTGAACCATTGCACT
CCAGCCTGGGTGACAGAATGAAACTCCGTCTTAAAAAAAAAAAAAAAGAA
TGTTTTCAAAAGTAAAATATTTTGCTCAGTTATTCAGATGTCAATTTCTT
ACCCTTTGTTAGGAAGAGCTTGATCATTACCAACTCTACATCATGAGACA
ACAAGGCAACAAAAGATGATGGAAATAACAATTTTTCTTTCTTCACTTAG
AACACTAGCTTTTCACCCAGGACATCAGCCTTCTCCCAGCTTCACATCCT
GTATCAATCAGACAGAAACAGAACTGATAGGTTAGATACAGATATATGTA
TAAAGAGAGTTAAGGAACTGGCTCACATTACTGTGGGGCTGGCAAGTCTG
AAATCTCCAGGGCAGGTGAACAGGCTGGAGACCTAGGAGGAGTTGACACT
GCAGTCCTGGCACAGAATTTTTTCCTCTCCAGGAAACCACAGTTTTTGCT
TTTAAGGCCTTCACCTGATTGCATGAGGCCCACCCATGCTATGGAGGGTA
GTCTCCTTTATTCAAAGTCAGTACCTTCACTGCAACAGCAAGCTTAGTGT
TTGATTAAATAACTGGGTACTATAGCCCAGCCAAGTTGACACTCAAAACT
GACCATCTCCCCACCTCAGACCCCATGATTTAGCACCTCCCCTGCTGTCT
GGTTAGCTTATCCTGATGTGCCCCTGTGTTTGTTTATTCATTCAATAAAC
ATTTATCAAGTATTTACTAGATGCCAAGCCCTTTTTCCCTAAGCATAGAG
GATATGCAGATGAATAAAATACCAGGACTAGTAATAATAGTAATGAAAGT
AATTGCAGATAACGTTTATTGAGCACTTACTGTGTGCCAGGCATTGTGCG
AGGCACATTACATGTGGTAGTTTTCTTACTAACTAACTCTGTGAGGTAGG
TCCAGAGAAGATAAGTCATTTGTTCATGGCCACATGTGAAGGGGCAGGAC
CAGGATTCCGTTTGAGTCAGCCCGACTCTAAAGCCCGGGCACATAACTAC
ATAACTGCATAGAAGCTGAGGGCCCAAAGCTGAATACTGATGGGTTGAGG
GGAGAACTAGAGGCTGTAGATGCCTGGTTTTGAGCCGTGTGGATGAAGAG
TGAAGGGAGAAGACTGCAGTTGGCTTAGGAAGTAAACATAGCAGCTGTAG
```

-continued

```
GGTGGGTCAGGCATATAAGCCTAGACGCCAGGTATGGGCGTGAGGGGAAG
GTATGTAGACAGAGGGACGGTGATGGAGCAAGGCCCTGTGGGACTCAGGG
AGAATGGGACCTAGAGCACCAGGAAGGGTTTGGCCTTGAACAAGGGGAGC
TATTCCCTGATTTTCATGCTGGTGGAAAGGCCACAGCATGGGTATAGTGG
TAGGTAGGAGTGAGCCGTGGAGGGAGAGTATCTGATGGTCCACTTTCACC
CTCCCTACAATTCCCAGTTTATATCAGGGACTTGAGCATCCATGGATTTT
GGTATCCACAGGGGGTCCTGGAACCAATCCCCCACAGATACTGAGGGACA
ACTATACAAGGACTAGGACTGCATTGGGCCTGAATTACAGAAAGTAAGTC
TTTCATATATTCACACTCTAGGCATTCCTGCCCTTGGAAGAAACAACATA
CCAGGAGCTGAGCTCCCTCCTCCTGTGATGCAAGAACAGTACCTATGTTG
GTGAGGGGTGGTCTGGAGTAGGCTCATACAGAGATGGGAAGGAGGAGTT
GAGGGTCTGCCAGGAAGCCCTGTGTTGGGAGGGAAGGGATGGCATTTTTG
GGACACATTGAAGCCTAGAGGCAGGAAACACTCCATCAGCTGAGTGGACT
GTGGCGATTCAGATCCGACGGGAGCACAAGGTGGAAAGGAAGGAACTGTG
GGAGTTGAGAAGAGAGGGAGCCTCTACAGAGGGATTGGGGCAAATAGGGG
CCACGTCCTCAGCCCACAGAGCATGTGCTGAAGTGCCCCAGGCACCCCAG
TGCACTCACAGGGCACCAGGGGATAGTGGACATTTTGAGGAAAACAGTAA
TACCTGACATTTGTTGGGACACCATACAAACTACTAGCTTGAAATAGTTT
ACAGGTTTATTTTAGGCCACACTGCATTCCTTTCAGTGACGTCGTATCT
TTAAGAAGCTGGGTTTTCAGCAGTTGCTGTGAAAACAAAAAAGGCTAATG
CTGTGTGAAAATCCGGGTGAAGAACAGGTAACGAGTGGGAGCACCTTGTC
TGATTCCAAGGCGTGGGAAATGGTGAGCTACCTGACAGGCACACGCATCC
CACTGGGAATTAGTTTTGGTTATTTAAGAATAATATTAACATTTTTCTTT
AGATTTATATGAATTATTTTTTCTAGTGGCTACTTAGAAATACTTACTAA
GTTAGATGTAATTACTTAAATCAGTGCAACTGTTGGCATTCCCAGCCACA
TTAGGGATTTCTTTTGGCCTAGAGGTCTATGGAGGAATTACTAAATTCCC
CATGTACCTATGTACTGAGAACTTTTGGGAAGCTCTGGGCCTGGTCCCAG
ATTTCAATTTTGTGGGCAAGAATGTACTTTACCAGAGTGAGGAGCAGCCT
GCAGGGCGTTTGGGCTGGAGGCGGGAGGTTAGTAAGGGGTTGCTGAAGTG
GTAGGCGGATGGTGCCGAAGAAGGCCTCACTAGGCAGTCATCATCAGGAT
AGGAAGTGGGCACGGGATTCAGGAGAAATCTGGACTTTACAGTGGACAGG
ATGTGGTGACTGAACGTGACAGTGTGGGAAAAAGAATGCAGGGTGATTCC
CGGGCTCATGGCTTGAGAAATGAGACCACTGTTGTGCCTCCAAGTGACAT
GGGAGGCTATAGAAAGTGACATGGAGGCTATAGAAAGTGACATGGGAGG
CCATAGAAAGTGACATGGGAGGCCATAGAAAGTGACATGGGAGGCCATAG
AAAGTGACAAGGGAGGCCATAGAAAGTGACATGGAGGCCATAGTGACAT
GGGAGGCCATAGAAAGTGACATGGGAGGCTATAGAAAGTGACATGGAGG
CCATAGAAAGTGACATGGGAGGCCATAGAAAGTGACATGGGAGGCCATAG
TGCATGGGAGGCCATAGAAAGTGACATGGGAGGCTATAGAAAGAGGAGA
TACAAGGTTCTAAGTGCAGGCGATAATGATCTCTATTTGGGACTGGCTTC
```

-continued

```
ATTTGAGGTGCCTTTAGGAGAGCCGAGTGGCCTATGCACAGCTGGGTCTG
CTATGCAGCAGGAAGGCTAAGTTGGAGACAGATGTGAGAACTAACCATGA
AGGAGGTAATAATGCAGACCAAGGGTCTGGTTGAAATTTCTTCTCCCCCA
GTCCAGGGTGCAGCGGGTGAGTGAAAATATGTGTGTTTGTGTGTCTGTCT
TCCTAGTCGGGAGAGAAGACTGAGTTTGTGGCTCTGCGGAGCATCACCAT
TTAAGGAGGGGAAAAGGAGACAGAAGGAATTACCAGAACACTCCAGAGG
GCTCCAAGACTGTATGGTGGGATCTAGATGGCCAGGAGGAGGGAGCAAA
AAGGAAAGAGTCATCCACAGTATCAGTAGGATGCCAGTTGAAGTGTTTTT
GCTGCCTCCCGGTTATGGGTGACTTTGATGAAAGCTGTCTTCTGGTGGTC
ATGGGGGTGGAGGCCAGATCACAAGGAAGCTGGGAATGGTAGATGAGATA
GTAGGGGCTTGCATATTCATTACTGTCTCGCAGAGAGAAACCTGAGGCTA
AGAGGGGTCTTGGATCAAAGGATGGGGTGGGTTTATCTGGTTTCGGGCT
TTTGTTTTTAATGAGAAGGAGTCATTTCTGTGCTGCTAGGAGGGATCAAT
GGAATAGGTGGGGTTAAAGATACAGTACGGAATCTACAGTTGATGGCTTG
ATGTGACAAGGTCCTCAAGGAGCCTGAAAGGAAGGGGTGGGGTCCAAGGG
CAAAACCGAGGTATGAGAAGAAGGATGCACAAGGATGGTTTGGAGTAGAC
AGTATTGTTGGTAGGGACATGAAGGAAGTTTAGTGGTCTATTGCAGCTAG
CCTGTGTTCCCAGTGAACCTGGAAACAAGGTTCTCATCTGTGCTCAGGCC
TCAGGCCAGAAAGGGCAAGGCAGCAGAGGGGCAAGGCAGCAGGCTGAGCC
CCATTTCCCCTTGCCATAATACTGCTGTGCCCCTCTGGTACCGAAAATCA
GGAGTTTCCAGTGCAATATAATATTATACAAGTTACACTGTATTATAATG
TGTATTGTCTTTTAGTGTGTTAACCAAATTACTGCAGTATTAAATGCAAA
TTATACTTTGTTTAACTGATTCTTCTCTTCATTTTTAGTTAGAAATCCTG
TGTTCTGTCAACATTCTCCAGTTTATATTCATTGCCTTAAGACTGGACAA
GATCATCCACTGGCCCTGGCTTGTATGTAACTTTTAAAATCCTTAAATAA
ACTTCTTTTTATTATAAAAGTAATTCATATTCACTGTACAAAGCTTGGA
AAAGACGGACAAGCAGAAGTAATAGCCTAATAGTCACCCATAATCCCACC
ATGGGGAGATAACATGGTTAGTGTTTTTATGTCTGTGTTTTATACAAACA
GTTTGGATATAACTGTGTGCACCATTTTGTATCCTGATTTTTTTGTTTTA
ATGTTGTATCATAAACATTTTATCATGTTAATAAAAGGTCTTTATAAACA
TGACTTCTAAAGTTTAATTGATACAAAATATTCTTCAAGTGCATGTATCA
GACCATCCTCTTATTTCTAAAATATGGTATTTCCATTGTTGCCAGTGTTG
AATGATTTAAATCATACTGCAGTATATATGTTTATGCATTAAAATTTTT
GCCTTTTGTTTTTGGTTGTTTTCTTAGGAAATAGTCCAGAAATAGTGTT
ACTGAGCTAGAGGTTGGGAACTATTTGAGATTCCTATATACGTATACTGC
ACTGCCAACTTGCTTTTCCAAAAGCCATACCTGGCCAGGCGCAGTGGCTT
ACACTTACAGTCCCAGCACTTTGGGAGGCCGAGGTGAGCTGATCACTTGA
GCTCAGGAGTTCGAGACCAACCTGTGCAATGTAGCAAGACCCTGTCTCAA
AAGAAAAAAAAAAAAGCCATACCCATTTACACTCTTGCTGGTGGTGGCA
TCTATGTCATGCTTCTAAACTGTGACTTCAGTTACTGGGCATTTGGTTGA
```

-continued

```
AATTAACTGTGAATAAATGGGTAGATGGATGCAGAGATAGAAAGATAAGT
GGCAAGGTAGAAATTAGAGAACACAGTATAGATTCCACTATTAAATGCAT
GGAAAAAGATGGAGACTAAAGGCAGAAGAGTTCCATTGCCACTGGGAGG
TAAGGTCATGCTAGTGTTTTTGTTCGGTTTTATTTTCTCTGTTGTTTGAT
GTATAATTTTGCATACAATATATTTTATGTATTAAATATAGCTACCCTTA
AAAAGTGAAAAGTATAGTAAAGAATTGGGAGCAGAGAAGAAATGAAGGGA
ACCTAAGTATACTCCATATTTAAAGATGGGAATAATCACTTCTGCCCAAA
GTCTTTGATAAAACATTCATAATAAAAAATATTCAGTCACTCATCCTACA
ACTTCACAGTGCTGTATCTGGAGAATGGTCATTGGGTTCAAAACTGTTTC
TGTTGTGACGTGAAGGAAACATATCTAAACAAGACCAAATTTTTTCGTAT
AAGATACTGTCAGGGAAAAAAAGATTAGTAATTTTGAGAGCTTTCCACA
AATGAGAAGAAAGATTTTTTCTGCCCTTCATCCTCTGTAGATCCCAGTTG
ATGAAGCAGTCTGAGTACATGTTTCCCATAGTGAGCAAGAGAAAACAAGG
AAGCCTATTGAGATCTAACATTCCACCCATGAAGGGAACTTCAGTAAAAA
GGAGAATCTCATCACAGAATGGGGAACGGGGAAGAAAGGCTGTGCATAGA
CTCTGCAGAGAAACCTACAATCAAGAACTGGTCAGGAGAAGTAAAATTCG
TATGCCAACTCAAATCATAGATCTAAAAGAAAATGTAAAACTATAGATCT
GTTAGGAAATAACATAGGACAGAATCTTTGGGGTTTGCAATTAGGCAGAG
AGTACTTAGAAATGGCACTGTTAATATGGTCCATACGAGAGAGAAATCAT
AAATTTGGACTTCCTCAAAATTAAAATGAAATGAAGACAGGCCACAGACT
GGGAGAAAATATTTGCAAAGCACACATCAAAACACTGACTTGCACCCAGA
ACATACAGAGAACTCTTAAAAACTCAAAACTGCAAAAAGAAACACCTAAA
AATTGGCAAAAGAGTTGACAATTTGCGAAGGGGATATACACATGGCGAAA
AAGCACAGGAAAGATGCTCAACGCCATTACAGGTTAGGGAAGACAAACT
ACAACCAGGATGAGGGCCCGAAACACATGGCTTCAGAATGGTGAAACTCA
GCAACACTGACGAGGCCACGTGCCTGGGAGGATGCAGAGGAACTGGGACA
CTCCAGTGTTACTGGCGGGAAGGCAGGTGGTACGGGCACTGTAGAAAATG
GTTTGGCCATCTCTGATGCAGTTAAAAGCGCACTTCCCGTGGGACTTGGC
TGCCCCACTCCTGGGTATAAGATTTACCCCCAGAGAAGTGAAAGCGCGCA
GCCTTGTAGAAACCCACACACCAGTGTTTGTAGCAGTCTTGTTTGCATTT
TGGATAGCGGCCTTGTTTGGTTTTCACAAACCACCCTCAGCGGACAGTCA
GATAAACTGTAGGCATCCATACAATGGAATACCACTCAGATCTGAGAGGG
AACGACCTGTGGATACAGGGAGGGAACAACTTGGATGAATCTCATTAGAG
ACATTATGTGGATGGCGGGAAGCCAGTCTCAACAGGTTACTTGTCTCGCG
ATGCCATCTACATAAAGTTCCAGCAGAGACAAAAGTACAGTGAGAGAACA
GATCAGTGTTTGCCGGGGCTAATGGTGGGACGGTGTGATAGTGAAGGGA
CAGCACGGAGAGTTTTGCAGGGTGACAGACCTCTTCTGCATCCTGCCAAC
GGCTGTGTGAATCTACTTGTGTGAAGACTCAGGGAACTCACACCAAAGGA
AGACGGTCACTTTTCCTACTGTATGATAGATAATTAATAAAAAGGGAGAA
CGGAGGAGTGTCGTCCCAGGAGGCAGGGCAGGAGGGCGAAGACGTGTCAC
```

-continued

```
AGGGGAGCCTGGCCAAGTGGCGCCCCCGGAACTCGTCCTCTGGGCTTGTG
TGTGGATGAGACAAGGTCTACCTGGTACGACAGGGACATACTGGGAATGC
GCCCTTGCCGTGGAGGCGGGGACCCGGCAGCGCTACGTATCCAGCATCAA
CCTGTATCCAGCATCAACCCGCCAAGTTCACTAACTTGGTAGGGGTGAGG
TTAGGGATCCTTAGGAGCCCAGGCAGCCAGACTTTCTGGGGAGCCCATTC
CCATTTGTGTTGCCAAAGTACCCCCAGCAGGTTGTGGGAATGTTGCCTGT
GAAGAGAGTCTGTTGGGGTGAGATCTTGTGTGTGTGCACAGGGTGACAGT
TGTGTCCCATTTCCCGGGAAGCTGTGATGGCAGCAGAACCTAGAGGAGCC
TGAGAGAGTGTGGGAGAGTGGGCCTCTGGAAGAGTAGAGGCTGCGGAGCC
AGGTGCAGGGCTGTCTGTCACCCAAAGGAAGAGGGACTGATGACTCACTG
AGCGTGTGTGTCCCTGGTGGCAGCAGGCCCCATAGTGAACATACCATAC
CTTTTCTGTCCTGAGCGATGCTCCCAGCAGTCCTGGGAGATGGAACGGTC
CTTATTCGGCTCACAGGAAGGACCGCCTTAACTGGACAGACACAGCAAGG
TGCTAAAGATGCCTTCCATCAGAGGCCAGGTTGGAAGCTCTAAAGAGACT
TCTCTTGCTGTTCTCTCACCCACCCCCAGGTTGTGTGTGTCCCGCTGTGG
ATTCTCATGTCCTTTCTGTGCCTGGTGGTCCTCTACTACATTGTGTGGTC
CGTCTTGTTCTTGCGCTCTATGGATGTGATTGCGGACAGCGCAGGACACA
CATAACCATGGCCCTGAGCTGGATGACCATCGTCGTGCCCCTTCTTACAT
TTGAGGTAAGCGTTCCACGGGAAGCCTCTTCAGCCCCTGAAGCTTGCGCT
TCCCCTGACAGGATTCTGCACCCCTAGAAAGGCAGCCTCTGTCCCTCGAG
CTCACAGTGAGCCCACTCCAGGAGAGGGGAGAGAACACAGCCATCTCCGA
GAGGGAGCTTCGGTGAAAGGAGAGCATCCTTCCTTTCTCTTGGGGGCAGC
ACGTGGGGCTGGCAGGGAGAAGAGTGCACCTTTTTAGCCATGGTGCGTCT
GTATGGCTCCAGTTTCCACTCTGGGGAAAGCAGAGTGGGATGTCAGATTT
GTGTATTGGAGTCAGGTGGAGAATTCTAGAATGGGAGCTGTTGACTCCTT
AGAACAAACACCCGGAGGAGTTTGCCATAAAACTGCTGGCACTGGGAACT
TTTCAAGTGGATAGGCTATTGCCGAGCTCTGAAGAGGGACATAAAAGCTC
ATTTGGAGCTTTCCCCAGGGATAGGTGGTTTCCTGCCTTTTTCTGGCGGT
GCTGATGTTCCCTCTTGTGGGAGCTCACGCGGGGTGGGGTGGTGGGGAG
GAACTGCCTAATGAAGTCTGGCTTCCGCCTCTGCCCATTTTCGGTGCTGG
CATCAACCGGGACTATGTCTCTTTCTTTAGATTCTGCTGGTTCACAAACT
GGATGGCCACAACGCCTTCTCCTGCATCCCGATCTTTGTCCCCCTTTGGC
TCTCGTTGATCACGCTGATGGCAACCACATTTGGACAGAAGGGAGGAAAC
CACTGTATGTACTCAGCATTTCAGAAGTCCTTGGTGTGTGTCTGGGGGGG
GACCAGGGGTGGGGGTGGCGGATAGAAGTCTAGGAAGGGATGAGTCCC
CGAGGGCCCCAATTTAGAAGCTTGTGTGGGAAAGTGAGGGCTGAGGAAAT
TCTGGGACCTTCTAAGGGAAGGGCATGCCGTAACTCTGGTGTTCTGCTGG
CCTGCACCGGGACTTTTCTCGCAGTGCACGCTGCCATTTGAGGTAGAACC
AGACACGGCAGGCAACCTCTCAGAGATCCCGTTCCCTCCTCTGCAAAATG
GGGATCAAGACAGATTCTTCCCAGGCCCGGGAGGGTTTGATGGAAAATCC
```

-continued

```
ACATCTCCCACCCAAACCTGGGATTCATCCTAGGTCCCTGTTGGCCGCTC
TGCCTCCCCATATCCTTGCTGCCATCACCCGAGTCTTGCCTGTCTTGCC
TTGCTAACACTCTATTCCCCTCCACCTGCTTGCTGAGGCAGACACTTCCA
AAACGATCTCTGCAGAGGGTGCCTTCCTGGCAAGGCTGTGGGCTCCATGG
CACGGAAGCCCAGAGCATTGCCCTTCGGAAAGCCAGTGGGTTTGGGGGCA
GGGCCTCACTGCAGCCCAGCAGCCCGGGCTGTGCTTGCTGTTTGTGCCTC
TGCCCCCTACCCCGCACCCGGGAGCAGGGAGGGCTTGCACCGAGCTGACA
CTCCAGTAGCCTACAGAGAGGAGTAGTGGGACTGGGAAAGTGGCTTTAAG
GTGGCTCCATGAGTTCAGGCCCCCTCCTGGCCAACCCGTGCATGACTACC
GCCCTCACGGATTCCAGAGGGTGACAGAAATCTTGTTCTTGGGTGGCACT
GTCATCCATGAGTTTATCCTGGCTGGAGAAGATTAGCGGAAGACACCGTA
GTCTGCGCACCACAGATATTTTGAGACTCACTGGAGCAGTAGTTCTCAAA
TTTGGGCATCCAGCAGAATCCCAAAAGGGCCAGGAAAAGGGGACCGCTGG
AGCCCACCCTAGCCCGACTCAGTTTCTGGAGGTCTGGGCTGGGGCCCGAG
AATGGCATCCCTAACTAGGCCCCGTGGACGCTGTCCCTGCCGGTCCGGGA
ACCCCACTCCAAGCACCACAGAGCTAGCATTTGCACTTCTTCCCCATTTT
GGGTACTCAAGCCCTGTTCAGGCTTTGTGACTCAGGAGTCTGGATAAAGT
ATGTTATGACATTGTAGGAGTGAAACTTCTTGTTACGGAAAGAAAGTTAA
CAGGAAGGTCAGTTGAGCCTCGTGTGTGAAATAAAAAATTCTTATTTTTC
AGGGTGGTTTGGTATCCGCAAAGATTTCTGTCAGTTTCTGCTTGAAATCT
TCCCATTTCTACGAGAATATGGAAACATTTCCTATGATCTCCATCACGAA
GATAATGAAGAAACCGAAGAGACCCCAGTTCCGGAGCCCCCTAAAATCGC
ACCCATGTTTCGAAAGAAGGCCAGGGTGGTCATTACCCAGAGCCCTGGGA
AGTATGTGCTCCCACCTCCCAAATTAAATATCGAAATGCCAGATTAGATG
CCACTTCCGGGGACAGAGCTTAAGTGGACTGGGACGCACTCTCTCCGCCT
TCCTCTGCCCCCTCGTTCACCCCGCAGACCAGAACCAGTACTGGAGCTGG
GTCTCCAGGTACGTCCATCTCATGCCTTGTTTGCATCCAGCGCCTATCAG
CCACTCACCACGACGGGACGCGGAAGTGGCAGGTGACGGGGGTGTGTGCC
AGCAGATGCGGATGCCAGGAAGAGTGTGAGAACAGGGGTGGGATTACCGT
CTGTCTGGGAGGGGCTCCAGGTACCCCTCTTCCCCGTCAGACCCACTGGG
AGATGGCTGCTTGCCAGGCCCCCAGAAGGAACATCTGTCTATACGGTGCT
GAAATCCCAATCAAAAGTATTGTTTAGAAATGTATTTCTCCACAGGGCTG
ACCTCCTGCAGCTCGCTGAGCACTCCCAGGTCCTCAGCACTCCCAGGTCG
TGGCTGGGCAGTCAGTAGGAACTGTAACTATGTCTCTGATGCACCACGT
GTTTAGACACAGCACAGTCCTTTTTTCTGTTCCTACTGTGGAAGTAGTTT
CTCTTTGGGCATGCTGACAGCAGTTTTTCATAGCCTCACGGATGAGCCCT
TTCTACGGGAGTGACTCCATGCTTGTATACAGAGTATTTATACAAATGTT
TTAGCATCTTCATATGCGGTGTTAACCCCTAGTTCTGTACAGCATATTCT
GTTCAAGTATTTTTTTACAAGCTTGTGCTGTAGGCACATGCCTTCTGCTG
CAGAAGTGGACGCCCGTGGCACACTCCCCCCCCCCCCCCGTGGGGTGCCA
```

-continued
CGCCTTCATGGGACATTGCCACTTCTGCCCTCGAACTCGTGCAGGTACGT
AGTAGCTGCTACTGCCACAACGGCAACACCAAGCAAGAGATGGTCCATGC
TTTTCTGACGTTCTCAGAATAGTGGCTAGCTTCAAACCTGACAAGCGCTG
CTTGAAGCCGGAACACTAGAGAATGTTGCTGAGAGCAGAAACGGCCACGC
GGGTCACGACTATGCGTGGGAAAGTCTCAAGCTTCCCTCCTGCCAGCAAC
AAGAAGGCTTTGGAGTAGGCATGATGTTTTCACGTGTGCGTGCCGTTTCT
CCAAGCACTGCAGGTTCCACCGTGTGTCAGAGGCTGCAAGTTTAACATCC
TCCTGCCTGAAAACAAATAGGTCCTTTGCTGAAAAGAGGGTAAAAAAAGA
GCTTTGATCTTCTCAGCCAGGAGAAGAGGGTGGTGTTTTCACGCGGGCAA
CTGCTCGCCGGCCTACATGGGGTTAATTCAAGTCTGCTGCGAGCACGACT
CCGCCCTTGGCACTGGCCTCCAGCAAGCCCTGTTCTCTTTGGGGTACAGG
GGAACGGGATGGTTTAGACTTTCCTGCTCAGTGTGTAAAAAATGTAGCTA
AAGCCACTATTTTTGCTCTCCTTAAGCTGTTCAATAAACCGGTTCCTCAT
TTTACACGTGCATGATGTGTATCTTCTTTGCTGGATGGGCCAGGAAACTG
GAGTGGTCCTCTCAGCCAGCCTCAGAGGAAAGAAATCTCTAGCTGGCACA
GGCAGCCAGTGAGTGAGGCTGGCGGCTGCAGGGGCACAGCCTTTAGAATG
AGTCCTTCAGTGCACAGGTCCCAGGGTATACGGGGTAGTGGGAGGAAGGA
GGGGACGCCTCGCAGATGCCACTGTTGGCTGGGCTACACCTTGCCACACT
TGTTACTGCTTAGGAGGCTTTCTGGAGTGTTCCTTGGGTGCTACGACAAT
CTGCAGCAGACACTGTCCTTTCACCGCTCCTGGTCCTCGTTTGCTCCCCA
GTGATGTCAACAGCTGAGGACTGCTCACGCTGCAACAAAGGCTCTGCAG
TCGCTGTCTAGCTTGCCCTAGTCGTCTCTAGAGTTCTGCCTGAACTGAAA
CTCAAGTGGGGTTCAGCTCATGACTTGTGGCAATTGACCAGGAAATTCAC
CAGTTGCTGTGGCTGGAAGGATTTTCAGTCCTGTGGGTTGTAACCAGAGG
CCACAGGTGGATTCTGCCTTAGGCTCATGAGATTTCCGACTTGCTGTTGA
AGAAAATGCCTTGTGAAGTGACAACAGTAGCTCTGACCCAACTGCCGGTG
CCTCGCTAGTTCCTATACGTCCCACTGGATCCTCACAGCCCCGGGAAGCA
GGTGCTACTACTCTTATCCCCGGGAGGAGACAGAGGCCGAGAGAGGTTAA
GTGACGTGCCCAAGTCACACAGCTCGGCAGCGGCCGGGTTGAGCATCAGC
AGTCTGTTTGCAGACCCCTCACTGTCACCCCCTGAGCCAGTGCGCCTTGG
GCCCTGCGGTCAGGATGTCTCAAGCGTGGAGGCATCACCGGTTCGTGGCA
GTCTCTGGAAGGTCACTGAGCTCTGTGCCCAGAATCGAGTCGGGGGAGTC
TGTGCAGAGGTGGCCCTGTGTGTGGGGACAGTGTGTGACACAGACACTGC
TTTGGATGGACACCTCTCCCGTGACCTCCTAGCATCCAATCCCAAAGGAA
CAACTGTTGCAGAGATGGACCGCTGGACACAAACCCACGTGCGTTTCTCT
GGAGACACTGGCCAAGGAAAACAAAACATGCTCGAAGGCCAACAGCTGCA
TGCCCCACCGCGATGTGACCGCAGACACCCGGGGTGTAGAAGGGTCTCTG
CCTGGTGGGGGACACGTGCAGGCCGAGGAGAGGCAGGAAGGAGGCTGCC
TCCGACTCCCCACTGGACTGCATGGCGACGGCGTGTGGTGGGCAGTCAG
CTAAGCCATTTGCGTAAGGGGCTGTCGGGCATCTGCGTGCTGGGGACCGA -continued
CAGTGTGGGTGTGTTAGGAGGATCTGTATGGAGCACATTGCTGCCTCTGG
CTAGGACAGGGTGGAAAGGGTGGCGTGGCTACAGGCTGACCCATGGGGAC
CGTCCTACCCTTTGTTCTGTGCTTCCGAGTGTCAGTCATGTGCTGGGGTC
TGTGGGCCCATGACTCAGACGGTGAGCTCTGACCTTCCTGAGCCAGGGGT
TTGGTGTAGTTGTGCCTGGCTCAGGAGCTCTAGGACAAGGGGACGGCTCC
AGGTCTGCATCTACGGTGTGGCAGGGCCCCTCGGCACTCTTGTGCACTAG
TGTCATCTTTCCCATTGAAATGACTGTGAGGACCAGAATGTGCACATGCA
GATGGGCAGCTACTTGTCTGCCTTGGCCCTTTATTACACAACTTGCTGGG
GGTGGAGATGCCACCCCCCGGCAGTCAGAGCCCCTTTATGATGTCATGGG
GCTGGTTACATGACTGCCAAGGGGTGCTGCTGGCCACACTGCACTAGCAA
GTTTGCCAGATGGAGGACAAGCGATCATTGAGTATGGCTCGCTGTGAAGA
AAGAAATTCGAGAGGACAGGATCATGGCTTGGAAAGGGTGCCTTTCCCTC
CCCAGTTGCAGTCAGAGACCTACCTTCACCCAGCAGATCCTTCCCCTGCC
TGGGACGACCCGGGGTCCACTGGGAGCCCTAACTTGAGGCTGCTGACAGA
AGAAATCGCTTTCCAACCTCTGGCCGAGGAAGCTTCGTTCAGAAGGCCGC
ACCCTGACGGTGACGTCCCGCCCCAGGGAGAAGATAATCTCCTCTCCCTC
CCCTTTCCACAGAAACTGTGGAGACTGGTCAGCAGCAACCAGTTTTCGTC
CATCTGGTGGGATGACAGTGGGGCTTGTAGAGTGATCAATCAAAAACTCT
TTGAAAAGGAGATTCTCAAAAGGGACGTCGCACACAAAGTGTTTGCCACA
ACTTCGATAAAGAGCTTCTTCCGCCAGCTAAACTTGTATGGCTTCCGAAA
ACGGCGTCAATGCACTTTCAGGACCTTCACCCGcATTTTCTCCGCAAAAA
GGCTGGTCTCCATCTTGAATAAGGTAATGAACGACAAGCCTCTGGAGGGG
TTAAGTCGGTGGGCTCTGGGGCCTGGTCGGGTGGAAGTCCCAGGACTGCC
TCCTGGGAAGTGGGCGACCTCAGGCAGGGTGTGGGGCCATCGCTGTGGGC
CTGTGTCCCCTCTGGGTGGAGGTGACATGAACTAAGAGTGAATGTGGGG
AGAGGGCTGAGGATGGTGCGGGCCCCTCTCGAGTGTGTAAAATATCACAG
GTGCCAAGTAGCCGTATCTGCGTGTCGTCCTCCCCGGGGCCAGCCATGTC
ATCTGGTGGTTGCTGTGTCCCCCTGACTCCACAGCACATTACCCTGTGAG
GTGAGCAGGCCAGGGGAGTCTGGTATTTGTACCACTGTCACCCTAGCTGG
TGTCTGGAGAGGTGCTCAAGTGGAAGCACTGAAGGGCGCCTGGCGCAGGA
GGTGCAGATGCTCCTGCTGCCCTTGGTAGGTGGGCCCCTGGTGTGGAAGA
GCCAGTACCCAGGGCCTCCAACCCAGCCGGGGTGCATTCTGTTGCCAGCT
GACACTGCATGGGGAGGCCCAGAATCTTCTTCCCTCCTGGTCTGCAACT
TCAAAGACCCTTTCCGCCGGCCATGGACACCCTAATCTGCCATTTTGAGG
CTTTTTCCAAGACGGAAAGGCCCGCCACAACTTCGTAAACCTTGACGATG
TGAACGCGAGTCCCCAGCTTCCTTTGGGGACTGGGACCTTTTCCAGAAAG
GCCTCCTGGGCCAGTAGAGTTCTCTTGCACAGGGGCGTAGATGGTTGGTA
GTTGTAGTCCATCCTTGTGACTTG SEQ ID NO: 13 (Stuffer 1-Short)
GGCCCAGGAGGCCTTTCTGGAAAAGGTCCCAGTCCCCAAGGAAGCTGGG
GACTCGCGTTCACATCGTCAAGGTTTACCAAGTTGTGGCGGGCCTTTCCG

```
TCTTGGAAAAAGCCTCAAAATGGCAGATTAGGGTGTCCATGGCCGGCGGA
AAGGGTCTTTGAAGTTGCAGACCAGGAGGGAAGAAGATTCTGGGCCTCCC
CCATGCAGTGTCAGCTGGCAACAGAATGCACCCCGGCTGGGTTGGAGGCC
CTGGGTACTGGCTCTTCCACACCAGGGGCCCACCTACCAAGGGCAGCAGG
AGCATCTGCACCTCCTGCGCCAGGCGCCCTTCAGTGCTTCCACTTGAGCA
CCTCTCCAGACACCAGCTAGGGTGACAGTGGTACAAATACCAGACTCCCC
TGGCCTGCTCACCTCACAGGGTAATGTGCTGTGGAGTCAGGGGGACACAG
CAACCACCAGATGACATGGCTGGCCCCGGGGAGGACGACACGCAGATACG
GCTACTTGGCACCTGTGATATTTTACACACTCGAGAGGGGCCCGCACCAT
CCTCAGCCCTCTCCCCACATTCACTCTTAGTTCATGTCACCTCCACCCAG
AGGGGGACACAGGCCCACAGCGATGGCCCCACACCCTGCCTGAGGTCGCC
CACTTCCCAGGAGGCAGTCCTGGGACTTCCACCCGACCAGGCCCCAGAGC
CCACCGACTTAACCCCTCCAGAGGCTTGTCGTTCATTACCTTATTCAAGA
TGGAGACCAGCCTTTTTGCGGAGAAAATGCGGGTGAAGGTCCTGAAAGTG
CATTGACGCCGTTTTCGGAAGCCATACAAGTTTAGCTGGCGGAAGAAGCT
CTTTATCGAAGTTGTGGCAAACACTTTGTGTGCGACGTCCCTTTTGAGAA
TCTCCTTTTCAAAGAGTTTTTGATTGATCACTCTACAAGCCCCACTGTCA
TCCCACCAGATGGACGAAAACTGGTTGCTGCTGACCAGTCTCCACAGTTT
CTGTGGAAAGGGGAGGGAGAGGAGATTATCTTCTCCCTGGGGCGGGACGT
CACCGTCAGGGTGCGGCCTTCTGAACGAAGCTTCCTCGGCCAGAGGTTGG
AAAGCGATTTCTTCTGTCAGCAGCCTCAAGTTAGGGCTCCCAGTGGACCC
CGGGTCGTCCCAGGCAGGGGAAGGATCTGCTGGGTGAAGGTAGGTCTCTG
ACTGCAACTGGGGAGGGAAAGGCACCCTTTCCAAGCCATGATCCTGTCCT
CTCGAATTTCTTTCTTCACAGCGAGCCATACTCAATGATCGCTTGTCCTC
CATCTGGCAAACTTGCTAGTCCAGTGTGGCCAGCAGCACCCCTTGGCAGT
CATGTAACCAGCCCCATGCATCATAAAGGGGCTCTGACTGCCGGGGGGT
GGCATCTCCACCCCCAGCAAGTTGTGTAATAAAGGGCCAAGGCAGACAAG
TAGCTGCCCATCTGCATGTGCACATTCTGGTCCTCACAGTCATTTCAATG
GGAAAGATGACACTAGTGCACAAGAGTGCCGAGGGGCCCTGCCACACCGT
AGATGCAGACCTGGAGCGGTCCCCTTGTCCTAGAGCTCCTGAGCCAGGCA
CAACTACAGCAAAGCCCTGGCTCAGGAAGGTCAGAGCTCACCGTCTGAGT
CATGGGCCACAGACCCCAGCACATGACTGACACTCGGAAGCACAGAACA
AAGGGTAGGACGGTGCCCATGGGTCAGGCTGTAGCCACGCCACCCTTTCC
ACCCTGTCCTAGCCAGAGGCAGCAATGTGCTCCATACAGATCCTCCTAAC
ACAGCCACACTGTCGGTCCCCAGCACGCAGATGCCCGACAGCCCCTTAGG
CAAATGGCTTAGCTGACTGCCCCACCACACGCCGTCGCCATGCAGTCGAG
TGGGGAGTCGGAGGCAGCCTCCTTCCTGCCTCTCCTCGGCCTGCACGTGT
CCCCCCACCAGGCAGAGACCCTTCTACACCCCGGGTGTCTGCGGTCACAT
CGCGGTGGGGCATGGAGCTGTTGGCCTTCGAGCATGTTTTGTTTTCCTTG
GCCAGTGTCTCCAGAGAAACGCACGTGGGTTTGTGTCCAGCGGTCCATCT
```

```
CTGCAACAGTTGTTCCTTTGGGATTGGATGCTAGGAGGTCACGGGAGAGG
TGTCCATCCAAAGCAGTGTCTGTGTCACACACTGTCCCCACACACAGGGC
CACCTCTGCACAGACTCCCCCGACTCGATTCTGGGCACAGAGCTCAGTGA
CCTTCCAGAGACTGCCACGAACCGGTGATGCCTCCACGCTTGAGACATCC
TGACCGCAGGGCCCAAGGCGCACTGGCTCAGGGGGTGACAGTGAGGGGTC
TGCAAACAGACTGCTGATGCTCAACCCGGCCGCTGCCGAGCTGTGTGACT
TGGGCACGTCACTTAACCTCTCTCGGCCTCTGTCTCCTCCCGGGGATAAG
AGTAGTAGCACCTGCTTCCCGGGGCTGTGAGGATCCAGTGGGACGTATAG
GAACTAGCGAGGCACCGGCAGTTGGGTCGAGCTACTGTTGTCACTTCACA
AGGCATTTTCTTCAACAGCAAGTCGGAAATCTCATGAGCCTAAGGCAGAA
TCCACCTGTGGCCTCTGGTTACAACCCACAGGACTGAAAATCCTTCCAGC
CACAGCAACTGGTGAATTTCCTGGTCAATTGCCACAAGTCATGAGCTGAA
CCCCACTTGAGTTTCAGTTCAGGCAGAACTCTAGAGACGACTAGGGCAAG
CTAGACAGCGACTGCAGAGCCTTTTGTTGCAGCGTGAGCAGTCCTCAGCT
GTTGACATCACTGGGGAGCAAACGAGGACCAGGAGCGGTGAAAGGACAGT
GTCTGCTGCAGATTGTCGTAGCACCCAAGGAACACTCCAGAAAGCCTCCT
AAGCAGTAACAAGTGTGGCAAGGTGTAGCCCAGCCAACAGTGGCATCTGC
GAGGCGTCCCCTCCTTCCTCCCACTACCCCGTATACCCTGGGACCTGTGC
ACTGAAGGACTCATTCTAAAGGCTGTGCCCCTGCAGCCGCCAGCCTCACT
CACTGGCTGCCTGTGCCAGCTAGAGATTTCTTTCCTCTGAGGCTGGCTGA
GAGGACCACTCCAGTTTCCTGGCCCATCCAGCAAAGAAGATACACATCAT
GCACGTGTAAAATGAGGAACCGGTTTATTGAACAGCTTAAGGAGAGCAAA
AATAGTGGCTTTAGCTACATTTTTTACACACTGAGCAGGAAAGTCTAAAC
CATCCCGTTCCCCTGTACCCCAAAGAGAACAGGGCTTGCTGGAGGCCAGT
GCCAAGGCGGAGTCGTGCTCGCAGCAGACTTGAATTAACCCCATGTAGG
CCGGCGAGCAGTTGCCCGCGTGAAAACACCACCCTCTTCTCCTGGCTGAG
AAGATCAAAGCTCTTTTTTTACCCTCTTTTCAGCAAAGGACCTATTTGTT
TTCAGGCAGGAGGATGTTAAACTTGCAGCCTCTGACACACGGTGGAACCT
GCAGTGCTTGGAGAAACGGCACGCACACGTGAAAACATCATGCCTACTCC
AAAGCCTTCTTGTTGCTGGCAGGAGGGAAGCTTGAGACTTTCCCACGCAT
AGTCGTGACCCGCGTGGCCGTTTCTGCTCTCAGCAACATTCTCTAGTGTT
CCGGCTTCAAGCAGCGCTTGTCAGGTTTGAAGCTAGCCACTATTCTGAGA
ACGTCAGAAAAGCATGGACCATCTCTTGCTTGGTGTTGCCGTTGTGGCAG
TAGCAGCTACTACGTACCTGCACGAGTTCCAGGGCAGAAGTGGCAATGTC
CCATGAAGGCGTGGCACCCCACGGGGGGGGGGGAGTGTGCCACGGGC
GTCCACTTCTGCAGCAGAAGGCATGTGCCTACAGCACAAGCTTGTAAAAA
AATACTTGAACAGAATATGCTGTACAGAACTAGGGGTTAACACCGCATAT
GAAGATGCTAAAACATTTGTATAAATACTCTGTATACAAGCATGGAGTCA
CTCCCGTAGAAAGGGCTCATCCGTGAGGCTATGAAAAACTGCTGTCAGCA
TGCCCAAAGAGAAACTACTTCCACAGTAGGAACAGAAAAAAGGACTGTGC
```

```
TGTGTCTAAACACGTGGTGCATCAGAGACATAGTTACAGTTCCTACTGAC
TGCCCCAGCCACGACCTGGGAGTGCTGAGGACCTGGGAGTGCTCAGCGAG
CTGCAGGAGGTCAGCCCTGTGGAGAAATACATTTCTAAACAATACTTTTG
ATTGGGATTTCAGCACCGTATAGACAGATGTTCCTTCTGGGGCCTGGCA
AGCAGCCATCTCCCAGTGGGTCTGACGGGAAGAGGGGTACCTGGAGCCC
CTCCCAGACAGACGGTAATCCCACCCCTGTTCTCACACTCTTCCTGGCAT
CCGCATCTGCTGGCACACACCCCCGTCACCTGCCACTTCCGCGTCCCGTC
GTGGTGAGTGGCTGATAGGCGCTGGATGCAAACAAGGCATGAGATGGACG
TACCTGGAGACCCAGCTCCAGTACTGGTTCTGGTCTGCGGGGTGAACGAG
GGGGCAGAGGAAGGCGGAGAGAGTGCGTCCCAGTCCACTTAAGCTCTGTC
CCCGGAAGTGGCATCTAATCTGGCATTTCGATATTTAATTTGGGAGGTGG
GAGCACATACTTCCCAGGGCTCTGGGTAATGACCACCCTGGCCTTCTTTC
GAAACATGGGTGCGATTTTAGGGGGCTCCGGAACTGGGGTCTCTTCGGTT
TCTTCATTATCTTCGTGATGGAGATCATAGGAAATGTTTCCATATTCTCG
TAGAAATGGGAAGATTTCAAGCAGAAACTGACAGAAATCTTTGCGGATAC
CAAACCACCCTGAAAAATAAGAATTTTTTATTTCACACACGAGGCTCAAC
TGACCTTCCTGTTAACTTTCTTTCCGTAACAAGAAGTTTCACTCCTACAA
TGTCATAACATACTTTATCCAGACTCCTGAGTCACAAAGCCTGAACAGGG
CTTGAGTACCCAAAATGGGGAAGAAGTGCAAATGCTAGCTCTGTGGTGCT
TGGAGTGGGGTTCCCGACCGGCAGGGACAGCGTCCACGGGGCCTAGTTA
GGGATGCCATTCTCGGGCCCCAGCCCAGACCTCCAGAAACTGAGTCGGGC
TAGGGTGGGCTCCAGCGGTCCCCTTTTCCTGGCCCTTTTGGGATTCTGCT
GGATGCCCAAATTTGAGAACTACTGCTCCAGTGAGTCTCAAAATATCTGT
GGTGCGCAGACTACGGTGTCTTCCGCTAATCTTCTCCAGCCAGGATAAAC
TCATGGATGACAGTGCCACCCAAGAaCAAGATTTCTGTCACCCTCTGGAA
TCCGTGAGGCGGTAGTCATGCACGGGTTGGCCAGGAGGGGGCCTGAACT
CATGGAGCCACCTTAAAGCCACTTTCCCAGTCCCACTACTCCTCTCTGTA
GGCTACTGGAGTGTCAGCTCGGTGCAAGCCCTCCCTGCTCCCGGGTGCGG
GGTAGGGGGCAGAGGCACAAACAGCAAGCACAGCCCGGGCTGCTGGGCTG
CAGTGAGGCCCTGCCCCCAAACCCACTGGCTTTCCGAAGGGCAATGCTCT
GGGCTTCCGTGCCATGGAGCCCACAGCCTTGCCAGGAAGGCACCCTCTGC
AGAGATCGTTTTGGAAGTGTCTGCCTCAGCAAGCAGGTGGAGGGGAATAG
AGTGTTAGCAAGGCAAGACAGGCAAGACTCGGGTGATGGCAGCAAGGATA
TGGGGGAGGCAGAGCGGCCAACAGGGACCTAGGATGAATCCCAGGTTTGG
GTGGGAGATGTGGATTTTCCATCAAACCGTCCCGGGCCTGGGAAGAATCT
GTCTTGATCCCCATTTTGCAGAGGAGGGAACGGGATCTCTGAGAGGTTGG
CTGCCGTGTCTGGTTCTACCTCAAATGGCAGCGTGCACTGCGAGAAAAGT
CCCGGTGCAGGCCAGCAGAACACCAGAGTTACGGCATGCCCTTCCCTTAG
AAGGTCCCAGAATTTCCTCAGCCCTCACTTTCCCACACAAGCTTCTAAAT
TGGGGCCCTCGGGGACTCATCCCTTCCTAGACTTCTATCCGCCACCCCCC
ACCCCCTGGTCCCCCCCAGACACACACCAAGGACTTCTGAAATGCTGAG
TACATACAGTGGTTTCCTCCCTTCTGTCCAAATGTGGTTGCCATCAGCGT
GATCAACGAGAGCCAAAGGGGGACAAAGATCGGGATGCAGGAGAAGGCGT
TGTGGCCATCCAGTTTGTGAACCAGCAGAATCTAAAGAAAGAGACATAGT
CCCGGTTGATGCCAGCACCGAAAATGGGCAGAGGCGGAAGCCAGACTTCA
TTAGGCAGTTCCTCCCCACCACCCCACCCCCGCGTGAGCTCCCACAAGAG
GGAACATCAGCACCGCCAGAAAAAGGCAGGAAACCACCTATCCCTGGGGA
AAGCTCGAAATGAGCTTTTATGTCCCTCTTCAGAGCTCGGCAATAGCCTA
TCCACTTGAAAAGTTCCCAGTGCCAGCAGTTTTATGGCAAACTCCTCCGG
GTGTTTGTTCTAAGGAGTCAACAGCTCCCATTCTAGAATTCTCCACGTGA
CTCCAATACACAAATCTGACATCCCACTCTGCTTTCCCCAGAGTGGAAAC
TGGAGCCATACAGAGGCACCATGGCTAAAAAGGTGCACTCTTCTCCCTGC
CAGCCCCACGTGCTGCCCCCAAGAGAAAGGAAGGATGCTCTCCTTTCACC
GAAGCTCCCTCTCGGAGATGGCTGTGTTCTCTCCCCTCTCCTGGAGTGGG
CTCACTGTGAGCTCGAGGGACAGAGGCTGCCTTTCTAGGGGTGCAGAATC
CTGTCAGGGGAAGCGCAAGCTTCAGGGGCTGAAGAGGCTTCCCGTGGAAC
GCTTACCTCAAATGTAAGAAGGGGCACGACGATGGTCATCCAGCTCAGGG
CCATGGTTATGTGTGTCCTGCGCTGTCCGCAATCACATCCATAGAGCGCA
AGAACAAGACGGACCACACAATGTAGTAGAGGACCACCAGGCACAGAAAG
GACATGAGAATCCACAGCGGGACACACACAACCTGGGGGTGGGTGAGAGA
ACAGCAAGAGAAGTCTCTTTAGAGCTTCCAACCTGGCCTCTGATGGAAGG
CATCTTTAGCACCTTGCTGTGTCTGTCCAGTTAAGGCGGTCCTTCCTGTG
AGCCGAATAAGGACCGTTCCATCTCCCAGGACTGCTGGGAGCATCGCTCA
GGACAGAAAAGGTATGGTATGTTCACTATGGGGCCTGCTGCCACCAGGGG
ACACACACGCTCAGTGAGTCATCAGTCCCTCTTCCTTTGGGTGACAGACA
GCCCTGCACCTGGCTCCGCAGCCTCTACTCTTCCAGAGGCCCACTCTCCC
ACACTCTCTCAGGCTCCTCTAGGTTCTGCTGCCATCACAGCTTCCCGGGA
AATGGGACACAACTGTCACCCTGTGCACACACACAAGATCTCACCCCAAC
AGACTCTCTTCACAGGCAACATTCCCACAACCTGCTGGGGGTACTTTGGC
AACACAAATGGGAATGGGCTCCCCAGAAAGTCTGGCTGCCTGGGCTCCTA
AGGATCCCTAACCTCACCCCTACCAAGTTAGTGAACTTGGCGGGTTGATG
CTGGATACAGGTTGATGCTGGATACGTAGCGCTGCCGGGTGACC
```

SEQ ID NO: 14 (p2-2)
```
GGGCGAATTGGGCCCGACGTCGCATGCTCCCGGCCGCCATGGCGGCCGCG
GGAATTCGATATCACTAGTCAATTCGCGGCCGGCCGATTGGGCCCGACGTC
GCATGCTCCCGGCCGCCATGGCGGCCGCGGGAATTCGATTCCTTAATTAA
GTCGACTGGGACCCAAACTTTGGAGTCGTTGACAGATGTGACAGGTGAAG
CCTGGGATGACATCGCCAAAAATGCAACGTCTCACTCATTGTCACTACTC
CCAGGGCTCAGTCGTCACTGGGGAAAATCTCCAGAAGGTAGCGCGGGCCA
AGGTGACAGGTGTCTGCCAAGATCTGCCCGCCAGACTCCCGGGCGGCGCG
```

-continued

```
CTCCCTCCCTGCAGGCCTTCAGCCCGTCAGCATCCCCTTCCTCGGGGCCC
TGCTCACTCCCAGCCTCCATCCCCTGCCATCTCCTCCGCCGGTCGCGTG
CGGACACAAGGATGGGGACCTCCCAGCGAGGAGCGCTCTGGGCGGGGCTC
CGGACGCATGCGCGGCCCTCGTACGGAAGCCCGGAAGGAGGGGCAGGGGG
CGGTGGCTCAGGTTTCTCCGGGCGGCGGCGGCGGCGGCGGCGGCGACGGC
GACGGCGACGGCAGCGGGGACGGCAGCAGTAGCGGGAGCAGCAGCGTGGA
CGCGGCTGGCGCTGGCGCCATGAACCCGCTGTAAGGCGCAGGCTGTGCAG
CACGGGGTGCGGGGAGGAGGAGGAGGACGCCGCGGTGAAGTTCTCCGCC
ATGAACCTGAGGGGCCTCTTCCAGGACTTCAACCCGAGGTGAGGCGGCGT
CGTTGGCGCCCCGGGAGTCCGCGCTGCGGGCTCGGGCGCGGGCTGGTGT
TCGGCTCCGGGGAGGCACGGCGGGCGAGATGCTGCAGCCCGAGGACCCGG
GCGCCTGCCCGAGCCTCCCTGCGGGTGCAAGCGGTCCCCAGGCAAAACAG
TCGGCCTCGGCGCCCGCCCGCTTCCTCCTCCCGTGCCCGGTGCTTTCAGC
CCCTGCCCGGCCACGGCCGGAAGGGCCCGGCCGCGAGCCCCGTCCTGCCC
CAAGGGAACCCCATTCTTTTCTGCTTGCTGTCCCTCATTGGTGTCCCAAC
TTCTTCGTCTCGGTTCCATCCTCTTCTGCGCCGCTGCGGGCCCTCCATTC
TCCGCGTCAGGGCCGTCTCACTCGACCCAACACCCCTACCCCCACCCCAG
CTGTTTCCTCCAGTTCCTCGCAGTCCTTGGGGTTTTCCTTGGGTTTATGC
CCATCCCTCTCTTGTTTGCTTCTTTGTTGAACGGATACCTGAAACACTGT
TGAATCCTTGGAGTCAGTGTCGGGGTATGGCAATACCTTATATAATGCAT
TTCTGGGTGAGCCTGATCATTTTCCATACTCATTTTCTCATCAGTCTTCA
CTACAAGTTTATTTGCAGGAAGTAGATATTGCTGTCCTTCTTTTCCAGAT
GGGGAACACCCAGTGGACAGTGTGGAGAAAACACTGGCTAAGCACTCAAG
CGCCTGTCCTTGCACTTGCCCGACTGTTTTGTAACTGTTCTTTACCCCAG
GCTGTGAGCTCCCTGAAGCTGAGACCATCTCCTGCTCATCTCAGTGTCCC
CAGCGCCTCCCACCCACCGTATCTGGCACATAGTAGGCACATATAAAATG
TTTGTGGAACTAAACTGAGCCCAAAGACTTGGATTGGAGACGAGGCCATA
TGTAACTGGGTGATTCTCTGCCCTTCTTTGGCCCTTCTGTAAAATGAGGA
GTTGGCCTAACTGATCTCTTAAATGCACTACTCTCCGAAAGGAGTATCCG
TTTCCCTTATTTGCCAGTTGGGAAGACGTGCTCAGTAAATATTTGTGTGC
TGTAACCTATGTTAGGTGCTTTAGATGCTGGCGGTCTCAGCATGGGGTGA
AGAAGGGCTTGTACACTTAAGATGCCTTACAGTACTGTGCAGTGCTGTAC
TGCGGGGCCAACTCTGGGGACCTATGCCTTGGCTGCTTGTTGAGGATGA
AAGGAAGTTTTAGGGGAGTATTTGTATGTTGAGGGTGCAGTCTCCCTAGG
GATGGTGACATTTTAACTTGTGAGTCATTGTGACTTTGTATGTGCCCTTA
TTCCACTTTGAGTTCATGTTCTGGTTAGGAGTGCCAGTGTCTCTAACACG
GTGCAGACATTATCATTGTTGGCTTCGAAGGCATAGAGGAGGTAACAGAA
CTAACTGCAGTCCCTTCCTCTGCTGCATCAGGGGGTTAAGATTGGTCTGC
AGGGTAGTAGGGTTGGTGCTGTGGCTGGACAAGCCCTGTATGTCTTCTAT
TTGGAGATGGTGATAAGAAAGTTAAGTAAAAACTGAATTGTTTTGTGCCC
```

-continued

```
TTGGGCAACTCACTTATCTATTGTTTTATCTGTAGAATGAGTATAATCTC
TCAGTGGGGTAGGGAGGCCAATTAAGGATTGATTACAAAGTGCCTTACAA
ATAGAAAGCTACAGTGACTTGTTTGCAAGGTGACAGAGAATTCAGAAGCC
TCAAGAAACTGCCTTAAGTGATCAAACAGGCTAACGGAGTTGCCAAAGCA
AAATAGTGCTGCACTGATACTACCTTTAACCGTTTTTTCCTTTAGCCCTT
TTCCCCCCAAAAAAATTAGTATATGAAATTACAGTGAAATACCTGGTATC
TAAGCAGATTTATAGTAATTCTCAACATATTCATCAATCTCTTAATTCTA
CCTGCATTAAAATGTATTTCTACCTGAAAAGTTTAAAGGTCTTTTATACT
CTGCCATTTTCCTGATTCATTGTTGCCAGAGGTAGTGAGTTCCTTAATTT
TACAGATATTTCAAGAGGACATTGGCCAGGTATTATTGGTAAATCAGATT
TGTTTTTTTAGCTGGTAGTGTTTCACCTCTCCTGAGCACTCCTAGTTTTT
GACAGTGTGCTTTAGTCTCCTTCCATGCTGAGGAAGGCCTTCTCTATAGG
AGAAAGAAAACTGAGGGGTGTACACAGGAAGTTACCTTATGCTGGGGACT
CAAACCTTGATGCTACTGCTTTGCTCCCTGCCTCTATTTTTGAACCAATT
CAACATCTCCCTCCTACCCCAGGACCTTGTCACACACTGTTCTCTTTACC
AGGAATGTTTCCCTCTCTTTTCCTCTCCTCCAGACCTAGTGAACTCCTAT
TTATCCTCACTTGGCACTTGCTAAGGGAAGCATTCCTGACTTCCCTGACC
AGATTTACTGCTCCCTGTTTCTACAGTTCCTGTAGTATTTACTACTCCTC
CATCATAGTGCATATTTGTACCCTTGTGTCTGTCTGGATGCTTATTTGAT
TAATACCTGCCTCCCCCACTAAACTTTAAGCTCCATGCGGTCAAGGCCGT
GACTGTGTCAGTATCGTAGCCTGCATACTTGGAATAGTACCTGGCTCAAT
AAATATTTGTGGAGTAAATAACTGAATAACTCTCCAGAGCCTATAAGATA
AATCTAGAGCTGCTGCTTTCAATCACTGCTTTCCTGGTGGTCTGTGGCCT
GGTTCTCTTTCTTCTCACACTCTTCCCACCTTCAGAGTGCAGCCATTGCT
TTGGAGAGATGGGAGAGAACATGGCACTAAGGCAGAATATGGCTATATTT
ACTTTGAAGAGCATGTCTTTGTCATAGAAATAGTCACTGTCATGGTTTGG
TGGGTCCCAAGGCATGGGTCATGGCTCCAGATCCCCTTTCCAGCCTTTTG
GATCTTGGTAAGTCTGAACCCACTGCTGCGTTGGCAAGGCTCTGGAAACT
ATAGTGACAGAGAATGATTCACAAGTGTCAACACTCAGATGTACAGGGCT
GCCAGCTGACCCACTCTACCTATTTCCATCTGGCACTGAACTGGTTGATC
ATGAACTTCTTTTCATAATTGCTTTTTAGTTATGCAGGTTAAGACATGCC
GAAACAGATGTACCGGACCCACAAACAAGTCCTTCCTTGAATGCCTGAGG
CTTCCTAACAGTGAAAGAGCCCTGTTCTTAGAGTAGGCAAACTGATTCTG
AGGCATTGTAGGTGGTAGGGATCTGGTAGTAGGTAGCATTAGGTGGGCTC
CCGGCACTCACCATGGAGCCTTGAAATTTTCTGCTACTTTGGGGGAGTTG
CTGGTTCAGAGAAGGCCCTTCCACCCTGGTAGCCATGTGGCACTGGAAGG
CTGTGAAAACTCTGCTGGGCCTTCTTAGTCATCTGTTGTGAGCTCCTGAT
GGGAGTGTGGTGTATCCCTCAGGTGTGCTAGACTGGAACAAAGGCTGAGA
AGTGTTGCTCTGGGGGTTCCAACTTGTGCGCATGGGGTACTGATGAGATC
AGTAGTGTTTGGAGACTTCTGTATGCTCCATCTTCAGAAGACATTCTCGA
```

-continued

```
GTCCATATAAGTTATCTTGTCTCTTGTTTGAAGCAGGAAAAAGGAATGCG
ATTGCTGGTAATATAGTTCACTAAAGTCAGCTACCTGGCCTCTAACAGTT
ATTTGCAAAGTATATTATAACATTGATTCCTCAAACATCTAGATTCCTAT
CTCGTGCCAAGTGATGTACTAGGTGCTCTAAGTACAAAAATAAAGGAATA
TAGTCCTCCTCTCAATGCGTAAGCCTAGTGGAAGAAGCAGAAATGAAGG
GAAATAAGAATTCAATAGAGTATGAGGCATTACAGTGAAAGAAACCAAAT
GTCTTAGAAGTACAAATGGCAGAGCTACTAATTCTGTCTCGAGCAGGCAG
GGAAGAGTCTATAGTGGAAATGACTTTTGAGCTAGATTTTGAATTGAGCT
AGTCTTTTGAGCCAGACTTTTGAGCTAGAATTGTAGGGTTGTCATCAGAC
CAGAGAGTAGGAAGGGTACCTTGTGAGGAAGAGAGAGAGAGATCAGATTG
TTACTGTGTCTATGTAGAAAAGGAAGACATAAGAAACTCCATTTTGATCT
GTACTAAGAAAAATTGTTTCTGCTTTGAGATGCTGTTAACCTGTAACTTT
AGTCCCAACCCTGTGCTCACAGAAACCTGTGCTGTAATGAATCAAGGTTT
AATGGATTTAGGGCTGTGCAGGATGTACCTTGTTAACAATATGTTTGCAG
GCAGTATGCTTGGTAAAAGTCATCGCCATTCTCCATTCTCGATTAACCAG
GGACACAGTGCACTGCGGAAGGCCGCAGGGACATCTGCCCAAGAAAGCCT
GGGTATTGTCCAAGGTTTCCCCCCACTGAGACAGCCTGAGATATGGCTT
GTGGGAAAGGAAAGACCTTACCACCCCCCAGCCCGACACCCGTAAAGTGT
CTGTGCTGAGGAGGAGTAGTGAAAGAGCGGGGCCTCTTTGCAGTTGAGAT
AAGAGGAAGGCTTCTGTCTCCTGCTCATCCCTGGGAATGGAATGTCTCTG
TGTAAAGCTGACCATTCCCATTCGTTCTATTCTGAGATAGGAGAAAACCA
CCCTGTGGCTGGAGGCGAAGTATGCTGGCAGCAATACTGCTCTGTTACTC
TTTGCTACACTGAGTTGTTTGGGTAAAGAGAAACATAAATCTAGCCTGCG
TGCACATCCAGGCACAGTACCTTTCCTTGAACTTATTCATGATACAGATT
CCTTTGCTCACGTTTCCCTGCTGACCTTCTCCCCACCTGTTGCCCTGCTA
CACTCCCCTCGCTAAGATAGTAAAAATAATGATCAGTAAATACTGAGGTA
AGTCAGAGGCTAGCGCTGGTGCGGGTCCTCCGTATGCTGAGTGCCGGTCC
CCTGGGCCCACTGTTCTTTCTCTATACTTTGTTTCTGTGTCTTATTTCTT
TTCTCAGTCTCGTCCCACCTGACGAGAAATACCCACAGGTGTGGAGGGGC
TGGCCCCTTTCAGTATCTCAGAAGGGACAAAGTACACAAAGGCATGGGT
CATGATAGTGCCTGGTATGTTCAGGTAGTGAAGAGGTCCATGTGGTATGA
GCACTGCAGATGATATGTGTCGTATGAATTAAAAATACATAGTTACTGCA
AATAGTTTTTACAGGTTATTGTTTTTAAGAAAGCAGTATCTAATGCACGA
GTGTACTGTCAGTACTGTCAATGAACTACTTACCACTCAAGTGACTGCTT
ACGCGTCGAATCACTAGTGAATTCGCGGCCGCCTGCAGGTCGACCATATG
GGAGAGCTCCCAACGCGTTGGATGCATAGCTTGAGTATTCTATAGTGTCA
CCTAAATAGCTTGGCGTAATCATGGTCATAGCTGTTTCCTGTGTGAAATT
GTTATCCGCTCACAATTCCACACAACATACGAGCCGGAAGCATAAAGTGT
AAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAAT
```

-continued

```
GAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGG
ATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAG
GACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAG
CCCGACCGCTGCGCCTTATCCGGTAACTATCGTCTTGAGTCCAACCCGGT
AAGACACGACTTATCGCCACTGGCAGCAGCCACTGGTAACAGGATTAGCA
GAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCC
AGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGC
TCAGTGGAACGAAAACTCACGTTAAGGGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCT
CCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTG
TCATGCCATCCGTAAGATGCTTTTCTGTGACTGGTGAGTACTCAACCAAG
TCATTCTGAGAATAGTGTATGCGGCGACCGAGTTGCTCTTGCCCGGCGTC
AATACGGGATAATACCGCGCCACATAGCAGAACTTTAAAAGTGCTCATCA
TTGGAAAACGTTCTTCGGGGCGAAAACTCTCAAGGATCTTACCGCTGTTG
AGATCCAGTTCGATGTAACCCACTCGTGCACCCAACTGATCTTCAGCATC
TTTTACTTTCACCAGCGTTTCTGGGTGAGCAAAAACAGGAAGGCAAAATG
CCGCAAAAAAGGGAATAAGGGCGACACGGAAATGTTGAATACTCATACTC
TTCCTTTTTCAATATTATTGAAGCATTTATCAGGGTTATTGTCTCATGAG
CGGATACATATTTGAATGTATTTAGAAAAATAAACAAATAGGGGTTCCGC
GCACATTTCCCCGAAAAGTGCCACCTGATGCGGTGTGAAATACCGCACAG
```

-continued

```
ATGCGTAAGGAGAAAATACCGCATCAGGAAATTGTAAGCGTTAATATTTT
GTTAAAATTCGCGTTAAATTTTTGTTAAATCAGGTCATTTTTTAACCAAT
AGGCCGAAATCGGCAAAATCCCTTATAAATCAAAAGAATAGACCGAGATA
GGGTTGAGTGTTGTTCCAGTTTGGAACAAGAGTCCACTATTAAAGAACGT
GGACTCCAACGTCAAAGGGCGAAAAACCGTCTATCAGGGCGATGGCCCAC
TACGTGAACCATCACCCTAATCAAGTTTTTTGGGGTCGAGGTGCCGTAAA
GCACTAAATCGGAACCCTAAAGGGAGCCCCCGATTTAGAGCTTGACGGGG
AAAGCCGGCGAACGTGGCGAGAAAGGAAGGGAAGAAAGCGAAAGGAGCGG
GCGCTAGGGCGCTGGCAAGTGTAGCGGTCACGCTGCGCGTAACCACCAGA
CCCGCCGCGCTTAATGCGCCGCTACAGGGCGCGTCCATTCGCCATTCAGG
GTGCGCAACTGTTGGGAAGGGCGATCGGTGCGGGCCTCTTCGCTATTACG
CCAGCTGGCGAAAGGGGATGTGCTGCAAGGCGATTAAGTTGGGTAACGC
CAGGGTTTTCCCAGTCACGACGTTGTAAAACGACGGCCAGTGAATTGTAA
TACGACTCACTATA
NEED SEQ ID NO: 15 (Stuffer 2)
GGCCGCGGGAATTCGATTCCTTAATTAAGTCGACTGGGACCCAAACTTTG
GAGTCGTTGACAGATGTGACAGGTGAAGCCTGGGATGAGATCGCCAAAAA
TGCAACGTCTCACTCATTGTCACTACTCCCAGGGCTCAGTCGTCACTGGG
GAAAATCTCCAGAAGGTAGCGCGGGCCAAGGTGACAGGTGTCTGCCAAGA
TCTGCCCGCCAGACTCCCGGGCGGCGCGCTCCCTCCCTGCAGGCCTTCAG
CCCGTCAGCATCCCCTTCCTCGGGGCCCTGCTCACTCCCAGCCTCCATCC
CCCTGCCATCTCCTCCGCCGGTCGCGTGCGGACACAAGGATGGGGACCTC
CCAGCGAGGAGCGCTCTGGGCGGGGCTCCGGACGCATGCGCGGCCCTCGT
ACGGAAGCCCGGAAGGAGGGGCAGGGGGCGGTGGCTCAGGTTTCTCCGGG
CGGCGGCGGCGGCGGCGGCGACGGCGACGGCGACGGCAGCGGGGACG
GCAGCAGTAGCGGGAGCAGCAGCGTGGACGCGGCTGGCGCTGGCGCCATG
AACCCGCTGTAAGGCGCAGGCTGTGCACCACGGGGTGCGGGGGAGGAGGA
GGAGGACGCCGCGGTGAAGTTCTCCGCCATGAACCTGAGGGGCCTCTTCC
AGGACTTCAACCCGAGGTGAGGCGGCGTCGTTGGCGCCCCCGGGAGTCCG
CGCTGCGGGCTCGGGCGCGGGCTGGTGTTCGGCTCCGGGGAGGCACGGCG
GGCGAGATGCTGCAGCCCGAGGACCCGGGCGCCTGCCCGAGCCTCCCTGC
GGGTGCAAGCGGTCCCCAGGCAAAACAGTCGGCCTCGGCGCCCGCCCGCT
TCCTCCTCCCGTGCCCGGTGCTTTCAGCCCCTGCCCGGCCACGGCCGGAA
GGGCCCGGCCGCGAGCCCCGTCCTGCCCCAAGGGAACCCCATTCTTTTCT
GCTTGCTGTCCCTCATTGGTGTCCCAACTTCTTCGTCTCGGTTCCATCCT
CTTCTGCGCCGCTGCGGGCCCTCCATTCTCCGCGTCAGGGCCGTCTCACT
CGACCCAACACCCCTACCCCCACCCCAGCTGTTTCCTCCAGTTCCTCGCA
GTCCTTGGGGTTTTCCTTGGGTTTATGCCCATCCCTCTCTTGTTTGCTTC
TTTGTTGAACGGATACCTGAAACACTGTTGAATCCTTGGAGTCAGTGTCG
GGGTATGGCAATACCTTATATAATGCATTTCTGGGTGAGCCTGATCATTT
TCCATACTCATTTTCTCATCAGTCTTCACTACAAGTTTATTTGCAGGAAG
```

-continued

```
TAGATATTGCTGTCCTTCTTTTCCAGATGGGGAACACCCAGTGGACAGTG
TGGAGAAAACACTGGCTAAGCACTCAAGCGCCTGTCCTTGCACTTGCCCG
ACTGTTTTGTAACTGTTCTTTACCCCAGGCTGTGAGCTCCCTGAAGCTGA
GACCATCTCCTGCTCATCTCAGTGTCCCCAGCGCCTCCCACCCACCGTAT
CTGGCACATAGTAGGCACATATAAAATGTTTGTGGAACTAAACTGAGCCC
AAAGACTTGGATTGGAGACGAGGCCATATGTAACTGGGTGATTCTCTGCC
CTTCTTTGGCCCTTCTGTAAAATGAGGAGTTGGCCTAACTGATCTCTTAA
ATGCACTACTCTCCGAAAGGAGTATCCGTTTCCCTTATTTGCCAGTTGGG
AAGACGTGCTCAGTAAATATTTGTGTGCTGTAACCTATGTTAGGTGCTTT
AGATGCTGGCGGTCTCAGCATGGGGTGAAGAAGGGCTTGTACACTTAAGA
TGCCTTACAGTACTGTGCAGTGCTGTACTGCGGGGGCCAACTCTGGGGAC
CTATGCCTTGGCTGCTTGTTGAGGATGAAAGGAAGTTTTAGGGGAGTATT
TGTATGTTGAGGGTGCAGTCTCCCTAGGGATGGTGACATTTTAACTTGTG
AGTCATTGTGACTTTGTATGTGCCCTTATTCCACTTTGAGTTCATGTTCT
GGTTAGGAGTGCCAGTGTCTCTAACACGGTGCAGACATTATCATTGTTGG
CTTCGAAGGCATAGAGGAGGTAACAGAACTAACTGCAGTCCCTTCCTCTG
CTGCATCAGGGGGTTAAGATTGGTCTGCAGGGTAGTAGGGTTGGTGCTGT
GGCTGGACAAGCCCTGTATGTCTTCTATTTGGAGATGGTGATAAGAAAGT
TAAGTAAAAACTGAATTGTTTTGTGCCCTTGGGCAACTCACTTATCTATT
GTTTTATCTGTAGAATGAGTATAATCTCTCAGTGGGGTAGGGAGGCCAAT
TAAGGATTGATTACAAAGTGCCTTACAAATAGAAAGCTACAGTGACTTGT
TTGCAAGGTGACAGAGAATTCAGAAGCCTCAAGAAACTGCCTTAAGTGAT
CAAACAGGCTAACGGAGTTGCCAAAAGCAAATAGTGCTGCACTGATACTA
CCTTTAACCGTTTTTTCCTTTAGCCCTTTTCCCCCCAAAAAAATTAGTAT
ATGAAATTACAGTGAAATACCTGGTATCTAAGCAGATTTATAGTAATTCT
CAACATATTCATCAATCTCTTAATTCTACCTGCATTAAAATGTATTTCTA
CCTGAAAAGTTTAAAGGTCTTTTATACTGTGCCATTTTCCTGATTCATTG
TTGCCAGAGGTAGTGAGTTCCTTAATTTTACAGATATTTCAAGAGGACAT
TGGCCAGGTATTATTGGTAAATCAGATTTGTTTTTTTAGCTGGTAGTGTT
TCACCTCTCCTGAGCACTCCTAGTTTTTGACAGTGTGCTTTAGTCTCCTT
CCATGCTGAGGAAGGCCTTCTCTATAGGAGAAAGAAAACTGAGGGGTGTA
CACAGGAAGTTACCTTATGCTGGGGACTCAAACCTTGATGCTACTGCTTT
GCTCCCTGCCTCTATTTTGAACCAATTCAACATCTCCCTCCTACCCCAG
GACCTTGTCACACACTGTTCTCTTTACCAGGAATGTTTCCCTCTCTTTTC
CTCTCCTCCAGACCTAGTGAACTCCTATTTATCCTCACTTGGCACTTGCT
AAGGGAAGCATTCCTGACTTCCCTGACCAGATTTACTGCTCCCTGTTTCT
ACAGTTCCTGTAGTATTTACTACTCCTCCATCATAGTGCATATTTGTACC
CTTGTGTCTGTCTGGATGCTTATTTGATTAATACCTGCCTCCCCCACTAA
ACTTTAAGCTCCATGGGTCAAGGCCGTGACTGTGTCAGTATCGTAGCCT
GCATACTTGGAATAGTACCTGGCTCAATAAATATTTGTGGAGTAAATAAC
```

TGAATAACTCTCCAGAGCCTATAAGATAAATCTAGAGCTGCTGCTTTCAA

TCACTGCTTTCCTGGTGGTCTGTGGCCTGGTTCTCTTTCTTCTCACACTC

TTCCCACCTTCAGAGTGCAGCCATTGCTTTGGAGAGATGGGAGAGAACAT

GGCACTAAGGCAGAATATGGCTATATTTACTTTGAAGAGCATGTCTTTGT

CATAGAAATAGTCACTGTCATGGTTTGGTGGGTCCCAAGGCATGGGTCAT

GGCTCCAGATCCCCTTTCCAGCCTTTTGGATCTTGGTAAGTCTGAACCCA

CTGCTGCGTTGGCAAGGCTCTGGAAACTATAGTGACAGAGAATGATTCAC

AAGTGTCAACACTCAGATGTACAGGGCTGCCAGCTGACCCACTCTACCTA

TTTCCATCTGGCACTGAACTGGTTGATCATGAACTTCTTTTCATAATTGC

TTTTTAGTTATGCAGGTTAAGACATGCCGAAACAGATGTACCGGACCCAC

AAACAAGTCCTTCCTTGAATGCCTGAGGCTTCCTAACAGTGAAAGAGCCC

TGTTCTTAGAGTAGGCAAACTGATTCTGAGGCATTGTAGGTGGTAGGGAT

CTGGTAGTAGGTAGCATTAGGTGGGCTCCCGGCACTCACCATGGAGCCTT

GAAATTTTCTGCTACTTTGGGGGAGTTGCTGGTTCAGAGAAGGCCCTTCC

ACCCTGGTAGCCATGTGGCACTGGAAGGCTGTGAAAACTCTGCTGGGCCT

TCTTAGTCATCTGTTGTGAGCTCCTGATGGGAGTGTGGTGTATCCCTCAG

GTGTGCTAGACTGGAACAAAGGCTGAGAAGTGTTGCTCTGGGGGTTCCAA

CTTGTGGGCATGGGGTACTGATGAGATCAGTAGTGTTTGGAGACTTCTGT

ATGCTCCATCTTCAGAAGACATTCTGGAGTCCATATAAGTTATCTTGTCT

CTTGTTTGAAGCAGGAAAAAGGAATGCGATTGCTGGTAATATAGTTCACT

AAAGTCAGCTACCTGGCCTCTAACAGTTATTTGCAAAGTATATTATAACA

TTGATTCCTCAAACATCTAGATTCCTATCTCGTGCCAAGTGATGTACTAG

GTGCTGTAAGTACAAAAATAAAGGAATATAGTCCTCCTCTCAATGCGTAA

GCCTAGTGGAAGAAGCAGAAATGAAAGGGAAAAAAGAATTCAATAGAGTA

TGAGGCATTACAGTGAAAGAAACCAAATGTCTTAGAAGTACAAATGGCAG

AGCTACTAATTCTGTCTCGAGCAGGCAGGGAAGAGTCTATAGTGGAAATG

ACTTTTGAGCTAGATTTTGAATTGAGCTAGTCTTTTGAGCCAGACTTTTG

AGCTAGAATTGTAGGGTTGTCATCAGACCAGAGAGTAGGAAGGGTACCTT

GTGAGGAAGAGAGAGAGAGATCAGATTGTTACTGTGTCTATGTAGAAAAG

GAAGACATAAGAAACTCCATTTTGATCTGTACTAAGAAAAATTGTTTCTG

CTTTGAGATGCTGTTAACCTGTAACTTTAGTCCCAACCCTGTGCTCACAG

AAACCTGTGCTGTAATGAATCAAGGTTTAATGGATTTAGGGCTGTGCAGG

ATGTACCTTGTTAACAATATGTTTGCAGGCAGTATGCTTGGTAAAAGTCA

TCGCCATTCTCCATTCTCGATTAACCAGGGACACAGTGCACTGCGGAAGG

CCGCAGGGACATCTGCCCAAGAAAGCCTGGGTATTGTCCAAGGTTTCCCC

CCACTGAGACAGCCTGAGATATGGCCTTGTGGGAAAGGAAAGACCTTACC

ACCCCCCAGCCCGACACCCGTAAAGTGTCTGTGCTGAGGAGGAGTAGTGA

AAGAGCGGGGCCTCTTTGCAGTTGAGATAAGAGGAAGGCTTCTGTCTCCT

GCTCATCCCTGGGAATGGAATGTCTCTGTGTAAAGCTGACCATTCCCATT

CGTTCTATTCTGAGATAGGAGAAAACCACCCTGTGGCTGGAGGCGAAGTA

TGCTGGCAGCAATACTGCTCTGTTACTCTTTGCTACACTGAGTTGTTTGG

GTAAAGAGAAACATAAATCTAGCCTGCGTGCACATCCAGGCACAGTACCT

TTCCTTGAACTTATTCATGATACAGATTCCTTTGCTCACGTTTCCCTGCT

GACCTTCTCCCCACCTGTTGCCCTGCTACACTCCCCTCGCTAAGATAGTA

AAAATAATGATCAGTAAATACTGAGGTAACTCAGAGGCTAGCGCTGGTGC

GGGTCCTCCGTATGCTGAGTGCCGGTCCCCTGGGCCCACTGTTCTTTCTC

TATACTTTGTTTCTGTGTCTTATTTCTTTTCTCAGTCTCGTCCCACCTGA

CGAGAAATACCCACAGGTGTGGAGGGGCTGGCCCCTTTCAGTATCTCAGA

AGGGACAAAGTACACAAAGGCATGGGTCATGATAGTGCCTGGTATGTTC

AGGTAGTGAAGAGGTCCATGTGGTATGAGCACTGCAGATGATATGTGTCG

TATGAATTAAAAATACATAGTTACTGCAAATAGTTTTTACAGGTTATTGT

TTTTAAGAAAGCAGTATCTAATGCACGAGTGTACTGTCAGTACTGTCAAT

GAACTACTTACCACTCAAGTGACTGCTTACGCGTCGAATCACTAGTGAAT

TCGC

SEQ ID NO: 16 (pTM-final)
GTACGGAAGCCCGGAAGGAGGGGCAGGGGGCGGTGGCTCAGGTTTCTCCG

GGCGGCCGCGGCGGCGGCGGCGGCGACGGCGACGGCGACGGCAGCGGGGA

CGGCAGCAGTAGCGGGAGCAGCAGCGTGGACGCGGCTGGCGCTGGCGCCA

TGAACCCGCTGTAAGGCGCAGGCTGTGCAGCACGGGGTGCGGGGAGGAG

GAGGAGGACGCCGCGGTGAAGTTCTCCGCCATGAACCTGAGGGGCCTCTT

CCAGGACTTCAACCCCGAGGTGAGGCGGCGTCGTTGGCGCCCCGGGAGTC

CGCGCTGCGGGCTCGGGCGCGGGCTGGTGTTCGGCTCCGGGGAGGCACGG

CGGGCGAGATGCTGCAGCCCGAGGACCCGGGCGCCTGCCCGAGCCTCCCT

GCGGGTGCAAGCGGTCCCCAGGCAAAACAGTCGGCCTCGGCGCCCGCCCG

CTTCCTCCTCCCGTGCCCGGTGCTTTCAGCCCCTGCCCGGCCACGGCCGG

AAGGGCCCGGCCGCGAGCCCCGTCCTGCCCCAAGGGAACCCCATTCTTTT

CTGCTTGCTGTCCCTCATTGGTGTCCCAACTTCTTCGTCTCGGTTCCATC

CTCTTCTGCGCCGCTGCGGGCCCTCCATTCTCCGCGTCAGGGCCGTCTCA

CTCGACCCAACACCCCTACCCCCACCCCAGCTGTTTCCTCCAGTTCCTCG

CAGTCCTTGGGGTTTTCCTTGGGTTTATGCCCATCCCTCTCTTGTTTGCT

TCTTTGTTGAACGGATACCTGAAACACTGTTGAATCCTTGGAGTCAGTGT

CGGGGTATGGCAATACCTTATATAATGCATTTCTGGGTGAGCCTGATCAT

TTTCCATACTCATTTTCTCATCAGTCTTCACTACAAGTTTATTTGCAGGA

AGTAGATATTGCTGTCCTTCTTTTCCAGATGGGGAACACCCAGTGGACAG

TGTGGAGAAAACACTGGCTAAGCACTCAAGCGCCTGTCCTTGCACTTGCC

CGACTGTTTTGTAACTGTTCTTTACCCCAGGCTGTGAGCTCCCTGAAGCT

GAGACCATCTCCTGCTCATCTCAGTGTCCCCAGCGCCTCCCACCCACCGT

ATCTGGCACATAGTAGGCACATATAAAATGTTTGTGGAACTAAACTGAGC

CCAAAGACTTGGATTGGAGACGAGGCCATATGTAACTGGGTGATTCTCTG

CCCTTCTTTGGCCCTTCTGTAAAATGAGGAGTTGGCCTAACTGATCTCTT

-continued

```
AAATGCACTACTCTCCGAAAGGAGTATCCGTTTCCCTTATTTGCCAGTTG
GGAAGACGTGCTCAGTAAATATTTGTGTGCTGTAACCTATGTTAGGTGCT
TTAGATGCTGGCGGTCTCAGCATGGGGTGAAGAAGGGCTTGTACACTTAA
GATGCCTTACAGTACTGTGCAGTGCTGTACTGCGGGGCCAACTCTGGGG
ACCTATGCCTTGGCTGCTTGTTGAGGATGAAAGGAAGTTTTAGGGGAGTA
TTTGTATGTTGAGGGTGCAGTCTCCCTAGGGATGGTGACATTTTAACTTG
TGAGTCATTGTGACTTTGTATGTGCCCTTATTCCACTTTGAGTTCATGTT
CTGGTTAGGAGTGCCAGTGTCTCTAACACGGTGCAGACATTATCATTGTT
GGCTTCGAAGGCATAGAGGAGGTAACAGAACTAACTGCAGTCCCTTCCTC
TGCTGCATCAGGGGGTTAAGATTGGTCTGCAGGGTAGTAGGGTTGGTGCT
GTGGCTGGACAAGCCCTGTATGTCTTCTATTTGGAGATGGTGATAAGAAA
GTTAAGTAAAAACTGAATTGTTTTGTGCCCTTGGGCAACTCACTTATCTA
TTGTTTTATCTGTAGAATGAGTATAATCTCTCAGTGGGGTAGGGAGGCCA
ATTAAGGATTGATTACAAAGTGCCTTACAAATAGAAAGCTACAGTGACTT
GTTTGCAAGGTGACAGAGAATTCAGAAGCCTCAAGAAACTGCCTTAAGTG
ATCAAACAGGCTAACGGAGTTGCCAAAGCAAAATAGTGCTGCACTGATAC
TACCTTTAACCGTTTTTTCCTTTAGCCCTTTTCCCCCCAAAAAAATTAGT
ATATGAAATTACAGTGAAATACCTGGTATCTAAGCAGATTTATAGTAATT
CTCAACATATTCATCAATCTCTTAATTCTACCTGCATTAAAATGTATTTC
TACCTGAAAAGTTTAAAGGTCTTTTATACTGTGCCATTTTCCTGATTCAT
TGTTGCCAGAGGTAGTGAGTTCCTTAATTTTACAGATATTTCAAGAGGAC
ATTGGCCAGGTATTATTGGTAAATCAGATTTGTTTTTTTAGCTGGTAGTG
TTTCACCTCTCCTGAGCACTCCAGTTTTTGACAGTGTGCTTTAGTCTCC
TTCCATGCTGAGGAAGGCCTTCTCTATAGGAGAAAGAAAACTGAGGGGTG
TACACAGGAAGTTACCTTATGCTGGGGACTCAAACCTTGATGCTACTGCT
TTGCTCCCTGCCTCTATTTTTGAACCAATTCAACATCTCCCTCCTACCCC
AGGACCTTGTCACACACTGTTCTCTTTACCAGGAATGTTTCCCTCTCTTT
TCCTGTCCTCCAGACCTAGTGAACTCCTATTTATCCTCACTTGGCACTTG
CTAAGGGAAGCATTCCTGACTTCCCTGACGAGATTTACTGCTCCCTGTTT
CTACAGTTCCTGTAGTATTTACTACTCCTCCATCATAGTGCATATTTGTA
CCCTTGTGTCTGTCTGGATGCTTATTTGATTAATACCTGCCTCCCGCACT
AAACTTTAAGCTCCATGGGGTCAAGGCCGTGACTGTGTCAGTATGGTAGC
CTGCATACTTGGAATAGTACCTGGCTCAATAAATATTTGTGGAGTAAATA
ACTGAATAACTCTCCAGAGCCTATAAGATAAATCTAGAGCTGCTGCTTTC
AATCACTGCTTTCCTGGTGGTCTGTGGCCTGGTTCTCTTTCTTCTCACAC
TCTTCCCACCTTCAGAGTGCAGCCATTGCTTTGGAGAGATGGGAGAGAAC
ATGGCACTAAGGCAGAATATGGCTATATTTACTTTGAAGAGCATGTCTTT
GTCATAGAAATAGTCACTGTCATGGTTTGGTGGGTCCCAAGGCATGGGTC
ATGGCTCCAGATCCCCTTTCCAGCCTTTTGGATCTTGGTAAGTCTGAACC
CACTGCTGCGTTGGCAAGGCTCTGGAAACTATAGTGACAGAGAATGATTC
```

-continued

```
ACAAGTGTCAACACTCAGATGTACAGGGCTGCCAGCTGACCCACTCTACC
TATTTCCATCTGGCACTGAACTGGTTGATCATGAACTTCTTTTCATAATT
GCTTTTTAGTTATGCAGGTTAAGACATGCCGAAACAGATGTACCGGACCC
ACAAACAAGTCCTTCCTTGAATGCCTGAGGCTTCCTAACAGTGAAAGAGC
CCTGTTCTTAGAGTAGGCAAACTGATTCTGAGGCATTGTAGGTGGTAGGG
ATCTGGTAGTAGGTAGCATTAGGTGGGCTCCCGGCACTCACCATGGAGCC
TTGAAATTTTCTGCTACTTTGGGGGAGTTGCTGGTTCAGAGAAGGCCCTT
CCACCCTGGTAGCCATGTGGCACTGGAAGGCTGTGAAAACTCTGCTGGGC
CTTCTTAGTCATCTGTTGTGAGCTCCTGATGGGAGTGTGGTGTATCCCTC
AGGTGTGCTAGACTGGAACAAAGGCTGAGAAGTGTTGCTCTGGGGGTTCC
AACTTGTGGGCATGGGGTACTGATGAGATCAGTAGTGTTTGGAGACTTCT
GTATGCTCCATCTTCAGAAGACATTCTGGAGTCCATATAAGTTATCTTGT
CTCTTGTTTGAAGCAGGAAAAAGGAATGCGATTGCTGGTAATATAGTTCA
CTAAAGTCAGCTACCTGGCCTCTAACAGTTATTTGCAAAGTATATTATAA
CATTGATTCCTCAAACATCTAGATTCCTATCTCGTGCCAAGTGATGTACT
AGGTGCTCTAAGTACAAAAATAAAGGAATATAGTCCTCCTCTCAATGCGT
AAGCCTAGTGGAAGAAGCAGAAATGAAAGGGAAATAAGAATTCAATAGAG
TATGACGCATTACAGTGAAAGAAACCAAATGTCTTAGAAGTACAAATGGC
AGAGCTACTAATTCTGTCTCGAGCAGGCAGGGAAGAGTCTATAGTGGAAA
TGACTTTTGAGCTAGATTTTGAATTGAGCTAGTCTTTTGAGCCAGACTTT
TGAGCTAGAATTGTAGGGTTGTCATCAGACCAGAGAGTAGGAAGGGTACC
TTGTGAGGAAGAGAGAGAGAGATCAGATTGTTACTGTGTCTATGTAGAAA
AGGAAGACATAAGAAACTCCATTTTGATCTGTACTAAGAAAAATTGTTTC
TGCTTTGAGATGCTGTTAACCTGTAACTTTAGTCCCAACCCTGTGCTCAC
AGAAACCTGTGCTGTAATGAATCAAGGTTTAATGGATTTAGGGCTGTGCA
GGATGTACCTTGTTAACAATATGTTTGCAGGCAGTATGCTTGGTAAAAGT
CATCGCCATTCTCCATTCTCGATTAACCAGGGACACAGTGCACTGCGGAA
GGCCGCAGGGACATCTGCCCAAGAAAGCCTGGGTATTGTCCAAGGTTTCC
CCCCACTGAGACAGCCTGAGATATGGCCTTGTGGGAAAGGAAAGACCTTA
CCACCCCCAGCCCGACACCCGTAAAGTGTCTGTGCTGAGGAGGAGTAGT
GAAAGAGCGGGGCCTCTTTGCAGTTGAGATAAGAGGAAGGCTTCTGTCTC
CTGCTCATCCCTGGGAATGGAATGTCTCTGTGTAAAGCTGACCATTCCCA
TTCGTTCTATTCTGAGATAGGAGAAAACCACCCTGTGGCTGGAGGCGAAG
TATGCTGGCAGCAATACTGCTCTGTTACTCTTTGCTACACTGAGTTGTTT
GGGTAAAGAGAAACATAAATCTAGCCTGCGTGCACATCCAGGCACAGTAC
CTTTCCTTGAACTTATTCATGATACAGATTCCTTTGCTCACGTTTCCCTG
CTGACCTTCTCCCCACCTGTTGCCCTGCTACACTCCCCTCGCTAAGATAG
TAAAAATAATGATCAGTAAATACTGAGGTAACTCAGAGGCTAGCGCTGGT
GCGGGTCCTCCGTATGCTGAGTGCCGGTCCCCTGGGCCCACTGTTCTTTC
TCTATACTTTGTTTCTGTGTCTTATTTCTTTTCTCAGTCTCGTCCCACCT
```

-continued

```
GACGAGAAATACCCACAGGTGTGGAGGGGCTGGCCCCTTTCAGTATCTCA
GAAGGGACAAAGTACACAAAGGCATGGGGTCATGATAGTGCCTGGTATGT
TCAGGTAGTGAAGAGGTCCATGTGGTATGAGCACTGCAGATGATATGTGT
CGTATGAATTAAAAATACATAGTTACTGCAAATAGTTTTTACAGGTTATT
GTTTTTAAGAAAGCAGTATCTAATGCACGAGTGTACTGTCAGTACTGTCA
ATGAACTACTTACCACTCAAGTGACTGCTTACGCGTCGAATCACTAGTGA
ATTCGCGGCCGCCTCGAGTCTAGAACTAGTGGATCCCCCAAACGGGCCCT
CTAGACGCGTTGACATTGATTATTGACTAGTTATTAATAGTAATCAATTA
CGGGGTCATTAGTTCATAGCCCATGATATCATATGGAGTTCCGCGTTACA
TAACTTACGGTAAATGGCCCGCCTGGCTGACCGCCCAACGACCCCCGCCC
ATTGACGTCAATAATGACGTATGTTCCCATAGTAACGCCAATAGGGACTT
TCCATTGACGTCAATGGGTGGAGTATTTACGGTAAACTGCCCACTTGGCA
GTACATCAAGTGTATCATATGCCAAGTACGCCCCCTATTGACGTCAATG
ACGGTAAATGGCCCGCCTGGCATTATGCCCAGTNCATGACCTTATGGGAC
TTTCCTACTTGGCAGACATCTACGTATTAGTCATCGCTATTACCATGGTG
ATGCGGTTTTGGCAGTACATCAATGGGCGTGGATAGCGGTTTGACTCACG
GGGATTTTCCAAGTCTCCACCCCATTGACGTCAATGGGAGTTTGTTTTGG
CACCAAAATCAACGGGACTTTCCAAAATGTCGTAACAACTCCGCCCCATT
GACGCAAATGGGCGGTAGGCGTGTACGGTGGGAGGTCTATATAAGCAGAG
CTCTCTGGCTAACTAGAGAACCCCTGCTTACTGGCTTATCGAGATATCTG
CAGAATTCATCTGTCGACTGCTACCGGCAGCGCGCAGCGGCAAGAAGTGT
CTGGGCTGGGACGGACAGGAGAGGCTGTCGCCATCGGCGTCCTGTGCCCC
TCTGCTCCGGCACGGCCCTGTCGCAGTGCCCGCGCTTTCCCCGGCGCCTG
CACGCGGCGCGCCTGGGTAACATGCTTGGGGTCCTGGTCCTTGGCGCGCT
GGCCCTGGCCGGCCTGGGGTTCCCCGCACCCGCAGAGCCGCAGCCGGGTG
GCAGCCAGTGCGTCGAGCACGACTGCTTCGCGCTCTACCCGGGCCCCGCG
ACCTTCCTCAATGCCAGTCAGATCTGCGACGGACTGCGGGGCCACCTAAT
GACAGTGCGCTCCTCGGTGGCTGCCGATGTCATTTCCTTGCTACTGAACG
GCGACGGCGGCGTTGGCCGCCGGCGCCTCTGGATCGGCCTGCAGCTGCCA
CCCGGCTGCGGCGACCCCAAGCGCCTCGGGCCCTGCGCGGCTTCCAGTG
GGTTACGGGAGACAACAACACCAGCTATAGCAGGTGGGCACGGCTCGACC
TCAATGGGCTCCCCTCTGGGGCCCGTTGTGCGTCGCTGTCTCCGCTGCT
GAGGCCACTGTGCCCAGCGAGCCGATCTGGGAGGAGCAGCAGTGCGAAGT
GAAGGCCGATGGCTTCCTCTGCGAGTTCCACTTCCCAGCCACCTGCAGGC
CACTGGCTGTGGAGCCCGGCGCCGCGGCTGCCGCCGTCTCGATCACCTAC
GGCACCCCGTTCGCGGCCCGCGGAGCGGACTTCCAGGCGCTGCCGGTGGG
CAGCTCCGCCGCGGTGGCTCCCCTCGGCTTACAGCTAATGTGCACCGCGC
CGCCCGGAGGGGTCCAGGGGCACTGGGCCAGGGAGGCGCCGGGCGCTTGG
GACTGCAGCGTGGAGAACGGCGGCTGCGAGCACGCGTGCAATGCGATCCC
TGGGGCTCCCCGCTGCCAGTGCCCAGCCGGCGCCGCCCTGCAGGCAGACG
```

-continued

```
GGCGCTCCTGCACCGCATCCGCGACGCAGTCCTGCAACGACCTCTGCGAG
CACTTCTGCGTTCCCAACCCCGACCAGCCGGGCTCCTACTCGTGCATGTG
CGAGAGCGGCTACCGGCTGGCGGCCGACCAACACCGGTGCGAGGACGTGG
ATGACTGCATACTGGAGCCCAGTCCGTGTCCGCAGCGCTGTGTCAACACA
CAGGGTGGCTTCGAGTGCCACTGCTACCCTAACTACGACCTGGTGGACGG
CGAGTGTGTGGAGCCCGTGGACCCGTGCTTCAGAGGCAACTGCGAGTACC
AGTGCCAGCCCCTGAACCAAACTAGCTACCTCTGCGTCTGCGCCGAGGGC
TTCGCGCCCATTCCCCACGAGCCGCACAGGTGCCAGATGTTTTGCAACCA
GACTGCCTGTCCAGCCGACTGCGACCCCAACACCCAGGCTAGCTGTGAGT
GCCCTGAAGGCTACATCCTGGACGACGGTTTCATCTGCACGGACATCGAC
GAGTGCGAAAACGGCGGCTTCTGCTCCGGGGTGTGCCACAACCTCCCCGG
TACCTTCGAGTGCATCTGCGGGCCCGACTCGGCCCTTGCCCGCCACATTG
GCACCGACTGTGACTCCGGCAAGGTGGACGGTGGCGACAGCGGCTCTGGC
GAGCCCCCGCCCAGCCCGACGCCCGGCTCCACCTTGACTCCTCCGGCCGT
GGGGCTCGTGCATTCGGGCTTGCTCATAGGCATCTCCATCGCGAGCCTGT
GCCTGGTGGTGGCGCTTTTGGCGCTCCTCTGCCACCTGCGCAAGAAGCAG
GGCGCCGCCAGGGCCAAGATGGAGTACAAGTGCGCGGCCCCTTCCAAGGA
GGTAGTGCTGCAGCACGTGCGGACCGAGCGGACGCCGCAGAGACTCTGAG
CGGCCTCCGTCCAGGAGCCTGGCTCCGTCCAGGAGCCTGTGCCTCCTCAC
CCCCAGCTTTGCTACCAAAGCACCTTAGCTGGCATTACAGCTGGAGAAGA
CCCTCCCCGCACCCCCCAAGCTGTTTTCTTCTATTCCATGGCTAACTGGC
GAGGGGTGATTAGAGGGAGGAGAATGAGCCTCGGCCTCTTCCGTGACGT
CACTGGACCACTGGGCAATGATGGCAATTTTGTAACGAAGACACAGACTG
CGATTTGTCCCAGGTCCTCACTACCGGGCGCAGGAGGGTGAGCGTTATTG
GTCGGCAGCCTTCTGGGCAGACCTTGACCTCGTGGGCTAGGGATGACTAA
AATATTTATTTTTTTAAGTATTTAGGTTTTTGTTTGTTTCCTTTGTTCT
TACCTGTATGTCTCCAGTATCCACTTTGCACAGCTCTCCGGTCTCTCTCT
CTCTACAAACTCCCACTTGTCATGTGACAGGTAAACTATCTTGGTGAATT
TTTTTTTCCTAGCCCTCTCACATTTATGAAGCAAGCCCCACTTATTCCCC
ATTCTTCCTAGTTTTCTCCTCCCAGGAACTGGGCCAACTCACCTGAGTCA
CCCTACCTGTGCCTGACCCTACTTCTTTTGCTCTTAGCTGTCTGCTCAGA
CAGAACCCCTACATGAAACAGAAACAAAAACACTAAAAATAAAAATGGCC
ATTTGCTTTTTCACCAGATTTGCTAATTTATCCTGAAATTTCAGATTCCC
AGAGCAAAATAATTTTAAACAAAGGTTGAGATGTAAAAGGTATTAAATTG
ATGTTGCTGGACTGTCATAGAAATTACACCCAAAGAGGTATTTATCTTTA
CTTTTAAACAGTGAGCCTGAATTTTGTTGCTGTTTTGATTTGTACTGAAA
AATGGTAATTGTTGCTAATCTTCTTATGCAATTTCCTTTTTTGTTATTAT
TACTTATTTTTGACAGTGTTGAAAATGTTCAGAAGGTTGCTCTAGATTGA
GAGAAGAGACAAACACCTCCCAGGAGACAGTTCAAGAAAGCTTCAAACTG
CATGATTCATGCCAATTAGCAATTGACTGTCACTGTTCCTTGTCACTGGT
```

-continued

```
AGACCAAAATAAAACCAGCTCTACTGGTCTTGTGGAATTGGGAGCTTGGG
AATGGATCCTGGAGGATGCCCAATTAGGGCCTAGCCTTAATCAGGTCCTC
AGAGAATTTCTACCATTTCAGAGAGGCCTTTTGGAATGTGGCCCCTGAAC
AAGAATTGGAAGCTGCCCTGCCCATGGGAGCTGGTTAGAAATGCAGAATC
CTAGGCTCCACCCCATCCAGTTCATGAGAATCTATATTTAACAAGATCTG
CAGGGGGTGTGTCTGCTCAGTAATTTGAGGACAACCATTCCAGACTGCTT
CCAATTTTCTGGAATACATGAAATATAGATCAGTTATAAGTAGCAGGCCA
AGTCAGGCCCTTATTTTCAAGAAACTGAGGAATTTTCTTTGTGTAGCTTT
GCTCTTTGGTAGAAAAGGCTAGGTACACAGCTCTAGACACTGCCACACAG
GGTCTGCAAGGTCTTTGGTTCAGCTAAGCTAGGAATGAAATCCTGCTTCA
GTGTATGGAAATAAATGTATCATAGAAATGTAACTTTTGTAAGACAAAGG
TTTTCCTCTTCTATTTTGTAAACTCAAATATTTGTACATAGTTATTTAT
TTATTGGAGATAATCTAGAACACAGGCAAAATCCTTGCTTATGACATCAC
TTGTACAAAATAAACAAATAACAATGTGAAAAAAAAAAAAAAAAAAAAA
AAAAAAAAAAAAAAAAGGTAGCAGTCGACAGATGAATTCCACCACACT
GGACTAGTGGATCCGAGCTCGGTACCAAGCTTAAGTTTGGGCTGCACGAA
TTCTGATGGCTCTCAAAATTCCTGCCTCCTTTAGGGATAAAAGACTTTAA
GACTTTTTAACAAAAAGAAAAAGAAAAAAAAAATTCCTGCCTCCTGGTG
TACACACACAGAAGGGTTCCCTCCCCTTGAATGTGACCAGGATCTGTGAA
AATAACGGGATAGCCGCTCCTGTGATTAGGTTATGTGGTAGACTAGAGCA
AGATTCTCCTGCTGGTTTTGAAGAAGTCAGCTGCCATGTTGTGAGACTGT
CATGGGCTAGGGCATGAGCCTTTAAATATCTGGGAGCAACCCCTGGCCAG
CAGCCAGTGAGAAAACGGGCCCTCAGTCCTACAATCACAAGGAACTAAAT
TCTGCCAACAACCTGAAGGAACTTTGAAGAGGATCATGAGTCCCTTGATT
CAGCTTGATGAGCCCCTGAGCAGAGGATACAGCTAACTTGTACTAGGGAA
GTATAAAAAACATGCATGGAATGATATATATCAACTTTAAGGATAATTG
TCATACTTCTGGGAATGAAGGGAAAGAAATGGGCTTTAGTTGTATTATG
ATCTTTAATTTCTCAAAAAAAATAAGATCAGAAGCAAATATGGCAAAATG
TTAATACTTTTGTGGGTACGTAGGTATTCAGCATACCCTTTTTTCTGAGT
TCAAAATATTTTATAATTAAAATGAAATGCAGGCCAGGCACAGTGGCTCA
TGCCTATAATACCAGCACTTTGCGAGGCCGAGGTGGGAGGATGGCTTGAG
GCCAGACCAGCCTGGCCAACATGGCAAACCCCATCTCTACTTAAAAAAA
AAAAAACTATATATATATATATGTGTGTGTGTGTATATATATATATGT
ATATATATTTATATATGTGTGTATATATATATATGTATATATATTTATAT
ATGTGTGTGTATATATATATATACACACACACATATATACATACATAC
ATACACACACACACACACAATTAGCCAGGCATGGTGGCGCACACCTGT
AGTCCCAGCTACTTGGGAGGCTGAGACATGAGAATTGCTTGAACCTGGGA
GGCAGAGTAGTTAGTGAGCTGAGATCATACCACTGCACTCCAGCCTGGTG
ACAGAGTGAGACTCTGTCTTAAAAAAAATAAAAATTAAAATTAAATGCAA
AAGGTCCAAGTGAATTGAAGAGGAAAGGGGTATCAAGGAAGGTTTTGTGG
```

-continued

```
AGGTGACGTTTGAGCTGGGTCTTAAATGACTTAAACATGGGATAAGAAGG
GAGGGAATAAGGACATTTCAGGTACGAGAAATAAGGAGCAAACAGTGGAA
ACAACCTAACGTCTGTCAACCAGTGAATGGATAACAAAAATGTAATTCAG
ATGGTATCCAACTTACGATGGTTCAACATGAGATTTTTCTGACTTTAGGA
TAGATTTATCAAAGTAGTAAATCCATTTTCAACTTATGATATTTTCAACT
TCAGATGGGTTTATCAGGACACAGTTGAGGAACACCTGTCTATCCATACA
ATTTGGCAATAAAAAGGAAATGAGTGCAGATATACTCCACAACATGAATG
AACCTTGAAAACATTAAGTGAGAGAAGCCAGATACAAAAGGCCACATATT
GTATGATTCTATTTATACAAAATGTCCAGAATAGGCAAATCTTATAGACA
GCAAGTAGGTAGATGATCAGTTTGCTAGGTGCTGGGGGAAGGGGAAATGG
GGAGTGATGGCTAAGGGGATTGGGTTTCTTTGTGGGGCAATGAAAATGTT
TTAAAATTGAGCGTGATAATGATTGCACAATGCTGCATATATATATAATC
TATAGATTATATATATATAAAGAGAGGCTGTTAGACAGTGATAAGTGATA
TATATATATATATACATAGAGAGAGAGAGAGAGAGAGAGAGGCTGTTA
GTGATAAGTGATCAGGAAAATAAAAGTATTGAGGAGGAATACGAAGTTGA
CGGTGTGAAAACATGAGATTTTATATAGGATGGCCAGGGAAGGCCTTAAT
GAGAAAGTGACTTATGAGTAAAAACAAGGGATCCTAAACCTTAGCATGCA
TCAGAATCACTCGGAAACTTGTTAAAGGATAGCTTGCTGGGCCTCATCAC
AGATATTTTGATTCGGTAGGTTCTTGTCTGATATTAATACTTTTGGTGTA
GGGAACCACATTTTGAGAACCACTGAGCTAAAGGAAGTAAAGGTTTCCCT
TAGTTTACTAGCTGGTAACACTGGCCCAGGAGGCCTTTCTGGAAAAGGTC
CCAGTCCCCAAAGGAAGCTGGGGACTCGCGTTCACATCGTCAAGGTTTAC
CAAGTTGTGGCGGGCCTTTCCGTCTTGGAAAAAGCCTCAAAATGGCAGAT
TAGGGTGTCCATGGCCGGCGGAAAGGGTCTTTGAAGTTGCAGACCAGGAG
GGAAGAAGATTCTGGGCCTCCCCCATGCAGTGTCAGCTGGCAACAGAATG
CACCCCGGCTGGGTTGGAGGCCCTGGGTACTGGCTCTTCCACACCAGGGG
CCCACCTACCAAGGGCAGCAGGAGCATCTGCACCTCCTGCGCCAGGCGCC
CTTCAGTGCTTCCACTTGAGCACCTCTCCAGACACCAGCTAGGGTGACAG
TGGTACAAATACCAGACTCCCCTGGCCTGCTCACCTCACAGGGTAATGTG
CTGTGGAGTCAGGGGACACAGCAACCACCAGATGACATGGCTGGCCCCG
GGGAGGACGACACGCAGATACGGCTACTTGGCACCTGTGATATTTTACAC
ACTCGAGAGGGCCCGCACCATCCTCAGCCCTCTCCCCACATTCACTCTT
AGTTCATGTCACCTCCACCCAGAGGGGACACAGGCCCACAGCGATGGCC
CCACACCCTGCCTGAGGTCGCCCACTTCCCAGGAGGCAGTCCTGGGACTT
CCACCCGACCAGGCCCCAGAGCCCACCGACTTAACCCCTCCAGAGGCTTG
TCGTTCATTACCTTATTCAAGATGGAGACCAGCCTTTTTGCGGAGAAAAT
GCGGGTGAAGGTCCTGAAAGTGCATTGACGCCGTTTTCGGAAGCCATACA
AGTTTAGCTGGCGGAAGAAGCTCTTTATCGAAGTTGTGGCAAACACTTTG
TGTGCGACGTCCCTTTTGAGAATCTCCTTTTCAAAGAGTTTTTGATTGAT
CACTCTACAAGCCCCACTGTCATCCCACCAGATGGACGAAAACTGGTTGC
```

-continued

```
TGCTGACCAGTCTCCACAGTTTCTGTGGAAAGGGGAGGGAGAGGAGATTA
TCTTCTCCCTGGGGCGGGACGTCACCGTCAGGGTGCGGCCTTCTGAACGA
AGCTTCCTCGGCCAGAGGTTGGAAAGCGATTTCTTCTGTCAGCAGCCTCA
AGTTAGGGCTCCCAGTGGACCCCGGGTCGTCCCAGGCAGGGGAAGGATCT
GCTGGGTGAAGGTAGGTCTCTGACTGCAACTGGGGAGGGAAAGGCACCCT
TTCCAAGCCATGATCCTGTCCTCTCGAATTTCTTTCTTCACAGCGAGCCA
TACTCAATGATCGCTTGTCCTCCATCTGGCAAACTTGCTAGTGCAGTGTG
GCCAGCAGCACCCCTTGGCAGTCATGTAACCAGCCCCATGACATCATAAA
GGGGCTCTGACTGCCGGGGGTGGCATCTCCACCCCCAGCAAGTTGTGTA
ATAAAGGGCCAAGGCAGACAAGTAGCTGCCCATCTGCATGTGCACATTCT
GGTCCTCACAGTCATTTCAATGGGAAAGATGACACTAGTGCACAAGAGTG
CCGAGCGGCCCTGCCACACCGTAGATGCAGACCTGGAGCGGTCCCCTTGT
CCTAGAGCTCCTGAGCCAGGCACAACTACACCAAAGCCCTGGCTCAGGAA
GGTCAGAGCTCACCGTCTGAGTCATGGGCCCACAGACCCCAGCACATGAC
TGACACTCGGAAGCACAGAACAAAGGGTAGGACGGTGCCCATGGGTCAGG
CTGTAGCCACGCCACCCTTTCCACCCTGTCCTAGCCAGAGGCAGCAATGT
GCTCCATACAGATCCTCCTAACACACCCACACTGTCGGTCCCCAGCACGC
AGATGCCCGACAGCCCCTTAGGCAAATGGCTTAGCTGACTGCCCCACCAC
ACGCCGTCGCCATGCAGTCCAGTGGGGAGTCGGAGGCAGCCTCCTTCCTG
CCTCTCCTCGGCCTGCACGTGTCCCCCCACCAGGCAGAGACCCTTCTACA
CCCCGGGTGTCTGCGGTCACATCGCGGTGGGGCATGCAGCTGTTGGCCTT
CGAGCATGTTTTGTTTTCCTTGGCCAGTGTCTCCAGAGAAACGCACGTGG
GTTTGTGTCCAGCGGTCCATCTCTGCAACAGTTGTTCCTTTGGGATTGGA
TGCTAGGAGGTCACGGGAGAGGTGTCCATCCAAAGCAGTGTCTGTGTCAC
ACACTGTCCCCACACAGGGCCACCTCTGCACAGACTCCCCCGACTCGA
TTCTGGGCACAGAGCTCAGTGACCTTCCAGAGACTGCCACGAACCGGTGA
TGCCTCCACGCTTGAGACATCCTGACCGCAGGGCCCAAGGCGCACTGGCT
CAGGGGGTGACAGTGAGGGGTCTGCAAACAGACTGCTGATGCTCAACCCG
GCCGCTGCCGAGCTGTGTGACTTGGGCACGTCACTTAACCTCTCTCGGCC
TCTGTCTCCTCCCGGGGATAAGAGTAGTAGCACCTGCTTCCCGGGGCTGT
GAGGATCCAGTGGGACGTATAGGAACTAGCGAGGCACCGGCAGTTGGGTC
AGAGCTACTGTTGTCACTTCACAAGGCATTTTCTTCAACAGCAAGTCGGA
AATCTCATGAGCCTAAGGCAGAATCCACCTGTGGCCTCTGGTTACAACCC
ACAGGACTGAAAATCCTTCCAGCCACAGCAACTGGTGAATTTCCTGGTCA
ATTGCCACAAGTCATGAGCTGAACCCCACTTGAGTTTCAGTTCAGCCAGA
ACTCTAGAGACGACTAGGGCAAGCTAGACAGCGACTGCAGAGCCTTTTGT
TGCAGCGTGAGCAGTCCTCAGCTGTTGACATCACTGGGGAGCAAACGAGG
ACCAGGAGCGGTGAAAGGACAGTGTCTGCTGCAGATTGTCGTAGCACCCA
AGGAACACTCCAGAAAGCCTCCTAAGCAGTAACAAGTGTGGCAAGGTGTA
GCCCAGCCAACAGTGGCATCTGCGAGGCGTCCCCTCCTTCCTCCCACTAC
CCCGTATACCCTGGGACCTGTGCACTGAAGGACTCATTCTAAAGGCTGTG
CCCCTGCAGCCGCCAGCCTCACTCACTGGCTGCCTGTGCCAGCTAGAGAT
TTCTTTCCTCTGAGGCTGGCTGAGAGGACCACTCCAGTTTCCTGGCCCAT
CCAGCAAAGAAGATACACATCATGCACGTGTAAAATGAGGAACCGGTTTA
TTGAACAGCTTAAGGAGAGCAAAAATAGTGGCTTTAGCTACATTTTTTAC
ACACTGAGCAGGAAAGTCTAAACCATCCCGTTCCCCTGTACCCCAAAGAG
AACAGGGCTTGCTGGAGGCCAGTGCCAAGGGCGGAGTCGTGCTCGCAGCA
GACTTGAATTAACCCCATGTAGGCCGGCGAGCAGTTGCCCGCGTGAAAAC
ACCACCCTCTTCTCCTGGCTGAGAAGATCAAAGCTCTTTTTTTACCCTCT
TTTCAGCAAAGGACCTATTTGTTTTCAGGCAGGAGGATGTTAAACTTGCA
GCCTCTGACACACGGTGGAACCTGCAGTGCTTGGAGAAACGGCACGCACA
CGTGAAAACATCATGCCTACTCCAAAGCCTTCTTGTTGCTGGCAGGAGGG
AAGCTTGAGACTTTCCCACGCATAGTCGTGACCCGCGTGGCCGTTTCTGC
TCTCAGCAACATTCTCTAGTGTTCCGGCTTCAAGCAGCGCTTGTCAGGTT
TGAAGCTAGCCACTATTCTGAGAACGTCAGAAAAGCATGGACCATCTCTT
GCTTGGTGTTGCCGTTGTGGCAGTAGCAGCTACTACGTACCTGCACGAGT
TCCAGGGCAGAAGTGGCAATGTCCCATGAAGGCGTGGCACCCCACGGGGG
GGGGGGGGAGTGTGCCACGGGCGTCCACTTCTGCAGCAGAAGGCATGTG
CCTACAGCACAAGCTTGTAAAAAAATACTTGAACAGAATATGCTGTACAG
AACTAGGGGTTAACACCGCATATGAAGATGCTAAAACATTTGTATAAATA
CTCTGTATACAAGCATGGAGTCACTCCCGTAGAAAGGGCTCATCCGTGAG
GCTATGAAAAACTGCTGTCAGCATGCCCAAAGAGAAACTACTTCCACAGT
AGGAACAGAAAAAAGGACTGTGCTGTGTCTAAACACGTGGTGCATCAGAG
ACATAGTTACAGTTCCTACTGACTGCCCCAGCCAGGACCTGGGAGTGCTG
AGGACCTGGGAGTGCTCAGCGAGCTGCAGGAGGTCAGCCCTGTGGAGAAA
TACATTTCTAAACAATACTTTTGATTGGGATTTCAGCACCGTATAGACAG
ATGTTCCTTCTGGGGCCTGGCAAGCAGCCATCTCCCAGTGGGTCTGACG
GGGAAGAGGGGTACCTGGAGCCCCTCCCAGACAGACGGTAATCCCACCCC
TGTTCTCACACTCTTCCTGGCATCCGCATGTGCTGGCACACACCCCGTC
ACCTGCCACTTCCGCGTCCCGTCGTGGTGAGTGGGTGATAGGCGCTGGAT
GCAAACAAGGCATGAGATGGACGTACCTGGAGACCCAGCTCCAGTACTGG
TTCTGGTCTGCGGGGTGAACGAGGGGGCAGAGGAAGGCGGAGAGAGTGCG
TCCCAGTCCACTTAAGCTCTGTCCCCGGAAGTGGCATCTAATCTGGCATT
TGGATATTTAATTTGGGAGGTGGGAGCACATACTTCCCAGGGCTCTGGGT
AATGACCACCCTGGCCTTCTTTCGAAACATGGGTGCGATTTAGGGGGCT
CCGGAACTGGGGTCTCTTCGGTTTCTTCATTATCTTCGTGATGGAGATCA
TAGGAAATGTTTCCATATTCTCGTAGAAATGGGAAGATTTCAAGCAGAAA
CTGACAGAAATCTTTGCGGATACCAAACCACCCTGAAAAATAAGAATTTT
TTATTTCACACACGAGGCTCAACTGACCTTCCTGTTAACTTTCTTTCCGT
AACAAGAAGTTTCACTCCTACAATGTCATAACATACTTTATCCAGACTCC
```

-continued

TGAGTCACAAAGCCTGAACAGGGCTTGAGTACCCAAAATGGGGAAGAAGT
GCAAATGCTAGCTCTGTGGTGCTTGGAGTGGGGTTCCCGGACCGGCAGGG
ACAGCGTCCACGGGGCCTAGTTAGGGATGCCATTCTCGGGCCCCAGCCCA
GACCTCCAGAAACTGAGTCGGGCTAGGGTGGGCTCCAGCGGTCCCCTTTT
CCTGGCCCTTTTGGGATTCTGCTGGATGCCCAAATTTGAGAACTACTGCT
CCAGTGAGTCTCAAAATATCTGTGGTGCGCAGACTACGGTGTCTTCCGCT
AATCTTCTCCAGCCAGGATAAACTCATGGATGACAGTGCCACCCAAGAAC
AAGATTTCTGTCACCCTCTGGAATCCGTGAGGGCGGTAGTCATGCACGGG
TTGGCCAGGAGGGGCCTGAACTCATGGAGCCACCTTAAAGCCACTTTCC
CAGTCCCACTACTCCTCTCTGTAGGCTACTCGAGTGTCAGCTCGGTGCAA
GCCCTCCCTGCTCCCGGGTGCGGGTAGGGGGCAGAGGCACAAACAGCAA
GCACAGCCCGGGCTGCTGGGCTGCAGTGAGGCCCTGCCCCCAAACCCACT
GGCTTTCCGAAGGGCAATGCTCTGGGCTTCCGTGCCATGGAGCCCACAGC
CTTGCCAGGAAGGCACCCTCTGCAGAGATCGTTTTGGAAGTGTCTGCCTC
AGCAAGCAGGTGGAGGGGAATAGAGTGTTAGCAAGGCAAGACAGGCAAGA
CTCGGGTGATGGCAGCAAGGATATGGGGGAGGCAGAGCGGCCAACAGGGA
CCTAGGATGAATCCCAGGTTTGGGTGGGAGATGTGGATTTTCCATCAAAC
CCTCCCGGGCCTGGGAAGAATCTGTCTTGATCCCCATTTTGCAGAGGAGG
GAACGGGATCTCTGAGAGGTTGCCTGCCGTGTCTGGTTCTACCTCAAATG
GCAGCGTGCACTGCGAGAAAAGTCCCGGTGCAGGCCAGCAGAACACCACA
GTTACGGCATGCCCTTCCCTTAGAAGGTCCCAGAATTTCCTCAGCCCTCA
CTTTCCCACACAAGCTTCTAAATTGGGGCCCTCGGGGACTCATCCCTTCC
TAGACTTCTATCCGCCACCCCCACCCCTGGTCCCCCCCAGACACACA
CCAAGGACTTCTGAAATGCTGAGTACATACAGTGGTTTCCTCCCTTCTGT
CCAAATGTGGTTGCCATCAGCGTGATCAACGAGAGCCAAAGGGGACAAA
GATCGGGATGCAGGAGAAGGCGTTGTGGCCATCCAGTTTGTGAACCAGCA
GAATCTAAAGAAAGAGACATAGTCCCGGTTGATGCCAGCACCGAAAATGG
GCAGAGGCGGAAGCCAGACTTCATTAGGCAGTTCCTCCCCACCACCCAC
CCCCGCGTGAGCTCCCACAAGAGGGAACATCAGCACCGCCAGAAAAAGGC
AGGAAACCACCTATCCCTGGGGAAAGCTCGAAATGAGCTTTTATGTCCCT
CTTCAGAGCTCGGCAATAGCCTATCCACTTGAAAAGTTCCCAGTGCCAGC
AGTTTTATGGCAAACTCCTCCGGGTGTTTGTTCTAAGGAGTCAACAGCTC
CCATTCTAGAATTCTCCACGTGACTCCAATACACAAATCTGACATCCCAC
TCTGCTTTCCCCAGAGTGGAAACTGGAGCCATACAGAGGCACCATGGCTA
AAAAGGTGCACTCTTCTCCCTGCCAGCCCCACGTGCTGCCCCAAGAGAA
AGGAAGGATGCTCTCCTTTCACCGAAGCTCCCTCTCGGAGATGGCTGTGT
TCTCTCCCCTCTCCTGGAGTGGGCTCACTGTGAGCTCGAGGGACAGAGGC
TGCCTTTCTAGGGGTGCAGAATCCTGTCAGGGGAAGCGCAAGCTTCAGGG
GCTGAAGACGCTTCCCGTGGAACGCTTACCTCAAATGTAAGAAGGGGCAC
GACGATGGTCATCCAGCTCAGGGCCATGGTTATGTGTGTCCTGCGCTGTC

-continued

CGCAATCACATCCATAGAGCGCAAGAACAAGACGGACCACACAATGTAGT
AGAGGACCACCAGGCACAGAAAGGACATGAGAATCCACAGCGGGACACAC
ACAACCTGGGGGTGGGTGAGAGAACAGCAAGAGAAGTCTCTTTAGAGCTT
CCAACCTGGCCTCTGATGGAAGGCATCTTTAGCACCTTGCTGTGTCTGTC
CAGTTAAGGCGGTCCTTCCTGTGAGCCGAATAAGGACCGTTCCATCTCCC
AGGACTGCTGGGAGCATCGCTCAGGACAGAAAAGGTATGGTATGTTCACT
ATGGGGCCTGCTGCCACCAGGGGACACACACGCTCAGTGAGTCATCAGTC
CCTCTTCCTTTGGGTGACAGACAGCCCTGCACCTGGCTCCGCAGCCTCTA
CTCTTCCAGAGGCCCACTCTCCCACACTCTCTCAGGCTCCTCTAGGTTCT
GCTGCCATCACAGCTTCCCGGGAAATGGGACACAACTGTCACCCTGTGCA
CACACACAAGATCTCACCCCAACAGACTCTCTTCACAGGCAACATTCCCA
CAACCTGCTGGGGGTACTTTGGCAACACAAATGGGAATGGGCTCCCCAGA
AAGTCTGGCTGCCTGGGCTCCTAAGGATCCCTAACCTCACCCCTACCAAG
TTAGTGAACTTGGCGGGTTGATGCTGGATACAGGTTGATGCTGGATACGT
AGCGCTGCCGGGTCGTGACCCCTAAGGAATTATCCAAACTCTTGTTTTTA
GATGCTTTATTATATCAAACTCTCCTTTAAACAAGTGGCCCATCTGCTGG
GATTTGGAAGCCTGTAATACTGAAATTTTCATCATAATGGAAATTTTAAA
AACAGAATTTGACCCACCTGTTTTTAAAACACTTTCATTACTTAACAAGA
GGTCTAATCTTGGGCAAGTCTTGAAATTTCTCTGGCCTTAGTTTCCCATG
TGTTAAATGAAACTTGAAGCAGTTGGTCTCTTATAGTCTCCTGACTCTAA
CATTCTAAGAATTATATTTGTACAATAACTCAAAAATCACATAATTTAAT
TTACCATATGGACTCCAAAATATATTTTCTCATTAGGCTAAACTTGATCT
GCATTTTCTGGATGTGTCCATATTCTTGGACTACACTAAAACATGATACC
AATGCTTCCTCTCACCATAAACCCTCACTTGCTTTCTACATTTAAGAAT
TTTATAGCTGGAAGAGTCCTTAACAGAAAATACCATCTAATAATTACCCC
TCAAAATCGAGAAAGTCCTATCTGTTCTTATGCTAGTTATAAGAATGAGG
CAGCATTTCACATAATGGTTATAAACACTGCCACAAGAAGATTCATGATG
TGTTGTTTATCTGTAGCTCTCATCATACTCTGTCATATAACTATAGCATT
AAGATTTTAATGTTCTATATATTCTTCTAAGACAGTGTTTACCAGAGTAA
GGCACAAAAGATCCACTGGTTTGCAAGAAAGATTAGAACTTTTAAATTTT
TTACCTCACCTTGTTTAATCTATATTTTTGTATGTATTTTGTAACATATA
TATTATTATTACCATAAATCATATATAATTTAAAATGCATATATTAGGGG
TAAATGCTCAGGAAACTTTTTATAAATTGGGCATGCAAATACAAGTTTGA
AGACTCACTGTTCTAGGTATTAAAAGTAAAGTTATAACCAAGTAAAGCTT
CCACCTTTTCATGTCTCAAAGCAGTTTATTGTTGGAGGTAAGATCTCTTA
GAAGCCTAAACAGGTCCAAGTACAGAATGAAGTAAGGCTAGCCCATAACT
TGTGGCAAGCAATTCATACTATTTCTCTCATGCTGAGCTCTCCTCAGTGA
AGCAGCTACTATAGACAACTGCAGCCTATTGGTAGCCTATTTTACAGGCA
GGAAAAAAATTACTTTTTATTCAAAGTGGAACTCAGGACATGGGGAGAAA
ATGAATACAAAAAATAGGGTCAATCCAAAGGCACACAGCAAATGAGTAAC

-continued
```
ACAGTTATGTTTTTTTCCCATTTGTATGAGGTCCCAGTAAATTCTAAGTA
AACTGCAAATTTAATAATACACTAAAAAAGCCATGCAATTGTTCAAATGA
ATCCCAGCATGGTACAAGGAGTACAGACACTAGAGTCTAAAAAACAAAAG
AATGCCATTATTGAGTTTTGAATTATATCAAGTAGTTACATCTCTACTT
AATAAATGAGAAAAACGAGGATAAGAGGCCATTTGATAAAATGAAAATAG
CCAAGAAGTGGTATTAGAGACTTGAATACAGGTATTCGGGTCCAAAGTTC
ATCTGCTCAAATACTAACTGGGGAAAAGAGGGAAAAATATTTATATACAT
ATATATCTGCACACAAAAATACCCCCAAAAGACAAAATGAGGCCAGGGAG
GGTGGCTCACACCCGTAATCCCGGTACTTTGGGAGGCTGAGGCAGGTGGA
TACCTGAGATGAGGAGTTGGAGATCAGCCTGGTCAACATGGTGAAACCCT
GTCTCTACTAAAGATAAAAAAATTAGCCAGGCATGGTGGCGTGCGCCTGT
AATCCCAGCTACTTGGGAGTCTGAGGCAGGAGAATCACTTGAACTGGGAA
GGGGAGGTTGCAGTGAGCCAAGATCGTACTACTGCACTCCAGCCTGGGCA
GCAGAGTGAGACTCCATCACAAAAATAAATAAATAAATAAAATACAATGA
AACAGAAAGTTCAAATAATCCCATAATCTTACCACCAAGAAATAACTTTC
ACTCGTTATACTTATTGATTTTTCCATAATAAATGTACTTTACTGTGACT
ATCATGAAAGAAAGTTATTTTAGAAACAGAGAACTGTTTCAGATCAAAT
CTATGTAGTAGAACAGAGCCATTAGGTGGGAAAGACGAGATCAAACTAAA
TCTCAGAAGGCCTAAAAGGCTAGGTCCATTCCAGCACTAAAAACTGACCA
GACAAGTAATGGCTTCAACAGCTTCTAAATATGGACAAAGCATGCTGAAA
GGGAAGGACAGGTCTAACAGTGGTATATGAAATGAACAGGAGGGGCAAAG
CTCATTTCTCCTCTGAAGTTTTCCAAAGATGCTGAGGAGGACATTAGTTT
GACATGACCCTGATATGGGACAAGATAATTTCACAGAAGTTTTACATGTT
AAAGTTTTCTTATAGATACTCATTCAAGTAAGCAATGAACACTAAAATCT
AAAGAAAGAAAAGAGCTTTAGAGTCAGGTCTGTATTCAAATTCAAGCTCT
ACCACTTACTGGTTCTGTGACTTTGGGCAAGTCTTTTAACCTTATTAAGT
CTTAATTTCCTGATTTGTAAAATGGGGATATCGTCTCCCTCACAGGATTG
TTGTGAAACTTTTATGAGATTAATGCCTTTATATTTGGCATAGTGTAAGT
AAACAATAACTGGCAGCTTCAAAAAAAAAAAGCAGTAGCATTCCATCAT
TATTATTGGTTACTCTCAAAAAGTTTTTCAATGTACTAGAAGATAAATAT
TCAAATACCTTAATATCTCCATTATTTTCAGGTAAACAGCATGCTCCTGA
ACAACCAATGGGTCAACAAATAAATTAAAAGGGAAATCTAAAAACATCTT
GATATTAAACTACATGGAAGCACAATATACCAAAACCAATGGTTCACACT
AGGAGAATTTTAAGGTACAAGAAAACTCTTTGAGATTTCTTAAAATAATA
GTATGTCTGAATTTATTGAGTGATTTACCAGAAACTGTTGTAAGAGCTCT
ACTTGCATTATAGCACTTAATCCTCTTAACTCTATGGCTGCTATTATCAA
CCTCACCCTAATCACATATGGGACACAGAGAGGTAAGTAACTTGCCCAA
GGTCAGAGTTAGGAAGTACTAAGCCATGCTTTGAATCAGTTGTCACGCTC
CGGAACTCACACTTTCAGCCACTACATAATACTGCTTTGCTATCTTTTAG
GAAACTATGTGAGTCTACCTCACATAGACTCACATAGGTTTGTTTTTTT
TTTTTTTTAAAGGCTATCTTTTCCCCCATCAATGTTTTTTGAAGGATCCC
AAATTAGAGTCCCACAGAGGCAGACAGCAGTACTTGACAATATGGACATT
TAAGGTTAATGTTGGATTCTACTGTCTTTTTACTACATGACCTAGGGAAC
GATAATTAACCTAGACTGCTTCCAAGGGTTAAATAACCCATTTAGTTATA
CTATGTAAATTATCTCTTAGTGATTGATTGAAAGCACACTGTTACTAATT
GACTCGGTATGAAGTGCTTTTTTTCTTCCCTTTCAAGATACATACCTTT
CCAGTTAAAGTTGAGAGATCATCTCCACCAATTACTTTTATGTCCCTCT
TGACTGGTCATTCTAGTTAAAAAAAAAAAAAACTATATATATATATATCT
ACACACACATATGTATATGTATATCCTTATCTACACACACAAACTTCAAA
TTAAATGAGAACTAGAAGATTTGAGAAGTTAGCTAGCTAATATCCATAGC
ATTATGATATTCTAAATGATATGAATTATAAGAATTAGGTTTCCTGAAAT
GAATGACTAGAAAACTTTCAAGTAGAGATTAGTAAAAATTAAAAAGTCCT
AATCGGCCATTACTGATTTGATGTTTTTAAGAGTCCTAAAAAATGGGTTA
CATCCATTTTAAGTGGGTAGTATTATAACAGCCACCCATCTTCAATCAC
AGTGATTTCTGAATTGTGAGGGAAGTTATTAGCATGACAGGTGTCTGGTT
CTGGCCCTGTACGATTCCCATGAGTCAACCAAATTGTAAGGGCTGGTCTA
TATCACACCCAACCCCAAGGATATGTCCCTCAAAAGTCTAGCCCAGGCCC
CGTCATCTTCAGCATCATCTGGGAAACCAGGTCTGATTAGTAGTCCTTTA
AGGAATACCTCTTAGGCTCCCATTTTACTGCTATCACAGAATCCAATAAA
ACCCTTACAGGAGATTCAATGGGAAATGCTCAACACCCACTGTAGTTGGT
GGTGACAATGACCATAATTTGGCTGTGCTGGATTCAGGACACAAAATTTG
GGTGAAAGAGCAGGTGAACAAAAGAGCTTCGACTTGCCCTAGCAGAGAGC
AAGCCATACCATACCACAAAGCCACAGCAATTACAACGGTGCAGTACCAG
CACAGTAAATGAACAAAGTAGAGCCCAGAAACAGACCCAGAACTATATGA
GGATTTAGTATACAATAAAGATGGTATTTCGAGTCAGTAGGGAAAAGATG
AATTATTCAATAAATGATGTTTCCCCAACTAGTAACCCATTTGGGAAAAA
ATAAAAGTATGGTCCCTACCTCACAGCATACACAAAAATAAATTCCAGAC
GGATTAAAATCTAAATGTAAAAAATAAAGCCATAAGTGGACTGGAAGAAA
ATAGAGAATTTTTTTTAACATCCGTAGAAAGGGTAAAAACCCAGGCATGA
CATGAACCAAAACTGAAGAGGTTCTGTAACAAATACCCCCTTTTATATAT
TGGGCTCCAACAATAAGAACCCATAGGAAAATGGAGAATGAACACAAATA
GACAATTTATAGAAGAGAAGGTTATAAGGTGTAAAATTATATCTATCTGA
GAAACAAACACTAAAACAATGTGATTCTACTGTTCTCCCACCCATACTGG
CAAAACTTAAGCCTGATAATATGCTGAGGGGAAATAAGCACTCTTGTTGG
TGAGAGTATTAATTGGCATACCTTCTTTTGAAAATGACATAGCAATACCT
GTTAAAATTGCAAACATGCATGTCACTTAATCCAGTAATCCCACTTCTGG
GAATCAATGCTACAAAAACACTGACAAGTATACAAAGATACATTCAAGAG
TGTTCACTGGGCCCGGTGCGGTGGCTTCATGCCTGTAATCCCAGGGAGGC
AGAGGCAAGACGATCGCTTGACCCCAGGAGTTCAAGGCCAGCCCGAGAAA
CACAGCAAGACCCTGTCTCTCTTTTTTTTATTTAAAAAATAAATGTTCAC
```

-continued

```
TGTATCAGTTGTTCACAAAAACAAACCAACATGTCCATTAACAGGGAACC
ATTTAAATTAATCAAGTTCATCTACACAATGTAATACCATGCAACTATTA
AAAAGCACCTGATAATCCAAAGCACACTGAGACAGAATAATGCTATTAAA
AACACCAAGTAGTGGAACACTGTGTTGCCTATCACACCATTTTTATTCAA
CATTTAAAAAAATTTGTAACAGCAATTACATCAGTAGTGACAATGGCGTT
TATGAGACTTTTCACTTTTATGTGCTTCTATTTTTGTTATGCTTCTATAT
ATACATCCATTTATTATGGAGTGTTACTTTCAAAAATCACAAATGGGCCA
GTATTATTTGGTGTTGCAAGGTGAGCATATCACTTCTGATATCAACCTTT
GCATATTACTTCTCAATTTAGGGAAATTACAGACATCCCTTATTCTAACT
AACTTAAAACCCAGCATTTCAAACATACAGAATTGATGGGGAAAAAAAG
AAAGAAGAAAGAAAGAAAGGCAACAAGCTTCAGATGACAGTGACTCACA
TCAAATTATTTATAAAATCTGTTAAATAGTGCCATCTTCTGGAGATACCT
GCTATTACAGTCCAACTCCAGTTGATGTCTTTACAGAGACAAGAGGAATA
AAGGAAAAATATTCAAGAACTGAAAAGTATGGAGTCATGGAAAAATTGC
TGTGATCCAAAAGGCTACGGTGATAGGACAGAAACAAGAGAACTCCAAGC
AGTAAGACACTGCTGTTCTATTAGCATCCAAACCTCCATACTCCTGTTTG
CCCCAAGGCTTTTTTAAAAAATAGAGACAGGATCTCACTATTTTGCTCAG
GCTGGTCTTGAACTCCTGGACTCAAGCTATCCTCCTGCCTCGGCCTCCTA
AAGTGCCGAGATTACAGGCTTGAGTCACCATACCTGGCTATTTATTTTTT
CTTAACTCTCTTGCCTGGCCTATAGCCACCATGGAGCTAATAAAGAATAT
TAATTTAAGAGTAATGGTATAGTTCACTACATTGGAATACAGGTATAAGT
GCCTACATTGTACATGAATGGCATACATGGATCAATTACCCCACCTGGGT
GGCCAAAGGAACTGCGCGAACCTCCCTCCTTGGCTGTCTGGAAGAAGCTT
CCCACTAGATGCCTTTAGTGAGTGCCTCCCTCATCTTTAATTATGGTTAA
GTCTAGGATAACAGGACTGGCAAACGTGAGGGGAAAGCTTCCTCCAGAGT
TGCTCTACCCTCTCCTCTACCGTCCTATCTCCTCACTCCTCTCAGCCAAG
GAGTCCAATCTGTCCTGAACTCAGAGCGTCACTGTCAACTACATAAAATT
GCCAGAGAAGCTCTTTGGGACTACAAACACATACCCTTAATGTCTTTATT
TCTATTTTGTCTACCTCTTCAGTCTAGGTGAAAAAATAGGAAGGATAATA
GGGAAGAACTTTGTTTATGCCTACTTATCCGCCCCTAGGAATTTTGAAAA
CCTCTAGGTAGCAATAAGAACTGCAGCATGGTATAGAAAAAGAGGAGGAA
AGCTGTATAGAAATGCATAATAAATGGGCAGGAAAAGAACTGCTTGGAAC
AAACAGGGAGGTTGAACTATAAGGAGAGAAAGCAGAGAGGCTAATCAACA
AGGCTGGGTTCCCAAGAGGGCATGAAGAGACTATTACTAAGGTAGGAATT
ACTAAGGGCTCCATGTCCCCTTAGTGGCTTAGTACTATGTAGCTTGCTTT
CTGCAGTGAACTTCAGACCCTTCTTTTAGGATCCTAGAATGGACTTTTTT
TTTTTATCGGAAAACAGTCATTCTCTCAACATTCAAGCAGGCCCCAAGTC
TACCACACTCAATCACATTTTCTCTTCATATCATAATCTCTCAACCATTC
TCTGTCCTTTTAACTGTTTTTCTATACCCTGATCAAATGCCAACAAAAGT
GAGAATGTTAGAATCATGTATTTTTAGAGGTAGACTGTATCTCAGATAAA
```

-continued

```
AAAAAGGGCAGATATTCCATTTTCCAAAATATGTATGCAGAAAAAATAA
GTATGAAAGGACATATGCTCAGGTAACAAGTTAATTTGTTTACTTGTATT
TTATGAATTCCCTAAAACCTACGTCACCCGCCCCGTTCCCACGCCCCGCG
CCACGTCACAAACTCCACCCCCTCATTATCATATTGGCTTCAATCCAAAA
TAAGGTATATTATTGATGATGTTAATTAACATGCATGGATCCATATGCGG
TGTGAAATACCGCACAGATGCGTAAGGAGAAAATACCGCATCAGGCGCTC
TTCCGCTTCCTCGCTCACTGACTCGCTGCGCTCGGTCGTTCGGCTGCGGC
GAGCGGTATCAGCTCACTCAAAGGCGGTAATACGGTTATCCACAGAATCA
GGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCG
ACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACC
CGGTAAGACACGACTTATCGCCACTGGCAGCAGCCACTGGTAACAGGATT
AGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGA
AGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTG
ACGCTCAGTGGAACGAAAACTCACGTTAAGGGATTTTGGTCATGAGATTA
TCAAAAAGGATCTTCACCTAGATCCTTTTAAATTAAAAATGAAGTTTTAA
ATCAATCTAAAGTATATATGAGTAAACTTGGTCTGACAGTTACCAATGCT
TAATCAGTGAGGCACCTATCTCAGCGATCTGTCTATTTCGTTCATCCATA
GTTGCCTGACTCCCCGTCGTGTAGATAACTACGATACGGGAGGGCTTACC
ATCTGGCCCCAGTGCTGCAATGATACCGCGAGACCCACGCTCACCGGCTC
CAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCA
TTGCTGCAGCCATGAGATTATCAAAAGGATCTTCACCTAGATCCTTTTC
ACGTAGAAAGCCAGTCCGCAGAAACGGTGCTGACCCCGGATGAATGTCAG
CTACTGGGCTATCTGGACAAGGGAAAACGCAAGCGCAAAGAGAAAGCAGG
TAGCTTGCAGTGGGCTTACATGGCGATAGCTAGACTGGGCGGTTTTATGG
ACAGCAAGCGAACCGGAATTGCCAGCTGGGGCGCCCTCTGGTAAGGTTGG
GAAGCCCTGCAAAGTAAACTGGATGGCTTTCTTGCCGCCAAGGATCTGAT
GGCGCAGGGGATCAAGCTCTGATCAAGAGACAGGATGAGGATCGTTTCGC
ATGATTGAACAAGATGGATTCACGCAGGTTCTCCGGCCGCTTGGGTGGA
GAGGCTATTCGGCTATGACTGGGCACAACAGACAATCGGCTGCTCTGATG
```

-continued

```
CCGCCGTGTTCCGGCTGTCAGCGCAGGGGCGCCCGGTTCTTTTTGTCAAG

ACCGACCTGTCCGGTGCCCTGAATGAACTGCAAGACGAGGCAGCGCGGCT

ATCGTGGCTGGCCACGACGGGCGTTCCTTGCGCAGCTGTGCTCGACGTTG

TCACTGAAGCGGGAAGGGACTGGCTGCTATTGGGCGAAGTGCCGGGGCAG

GATCTCCTGTCATCTCACCTTGCTCCTGCCGAGAAAGTATCCATCATGGC

TGATGCAATGCGGCGGCTGCATACGCTTGATCCGGCTACCTGCCCATTCG

ACCACCAAGCGAAACATCGCATCGAGCGAGCACGTACTCGGATGGAAGCC

GGTCTTGTCGATCAGGATGATCTGGACGAAGAGCATCAGGGGCTCGCGCC

AGCCGAACTGTTCGCCAGGCTCAAGGCGAGCATGCCCGACGGCGAGGATC

TCGTCGTGACCCATGGCGATGCCTGCTTGCCGAATATCATGGTGGAAAAT

GGCCGCTTTTCTGGATTCATCGACTGTGGCCGGCTGGGTGTGGCGGACCG

CTATCAGGACATAGCGTTGGCTACCCGTGATATTGCTGAAGAGCTTGGCG

GCGAATGGGCTGACCGCTTCCTCGTGCTTTACGGTATCGCCGCTCCCGAT

TCGCAGCGCATCGCCTTCTATCGCCTTCTTGACGAGTTCTTCTGAATTTT

GTTAAAATTTTGTTAAATCAGCTCATTTTTTAACCAATAGGCCGAAATC

GGCAAAATCCCTTATAAATCAAAAGAATAGACCGAGATAGGGTTGAGTGT
```

```
TGTTCCAGTTTGGAACAAGAGTCCACTATTAAAGAACGTGGACTCCAACG

TCAAAGGGCGAAAAACCGTCTATCAGGGCGATGGCCCACTACGTGAACCA

TCACCCTAATCAAGTTTTTTGGGGTCGAGGTGCCGTAAAGCACTAAATCG

GAACCCTAAAGGGAGCCCCCGATTTAGAGCTTGACGGGGAAAGCCGGCGA

ACGTGGCGAGAAAGGAAGGGAAGAAAGCGAAAGGAGCGGGCGCTAGGGCG

CTGGCAAGTGTAGCGGTCACGCTGCGCGTAACCACCACACCCGCCGCGCT

TAATGCGCCGCTACAGGGCGCGTCCATTCGCCATTCAGGATCGAATTAAT

TCTTAATTAACATCATCAATAATATACCTTATTTTGGATTGAAGCCAATA

TGATAATGAGGGGGTGGAGTTTGTGACGTGGCGCGGGGCGTGGGAACGGG

GCGGGTGACGTAGTAGTGTGGCGGAAGTGTGATGTTGCAAGTGTGGCGGA

ACACATGTAAGCGACGGATGTGGCAAAAGTGACGTTTTTGGTGTGCGCCG

GTGTACACAGGAAGTGACAATTTTCGCGCGGTTTTAGGCGGATGTTGTAG

TAAATTTGGGCGTAACCGAGTAAGATTTGGCCATTTTCGCGGGAAAACTG

AATAAGAGGAAGTGAAATCTGAATAATTTTGTGTTACTCATAGCGCGTAA

TACTG
```

What is claimed is:

1. A method for treating a vascular disease in a mammal, said method comprising the steps of:
   infecting a segment of blood vessel in vitro using a gutless adenoviral vector comprising a polynucleotide encoding a functional thrombomodulin protein or its variant, wherein said polynucleotide encoding the thrombomodulin protein is under the control of a regulatory element; and
   grafting the virus-treated blood vessel in said mammal;
   wherein the thrombomodulin protein or its variant is expressed in an amount sufficient to reduce re-occlusion or intimal hyperplasia in the grafted blood vessel, and wherein said gutless adenoviral vector comprises the nucleotide sequence of SEQ ID NO: 13 or SEQ ID NO: 15.

2. The method of claim 1, wherein said gutless adenoviral vector comprises the nucleotide sequence of SEQ ID NO: 13 and SEQ ID NO: 15.

3. The method of claim 1, wherein said gutless adenoviral vector is produced by transfecting 293FLP cells with a linearized plasmid having the nucleotide sequence of SEQ ID NO: 16 followed with infection of a helper virus.

4. The method of claim 1, wherein said thrombomodulin protein has the amino acid sequence of SEQ ID NO: 2.

5. The method of claim 1, wherein said regulatory element is a promoter.

6. The method of claim 5, wherein said regulatory element is a CMV promoter or a RSV promoter.

7. The method of claim 1, wherein said infecting step further comprises:
   filling the blood vessel with a complete viral delivery system comprising of 1:1 mixture of Ham's F12 medium and DMEM, an effective amount of the gutless adenovirus vector, and an acellular oxygen carrier; and
   incubating the blood vessel with the complete viral delivery system for a desired period of time.

8. The method of claim 7, wherein said acellular oxygen carrier is selected from the group consisting of unmodified hemoglobin, chemically modified hemoglobin and perfluorochemical emulsions.

9. The method of claim 8, wherein said unmodified hemoglobin or chemically modified hemoglobin is used in the range of 3 g/dl to 10 g/dl.

10. The method of claim 9, wherein the complete viral delivery system further comprises at least one of L-glutamine, sodium bicarbonate, or antibiotic-antimycotic.

11. The method of claim 10, wherein the desired period of time is between 10 to 45 minutes.

* * * * *

SEQUENCE LISTING

<160> NUMBER OF SEQ ID NOS: 16

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 1

```
catcatcaat aatataacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactggtacc gcggccgcct     360
cgagtctaga actagtggat ccccgggct gcaggaattc tgatggctct caaaattcct      420
gcctccttta gggataaaag actttaagac tttttaacaa aaaagaaaaa gaaaaaaaaa     480
attcctgcct cctggtgtac acacacagaa gggttccctc cccttgaatg tgaccaggat     540
ctgtgaaaat aacgggatag ccgctcctgt gattaggtta tgtggtagac tagagcaaga     600
ttctcctgct ggttttgaag aagtcagctg ccatgttgtg agactgtcat gggctagggc     660
atgagccttt aaatatctgg gagcaaccc tggccagcag ccagtgagaa acgggccct      720 cagtcctaca atcacaagga actaaattct gccaacaacc tgaaggaact ttgaagagga     780
tcatgagtcc cttgattcag cttgatgagc ccctgagcag aggatacagc taacttgtac     840
```

-continued

```
tagggaagta taaaaaacat gcatgggaat gatatatatc aactttaagg ataattgtca      900
tacttctggg aatgaaggga agaaatgggg ctttagttg tattatgatc tttaatttct       960
caaaaaaaat aagatcagaa gcaaatatgg caaaatgtta atacttttgt gggtacgtag     1020
gtattcagca tacccttttt tctgagttca aaatatttta taattaaaat gaaatgcagg     1080
ccaggcacag tggctcatgc ctataatacc agcactttgc gaggccgagg tgggaggatg     1140
gcttgaggcc agaccagcct ggccaacatg gcaaacccc atctctactt aaaaaaaaaa      1200
aaactatata tatatatatg tgtgtgtgtg tgtatatata tatatgtata tatatttata    1260
tatgtgtgta tatatatata tgtatatata tttatatatg tgtgtgtata tatatatata    1320
cacacacaca catatataca tacatacata cacacacaca cacacacaat tagccaggca    1380
tggtggcgca cacctgtagt cccagctact tgggaggctg agacatgaga attgcttgaa    1440
cctgggaggc agagtagtta gtgagctgag atcataccac tgcactccag cctggtgaca    1500
gagtgagact ctgtcttaaa aaaataaaa attaaaatta aatgcaaaag gtccaagtga     1560
attgaagagg aaaggggtat caaggaaggt tttgtggagg tgacgtttga gctgggtctt    1620
aaatgactta aacatgggat aagaagggag ggaataagga catttcaggt acgagaaata    1680
aggagcaaac agtggaaaca acctaacgtc tgtcaaccag tgaatggata acaaaaatgt    1740
aattcagatg gtatccaact tacgatggtt caacatgaga tttttctgac tttaggatag    1800
atttatcaaa gtagtaaatc cattttcaac ttatgatatt ttcaacttca gatgggttta    1860
tcaggacaca gttgaggaac acctgtctat ccatacaatt tggcaataaa aggaaatga     1920
gtgcagatat actccacaac atgaatgaac cttgaaaaca ttaagtgaga gaagccagat    1980
acaaaaggcc acatattgta tgattctatt tatacaaaat gtccagaata ggcaaatctt    2040
atagacagca agtaggtaga tgatcagttt gctaggtgct gggggaaggg gaaatgggga   2100
gtgatggcta aggggattgg gtttctttgt ggggcaatga aaatgtttta aaattgagcg    2160
tgataatgat tgcacaatgc tgcatatata tataatctat agattatata tatataaaga   2220
gaggctgtta gacagtgata agtgatatat atatatatat acatagagag agagagagag    2280
agagagagag gctgttagtg ataagtgatc aggaaaataa aagtattgag gaggaatacg    2340
aagttgacgg tgtgaaaaca tgagatttta tataggatgg ccagggaagg ccttaatgag    2400
aaagtgactt atgagtaaaa acaagggatc ctaaaccttta gcatgcatca gaatcactcg    2460
gaaacttgtt aaagcatagc ttgctgggcc tcatcacaga tattttgatt cggtaggttc    2520
ttgtctgata ttaatacttt tggtctaggg aaccacattt tgagaaccac tgagctaaag    2580
gaagtaaagg tttcccttag tttactagct ggtaacccta ggaaactgct tagcctctcg    2640
gtgctaagat acaaaatact ttagcacata ataacacatg gaaatagtc tataaattat     2700
aaatattatt ttttatgtac caaatattac ataagacaaa atctaagcaa gatatatata    2760
tatatacata aaatataaga tatatatgta tatattatat atagataaat agagagagag    2820
agttatgttt agaaagaaaa tacttcaaac taaaaaaaga gaggtaggaa gtataccatt    2880
ccattattgg taaaaacaaa ttactaagta gtctttacaa aaaaccaatc tcactccttt    2940
agaacacaag cccaccatta aaactgatgc agaggaattt ctctccctgg cttacccttta   3000
ggatggtgca tactaagtta gaaaagtcat aaatgttata ttaaaagtaa atgtgaactt     3060
acttccacaa tcaagacatt ctagaagaaa aagagaaatg aaaatcagta caatgaataa    3120
aacggtattt ccaattataa gtcaaatcac atcataacaa ccctaaggaa ttatccaaac    3180
tcttgttttt agatgcttta ttatatcaaa ctctcccttta aacaagtggc ccatctgctg    3240
```

```
ggatttggaa gcctgtaata ctgaaatttt catcataatg gaaattttaa aaacagaatt    3300
tgacccacct gttttaaaa cactttcatt acttaacaag aggtctaatc ttgggcaagt    3360
cttgaaattt ctctggcctt agtttcccat gtgttaaatg aaacttgaag cagttggtct    3420
cttatagtct cctgactcta acattctaag aattatattt gtacaataac tcaaaaatca    3480
cataatttaa tttaccatat ggactccaaa atatatttc tcattaggct aaacttgatc    3540
tgcattttct ggatgtgtcc atattcttgg actacactaa acatgatac caatgcttcc    3600 tctcaccata aaccctcact tcgctttcta catttaagaa ttttatagct ggaagagtcc    3660
ttaacagaaa ataccatcta ataattaccc ctcaaaatcg agaaagtcct atctgttctt    3720
atgctagtta taagaatgag gcagcatttc acataatggt tataaacact gccacaagaa    3780
gattcatgat gtgttgttta tctgtagctc tcatcatact ctgtcatata actatagcat    3840
taagatttta atgttctata tattcttcta agacagtgtt taccagagta aggcacaaaa    3900
gatccactgg tttgcaagaa agattagaac ttttaaattt tttacctcac cttgtttaat    3960
ctatattttt gtatgtattt tgtaacatat atattattat taccataaat catatataat    4020
ttaaaatgca tatattaggg gtaaatgctc aggaaacttt ttataaattg ggcatgcaaa    4080
tacaagtttg aagactcact gttctaggta ttaaaagtaa agttataacc aagtaaagct    4140
tccacctttt catgtctcaa agcagtttat tgttggaggt aagatctctt agaagcctaa    4200
acaggtccaa gtacagaatg aagtaaggct agcccataac ttgtggcaag caattcatac    4260
tatttctctc atgctgagct ctcctcagtg aagcagctac tatagacaac tgcagcctat    4320
tggtagccta ttttacaggc aggaaaaaaa ttacttttta ttcaaagtgg aactcaggac    4380
atggggagaa aatgaataca aaaaataggg tcaatccaaa ggcacacagc aaatgagtaa    4440
cacagttatg ttttttttccc atttgtatga ggtcccagta aattctaagt aaactgcaaa    4500
tttaataata cactaaaaaa gccatgcaat tgttcaaatg aatcccagca tggtacaagg    4560
agtacagaca ctagagtcta aaaaacaaaa gaatgccatt attgagtttt tgaattatat    4620
caagtagtta catctctact taataaatga gaaaacgag gataagaggc catttgataa    4680
aatgaaaata gccaagaagt ggtattagag acttgaatac aggtattcgg gtccaaagtt    4740
catctgctca aatactaact ggggaaaaga gggaaaaata tttatataca tatatatctg    4800
cacacaaaaa tacccccaaa agacaaaatg aggccaggca gggtggctca cacccgtaat    4860
cccggtactt tgggaggctg aggcaggtgg atacctgaga tcaggagttg gagatcagcc    4920
tggtcaacat ggtgaaaccc tgtctctact aaagataaaa aaattagcca ggcatggtgg    4980
cgtgcgcctg taatcccagc tacttgggag tctgaggcag gagaatcact tgaactggga    5040
aggggaggtt gcagtgagcc aagatcgtac tactgcactc cagcctgggc agcagagtga    5100
gactccatca caaaaataaa taaataaata aaatacaatg aaacagaaag ttcaaataat    5160
cccataatct taccaccaag aaataacttt cactcgttat acttattgat ttttccataa    5220
taaatgtact ttactgtgac tatcatgaaa agaaagttat tttagaaaca gagaactgtt    5280
tcagatcaaa tctatgtagt agaacagagc cattaggtgg gaaagacgag atcaaactaa    5340
atctcagaag gcctaaaagg ctaggtccat tccagcacta aaaactgacc agacaagtaa    5400
tggcttcaac agcttctaaa tatggacaaa gcatgctgaa agggaaggac aggtctaaca    5460
gtggtatatg aaatgaacag gaggggcaaa gctcatttct cctctgaagt tttccaaaga    5520
tgctgaggag gacattagtt tgacatgacc ctgatatggg acaagataat ttcacagaag    5580
```

```
ttttacatgt taaagttttc ttatagatac tcattcaagt aagcaatgaa cactaaaatc   5640
taaagaaaga aaagagcttt agagtcaggt ctgtattcaa attcaagctc taccacttac   5700
tggttctgtg actttgggca agtcttttaa ccttattaag tcttaatttc ctgatttgta   5760
aaatggggat atcgtctccc tcacaggatt gttgtgaaac ttttatgaga ttaatgcctt   5820
tatatttggc atagtgtaag taaacaataa ctggcagctt caaaaaaaaa aagcagtagc   5880
attccatcat ttattattgg ttactctcaa aaagttttc aatgtactag aagataaata   5940
ttcaaatacc ttaatatctc cattattttc aggtaaacag catgctcctg aacaaccaat   6000
gggtcaacaa ataaattaaa agggaaatct aaaaacatct tgatattaaa ctacatggaa   6060
gcacaatata ccaaaaccaa tggttcacac taggagaatt ttaaggtaca agaaaactct   6120
ttgagatttc ttaaaataat agtatgtctg aatttattga gtgatttacc agaaactgtt   6180
gtaagagctc tacttgcatt atagcactta atcctcttaa ctctatggct gctattatca   6240
acctcaccct aatcacatat gggacacaga gaggttaagt aacttgccca aggtcagagt   6300
taggaagtac taagccatgc tttgaatcag ttgtcaggct ccggaactca cactttcagc   6360
cactacataa tactgctttg ctatctttta ggaaactatg tgagtctacc tcacatagac   6420
tcacataggt ttgtttttt ttttttttta aaggctatct tttcccccat caatgttttt   6480
tgaaggatcc caaattagag tcccacagag gcagacagca gtacttgaca atatggacat   6540
ttaaggttaa tgttggattc tactgtcttt ttactacatg acctagggaa cgataattaa   6600
cctagactgc ttccaagggt taaataaccc atttagttat actatgtaaa ttatctctta   6660
gtgattgatt gaaagcacac tgttactaat tgactcggta tgaagtgctt tttttcttc   6720 cctttcaaga tacataccttt ccagttaaa gttgagagat catctccacc aattacttt   6780 atgtcccctg ttgactggtc attctagtta aaaaaaaaaa aaactatata tatatatatc   6840
tacacacaca tatgtatatg tatatcctta tgtacacaca caaacttcaa attaaatgag   6900
aactagaaga tttgagaagt tagctagcta atatccatag cattatgata ttctaaatga   6960
tatgaattat aagaattagg tttcctgaaa tgaatgacta gaaaactttc aagtagagat   7020
tagtaaaaat taaaaagtcc taatcggcca ttactgattt gatgtttta agagtcctaa   7080 aaaatgggtt acatccattt ttaagtgggt agtattataa cagccaccca tcttcaatca   7140
cagtgatttc tgaattgtga gggaagttat tagcatgaca ggtgtctggt tctggccctg   7200
tacgattccc atgagtcaag caaattgtaa gggctggtct atatcacacc caaccccaag   7260
gatatgtccc tcaaaagtct agcccaggcc ccgtcatctt cagcatcatc tgggaaacca   7320
ggtctgatta gtagtccttt aaggaatacc tcttaggctc ccatttact gctatcacag   7380 aatccaataa aacccttaca ggagattcaa tgggaaatgc tcaacaccca ctgtagttgg   7440
tggtgacaat gaccataatt tggctgtgct ggattcagga cagaaatttt gggtgaaaga   7500
gcaggtgaac aaaagagctt cgacttgccc tagcagagag caagccatac cataccacaa   7560
agccacagca attacaacgg tgcagtacca gcacagtaaa tgaacaaagt agagcccaga   7620
aacagaccca gaactatatg aggattagt atacaataaa gatggtattt cgagtcagta   7680
gggaaaagat gaattattca ataaatgatg tttggccaac tagtaaccca tttgggaaaa   7740
aataaaagta tggtccctac ctcacagcat acacaaaaat aaattccaga cggattaaaa   7800
tctaaatgta aaaataaag ccataagtgg actggaagaa atagagaat ttttttttaac   7860 atccgtagaa agggtaaaaa cccaggcatg acatgaacca aaactgaaga ggttctgtaa   7920 caaataccccc cttttatata ttgggctcca acaataagaa cccataggaa aatggagaat   7980
```

```
gaacacaaat agacaattta tagaagagaa ggttataagg tgtaaaatta tatctatctg    8040
agaaacaaac actaaaacaa tgtgattcta ctgttctccc acccatactg gcaaaactta    8100
agcctgataa tatgctgagg ggaaataagc actcttgttg gtgagagtat taattggcat    8160
agcttctttt gaaaatgaca tagcaatacc tgttaaaatt gcaaacatgc atgtcactta    8220
atccagtaat cccacttctg ggaatcaatg ctacaaaaac actgacaagt atacaaagat    8280
acattcaaga gtgttcactg ggccgggtgc ggtggcttca tgcctgtaat cccagggagg    8340
cagaggcaag acgatcgctt gaccccagga gttcaaggcc agcccgagaa acacagcaag    8400
accctgtctc tctttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaacaccaag tagtggaaca ctgtgttgcc tatgcacacca ttttttattca   8640 acatttaaac aaatttgtaa cagcaattac atgagtagtg acaatggcgt ttatgagact    8700
tttcactttt atgtgcttct atttttgtta tgcttctata tatacatcca tttattatgg    8760
agtgttactt tcaaaaatca caaatgggcc agtattattt ggtgttgcaa ggtgagcata    8820
tgacttctga tatcaacctt tgcatattac ttctcaattt agggaaatta cagacatccc    8880
ttattctaac taacttaaaa cccagcattt caaacataca gaattgatgg ggaaaaaaaa    8940
gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
agttgatgtc tttacagaga caagaggaat aaaggaaaaa atattcaaga actgaaaagt    9120
atggagtcat ggaaaaattg ctgtgatcca aaggctacgg tgataggaca agaaacaaga    9180
gaactccaag cagtaagaca ctgctgttct attagcatcc aaacctccat actcctgttt    9240
gccccaaggc ttttttaaaa aatagagaca ggatctcact attttgctca ggctggtctt    9300
gaactcctgg actcaagcta tcctcctgcc tcggcctcct aaagtgccga gattacaggc    9360
ttgagtcacc atacctggct atttattttt tcttaactct cttgcctggc ctatagccac    9420
catggaagct aataaagaat attaatttaa gagtaatggt atagttcact acattggaat    9480
acaggtataa gtgcctacat tgtacatgaa tggcatacat ggatcaatta ccccaccctgg   9540 gtggccaaag gaactgcgcg aacctccctc cttggctgtc tggaacaagc ttcccactag    9600 atcccttttac tgagtgcctc cctcatcttt aattatggtt aagtctagga taacaggact    9660
ggcaaaggtg aggggaaagc ttcctccaga gttgctctac cctctcctct accgtcctat    9720
ctcctcactc ctctcagcca aggagtccaa tctgtcctga actcagagcg tcactgtcaa    9780
ctacataaaa ttgccagaga agctctttgg gactacaaac atacccctt aatgtcttta     9840 tttctatttt gtctacctct tcagtctagg tgaaaaaata ggaaggataa tagggaagaa    9900
ctttgtttat gcctacttat ccgcccctag gaattttgaa aacctctagg tagcaataag    9960
aactgcagca tggtatagaa aaagaggagg aaagctgtat agaaatgcat aataaatggg   10020
caggaaaaga actgcttgga acaaacaggg aggttgaact ataaggagag aaagcagaga   10080
ggctaatcaa caaggctggg ttcccaagag ggcatgatga gactattact aaggtaggaa   10140
ttactaaggg ctccatgtcc ccttagtggc ttagtactat gtagcttgct ttctgcagtg   10200
aacttcagac ccttctttta ggatcctaga atggactttt ttttttttatc ggaaaacagt   10260 cattctctca acattcaagc aggccccaag tctaccacac tcaatcacat tttctcttca   10320
```

```
tatcataatc tctcaaccat tctctgtcct tttaactgtt tttctatacc ctgatcaaat    10380
gccaacaaaa gtgagaatgt tagaatcatg tatttttaga ggtagactgt atctcagata    10440
aaaaaaaagg gcagatattc cattttccaa aatatgtatg cagaaaaaat aagtatgaaa    10500
ggacatatgc tcaggtaaca agttaatttg tttacttgta ttttatgaat tccctaaaac    10560
ctacgtcacc cgccccgttc ccacgccccg cgccacgtca caaactccac ccctcatta    10620 tcatattggc ttcaatccaa aataaggtat attattgatg atgttaatta acatgcatgg    10680
atccatatgc ggtgtgaaat accgcacaga tgcgtaagga gaaataccg catcaggcgc    10740 tcttccgctt cctcgctcac tgactcgctg cgctcggtcg ttcggctgcg gcgagcggta    10800
tcagctcact caaaggcggt aatacggtta tccacagaat cagggataa cgcaggaaag    10860 aacatgtgag caaaaggcca gcaaaaggcc aggaaccgta aaaaggccgc gttgctggcg    10920 ttttccata ggctccgccc ccctgacgag catcacaaaa atcgacgctc aagtcagagg    10980
tggcgaaacc cgacaggact ataaagatac caggcgtttc cccctggaag ctccctcgtg    11040
cgctctcctg ttccgaccct gccgcttacc ggatacctgt ccgcctttct cccttcggga    11100
agcgtggcgc tttctcatag ctcacgctgt aggtatctca gttcggtgta ggtcgttcgc    11160
tccaagctgg gctgtgtgca cgaacccccc gttcagcccg accgctgcgc cttatccggt    11220
aactatcgtc ttgagtccaa cccggtaaga cacgacttat cgccactggc agcagccact    11280
ggtaacagga ttagcagagc gaggtatgta ggcggtgcta cagagttctt gaagtggtgg    11340
cctaactacg gctacactag aaggacagta tttggtatct gcgctctgct gaagccagtt    11400
accttcggaa aaagagttgg tagctcttga tccggcaaac aaaccaccgc tggtagcggt    11460
ggtttttttg tttgcaagca gcagattacg cgcagaaaaa aaggatctca agaagatcct    11520
ttgatctttt ctacggggtc tgacgctcag tggaacgaaa actcacgtta agggattttg    11580
gtcatgagat tatcaaaaag gatcttcacc tagatccttt taaattaaaa atgaagtttt    11640
aaatcaatct aaagtatata tgagtaaact tggtctgaca gttaccaatg cttaatcagt    11700
gaggcaccta tctcagcgat ctgtctattt cgttcatcca tagttgcctg actccccgtc    11760
gtgtagataa ctacgatacg ggagggctta ccatctggcc ccagtgctgc aatgataccg    11820
cgagacccac gctcaccggc tccagattta tcagcaataa accagccagc cggaagggcc    11880
gagcgcagaa gtggtcctgc aactttatcc gcctccatcc agtctattaa ttgttgccgg    11940
gaagctagag taagtagttc gccagttaat agtttgcgca acgttgttgc cattgctgca    12000
gccatgagat tatcaaaaag gatcttcacc tagatccttt tcacgtagaa agccagtccg    12060
cagaaacggt gctgacccccg gatgaatgtc agctactggg ctatctggac aagggaaaac    12120
gcaagcgcaa agagaaagca ggtagcttgc agtgggctta catggcgata gctagactgg    12180
gcggttttat ggacagcaag cgaaccggaa ttgccagctg ggcgccctc tggtaaggtt    12240 gggaagccct gcaaagtaaa ctggatggct ttcttgccgc caaggatctg atggcgcagg    12300
ggatcaagct ctgatcaaga cacaggatga ggatcgtttc gcatgattga acaagatgga    12360
ttgcacgcag gttctccggc cgcttgggtg gagaggctat tcggctatga ctgggcacaa    12420
cagacaatcg gctgctctga tgccgccgtg ttccggctgt cagcgcaggg gcgcccggtt    12480 cttttttgtca agaccgacct gtccggtgcc ctgaatgaac tgcaagacga ggcagcgcgg    12540
ctatcgtggc tggccacgac gggcgttcct tgcgcagctg tgctcgacgt tgtcactgaa    12600
gcgggaaggg actggctgct attgggcgaa gtgccggggc aggatctcct gtcatctcac    12660
cttgctcctg ccgagaaagt atccatcatg gctgatgcaa tgcggcggct gcatacgctt    12720
```

```
gatccggcta cctgcccatt cgaccaccaa gcgaaacatc gcatcgagcg agcacgtact   12780
cggatggaag ccggtcttgt cgatcaggat gatctggacg aagagcatca ggggctcgcg   12840
ccagccgaac tgttcgccag gctcaaggcg agcatgcccg acggcgagga tctcgtcgtg   12900
acccatggcg atgcctgctt gccgaatatc atggtggaaa atggccgctt ttctggattc   12960
atcgactgtg gccggctggg tgtggcggac cgctatcagg acatagcgtt ggctacccgt   13020
gatattgctg aagagcttgg cggcgaatgg gctgaccgct tcctcgtgct ttacggtatc   13080
gccgctcccg attcgcagcg catcgccttc tatcgccttc ttgacgagtt cttctgaatt   13140
ttgttaaaat ttttgttaaa tcagctcatt ttttaaccaa taggccgaaa tcggcaaaat   13200
cccttataaa tcaaaagaat agaccgagat agggttgagt gttgttccag tttggaacaa   13260
gagtccacta ttaaagaacg tggactccaa cgtcaagggc gaaaaaccgt ctatcaggg    13320 cgatggccca ctacgtgaac catcaccccta atcaagtttt ttggggtcga ggtgccgtaa   13380
agcactaaat cggaacccta aagggagccc ccgatttaga gcttgacggg gaaagccggc   13440
gaacgtggcg agaaaggaag ggaagaaagc gaaaggagcg ggcgctaggg cgctggcaag   13500
tgtagcggtc acgctgcgcg taaccaccac acccgccgcg cttaatgcgc cgctacaggg   13560
cgcgtccatt cgccattcag gatcgaatta attcttaatt aa                      13602
```

<210> SEQ ID NO 2
<211> LENGTH: 575
<212> TYPE: PRT
<213> ORGANISM: Homo sapiens

<400> SEQUENCE: 2

```
Met Leu Gly Val Leu Val Leu Gly Ala Leu Ala Leu Ala Gly Leu Gly
  1               5                  10                  15

Phe Pro Ala Pro Ala Glu Pro Gln Pro Gly Gly Ser Gln Cys Val Glu
             20                  25                  30

His Asp Cys Phe Ala Leu Tyr Pro Gly Pro Ala Thr Phe Leu Asn Ala
         35                  40                  45

Ser Gln Ile Cys Asp Gly Leu Arg Gly His Leu Met Thr Val Arg Ser
     50                  55                  60

Ser Val Ala Ala Asp Val Ile Ser Leu Leu Leu Asn Gly Asp Gly Gly
 65                  70                  75                  80

Val Gly Arg Arg Arg Leu Trp Ile Gly Leu Gln Leu Pro Pro Gly Cys
                 85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
```

```
            210                 215                 220
Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
        450                 455                 460

Ile Cys Gly Pro Asp Ser Ala Leu Ala Arg His Ile Gly Thr Asp Cys
465                 470                 475                 480

Asp Ser Gly Lys Val Asp Gly Asp Ser Gly Ser Gly Glu Pro Pro
                485                 490                 495

Pro Ser Pro Thr Pro Gly Ser Thr Leu Thr Pro Pro Ala Val Gly Leu
            500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575

<210> SEQ ID NO 3
<211> LENGTH: 1725
<212> TYPE: DNA
<213> ORGANISM: Homo sapiens

<400> SEQUENCE: 3
atgcttgggg tcctggtcct tggcgcgctg gccctggccg gctgggggtt ccccgcaccc        60
gcagagccgc agccgggtgg cagccagtgc gtcgagcacg actgcttcgc gctctacccg       120
```

| | |
|---|---|
| ggccccgcga ccttcctcaa tgccagtcag atctgcgacg gactgcgggg ccacctaatg | 180 |
| acagtgcgct cctcggtggc tgccgatgtc atttccttgc tactgaacgg cgacggcggc | 240 |
| gttggccgcc ggcgcctctg gatcggcctg cagctgccac ccggctgcgg cgaccccaag | 300 |
| cgcctcgggc ccctgcgcgg cttccagtgg gttacgggag acaacaacac cagctatagc | 360 |
| aggtgggcac ggctcgacct caatgggggct ccctctgcg gcccgttgtg cgtcgctgtc | 420 |
| tccgctgctg aggccactgt gcccagcgag ccgatctggg aggagcagca gtgcgaagtg | 480 |
| aaggccgatg gcttcctctg cgagttccac ttcccagcca cctgcaggcc actggctgtg | 540 |
| gagcccggcg ccgcggctgc cgccgtctcg atcacctacg gcacccccgtt cgcggcccgc | 600 |
| ggagcggact ccaggcgct gccggtgggc agctccgccg cggtggctcc cctcggctta | 660 |
| cagctaatgt gcaccgcgcc gcccggagcg gtccagggc actgggccag ggaggcgccg | 720 |
| ggcgcttggg actgcagcgt ggagaacggc ggctgcgagc acgcgtgcaa tgcgatccct | 780 |
| ggggctcccc gctgccagtg cccagccggc gccgccctgc aggcagacgg gcgctcctgc | 840 |
| accgcatccg cgacgcagtc ctgcaacgac ctctgcgagc acttctgcgt tcccaacccc | 900 |
| gaccagccgg gctcctactc gtgcatgtgc gagaccggct accggctggc ggccgaccaa | 960 |
| caccggtgcg aggacgtgga tgactgcata ctggagccca gtccgtgtcc gcagcgctgt | 1020 |
| gtcaacacac agggtggctt cgagtgccac tgctacccta actacgacct ggtggacggc | 1080 |
| gagtgtgtgg agcccgtgga cccgtgcttc agagccaact gcgagtacca gtgccagccc | 1140 |
| ctgaaccaaa ctagctacct ctgcgtctgc gccgagggct tcgcgcccat tccccacgag | 1200 |
| ccgcacaggt gccagatgtt ttgcaaccag actgcctgtc cagccgactg cgaccccaac | 1260 |
| acccaggcta gctgtgagtg ccctgaaggc tacatcctgg acgacggttt catctgcacg | 1320 |
| gacatcgacg agtgcgaaaa cggcggcttc tgctccgggg tgtgccacaa cctccccggt | 1380 |
| accttcgagt gcatctgcgg gccccgactcg gcccttgccc gccacattgg caccgactgt | 1440 |
| gactccggca aggtggacgg tggcgacagc ggctctggcg agcccccgcc cagcccgacg | 1500 |
| cccggctcca ccttgactcc tccggccgtg gggctcgtgc attcgggctt gctcataggc | 1560 |
| atctccatcg cgagcctgtg cctggtggtg gcgcttttgg cgctcctctg ccacctgcgc | 1620 |
| aagaagcagg gcgccgccag ggccaagatg gagtacaagt gcgcggcccc ttccaaggag | 1680 |
| gtagtgctgc agcacgtgcg gaccgagcgg acgccgcaga gactc | 1725 |

<210> SEQ ID NO 4
<211> LENGTH: 649
<212> TYPE: DNA
<213> ORGANISM: Homo sapiens
<220> FEATURE:
<221> NAME/KEY: modified_base
<222> LOCATION: (335)
<223> OTHER INFORMATION: a, c, g, t, unknown or other

<400> SEQUENCE: 4

| | |
|---|---|
| tctagacgcg ttgacattga ttattgacta gttattaata gtaatcaatt acgggggtcat | 60 |
| tagttcatag cccatgatat catatggagt tccgcgttac ataacttacg gtaaatggcc | 120 |
| cgcctggctg accgcccaac gacccccgcc cattgacgtc aataatgacg tatgttccca | 180 |
| tagtaacgcc aatagggact ttccattgac gtcaatgggt ggagtattta cggtaaactg | 240 |
| cccacttggc agtacatcaa gtgtatcata tgccaagtac gccccctat tgacgtcaat | 300 |
| gacggtaaat ggcccgcctg gcattatgcc cagtncatga cctttatggga cttttcctact | 360 |

-continued

| | |
|---|---|
| tggcagacat ctacgtatta gtcatcgcta ttaccatggt gatgcggttt tggcagtaca | 420 |
| tcaatgggcg tggatagcgg tttgactcac ggggattttc caagtctcca ccccattgac | 480 |
| gtcaatggga gtttgttttg gcaccaaaat caacgggact ttccaaaatg tcgtaacaac | 540 |
| tccgccccat tgacgcaaat gggcggtagg cgtgtacggt gggaggtcta tataagcaga | 600 |
| gctctctggc taactagaga acccctgctt actggcttat cgagatatc | 649 |

<210> SEQ ID NO 5
<211> LENGTH: 3693
<212> TYPE: DNA
<213> ORGANISM: Homo sapiens

<400> SEQUENCE: 5

| | |
|---|---|
| ggcagcgcgc agcggcaaga agtgtctggg ctgggacgga caggagaggc tgtcgccatc | 60 |
| ggcgtcctgt gcccctctgc tccggcacgg ccctgtcgca gtgcccgcgc tttccccggc | 120 |
| gcctgcacgc ggcgcgcctg ggtaacatgc ttggggtcct ggtccttggc gcgctggccc | 180 |
| tggccggcct ggggttcccc gcacccgcag agccgcagcc gggtggcagc cagtgcgtcg | 240 |
| agcacgactg cttcgcgctc tacccggggcc ccgcgacctt cctcaatgcc agtcagatct | 300 |
| gcgacggact gcggggccac ctaatgacag tgcgctcctc ggtggctgcc gatgtcattt | 360 |
| ccttgctact gaacgcgac ggcggcgttg gccgccggcg cctctggatc ggcctgcagc | 420 |
| tgccacccgg ctgcggcgac cccaagcgcc tcgggcccct gcgcggcttc cagtgggtta | 480 |
| cgggagacaa caacaccagc tatagcaggt gggcacggct cgacctcaat ggggctcccc | 540 |
| tctgcggccc gttgtgcgtc gctgtctccg ctgctgaggc cactgtgccc agcgagccga | 600 |
| tctgggagga gcagcagtgc gaagtgaagg ccgatggctt cctctgcgag ttccacttcc | 660 |
| cagccacctg caggccactg gctgtggagc ccggcgccgc ggctgccgcc gtctcgatca | 720 |
| cctacgcac cccgttcgcg gcccgcgag cggacttcca ggcgctgccg gtgggcagct | 780 |
| ccgccgcgt ggctccccctc ggcttacagc taatgtgcac cgcgccgccc ggagcggtcc | 840 |
| aggggcactg ggccagggag gcgccgggcg cttgggactg cagcgtggag aacggcggct | 900 |
| gcgagcacgc gtgcaatgcg atccctgggg ctccccgctg ccagtgccca gccggcgccg | 960 |
| ccctgcagg agacgggcgc tcctgcaccg catccgcgac gcagtcctgc aacgacctct | 1020 |
| gcgagcactt ctgcgttccc aaccccgacc agccgggctc ctactcgtgc atgtgcgaga | 1080 |
| ccggctaccg gctggcggcc gaccaacacc ggtgcgagga cgtggatgac tgcatactgg | 1140 |
| agcccagtcc gtgtccgcag cgctgtgtca acacacaggg tggcttcgag tgccactgct | 1200 |
| accctaacta cgacctggtg gacggcgagt gtgtggagcc cgtggaccg tgcttcagag | 1260 |
| ccaactgcga gtaccagtgc cagcccctga accaaactag ctacctctgc gtctgcgccg | 1320 |
| agggcttcgc gcccattccc cacgagccgc acaggtgcca gatgttttgc aaccagactg | 1380 |
| cctgtccagc cgactgcgac cccaacaccc aggctagctg tgagtgccct gaaggctaca | 1440 |
| tcctggacga cggtttcatc tgcacggaca tcgacgagtg cgaaaacggc ggcttctgct | 1500 |
| ccgggggtgtg ccacaacctc cccggtacct tcgagtgcat ctgcgggccc gactcggccc | 1560 |
| ttgcccgcca cattggcacc gactgtgact ccggcaaggt ggacggtggc acagcggct | 1620 |
| ctggcgagcc cccgcccagc ccgacgcccg gctccacctt gactcctccg gccgtggggc | 1680 |
| tcgtgcattc gggcttgctc ataggcatct ccatcgcgag cctgtgcctg gtggtggcgc | 1740 |
| ttttggcgct cctctgccac ctgcgcaaga agcagggcgc cgccagggcc aagatggagt | 1800 |
| acaagtgcgc ggccccttcc aaggaggtag tgctgcagca cgtgcggacc gagcggacgc | 1860 |

```
cgcagagact ctgagcggcc tccgtccagg agcctggctc cgtccaggag cctgtgcctc    1920
ctcaccccca gctttgctac caaagcacct tagctggcat tacagctgga gaagaccctc    1980
cccgcacccc ccaagctgtt ttcttctatt ccatggctaa ctggcgaggg ggtgattaga    2040
gggaggagaa tgagcctcgg cctcttccgt gacgtcactg gaccactggg caatgatggc    2100
aattttgtaa cgaagacaca gactgcgatt tgtcccaggt cctcactacc gggcgcagga    2160
gggtgagcgt tattggtcgg cagccttctg ggcagacctt gacctcgtgg gctagggatg    2220
actaaaatat ttatttttt taagtattta ggttttttgtt tgtttccttt gttcttacct     2280
gtatgtctcc agtatccact tgcacagct ctccggtctc tctctctcta caaactccca     2340
cttgtcatgt gacaggtaaa ctatcttggt gaatttttt ttcctagccc tctcacattt      2400
atgaagcaag ccccacttat tccccattct tcctagtttt ctcctcccag gaactgggcc    2460
aactcacctg agtcacccta cctgtgcctg accctacttc ttttgctctt agctgtctgc    2520
tcagacagaa ccctacatg aaacagaaac aaaacacta aaataaaaa tggccatttg       2580 cttttttcacc agatttgcta atttatcctg aaatttcaga ttcccagagc aaaataattt    2640
taaacaaagg ttgagatgta aaaggtatta aattgatgtt gctggactgt catagaaatt    2700
acacccaaag aggtatttat cttactttt aaacagtgag cctgaatttt gttgctgttt      2760
tgatttgtac tgaaaaatgg taattgttgc taatcttctt atgcaatttc ctttttttgtt   2820 attattactt attttgaca gtgttgaaaa tgttcagaag gttgctctag attgagagaa      2880
gagacaaaca cctcccagga gacagttcaa gaaagcttca aactgcatga ttcatgccaa    2940
ttagcaattg actgtcactg ttccttgtca ctggtagacc aaaataaaac cagctctact    3000
ggtcttgtgg aattgggagc ttgggaatgg atcctggagg atgcccaatt agggcctagc    3060
cttaatcagg tcctcagaga atttctacca tttcagagag ccttttgga atgtggcccc     3120 tgaacaagaa ttggaagctg ccctgcccat gggagctggt tagaaatgca gaatcctagg    3180
ctccacccca tccagttcat gagaatctat atttaacaag atctgcaggg ggtgtgtctg    3240
ctcagtaatt tgaggacaac cattccagac tgcttccaat tttctggaat acatgaaata    3300
tagatcagtt ataagtagca ggccaagtca ggcccttatt ttcaagaaac tgaggaattt    3360
tctttgtgta gctttgctct ttggtagaaa aggctaggta cacagctcta gacactgcca    3420
cacagggtct gcaaggtctt tggttcagct aagctaggaa tgaaatcctg cttcagtgta    3480
tggaaataaa tgtatcatag aaatgtaact tttgtaagac aaaggttttc ctcttctatt    3540
ttgtaaactc aaaatatttg tacatagtta tttatttatt ggagataatc tagaacacag    3600
gcaaaatcct tgcttatgac atcacttgta caaaataaac aaataacaat gtgaaaaaaa    3660
aaaaaaaaaa aaaaaaaaa aaaaaaaaa aaa                                   3693

<210> SEQ ID NO 6
<211> LENGTH: 4457
<212> TYPE: DNA
<213> ORGANISM: Homo sapiens
<220> FEATURE:
<221> NAME/KEY: modified_base
<222> LOCATION: (349)
<223> OTHER INFORMATION: a, c, g, t, unknown or other

<400> SEQUENCE: 6
gtttaaacgg gccctctaga cgcgttgaca ttgattattg actagttatt aatagtaatc      60
aattacgggg tcattagttc atagcccatg atatcatatg gagttccgcg ttacataact    120
```

```
tacggtaaat ggcccgcctg gctgaccgcc caacgacccc cgcccattga cgtcaataat     180
gacgtatgtt cccatagtaa cgccaatagg gactttccat tgacgtcaat gggtggagta     240
tttacggtaa actgcccact tggcagtaca tcaagtgtat catatgccaa gtacgccccc     300
ctattgacgt caatgacggt aaatggcccg cctggcatta tgcccagtnc atgaccttat     360
gggactttcc tacttggcag acatctacgt attagtcatc gctattacca tggtgatgcg     420
gttttggcag tacatcaatg ggcgtggata gcggtttgac tcacgggat ttccaagtc      480 tccaccccat tgacgtcaat gggagtttgt tttggcacca aaatcaacgg gactttccaa     540
aatgtcgtaa caactccgcc ccattgacgc aaatgggcgg taggcgtgta cggtgggagg     600
tctatataag cagagctctc tggctaacta gagaacccct gcttactggc ttatcgagat     660
atctgcagaa ttcatctgtc gactgctacc ggcagcgcgc agcggcaaga agtgtctggg     720
ctgggacgga caggagaggc tgtcgccatc ggcgtcctgt gcccctctgc tccggcacgg     780
ccctgtcgca gtgcccgcgc tttccccggc gcctgcacgc ggcgcgcctg ggtaacatgc     840
ttggggtcct ggtccttggc gcgctggccc tggccggcct ggggttcccc gcacccgcag     900
agccgcagcc gggtggcagc cagtgcgtcg agcacgactg cttcgcgctc tacccggggcc    960 ccgcgacctt cctcaatgcc agtcagatct gcgacggact gcggggccac ctaatgacag    1020
tgcgctcctc ggtggctgcc gatgtcattt ccttgctact gaacggcgac ggcggcgttg    1080
gccgccggcg cctctggatc ggcctgcagc tgccacccgg ctgcggcgac cccaagcgcc    1140
tcgggcccct cgcgcggcttc cagtgggtta cgggagacaa caacaccagc tatagcaggt    1200
gggcacggct cgacctcaat ggggctcccc tctgcggccc gttgtgcgtc gctgtctccg    1260
ctgctgaggc cactgtgccc agcgagccga tctgggagga gcagcagtgc gaagtgaagg    1320
ccgatggctt cctctgcgag ttccacttcc cagccacctg caggccactg gctgtggagc    1380
ccggcgccgc ggctgccgcc gtctcgatca cctacggcac cccgttcgcg gcccgcggag    1440
cggacttcca ggcgctgccg gtgggcagct ccgccgcggt ggctcccctc ggcttacagc    1500
taatgtgcac cgcgccgccc ggagcggtcc aggggcactg gccaggag gcgccgggcg       1560 cttgggactg cagcgtggag aacggcggct gcgagcacgc gtgcaatgcg atccctgggg    1620
ctccccgctg ccagtgccca gccggcgccc cctgcaggc agacgggcgc tcctgcaccg     1680
catccgcgac gcagtcctgc aacgacctct gcgagcactt ctgcgttccc aaccccgacc    1740
agccgggctc ctactcgtgc atgtgcgaga ccggctaccg gctggcggcc gaccaacacc    1800
ggtgcgagga cgtggatgac tgcatactgg agcccagtcc gtgtccgcag cgctgtgtca    1860
acacacaggg tggcttcgag tgccactgct accctaacta cgacctggtg gacggcgagt    1920
gtgtggagcc cgtggacccg tgcttcagag ccaactgcga gtaccagtgc cagccctga    1980 accaaactag ctacctctgc gtctgcgccg agggcttcgc gcccattccc acgagccgc     2040 acaggtgcca gatgttttgc aaccagactg cctgtccagc cgactgcgac cccaacaccc    2100
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc cccgcccagc cgacgccccg    2340
gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
```

-continued

```
tgctgcagca cgtgcggacc gagcggacgc cgcagagact ctgagcggcc tccgtccagg    2580
agcctggctc cgtccaggag cctgtgcctc ctcaccccca gctttgctac caaagcacct    2640
tagctggcat tacagctgga gaagaccctc cccgcacccc ccaagctgtt ttcttctatt    2700
ccatggctaa ctggcgaggg ggtgattaga gggaggagaa tgagcctcgg cctcttccgt    2760
gacgtcactg gaccactggg caatgatggc aattttgtaa cgaagacaca gactgcgatt    2820
tgtcccaggt cctcactacc gggcgcagga gggtgagcgt tattggtcgg cagccttctg    2880
ggcagacctt gacctcgtgg gctagggatg actaaaatat ttatttttt taagtattta     2940 ggttttgtt tgtttccttt gttcttacct gtatgtctcc agtatccact ttgcacagct     3000
ctccggtctc tctctctcta caaactccca cttgtcatgt gacaggtaaa ctatcttggt    3060 gaatttttt ttcctagccc tctcacattt atgaagcaag ccccacttat tccccattct     3120
tcctagtttt ctcctcccag gaactgggcc aactcacctg agtcacccta cctgtgcctg    3180
accctacttc ttttgctctt agctgtctgc tcagacagaa cccctacatg aaacagaaac    3240
aaaaacacta aaaataaaaa tggccatttg cttttttcacc agatttgcta atttatcctg    3300
aaatttcaga ttcccagagc aaaataattt taaacaaagg ttgagatgta aaaggtatta    3360
aattgatgtt gctggactgt catagaaatt acacccaaag aggtatttat ctttactttt    3420
aaacagtgag cctgaatttt gttgctgttt tgatttgtac tgaaaaatgg taattgttgc    3480
taatcttctt atgcaatttc ctttttttgtt attattactt attttttgaca gtgttgaaaa   3540 tgttcagaag gttgctctag attgagagaa gagacaaaca cctcccagga gacagttcaa    3600
gaaagcttca aactgcatga ttcatgccaa ttagcaattg actgtcactg ttccttgtca    3660
ctggtagacc aaaataaaac cagctctact ggtcttgtgg aattgggagc ttgggaatgg    3720
atcctggagg atgcccaatt agggcctagc cttaatcagg tcctcagaga atttctacca    3780
tttcagagag gccttttgga atgtggcccc tgaacaagaa ttggaagctg ccctgcccat    3840
gggagctggt tagaaatgca gaatcctagg ctccacccca tccagttcat gagaatctat    3900
atttaacaag atctgcaggg ggtgtgtctg ctcagtaatt tgaggacaac cattccagac    3960
tgcttccaat tttctggaat acatgaaata tagatcagtt ataagtagca ggccaagtca    4020 ggccccttatt ttcaagaaac tgaggaattt tctttgtgta gctttgctct ttggtagaaa    4080
aggctaggta cacagctcta gacactgcca cacagggtct gcaaggtctt tggttcagct    4140
aagctaggaa tgaaatcctg cttcagtgta tggaaataaa tgtatcatag aaatgtaact    4200
tttgtaagac aaaggttttc ctcttctatt ttgtaaactc aaaatatttg tacatagtta    4260
tttatttatt ggagataatc tagaacacag gcaaaatcct tgcttatgac atcacttgta    4320
caaaataaac aaataacaat gtgaaaaaaa aaaaaaaaa aaaaaaaaa aaaaaaaaa       4380 aaaggtagca gtcgacagat gaattccacc acactggact agtggatccg agctcggtac    4440
caagcttaag tttaaac                                                   4457
```

<210> SEQ ID NO 7
<211> LENGTH: 17534
<212> TYPE: DNA
<213> ORGANISM: Artificial Sequence
<220> FEATURE:
<221> NAME/KEY: modified_base
<222> LOCATION: (730)
<223> OTHER INFORMATION: a, c, g, t, unknown or other
<220> FEATURE:
<223> OTHER INFORMATION: Description of Artificial Sequence: Synthetic plasmid

<400> SEQUENCE: 7

```
catcatcaat aatatacctt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgttttg    180
gtgtgcgccg gtgtacacag gaagtgacaa ttttcgcgcg gttttaggcg gatgttgtag   240
taaatttggg cgtaaccgag taagatttgg ccattttcgc gggaaaactg aataagagga   300
agtgaaatct gaataatttt gtgttactca tagcgcgtaa tactggtacc gcggccgcct   360
cgagtctaga actagtggat cccccaaacg ggccctctag acgcgttgac attgattatt   420
gactagttat taatagtaat caattacggg gtcattagtt catagcccat gatatcatat   480
ggagttccgc gttacataac ttacggtaaa tggcccgcct ggctgaccgc ccaacgaccc   540
ccgcccattg acgtcaataa tgacgtatgt tcccatagta acgccaatag ggactttcca   600
ttgacgtcaa tgggtggagt atttacggta aactgcccac ttggcagtac atcaagtgta   660
tcatatgcca gtacgccccc ctattgacg tcaatgacgg taaatggccc gcctggcatt    720
atgcccagtn catgacctta tgggactttc ctacttggca gacatctacg tattagtcat   780
cgctattacc atggtgatgc ggttttggca gtacatcaat gggcgtggat agcggtttga   840
ctcacgggga ttttccaagt ctccacccca ttgacgtcaa tgggagtttg ttttggcacc   900
aaaatcaacg ggactttcca aaatgtcgta caactccgc cccattgacg caaatgggcg    960
gtaggcgtgt acggtgggag gtctatataa gcagagctct ctggctaact agagaacccc  1020
tgcttactgg cttatcgaga tatctgcaga attcatctgt cgactgctac cggcagcgcg  1080
cagcggcaag aagtgtctgg gctgggacgg acaggagagg ctgtcgccat cggcgtcctg  1140
tgcccctctg ctccggcacg gccctgtcgc agtgccgcg ctttcccgg cgcctgcacg    1200
cggcgcgcct gggtaacatg cttggggtcc tggtccttgg cgcgctggcc ctggccggcc  1260
tggggttccc cgcacccgca gagccgcagc cgggtggcag ccagtgcgtc gagcacgact  1320
gcttcgcgct ctaccgggc cccgcgacct tcctcaatgc cagtcagatc tgcgacggac   1380
tgcggggcca cctaatgaca gtgcgctcct cggtggctgc cgatgtcatt tccttgctac  1440
tgaacggcga cggcggcgtt ggccgccggc gcctctggat cggcctgcag ctgccacccg  1500
gctgcggcga ccccaagcgc ctcgggcccc tgcgcggctt ccagtgggtt acgggagaca  1560
acaacaccag ctatagcagg tgggcacggc tcgacctcaa tggggctccc ctctgcggcc  1620
cgttgtgcgt cgctgtctcc gctgctgagg ccactgtgcc cagcgagccg atctgggagg  1680
agcagcagtg cgaagtgaag gccgatggct tcctctgcga gttccacttc cagccacct   1740
gcaggccact ggctgtggag cccggcgccg cggctgccgc cgtctcgatc acctacggca   1800
ccccgttcgc ggcccgcgga gcggacttcc aggcgctgcc ggtgggcagc tccgccgcgg  1860
tggctcccct cggcttacag ctaatgtgca ccgcgccgcc cggagcggtc caggggcact  1920
gggccaggga ggcgccgggc gcttgggact gcagcgtgga gaacggcggc tgcgagcacg  1980
cgtgcaatgc gatccctggg gctccccgct gccagtgccc agccggcgcc gccctgcagg  2040
cagacgggcg ctcctgcacc gcatccgcga cgcagtcctg caacgacctc tgcgagcact  2100
tctgcgttcc caaccccgac cagccgggct cctactcgtg catgtgcgag accggctacc  2160
ggctggcggc cgaccaacac cggtgcgagg acgtggatga ctgcatactg gagcccagtc  2220
cgtgtccgca gcgctgtgtc aacacacagg gtggcttcga gtgccactgc taccctaact  2280
```

```
acgacctggt ggacggcgag tgtgtggagc ccgtggaccc gtgcttcaga gccaactgcg   2340
agtaccagtg ccagcccctg aaccaaacta gctacctctg cgtctgcgcc gagggcttcg   2400
cgcccattcc ccacgagccg cacaggtgcc agatgttttg caaccagact gcctgtccag   2460
ccgactgcga ccccaacacc caggctagct gtgagtgcca tgaaggctac atcctggacg   2520
acggtttcat ctgcacggac atcgacgagt gcgaaaacgg cggcttctgc tccggggtgt   2580
gccacaacct ccccggtacc ttcgagtgca tctgcgggcc cgactcggcc cttgcccgcc   2640
acattggcac cgactgtgac tccggcaagg tggacggtgg cgacagcggc tctggcgagc   2700
ccccgcccag cccgacgccc ggctccacct tgactcctcc ggccgtgggg ctcgtgcatt   2760
cgggcttgct cataggcatc tccatcgcga gcctgtgcct ggtggtggcg cttttggcgc   2820
tcctctgcca cctgcgcaag aagcagggcg ccgccagggc caagatggag tacaagtgcg   2880
cggccccttc caaggaggta gtgctgcagc acgtgcggac cgagcggacg ccgcagagac   2940
tctgagcggc ctccgtccag gagcctggct ccgtccagga gcctgtgcct cctcaccccc   3000
agctttgcta ccaaagcacc ttagctggca ttacagctgg agaagaccct ccccgcaccc   3060
cccaagctgt tttcttctat tccatggcta actggcgagg gggtgattag agggaggaga   3120
atgagcctcg gcctcttccg tgacgtcact ggaccactgg gcaatgatgg caattttgta   3180
acgaagacac agactgcgat tgtcccagg tcctcactac cgggcgcagg agggtgagcg   3240
ttattggtcg gcagccttct gggcagacct tgacctcgtg ggctagggat gactaaaata   3300
tttattttt ttaagtattt aggtttttgt ttgtttcctt tgttcttacc tgtatgtctc   3360
cagtatccac tttgcacagc tctccggtct ctctctctct acaaactccc acttgtcatg   3420
tgacaggtaa actatcttgg tgaatttttt tttcctagcc ctctcacatt tatgaagcaa   3480
gccccactta ttcccattc ttcctagttt tctcctccca ggaactgggc caactcacct   3540
gagtcaccct acctgtgcct gaccctactt cttttgctct tagctgtctg ctcagacaga   3600
acccctacat gaaacagaaa caaaaacact aaaaataaaa atggccatt gctttttcac   3660
cagatttgct aatttatcct gaaatttcag attcccagag caaaataatt ttaaacaaag   3720
gttgagatgt aaaaggtatt aaattgatgt tgctggactg tcatagaaat tacacccaaa   3780
gaggtattta tctttacttt taaacagtga gcctgaattt tgttgctgtt ttgatttgta   3840
ctgaaaaatg gtaattgttg ctaatcttct tatgcaattt ccttttttgt tattattact   3900
tatttttgac agtgttgaaa atgttcagaa ggttgctcta gattgagaga agagacaaac   3960
acctcccagg agacagttca agaaagcttc aaactgcatg attcatgcca attagcaatt   4020
gactgtcact gttccttgtc actggtagac caaaataaaa ccagctctac tggtcttgtg   4080
gaattgggag cttgggaatg gatcctggag gatgcccaat tagggcctag ccttaatcag   4140
gtcctcagag aatttctacc atttcagaga ggccttttgg aatgtggccc ctgaacaaga   4200
attggaagct gccctgccca tgggagctgg ttagaaatgc agaatcctag gctccacccc   4260
atccagttca tgagaatcta tatttaacaa gatctgcagg gggtgtgtct gctcagtaat   4320
ttgaggacaa ccattccaga ctgcttccaa ttttctggaa tacatgaaat atagatcagt   4380
tataagtagc aggccaagtc aggcccttat tttcaagaaa ctgaggaatt tctttgtgt   4440
agctttgctc tttggtagaa aaggctaggt acacagctct agacactgcc acacagggtc   4500
tgcaaggtct ttggttcagc taagctagga atgaaatcct gcttcagtgt atggaaataa   4560
atgtatcata gaaatgtaac ttttgtaaga caaaggtttt cctcttctat tttgtaaact   4620
caaaatattt gtacatagtt atttatttat tggagataat ctagaacaca ggcaaaatcc   4680
```

```
ttgcttatga catcacttgt acaaaataaa caaataacaa tgtgaaaaaa aaaaaaaaaa    4740
aaaaaaaaaa aaaaaaaaaa aaaaggtagc agtcgacaga tgaattccac cacactggac    4800
tagtggatcc gagctcggta ccaagcttaa gtttgggctg caggaattct gatggctctc    4860
aaaattcctg cctcctttag ggataaaaga ctttaagact ttttaacaaa aagaaaaag     4920
aaaaaaaaaa ttcctgcctc ctggtgtaca cacacagaag ggttccctcc ccttgaatgt    4980
gaccaggatc tgtgaaaata cgggatagc cgctcctgtg attaggttat gtggtagact    5040
agagcaagat tctcctgctg gttttgaaga agtcagctgc catgttgtga gactgtcatg    5100
ggctagggca tgagccttta aatatctggg agcaacccct ggccagcagc cagtgagaaa    5160
acgggccctc agtcctacaa tcacaaggaa ctaaattctg ccaacaacct gaaggaactt    5220
tgaagaggat catgagtccc ttgattcagc ttgatgagcc cctgagcaga ggatacagct    5280
aacttgtact agggaagtat aaaaaacatg catgggaatg atatatatca actttaagga    5340
taattgtcat acttctggga atgaagggaa agaaatgggg ctttagttgt attatgatct    5400
ttaatttctc aaaaaaaata agatcagaag caaatatggc aaaatgttaa tacttttgtg    5460
ggtacgtagg tattcagcat accctttttt ctgagttcaa aatattttat aattaaaatg    5520
aaatgcaggc caggcacagt ggctcatgcc tataatacca gcactttgcg aggccgaggt    5580
gggaggatgg cttgaggcca gaccagcctg gccaacatgg caaaacccca tctctactta    5640
aaaaaaaaaa aactatatat atatatatgt gtgtgtgtgt gtatatatat atatgtatat    5700
atatttatat atgtgtgtat atatatatat gtatatatat ttatatatgt gtgtgtatat    5760
atatatatac acacacacac atatatacat acatacatac acacacacac acacacaatt    5820
agccaggcat ggtggcgcac acctgtagtc ccagctactt gggaggctga gacatgagaa    5880
ttgcttgaac ctgggaggca gagtagttag tgagctgaga tcataccact gcactccagc    5940
ctggtgacag agtgagactc tgtcttaaaa aaaataaaaa ttaaaattaa atgcaaaagg    6000
tccaagtgaa ttgaagagga aaggggtatc aaggaaggtt ttgtggaggt gacgtttgag    6060
ctgggtctta aatgacttaa acatgggata agaaggagg gaataaggac atttcaggta    6120
cgagaaataa ggagcaaaca gtggaaacaa cctaacgtct gtcaaccagt gaatggataa    6180
caaaaatgta attcagatgg tatccaactt acgatggttc aacatgagat ttttctgact    6240
ttaggataga tttatcaaag tagtaaatcc attttcaact tatgatattt tcaacttcag    6300
atgggtttat caggacacag ttgaggaaca cctgtctatc catacaattt ggcaataaaa    6360
aggaaatgag tgcagatata ctccacaaca tgaatgaacc ttgaaaacat taagtgagag    6420
aagccagata caaaaggcca catattgtat gattctattt atacaaaatg tccagaatag    6480
gcaaatctta tagacagcaa gtaggtagat gatcagtttg ctaggtgctg ggggaagggg    6540
aaatggggag tgatggctaa ggggattggg tttctttgtg gggcaatgaa atgttttaa     6600
aattgagcgt gataatgatt gcacaatgct gcatatatat ataatctata gattatatat    6660
atataaagag aggctgttag acagtgataa gtgatatata tatatatata catagagaga    6720
gagagagaga gagagagagg ctgttagtga taagtgatca ggaaaataaa agtattgagg    6780
aggaatacga agttgacggt gtgaaaacat gagattttat ataggatggc cagggaaggc    6840
cttaatgaga aagtgactta tgagtaaaaa caagggatcc taaaccttag catgcatcag    6900
aatcactcgg aaacttgtta aagcatagct tgctgggcct catcacagat attttgattc    6960
ggtaggttct tgtctgatat taatacttt ggtctaggga accacatttt gagaaccact     7020
```

```
gagctaaagg aagtaaaggt ttcccttagt ttactagctg gtaacactgg cccaggaggc    7080 cttttctggtg acccctaagg aattatccaa actcttgttt ttagatgctt tattatatca    7140
aactctcctt taaacaagtg gcccatctgc tgggatttgg aagcctgtaa tactgaaatt    7200
ttcatcataa tggaaatttt aaaaacagaa tttgacccac ctgttttaa aacactttca    7260 ttacttaaca agaggtctaa tcttgggcaa gtcttgaaat ttctctggcc ttagtttccc    7320
atgtgttaaa tgaaacttga agcagttggt ctcttatagt ctcctgactc taacattcta    7380
agaattatat ttgtacaata actcaaaaat cacataattt aatttaccat atggactcca    7440
aaatatattt tctcattagg ctaaacttga tctgcatttt ctggatgtgt ccatattctt    7500
ggactacact aaaacatgat accaatgctt cctctcacca taaaccctca cttcgctttc    7560
tacatttaag aattttatag ctggaagagt ccttaacaga aaataccatc taataattac    7620
ccctcaaaat cgagaaagtc ctatctgttc ttatgctagt tataagaatg aggcagcatt    7680
tcacataatg gttataaaca ctgccacaag aagattcatg atgtgttgtt tatctgtagc    7740
tctcatcata ctctgtcata taactatagc attaagattt taatgttcta tatattcttc    7800
taagacagtg tttaccagag taaggcacaa aagatccact ggtttgcaag aaagattaga    7860
acttttaaat ttttttaccctc accttgttta atctatattt ttgtatgtat tttgtaacat    7920
atatattatt attaccataa atcatatata atttaaaatg catatattag gggtaaatgc    7980
tcaggaaact ttttataaat tgggcatgca aatacaagtt tgaagactca ctgttctagg    8040
tattaaaagt aaagttataa ccaagtaaag cttccacctt ttcatgtctc aaagcagttt    8100
attgttggag gtaagatctc ttagaagcct aaacaggtcc aagtacagaa tgaagtaagg    8160
ctagcccata acttgtggca agcaattcat actatttctc tcatgctgag ctctcctcag    8220
tgaagcagct actatagaca actgcagcct attggtagcc tattttacag gcaggaaaaa    8280
aattactttt tattcaaagt ggaactcagg acatggggag aaaatgaata caaaaaatag    8340
ggtcaatcca aaggcacaca gcaaatgagt aacacagtta tgttttttc ccatttgtat    8400 gaggtcccag taaattctaa gtaaactgca aatttaataa tacactaaaa aagccatgca    8460
attgttcaaa tgaatcccag catggtacaa ggagtacaga cactagagtc taaaaaacaa    8520
aagaatgcca ttattgagtt tttgaattat atcaagtagt tacatctcta cttaataaat    8580
gagaaaaacg aggataagag gccatttgat aaaatgaaaa tagccaagaa gtggtattag    8640
agacttgaat acaggtattc gggtccaaag ttcatctgct caaatactaa ctggggaaaa    8700
gagggaaaaa tatttatata catatatatc tgcacacaaa aataccccca aaagacaaaa    8760
tgaggccagg cagggtggct cacacccgta atcccggtac tttgggaggc tgaggcaggt    8820
ggatacctga gatcaggagt tggagatcag cctggtcaac atggtgaaac cctgtctcta    8880
ctaaagataa aaaaattagc caggcatggt ggcgtgcgcc tgtaatccca gctacttggg    8940
agtctgaggc aggagaatca cttgaactgg aagggagg ttgcagtgag ccaagatcgt    9000
actactgcac tccagcctgg gcagcagagt gagactccat cacaaaaata aataaataaa    9060
taaaatacaa tgaaacagaa agttcaaata atcccataat cttaccacca agaaataact    9120
ttcactcgtt atacttattg attttccat aataaatgta ctttactgtg actatcatga    9180
aaagaaagtt attttagaaa cagagaactg tttcagatca aatctatgta gtagaacaga    9240
gccattaggt gggaaagacg agatcaaact aaatctcaga aggcctaaaa ggctaggtcc    9300
attccagcac taaaaactga ccagacaagt aatggcttca acagcttcta aatatggaca    9360
aagcatgctg aaagggaagg acaggtctaa cagtggtata tgaaatgaac aggaggggca    9420
```

```
aagctcattt ctcctctgaa gttttccaaa gatgctgagg aggacattag tttgacatga    9480
ccctgatatg ggacaagata atttcacaga agttttacat gttaaagttt tcttatagat    9540
actcattcaa gtaagcaatg aacactaaaa tctaaagaaa gaaaagagct ttagagtcag    9600
gtctgtattc aaattcaagc tctaccactt actggttctg tgactttggg caagtctttt    9660
aaccttatta agtcttaatt tcctgatttg taaaatgggg atatcgtctc cctcacagga    9720
ttgttgtgaa acttttatga gattaatgcc tttatatttg gcatagtgta agtaaacaat    9780
aactggcagc ttcaaaaaaa aaagcagta gcattccatc atttattatt ggttactctc    9840
aaaaagtttt tcaatgtact agaagataaa tattcaaata ccttaatatc tccattattt    9900
tcaggtaaac agcatgctcc tgaacaacca atgggtcaac aaataaatta aagggaaat    9960 ctaaaaacat cttgatatta aactacatgg aagcacaata taccaaaacc aatggttcac   10020
actaggagaa tttaaggta caagaaaact ctttgagatt tcttaaaata atagtatgtc    10080
tgaatttatt gagtgattta ccagaaactg ttgtaagagc tctacttgca ttatagcact   10140
taatcctctt aactctatgg ctgctattat caacctcacc ctaatcacat atgggacaca   10200
gagaggttaa gtaacttgcc caaggtcaga gttaggaagt actaagccat gctttgaatc   10260
agttgtcagg ctccggaact cacactttca gccactacat aatactgctt tgctatcttt   10320
taggaaacta tgtgagtcta cctcacatag actcacatag gtttgttttt tttttttttt   10380
taaaggctat cttttccccc atcaatgttt tttgaaggat cccaaattag agtcccacag   10440
aggcagacag cagtacttga caatatgac attttaaggt aatgttggat tctactgtct    10500
ttttactaca tgacctaggg aacgataatt aacctagact gcttccaagg gttaaataac   10560
ccatttagtt atactatgta aattatctct tagtgattga ttgaaagcac actgttacta   10620
attgactcgg tatgaagtgc ttttttttct tcccttcaa gatacatacc tttccagtta    10680
aagttgagag atcatctcca ccaattactt ttatgtcccc tgttgactgg tcattctagt   10740
taaaaaaaaa aaaactata tatatatata tctacacaca catatgtata tgtatatcct    10800
tatgtacaca cacaaacttc aaattaaatg agaactagaa gatttgagaa gttagctagc   10860
taatatccat agcattatga tattctaaat gatatgaatt ataagaatta ggtttcctga   10920
aatgaatgac tagaaaactt tcaagtagag attagtaaaa attaaaaagt cctaatcggc   10980
cattactgat ttgatgtttt taagagtcct aaaaaatggg ttacatccat ttttaagtgg   11040
gtagtattat aacagccacc catcttcaat cacagtgatt tctgaattgt gagggaagtt   11100
attagcatga caggtgtctg gttctggccc tgtacgattc ccatgagtca agcaaattgt   11160
aagggctggt ctatatcaca cccaacccca aggatatgtc cctcaaaagt ctagcccagg   11220
ccccgtcatc ttcagcatca tctgggaaac caggtctgat tagtagtcct ttaaggaata   11280
cctcttaggc tcccatttta ctgctatcac agaatccaat aaaaccctta caggagattc   11340
aatgggaaat gctcaacacc cactgtagtt ggtggtgaca atgaccataa tttggctgtg   11400
ctggattcag gacagaaaat ttgggtgaaa gagcaggtga acaaagagc ttcgacttgc    11460 cctagcagag agcaagccat accataccac aaagccacag caattacaac ggtgcagtac   11520
cagcacagta aatgaacaaa gtagagccca gaaacagacc cagaactata tgaggattta   11580
gtatacaata aagatggtat ttcgagtcag tagggaaaag atgaattatt caataaatga   11640
tgtttggcca actagtaacc catttgggaa aaaataaaag tatggtccct acctcacagc   11700
atacacaaaa ataaattcca gacggattaa aatctaaatg taaaaaataa agccataagt   11760
```

```
ggactggaag aaaatagaga attttttta acatccgtag aaagggtaaa aacccaggca   11820
tgacatgaac caaaactgaa gaggttctgt aacaaatacc cccttttata tattgggctc   11880
caacaataag aacccatagg aaaatggaga atgaacacaa atagacaatt tatagaagag   11940
aaggttataa ggtgtaaaat tatatctatc tgagaaacaa acactaaaac aatgtgattc   12000
tactgttctc ccacccatac tggcaaaact taagcctgat aatatgctga ggggaaataa   12060
gcactcttgt tggtgagagt attaattggc atagcttctt ttgaaaatga catagcaata   12120
cctgttaaaa ttgcaaacat gcatgtcact taatccagta atcccacttc tgggaatcaa   12180
tgctacaaaa acactgacaa gtatacaaag atacattcaa gagtgttcac tgggccgggt   12240
gcggtggctt catgcctgta atcccaggga ggcagaggca agacgatcgc ttgaccccag   12300
gagttcaagg ccagcccgag aaacacagca agaccctgtc tctctttttt ttatttaaaa   12360
aataaatgtt cactgtatca gttgttcaca aaaacaaacc aacatgtcca ttaacaggga   12420
accatttaaa ttaatcaagt tcatctacac aatgtaatac catgcaacta ttaaaaagca   12480
cctgataatc caaagcacac tgagacagaa taatgctatt aaaaacacca agtagtggaa   12540
cactgtgttg cctatgacac cattttatt caacatttaa acaaatttgt aacagcaatt   12600
acatgagtag tgacaatggc gtttatgaga cttttcactt ttatgtgctt ctattttgt   12660
tatgcttcta tatatacatc catttattat ggagtgttac tttcaaaaat cacaaatggg   12720
ccagtattat ttggtgttgc aaggtgagca tatgacttct gatatcaacc tttgcatatt   12780
acttctcaat ttagggaaat tacagacatc ccttattcta actaacttaa aacccagcat   12840
ttcaaacata cagaattgat ggggaaaaaa aagaaagaag aaagaaagaa aaggcaacaa   12900
gcttcagatg acagtgactc acatcaaatt atttataaaa tctgttaaat agtgccatct   12960
tctggagata cctggtatta cagtccaact ccagttgatg tctttacaga gacaagagga   13020
ataaaggaaa aaatattcaa gaactgaaaa gtatggagtc atggaaaaat tgctgtgatc   13080
caaaggctac ggtgatagga caagaaacaa gagaactcca agcagtaaga cactgctgtt   13140
ctattagcat ccaaacctcc atactcctgt ttgccccaag gctttttttaa aaaatagaga   13200
caggatctca ctattttgct caggctggtc ttgaactcct ggactcaagc tatcctcctg   13260
cctcggcctc ctaaagtgcc gagattacag gcttgagtca ccatacctgg ctatttattt   13320
tttcttaact ctcttgcctg gcctatagcc accatggaag ctaataaaga atattaattt   13380
aagagtaatg gtatagttca ctacattgga atacaggtat aagtgcctac attgtacatg   13440
aatggcatac atggatcaat tacccccacct gggtggccaa aggaactgcg cgaacctccc   13500
tccttggctg tctggaacaa gcttcccact agatcccttt actgagtgcc tccctcatct   13560
ttaattatgg ttaagtctag gataacagga ctggcaaagg tgaggggaaa gcttcctcca   13620
gagttgctct accctctcct ctaccgtcct atctcctcac tcctctcagc caaggagtcc   13680
aatctgtcct gaactcagag cgtcactgtc aactacataa aattgccaga gaagctcttt   13740
gggactacaa acacataccc ttaatgtctt tatttctatt ttgtctacct cttcagtcta   13800
ggtgaaaaaa taggaaggat aatagggaag aactttgttt atgcctactt atccgccct   13860
aggaattttg aaaacctcta ggtagcaata agaactgcag catggtatag aaaaagagga   13920
ggaaagctgt atagaaatgc ataataaatg ggcaggaaaa gaactgcttg aacaaacag   13980
ggaggttgaa ctataaggag agaaagcaga gaggctaatc aacaaggctg ggttcccaag   14040
agggcatgat gagactatta ctaaggtagg aattactaag ggctccatgt cccccttagtg   14100
gcttagtact atgtagcttg ctttctgcag tgaacttcag acccttcttt taggatccta   14160
```

```
gaatggactt ttttttttta tcggaaaaca gtcattctct caacattcaa gcaggcccca    14220
agtctaccac actcaatcac attttctctt catatcataa tctctcaacc attctctgtc    14280
cttttaactg tttttctata ccctgatcaa atgccaacaa aagtgagaat gttagaatca    14340
tgtattttta gaggtagact gtatctcaga taaaaaaaaa gggcagatat tccattttcc    14400
aaaatatgta tgcagaaaaa ataagtatga aaggacatat gctcaggtaa caagttaatt    14460
tgtttacttg tattttatga attccctaaa acctacgtca cccgcccgt tcccacgccc     14520 cgcgccacgt cacaaactcc acccctcat tatcatattg gcttcaatcc aaaataaggt     14580
atattattga tgatgttaat taacatgcat ggatccatat gcggtgtgaa ataccgcaca    14640
gatgcgtaag gagaaaatac cgcatcaggc gctcttccgc ttcctcgctc actgactcgc    14700
tgcgctcggt cgttcggctg cggcgagcgg tatcagctca ctcaaaggcg gtaatacggt    14760
tatccacaga atcaggggat aacgcaggaa agaacatgtg agcaaaaggc cagcaaaagg    14820
ccaggaaccg taaaaaggcc gcgttgctgg cgttttttcca taggctccgc cccctgacg    14880 agcatcacaa aaatcgacgc tcaagtcaga ggtggcgaaa cccgacagga ctataaagat    14940
accaggcgtt ccccctgga agctccctcg tgcgctctcc tgttccgacc ctgccgctta    15000
ccggatacct gtccgccttt ctcccttcgg gaagcgtggc gctttctcat agctcacgct    15060
gtaggtatct cagttcggtg taggtcgttc gctccaagct gggctgtgtg cacgaacccc    15120
ccgttcagcc cgaccgctgc gccttatccg gtaactatcg tcttgagtcc aacccggtaa    15180
gacacgactt atcgccactg gcagcagcca ctggtaacag gattagcaga gcgaggtatg    15240
taggcggtgc tacagagttc ttgaagtggt ggcctaacta cggctacact agaaggacag    15300
tatttggtat ctgcgctctg ctgaagccag ttaccttcgg aaaaagagtt ggtagctctt    15360
gatccggcaa acaaaccacc gctggtagcg gtggttttttt tgtttgcaag cagcagatta    15420
cgcgcagaaa aaaaggatct caagaagatc ctttgatctt ttctacgggg tctgacgctc    15480
agtggaacga aaactcacgt taagggattt tggtcatgag attatcaaaa aggatcttca    15540
cctagatcct tttaaattaa aaatgaagtt ttaaatcaat ctaaagtata tatgagtaaa    15600
cttggtctga cagttaccaa tgcttaatca gtgaggcacc tatctcagcg atctgtctat    15660
ttcgttcatc catagttgcc tgactccccg tcgtgtagat aactacgata cgggagggct    15720
taccatctgg ccccagtgct gcaatgatac cgcgagaccc acgctcaccg gctccagatt    15780
tatcagcaat aaaccagcca gccggaaggg ccgagcgcag aagtggtcct gcaactttat    15840
ccgcctccat ccagtctatt aattgttgcc gggaagctag agtaagtagt tcgccagtta    15900
atagtttgcg caacgttgtt gccattgctg cagccatgag attatcaaaa aggatcttca    15960
cctagatcct tttcacgtag aaagccagtc cgcagaaacg gtgctgaccc cggatgaatg    16020
tcagctactg ggctatctgg acaagggaaa acgcaagcgc aaagagaaag caggtagctt    16080
gcagtgggct tacatggcga tagctagact gggcggtttt atggacagca agcgaaccgg    16140
aattgccagc tggggcgccc tctggtaagg ttgggaagcc ctgcaaagta aactggatgg    16200
ctttcttgcc gccaaggatc tgatggcgca ggggatcaag ctctgatcaa gagacaggat    16260
gaggatcgtt tcgcatgatt gaacaagatg gattgcacgc aggttctccg gccgcttggg    16320
tggagaggct attcggctat gactgggcac aacagacaat cggctgctct gatgccgccg    16380
tgttccggct gtcagcgcag gggcgcccgg ttcttttttgt caagaccgac ctgtccggtg    16440
ccctgaatga actgcaagac gaggcagcgc ggctatcgtg gctggccacg acgggcgttc    16500
```

-continued

```
cttgcgcagc tgtgctcgac gttgtcactg aagcgggaag ggactggctg ctattgggcg    16560
aagtgccggg gcaggatctc ctgtcatctc accttgctcc tgccgagaaa gtatccatca    16620
tggctgatgc aatgcggcgg ctgcatacgc ttgatccggc tacctgccca ttcgaccacc    16680
aagcgaaaca tcgcatcgag cgagcacgta ctcggatgga agccggtctt gtcgatcagg    16740
atgatctgga cgaagagcat caggggctcg cgccagccga actgttcgcc aggctcaagg    16800
cgagcatgcc cgacggcgag gatctcgtcg tgacccatgg cgatgcctgc ttgccgaata    16860
tcatggtgga aaatggccgc ttttctggat tcatcgactg tggccggctg ggtgtggcgg    16920
accgctatca ggacatagcg ttggctaccc gtgatattgc tgaagagctt ggcggcgaat    16980
gggctgaccg cttcctcgtg ctttacggta tcgccgctcc cgattcgcag cgcatcgcct    17040
tctatcgcct tcttgacgag ttcttctgaa ttttgttaaa attttgtta aatcagctca     17100 tttttaacc aataggccga aatcggcaaa atcccttata aatcaaaaga atagaccgag     17160 ataggttga gtgttgttcc agtttggaac aagagtccac tattaaagaa cgtggactcc     17220
aacgtcaaag ggcgaaaaac cgtctatcag ggcgatggcc cactacgtga accatcaccc    17280
taatcaagtt ttttggggtc gaggtgccgt aaagcactaa atcggaaccc taaagggagc    17340
ccccgattta gagcttgacg gggaaagccg gcgaacgtgg cgagaaagga agggaagaaa    17400
gcgaaaggag cgggcgctag ggcgctggca agtgtagcgg tcacgctgcg cgtaaccacc    17460
acacccgccg cgcttaatgc gccgctacag ggcgcgtcca ttcgccattc aggatcgaat    17520
taattcttaa ttaa                                                     17534
```

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gtaacactgg cccaggaggc ctttctggtg acccc                              35

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
tgaccgggtc ctccggaaag accactgggg att                                33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tagttccttc tgcctggaat ac                                            22

<210> SEQ ID NO 11
<211> LENGTH: 22
<212> TYPE: DNA

<213> ORGANISM: Artificial Sequence
<220> FEATURE:
<223> OTHER INFORMATION: Description of Artificial Sequence: Synthetic primer

<400> SEQUENCE: 11

```
caagtcacaa ggatggacta ca                                              22
```

<210> SEQ ID NO 12
<211> LENGTH: 18524
<212> TYPE: DNA
<213> ORGANISM: Homo sapiens

<400> SEQUENCE: 12

```
tagttccttc tgcctggaat acttcctcat ctcacttgct ttcctgcctg gcagcttcct     60
acttgccctc tggaaccagc tctagggtca ccacatctct gcttctgagt gcctcctcag    120
acacagtctg tatttcctct tccaagctct catcacaaac attgtgctgt attatatgtt    180
tctgtgtggt cttccttcta tgaggaagcc ttggaaagca ggagacttat tttagtcttc    240
tttatgtttc ttttattccc aacacattat gtctgcccca tagacctttt caataaatga    300
ttattgagtt agtgactcct tttacatgct gacaaatgtg gctcttatta ctccccattt    360
cagtatcaca tatttgtaaa agtgaatcct tcttaatcgt tttacttttc tcctagtaaa    420
ttcctcatct atgcctgtct gctgctgttc tctgtgctgc tggcccttcg tttggatggc    480
atcatacagt ggagttactg ggctgtcttt gctccaatat ggctgtggaa gttaatggtc    540
attgttggag cctcagttgg aactggagtc tgggcacgaa atcctcaata tcggtaatac    600
tgctttatac aacccattgg tctctagcat gagggagcaa tatcttgact tttctcactt    660
ttgatgaagt aaggaccatt ttattttcta cctatctggg gtcttagaac tatagtataa    720
gctaacagat ctcttctgtg tttttgaaaa tttagtcttt ggtatgtatt ttcttacaaa    780
agcagtgcca tttgggggta agttgccagc cagctcacag atgcctatat aatccaaaat    840
gcacccaaaa tacagaactg gtatgccata ctagactaag cagcatgaaa ccaccctgtt    900
tttaggaaaa gacactcata ttatgtttgg tcatgaaaga tctttctcca atacagtttt    960
ggaactgggg ctccccttgt cccaccctcc tagtcccaga gctttaggac tattagcagt   1020
gtaggggagg tggcttgacc aggagaccat gagtccctga gacagcagct ggggaatgag   1080
gaaagtcaaa gattggatgc gagaaggaa agcagagcct ttggggcag gggagagggg    1140
tacccttttac cgtttccaac tcttgccctc cctgctcttg gatgcctccg ctggcccaaa   1200
ttcctgggag ttgctcacgc cagcatgcaa cctgcttgtt gctgggacct gcgagagtct   1260
ttcccttctc tgccacagag actgtaacta cataaaggga aaaagggga cttaagactg    1320
ggaggctatt atgaacctcc actgggaaaa tgaggagtac aggaattccc agaaggcagc   1380
tgctcatgtg ggaaaagtgt aaagttgaaa ctaccgcacc tttttttttt tttttttttt   1440
tttttttttt ttgagacaga gtttcgctct tgttcccag gctggagtgc aatggtgtga   1500
tctcggccca ctgcagcctc cacatcccgg gttcaagtga ttctcctgcc tcggcctcct   1560
gagtagctgg gattacaggc acctgccacc atgcccagct aatttttttgt attttttagta   1620
gagatagggt ttcaccatgc caggctagtt ttgaactcct gacatcaggt gatccacccg   1680
ccttggcctc ctgaagtgct gggattacag gtgtgagcca ccacgtccgg ccactacatc   1740
aactttttaa attttttgttt actaaatatg aaaatgattc agattgtgta aattacatat   1800
cacatacatg tctaagaact gtaaaacagt tacacagaga gccttggcag gtgagggaca   1860
```

-continued

```
ttcatgtata gctgtttcag agttcttaga tttttttga aagattgatg acctgtgtgg    1920
ctgtatgtgt tttattttt tatgagatat tttcagatat ctaatattaa ttgcttctca    1980
aagaatgcaa agttaaataa acatttaggt tctactaatt gatatttaga atatattcaa   2040
acttctcttt gttggtctta tttaagatgt tttgagcaag gaaaggaatt gtgtatgtgg   2100
ggttgaatgt aaggaatgta caggcgtggt cattctcatg ttaacattaa ccagtggaac   2160
atggttgggt cctacaggaa taacctctga tagcattttc tctatgatct aacttccggt   2220
gtatttgtca cccacaatac atgtatatca taaatgttca tctgtatttt gaataaacat   2280
tgtaggcctt tcagatgcat tatagagcct tttcctgatt agcggcctta ccattgctca   2340
attgtagatc tgttaaggtt attgtgcatg atacttagct aattaaactg attttgtttg   2400
agaacagttt taactcttgt tcttctttct ctttcatgtg caggtgttaa tttatcttaa   2460
tggaatagaa aggaaaatga aaatcattta tacgttttat ttgcatttaa aaatagcacc   2520
taacaatagt tactactatc ttgaaatata actggcactt gttcatagaa ctagagttat   2580
ttttataata ttgtgtgaag ggtggtttac atggtttctt gaaaaatgag gatcatgaga   2640
cttaaggggt atttgcctgg ttttagcagc agaagcaaat cagcttgaat aatcttggaa   2700
gtaactcttg ttgttgaatt taaagatgtg aacagaagtg tttatgtaca ttgtcaggga   2760
aataagaact ggctattact tttgagaata tccttatacg gttaaaacat taaattctgg   2820
tttggttgta atgttcattt tgtattatgt agtagttctt cgatgtttca gagattgcct   2880
accaaagctt aggtttaagt tagctttcta cctgatttcc ctttgctttt gtcaaatttt   2940
caagtaaaat tcaaagtata aatataagtt ggtatttgcc ctgaactgct tgcttatagt   3000
ggagattctg aactgagggt gttttcttct tctctccctt ttttagagca gaaggagaaa   3060
cgtgtgtgga gtttaaagcc atgttgattg cagtgggcat ccacttgctc ttgttgatgt   3120
ttgaagttct ggtctgtgac agaatcgaga gaggaagcca tttctggctc ctggtcttca   3180
tgccgctgtt ctttgtttcc ccggtgtctg ttgcagcttg cgtttggggc tttcgacatg   3240
acaggtcact agaggtgaga tttcatatat ttaagaatgt tttccacttt gggaggtcaa   3300
ggcaggtgga tcacttgagg tcaggagttt gagaccagcc tggccaacat ggtgaaaccc   3360
catctctact aataatacaa aaattagccg ggtgtggtgg catgcgccag taatcccagc   3420
ttctccggag gctgaggcgg gagaatctct tgaacccagg aggcggaggt tgcagtgagc   3480
caagattgaa ccattgcact ccagcctggg tgacagaatg aaactccgtc ttaaaaaaaa   3540 aaaaaagaa tgttttcaaa agtaaatat tttgctcagt tattcagatg tcaatttctt    3600 acccttgtt aggaagagct tgatcattac caactctaca tcatgagaca acaaggcaac    3660
aaaagatgat ggaaataaca attttctttt cttcacttag aacactagct tttcacccag   3720
gacatcagcc ttctcccagc ttcacatcct gtatcaatca gacagaaaca gaactgatag   3780
gttagataca gatatatgta taagagagt taaggaactg gctcacatta ctgtgggct    3840 ggcaagtctg aaatctccag ggcaggtgaa caggctggag acctaggagg agttgacact   3900
gcagtcctgg cacagaattt tttcctctcc aggaaaccac agttttgct tttaaggcct    3960 tcacctgatt gcatgaggcc cacccatgct atggagggta gtctccttta ttcaaagtca   4020
gtaccttcac tgcaacagca agcttagtgt ttgattaaat aactgggtac tatagcccag   4080
ccaagttgac actcaaaact gaccatctcc ccacctcaga ccccatgatt tagcacctcc   4140
cctgctgtct ggttagctta tcctgatgtg ccctgtgtt tgtttattca ttcaataaac    4200
atttatcaag tatttactag atgccaagcc cttttccct aagcatagag gatatgcaga    4260
```

```
tgaataaaat accaggacta gtaataatag taatgaaagt aattgcagat aacgtttatt    4320
gagcacttac tgtgtgccag gcattgtgcg aggcacatta catgtggtag ttttcttact    4380
aactaactct gtgaggtagg tccagagaag ataagtcatt tgttcatggc cacatgtgaa    4440
ggggcaggac caggattccg tttgagtcag cccgactcta aagcccgggc ataaactac     4500
ataactgcat agaagctgag ggcccaaagc tgaatactga tgggttgagg ggagaactag    4560
aggctgtaga tgcctggttt tgagccgtgt ggatgaagag tgaagggaga agactgcagt    4620
tggcttagga agtaaacata gcagctgtag ggtgggtcag gcatataagc ctagacccca    4680
ggtatgggcg tgaggggaag gtatgtagac agagggacgg tgatggagca aggccctgtg    4740
ggactcaggg agaatgggac ctagagcacc aggaagggtt tggccttgaa caaggggagc    4800
tattccctga ttttcatgct ggtggaaagg ccacagcatg ggtatagtgg taggtaggag    4860
tgagccgtgg agggagagta tctgatggtc cactttcacc ctccctacaa ttcccagttt    4920
atatcaggga cttgagcatc catggatttt ggtatccaca gggggtcctg gaaccaatcc    4980
cccacagata ctgagggaca actatacaag gactaggact gcattgggcc tgaattacag    5040
aaagtaagtc tttcatatat tcacactcta ggcattcctg cccttggaag aaacaacata    5100
ccaggagctg agctccctcc tcctgtgatg caagaacagt acctatgttg gtgaggggt     5160
ggtctggagt aggctcatac agagatggga aggaggagtt gagggtctgc caggaagccc    5220
tgtgttggga gggaagggat ggcatttttg ggacacattg aagcctagag gcaggaaaca    5280
ctccatcagc tgagtggact gtggcgattc agatccgacg ggagcacaag gtggaaggaa    5340
aggaactgtg ggagttgaga agagaggag cctctacaga gggattgggg caaatagggg     5400
ccacgtcctc agcccacaga gcatgtgctg aagtgcccca ggcacccccag tgcactcaca   5460
gggcaccagg ggatagtgga catttttgagg aaaacagtaa tacctgacat tgttgggac    5520
accatacaaa ctactagctt gaaatagttt acaggtttat ttttaggcca cactgcattc    5580
ctttcagtga cgtcgtatct ttaagaagct gggttttcag cagttgctgt gaaaacaaaa    5640
aaggctaatg ctgtgtgaaa atccgggtga agaacaggta acgagtggga gcaccttgtc    5700
tgattccaag gcgtgggaaa tggtgagcta cctgacaggc acacgcatcc cactgggaat    5760
tagttttggt tatttaagaa taatattaac attttttcttt agatttatat gaattatttt   5820
ttctagtggc tacttagaaa tacttactaa gttagatgta attacttaaa tcagtgcaac    5880
tgttggcatt cccagccaca ttagggattt cttttggcct agaggtctat ggaggaatta    5940
ctaaattccc catgtaccta tgtactgaga acttttggga agctctgggc ctggtcccag    6000
atttcaattt tgtgggcaag aatgtacttt accagagtga ggagcagcct gcagggcgtt    6060
tgggctggag gcgggaggtt agtaagggt tgctgaagtg gtaggcggat ggtgccgaag     6120
aaggcctcac taggcagtca tcatcaggat aggaagtggg cacgggattc aggagaaatc    6180
tggactttac agtggacagg atgtggtgac tgaacgtgac agtgtgggaa aaagaatgca    6240
gggtgattcc cgggctcatg gcttgagaaa tgagaccact gttgtgcctc caagtgacat    6300
gggaggctat agaaagtgac atgggaggct atagaaagtg acatgggagg ccatagaaag    6360
tgacatggga ggccatagaa agtgacatgg gaggccatag aaagtgacaa gggaggccat    6420
agaaagtgac atgggaggcc atagtgacat gggaggccat agaaagtgac atgggaggct    6480
atagaaagtg acatgggagg ccatagaaag tgacatggga ggccatagaa agtgacatgg    6540
gaggccatag tgacatggga ggccatagaa agtgacatgg gaggctatag aaagaggaga    6600
```

```
tacaaggttc taagtgcagg cgataatgat ctctatttgg gactggcttc atttgaggtg    6660
cctttaggag agccgagtgg cctatgcaca gctgggtctg ctatgcagca ggaaggctaa    6720
gttggagaca gatgtgagaa ctaaccatga aggaggtaat aatgcagacc aagggtctgg    6780
ttgaaatttc ttctccccca gtccagggtg cagcgggtga gtgaaaatat gtgtgtttgt    6840
gtgtctgtct tcctagtcgg gagagaagac tgagtttgtg gctctgcgga gcatcaccat    6900
ttaaggaggg ggaaaaggag acagaaggaa ttaccagaac actccagagg gctccaagac    6960
tgtatggtgg gatctagatg gccaggagga ggggagcaaa aaggaaagag tcatccacag    7020
tatcagtagg atgccagttg aagtgttttt gctgcctccc ggttatcggt gactttgatg    7080
aaagctgtct tctggtggtc atggggtgg aggccagatc acaaggaagc tgggaatggt    7140
agatgagata gtagggctt gcatattcat tactgtctcg cagagagaaa cctgaggcta    7200
agaggggtct tggatcaaag gatggggtgg gtttatctgg tttcggggct tttgttttta    7260
atgagaagga gtcatttctg tgctgctagg agggatcaat ggaataggtg gggttaaaga    7320
tacagtacgg aatctacagt tgatggcttg atgtgacaag gtcctcaagg agcctgaaag    7380
gaaggggtgg ggtccaaggg caaaaccgag gtatgagaag aaggatgcac aaggatggtt    7440
tcgagtagac agtattgttg gtagggacat gaaggaagtt tagtggtcta ttgcagctag    7500
cctgtgttcc cagtgaacct ggaaacaagg ttctcatctg tgctcaggcc tcaggccaga    7560
aagggcaagg cagcagaggg gcaaggcagc aggctgagcc ccatttcccc ttgccataat    7620
actgctgtgc ccctctggta ccgaaaatca ggagtttcca gtgcaatata atattataca    7680
agttacactg tattataatg tgtattgtct tttagtgtgt taaccaaatt actgcagtat    7740
taaatgcaaa ttatactttg tttaactgat tcttctcttc attttagtt agaaatcctg    7800 tgttctgtca acattctcca gtttatattc attgccttaa gactggacaa gatcatccac    7860
tggccctggc ttgtatgtaa cttttaaaat ccttaaataa acttcttttt tattataaaa    7920
gtaattcata ttcactgtac aaagcttgga aaagacggac aagcagaagt aatagcctaa    7980
tagtcaccca taatcccacc atggggagat aacatggtta gtgtttttat gtctgtgttt    8040
tatacaaaca gtttggatat aactgtgtgc accattttgt atcctgattt ttttgtttta    8100
atgttgtatc ataaacattt tatcatgtta ataaaaggtc tttataaaca tgacttctaa    8160
agtttaattg atacaaaata ttcttcaagt gcatgtatca gaccatcctc ttatttctaa    8220
aatatggtat ttccattgtt gccagtgttg aatgatttta aatcatactg cagtatatat    8280
gtttatgcat taaaatttt gccttttgtt ttttggttgt tttcttagga aatagtccag    8340
aaatagtgtt actgagctag aggttgggaa ctatttgaga ttcctatata cgtatactgc    8400
actgccaact tgcttttcca aaagccatac ctggccaggc gcagtggctt acacttacag    8460
tcccagcact ttgggaggcc gaggtgagct gatcacttga gctcaggagt tcgagaccaa    8520
cctgtgcaat gtagcaagac cctgtctcaa aagaaaaaaa aaaaaagcca tacccattta    8580
cactcttgct ggtggtggca tctatgtcat gcttctaaac tgtgacttca gttactgggc    8640
atttggttga aattaactgt gaataaatgg gtagatggat gcagagatag aaagataagt    8700
ggcaaggtag aaattagaga acacagtata gattccacta ttaaatgcat ggaaaaaaga    8760
tggagactaa aggcagaaga gttccattgc cactgggagg taaggtcatg ctagtgtttt    8820
tgttcggttt tattttctct gttgtttgat gtataatttt gcatacaata tattttatgt    8880
attaaatata gctacccttaa aaagtgaaa agtatagtaa agaattggga gcagagaaga    8940
aatgaaggga acctaagtat actccatatt taaagatggg aataatcact tctgcccaaa    9000
```

```
gtctttgata aaacattcat aataaaaaat attcagtcac tcatcctaca acttcacagt    9060
gctgtatctg gagaatggtc attgggttca aaactgtttc tgttgtgacg tgaaggaaac    9120
atatctaaac aagaccaaat tttttcgtat aagatactgt cagggaaaaa aaagattagt    9180
aattttgaga gctttccaca aatgagaaga aagatttttt ctgcccttca tcctctgtag    9240
atcccagttg atgaagcagt ctgagtacat gtttcccata gtgagcaaga gaaacaagg     9300 aagcctattg agatctaaca ttccacccat gaagggaact tcagtaaaaa ggagaatctc    9360
atcacagaat ggggaacggg gaagaaaggc tgtgcataga ctctgcagag aaacctacaa    9420
tcaagaactg gtcaggagaa gtaaaattcg tatgccaact caaatcatag atctaaaaga    9480
aaatgtaaaa ctatagatct gttaggaaat aacataggac agaatctttg ggtttgcaa     9540 ttaggcagag agtacttaga aatggcactg ttaatatggt ccatacgaga gagaaatcat    9600
aaatttggac ttcctcaaaa ttaaaatgaa atgaagacag gccacagact gggagaaaat    9660
atttgcaaag cacacatcaa aacactgact tgcacccaga acatacagag aactcttaaa    9720
aactcaaaac tgcaaaaaga aacacctaaa aattggcaaa agagttgaca atttgcgaag    9780
gggatataca catggcgaaa aagcacagga aaagatgctc aacgccatta caggttaggg    9840
aagcaaaact acaaccagga tgagggcccg aaacacatgg cttcagaatg gtgaaactca    9900
gcaacactga cgaggccacg tgcctgggag gatgcagagg aactgggaca ctccagtgtt    9960
actggcggga aggcaggtgg tacgggcact gtagaaaatg gtttggccat ctctgatgca   10020
gttaaaagcg cacttcccgt gggacttggc tgccccactc ctgggtataa gatttacccc   10080
cagagaagtg aaagcgcgca gccttgtaga aacccacaca ccagtgtttg tagcagtctt   10140
gtttgcattt tggatagcgg ccttgtttgg ttttcacaaa ccaccctcag cggacagtca   10200
gataaactgt aggcatccat acaatggaat accactcaga tctgagaggg aacgacctgt   10260
ggatacaggg agggaacaac ttggatgaat ctcattagag acattatgtg gatggcggga   10320
agccagtctc aacaggttac ttgtctcgcg atgccatcta cataaagttc cagcagagac   10380
aaaagtacag tgagagaaca gatcagtgtt tgccggggct aatggtgggg acggtgtgat   10440
agtgaaggga cagcacggag agttttgcag ggtgacagac ctcttctgca tcctgccaac   10500
ggctgtgtga atctacttgt gtgaagactc agggaactca caccaaagga agacggtcac   10560
ttttcctact gtatgataga taattaataa aaagggagaa cggaggagtg tcgtcccagg   10620
aggcagggca ggagggcgaa gacgtgtcac aggggagcct ggccaagtgg cgccccggaa   10680
actcgtcctc tgggcttgtg tgtggatgag acaaggtcta cctggtacga cagggacata   10740
ctgggaatgc gcccttgccg tggaggcggg gacccggcag cgctacgtat ccagcatcaa   10800
cctgtatcca gcatcaaccc gccaagttca ctaacttggt aggggtgagg ttagggatcc   10860
ttaggagccc aggcagccag actttctggg gagcccattc ccatttgtgt tgccaaagta   10920
cccccagcag gttgtgggaa tgttgcctgt gaagagagtc tgttggggtg agatcttgtg   10980
tgtgtgcaca gggtgacagt tgtgtcccat ttcccgggaa gctgtgatgg cagcagaacc   11040
tagaggagcc tgagagagtg tgggagagtg ggcctctgga agagtagagg ctgcggagcc   11100
aggtgcaggg ctgtctgtca cccaaaggaa gagggactga tgactcactg agcgtgtgtg   11160 tccctggtg gcagcaggcc ccatagtgaa cataccatac ctttctgtc ctgagcgatg      11220 ctcccagcag tcctgggaga tggaacggtc cttattcggc tcacaggaag gaccgcctta   11280
actggacaga cacagcaagg tgctaaagat gccttccatc agaggccagg ttggaagctc   11340
```

```
taaagagact tctcttgctg ttctctcacc cacccccagg ttgtgtgtgt cccgctgtgg   11400
attctcatgt cctttctgtg cctggtggtc ctctactaca ttgtgtggtc cgtcttgttc   11460
ttgcgctcta tggatgtgat tgcggacagc gcaggacaca cataaccatg gccctgagct   11520
ggatgaccat cgtcgtgccc cttcttacat ttgaggtaag cgttccacgg gaagcctctt   11580
cagcccctga agcttgcgct tcccctgaca ggattctgca cccctagaaa ggcagcctct   11640
gtccctcgag ctcacagtga gcccactcca ggagagggga gagaacacag ccatctccga   11700
gagggagctt cggtgaaagg agagcatcct tcctttctct tggggcagc acgtgggct    11760 ggcagggaga agagtgcacc ttttagcca tggtgcctct gtatggctcc agtttccact    11820
ctggggaaag cagagtggga tgtcagattt gtgtattgga gtcacgtgga gaattctaga   11880
atgggagctg ttgactcctt agaacaaaca cccggaggag tttgccataa aactgctggc   11940
actgggaact tttcaagtgg ataggctatt gccgagctct gaagagggac ataaaagctc   12000
atttcgagct ttccccaggg ataggtgttt tcctgccttt ttctggcggt gctgatgttc   12060
cctcttgtgg gagctcacgc gggggtgggg tggtgggag gaactgccta atgaagtctg    12120
gcttccgcct ctgcccattt tcggtgctgg catcaaccgg gactatgtct ctttctttag   12180
attctgctgg ttcacaaact ggatggccac aacgccttct cctgcatccc gatctttgtc   12240
cccctttggc tctcgttgat cacgctgatg gcaaccacat ttggacagaa gggaggaaac   12300
cactgtatgt actcagcatt tcagaagtcc ttggtgtgtg tctggggggg gaccaggggg   12360 tgggggggtgg cggatagaag tctaggaagg gatgagtccc cgagggcccc aatttagaag  12420
cttgtgtggg aaagtgaggg ctgaggaaat tctgggacct tctaagggaa gggcatgccg   12480
taactctggt gttctgctgg cctgcaccgg gacttttctc gcagtgcacg ctgccatttg   12540
aggtagaacc agacacggca ggcaacctct cagagatccc gttccctcct ctgcaaaatg   12600
gggatcaaga cagattcttc ccaggcccgg gagggtttga tggaaaatcc acatctccca   12660
cccaaacctg ggattcatcc taggtccctg ttggccgctc tgcctccccc atatccttgc   12720
tgccatcacc cgagtcttgc ctgtcttgcc ttgctaacac tctattcccc tccacctgct   12780
tgctgaggca gacacttcca aaacgatctc tgcagagggt gccttcctgg caaggctgtg   12840
ggctccatgg cacggaagcc cagagcattg ccctttcggaa agccagtggg tttgggggca   12900
gggcctcact gcagcccagc agcccgggct gtgcttgctg tttgtgcctc tgcccctac    12960 cccgcacccg ggagcaggga gggcttgcac cgagctgaca ctccagtagc ctacagagag   13020
gagtagtggg actgggaaag tggctttaag gtggctccat gagttcaggc cccctcctgg   13080
ccaacccgtg catgactacc gccctcacgg attccagagg gtgacagaaa tcttgttctt   13140
gggtggcact gtcatccatg agtttatcct ggctggagaa gattagcgga agacaccgta   13200
gtctgcgcac cacagatatt ttgagactca ctggagcagt agttctcaaa tttgggcatc   13260
cagcagaatc ccaaaaggc caggaaaagg gaccgctgg agcccaccct agcccgactc     13320
agtttctgga ggtctgggct ggggcccgag aatggcatcc ctaactaggc cccgtggacg   13380
ctgtccctgc cggtccggga accccactcc aagcaccaca gagctagcat ttgcacttct   13440
tccccatttt gggtactcaa gccctgttca ggctttgtga ctcaggagtc tggataaagt   13500
atgttatgac attgtaggag tgaaacttct tgttacggaa agaagttaa caggaaggtc    13560 agttgagcct cgtgtgtgaa ataaaaaatt cttattttc agggtggttt ggtatccgca    13620
aagatttctg tcagttttctg cttgaaatct tcccatttct acgagaatat ggaaacattt   13680
cctatgatct ccatcacgaa gataatgaag aaaccgaaga gaccccagtt ccggagcccc   13740
```

```
ctaaaatcgc acccatgttt cgaaagaagg ccagggtggt cattacccag agccctggga   13800
agtatgtgct cccacctccc aaattaaata tcgaaatgcc agattagatg ccacttccgg   13860
ggacagagct taagtggact gggacgcact ctctccgcct tcctctgccc cctcgttcac   13920
cccgcagacc agaaccagta ctggagctgg gtctccaggt acgtccatct catgccttgt   13980
ttgcatccag cgcctatcag ccactcacca cgacgggacg cggaagtggc aggtgacggg   14040
ggtgtgtgcc agcagatgcg gatgccagga agagtgtgag aacaggggtg ggattaccgt   14100
ctgtctggga ggggctccag gtacccctct tccccgtcag acccactggg agatggctgc   14160
ttgccaggcc cccagaagga acatctgtct atacggtgct gaaatcccaa tcaaaagtat   14220
tgtttagaaa tgtatttctc cacagggctg acctcctgca gctcgctgag cactcccagg   14280
tcctcagcac tcccaggtcg tggctggggc agtcagtagg aactgtaact atgtctctga   14340
tgcaccacgt gtttagacac agcacagtcc ttttttctgt tcctactgtg aagtagttt   14400
ctctttgggc atgctgacag cagttttttca tagcctcacg gatgagccct ttctacggga   14460
gtgactccat gcttgtatac agagtattta tacaaatgtt ttagcatctt catatgcggt   14520
gttaacccct agttctgtac agcatattct gttcaagtat ttttttacaa gcttgtgctg   14580
taggcacatg ccttctgctg cagaagtgga cgcccgtggc acactccccc ccccccccg   14640
tggggtgcca cgccttcatg ggacattgcc acttctgccc tggaactcgt gcaggtacgt   14700
agtagctgct actgccacaa cggcaacacc aagcaagaga tggtccatgc tttctgacg   14760
ttctcagaat agtggctagc ttcaaacctg acaagcgctg cttgaagccg aacactaga   14820
gaatgttgct gagagcagaa acggccacgc gggtcacgac tatgcgtggg aaagtctcaa   14880
gcttccctcc tgccagcaac aagaaggctt tggagtaggc atgatgtttt cacgtgtgcg   14940
tgccgtttct ccaagcactg caggttccac cgtgtgtcag aggctgcaag tttaacatcc   15000
tcctgcctga aaacaaatag gtcctttgct gaaaagaggg taaaaaaaga ctttgatct   15060
tctcagccag gagaagaggg tggtgttttc acgcgggcaa ctgctcgccg gcctacatgg   15120
ggttaattca agtctgctgc gagcacgact ccgcccttgg cactggcctc cagcaagccc   15180
tgttctcttt ggggtacagg ggaacgggat ggtttagact ttcctgctca gtgtgtaaaa   15240
aatgtagcta aagccactat ttttgctctc cttaagctgt tcaataaacc ggttcctcat   15300
tttacacgtg catgatgtgt atcttctttg ctggatgggc caggaaactg gagtggtcct   15360
ctcagccagc ctcagaggaa agaaatctct agctggcaca gcagccagt gagtgaggct   15420
ggcggctgca ggggcacagc ctttagaatg agtccttcag tgcacaggtc ccagggtata   15480
cggggtagtg ggaggaagga ggggacgcct cgcagatgcc actgttggct gggctacacc   15540
ttgccacact tgttactgct taggaggctt tctggagtgt tccttgggtg ctacgacaat   15600
ctgcagcaga cactgtcctt tcaccgctcc tggtcctcgt ttgctcccca gtgatgtcaa   15660
cagctgagga ctgctcacgc tgcaacaaaa ggctctgcag tcgctgtcta gcttgcccta   15720
gtcgtctcta gagttctgcc tgaactgaaa ctcaagtggg gttcagctca tgacttgtgg   15780
caattgacca ggaaattcac cagttgctgt ggctggaagg atttttcagtc ctgtgggttg   15840
taaccagagg ccacaggtgg attctgcctt aggctcatga gatttccgac ttgctgttga   15900
agaaaatgcc ttgtgaagtg acaacagtag ctctgaccca actgccggtg cctcgctagt   15960
tcctatacgt cccactggat cctcacagcc ccgggaagca ggtgctacta ctcttatccc   16020
cgggaggaga cagaggccga gagaggttaa gtgacgtgcc caagtcacac agctcggcag   16080
```

```
cggccgggtt gagcatcagc agtctgtttg cagacccctc actgtcaccc cctgagccag    16140
tgcgccttgg gccctgcggt caggatgtct caagcgtgga ggcatcaccg gttcgtggca    16200
gtctctggaa ggtcactgag ctctgtgccc agaatcgagt cggggagtc tgtgcagagg     16260
tggccctgtg tgtggggaca gtgtgtgaca cagacactgc tttggatgga cacctctccc    16320
gtgacctcct agcatccaat cccaaaggaa caactgttgc agagatggac cgctggacac    16380
aaacccacgt gcgtttctct ggagacactg gccaaggaaa acaaaacatg ctcgaaggcc    16440
aacagctgca tgccccaccg cgatgtgacc gcagacaccc ggggtgtaga agggtctctg    16500
cctggtgggg ggacacgtgc aggccgagga gaggcaggaa ggaggctgcc tccgactccc    16560
cactggactg catggcgacg gcgtgtggtg gggcagtcag ctaagccatt tgcctaaggg    16620
gctgtcgggc atctgcgtgc tggggaccga cagtgtgggt gtgttaggag gatctgtatg    16680
gagcacattg ctgcctctgg ctaggacagg gtggaaaggg tggcgtggct acagcctgac    16740
ccatgggcac cgtcctaccc tttgttctgt gcttccgagt gtcagtcatg tgctggggtc    16800
tgtgggccca tgactcagac ggtgagctct gaccttcctg agccagggct tgctgtagt    16860
tgtgcctggc tcaggagctc taggacaagg ggaccgctcc aggtctgcat ctacggtgtg    16920
gcagggcccc tcggcactct tgtgcactag tgtcatcttt cccattgaaa tgactgtgag    16980
gaccagaatg tgcacatgca gatgggcagc tacttgtctg ccttggccct ttattacaca    17040
acttgctggg ggtggagatg ccacccccg gcagtcagag ccccttatg atgtcatggg      17100
gctggttaca tgactgccaa ggggtgctgc tggccacact gcactagcaa gtttgccaga    17160
tggaggacaa gcgatcattg agtatggctc gctgtgaaga aagaaattcg agaggacagg    17220
atcatggctt ggaaagggtg cctttccctc cccagttgca gtcagagacc taccttcacc    17280
cagcagatcc ttcccctgcc tgggacgacc cggggtccac tgggagccct aacttgaggc    17340
tgctgacaga agaaatcgct ttccaacctc tggccgagga agcttcgttc agaaggccgc    17400
accctgacgg tgacgtcccg ccccagggag aagataatct cctctcccct ccctttccac    17460
agaaactgtg gagactggtc agcagcaacc agttttcgtc catctggtgg gatgacagtg    17520
gggcttgtag agtgatcaat caaaaactct ttgaaaagga gattctcaaa agggacgtcg    17580
cacacaaagt gtttgccaca acttcgataa agagcttctt ccgccagcta aacttgtatg    17640
gcttccgaaa acggcgtcaa tgcactttca ggaccttcac ccgcattttc tccgcaaaaa    17700
ggctggtctc catcttgaat aaggtaatga acgacaagcc tctggagggg ttaagtcggt    17760
gggctctggg gcctggtcgg gtggaagtcc caggactgcc tcctgggaag tgggcgacct    17820
caggcagggt gtgggccat cgctgtgggc ctgtgtcccc ctctggtgg aggtgacatg       17880
aactaagagt gaatgtgggg agagggctga ggatggtgcg ggcccctctc gagtgtgtaa    17940
aatatcacag gtgccaagta gccgtatctg cgtgtcgtcc tccccggggc cagccatgtc    18000
atctggtggt tgctgtgtcc ccctgactcc acagcacatt accctgtgag gtgagcaggc    18060
caggggagtc tggtatttgt accactgtca ccctagctgg tgtctggaga ggtgctcaag    18120
tggaagcact gaagggcgcc tggcgcagga ggtgcagatg ctcctgctgc ccttggtagg    18180
tgggcccctg gtgtggaaga gccagtaccc agggcctcca acccagccgg ggtgcattct    18240
gttgccagct gacactgcat gggggaggcc cagaatcttc ttccctcctg gtctgcaact    18300
tcaaagaccc tttccgccgg ccatggacac cctaatctgc cattttgagg cttttttccaa   18360
gacggaaagg cccgccacaa cttggtaaac cttgacgatg tgaacgcgag tccccagctt    18420
cctttgggga ctgggacctt ttccagaaag gcctcctggg ccagtagagt tctcttgcac    18480
``` agggggcgtag atggttggta gttgtagtcc atccttgtga cttg   18524

<210> SEQ ID NO 13
<211> LENGTH: 7695
<212> TYPE: DNA
<213> ORGANISM: Homo sapiens

<400> SEQUENCE: 13

| | | | | | |
|---|---|---|---|---|---|
| ggcccaggag | gcctttctgg | aaaaggtccc | agtccccaaa | ggaagctggg | gactcgcgtt | 60 |
| cacatcgtca | aggtttacca | agttgtggcg | ggcctttccg | tcttggaaaa | agcctcaaaa | 120 |
| tggcagatta | gggtgtccat | ggccggcgga | aagggtcttt | gaagttgcag | accaggaggg | 180 |
| aagaagattc | tgggcctccc | ccatgcagtg | tcagctggca | acagaatgca | ccccggctgg | 240 |
| gttggaggcc | ctgggtactg | gctcttccac | accaggggcc | cacctaccaa | gggcagcagg | 300 |
| agcatctgca | cctcctgcgc | caggcgccct | tcagtgcttc | cacttgagca | cctctccaga | 360 |
| caccagctag | ggtgacagtg | gtacaaatac | cagactcccc | tggcctgctc | acctcacagg | 420 |
| gtaatgtgct | gtggagtcag | ggggacacag | caaccaccag | atgacatggc | tggccccggg | 480 |
| gaggacgaca | cgcagatacg | gctacttggc | acctgtgata | ttttacacac | tcgagagggg | 540 |
| cccgcaccat | cctcagccct | ctccccacat | tcactcttag | ttcatgtcac | ctccacccag | 600 |
| agggggacac | aggcccacag | cgatggcccc | acaccctgcc | tgaggtcgcc | cacttcccag | 660 |
| gaggcagtcc | tgggacttcc | acccgaccag | gccccagagc | ccaccgactt | aaccccctcca | 720 |
| gaggcttgtc | gttcattacc | ttattcaaga | tggagaccag | ccttttttgcg | gagaaaatgc | 780 |
| gggtgaaggt | cctgaaagtg | cattgacgcc | gttttcggaa | gccatacaag | tttagctggc | 840 |
| ggaagaagct | ctttatcgaa | gttgtggcaa | acactttgtg | tgcgacgtcc | cttttgagaa | 900 |
| tctcctttc | aaagagtttt | tgattgatca | ctctacaagc | cccactgtca | tcccaccaga | 960 |
| tggacgaaaa | ctggttgctg | ctgaccagtc | tccacagttt | ctgtggaaag | gggagggaga | 1020 |
| ggagattatc | ttctccctgg | ggcgggacgt | caccgtcagg | gtgcggcctt | ctgaacgaag | 1080 |
| cttcctcggc | cagaggttgg | aaagcgattt | cttctgtcag | cagcctcaag | ttagggctcc | 1140 |
| cagtggaccc | cgggtcgtcc | caggcagggg | aaggatctgc | tgggtgaagg | taggtctctg | 1200 |
| actgcaactg | ggagggaaa | ggcacccttt | ccaagccatg | atcctgtcct | ctcgaatttc | 1260 |
| tttcttcaca | gcgagccata | ctcaatgatc | gcttgtcctc | catctggcaa | acttgctagt | 1320 |
| gcagtgtggc | cagcagcacc | ccttggcagt | catgtaacca | gccccatgac | atcataaagg | 1380 |
| ggctctgact | gccgggggggt | ggcatctcca | ccccagcaa | gttgtgtaat | aaagggccaa | 1440 |
| ggcagacaag | tagctgccca | tctgcatgtg | cacattctgg | tcctcacagt | catttcaatg | 1500 |
| ggaaagatga | cactagtgca | caagagtgcc | gagggggccct | gccacaccgt | agatgcagac | 1560 |
| ctggagcggt | ccccttgtcc | tagagctcct | gagccaggca | caactacagc | aaaagccctgg | 1620 |
| ctcaggaagg | tcagagctca | ccgtctgagt | catgggccca | cagaccccag | cacatgactg | 1680 |
| acactcggaa | gcacagaaca | aagggtagga | cggtgcccat | gggtcaggct | gtagccacgc | 1740 |
| cacccctttcc | accctgtcct | agccagaggc | agcaatgtgc | tccatacaga | tcctcctaac | 1800 |
| acacccacac | tgtcggtccc | cagcacgcag | atgcccgaca | gcccttagg | caaatggctt | 1860 |
| agctgactgc | cccaccacac | gccgtcgcca | tgcagtccag | tggggagtcg | gaggcagcct | 1920 |
| ccttcctgcc | tctcctcggc | ctgcacgtgt | ccccccacca | ggcagagacc | cttctacacc | 1980 |
| ccgggtgtct | gcggtcacat | cgcggtgggg | catgcagctg | ttggccttcg | agcatgtttt | 2040 |

```
gttttccttg gccagtgtct ccagagaaac gcacgtgggt ttgtgtccag cggtccatct    2100
ctgcaacagt tgttcctttg ggattggatg ctaggaggtc acgggagagg tgtccatcca    2160
aagcagtgtc tgtgtcacac actgtcccca cacacagggc cacctctgca cagactcccc    2220
cgactcgatt ctgggcacag agctcagtga ccttccagag actgccacga accggtgatg    2280
cctccacgct tgagacatcc tgaccgcagg gcccaaggcg cactggctca ggggtgaca    2340 gtgagggtc tgcaaacaga ctgctgatgc tcaacccggc cgctgccgag ctgtgtgact    2400
tgggcacgtc acttaacctc tctcggcctc tgtctcctcc cggggataag agtagtagca    2460
cctgcttccc ggggctgtga ggatccagtg ggacgtatag gaactagcga ggcaccggca    2520
gttgggtcag agctactgtt gtcacttcac aaggcatttt cttcaacagc aagtcggaaa    2580
tctcatgagc ctaaggcaga atccacctgt ggcctctggt tacaacccac aggactgaaa    2640
atccttccag ccacagcaac tggtgaattt cctggtcaat tgccacaagt catgagctga    2700
accccacttg agtttcagtt caggcagaac tctagacg actagggcaa gctagacagc       2760
gactgcagag cctttgttg cagcgtgagc agtcctcagc tgttgacatc actggggagc       2820
aaacgaggac caggagcggt gaaaggacag tgtctgctgc agattgtcgt agcacccaag    2880
gaacactcca gaaagcctcc taagcagtaa caagtgtggc aaggtgtagc ccagccaaca    2940
gtggcatctg cgaggcgtcc cctccttcct cccactaccc cgtataccct gggacctgtg    3000
cactgaagga ctcattctaa aggctgtgcc cctgcagccg ccagcctcac tcactggctg    3060
cctgtgccag ctagagattt ctttcctctg aggctggctg agaggaccac tccagtttcc    3120
tggcccatcc agcaaagaag atacacatca tgcacgtgta aaatgaggaa ccggtttatt    3180
gaacagctta aggagagcaa aaatagtggc tttagctaca ttttttacac actgagcagg    3240
aaagtctaaa ccatcccgtt ccctgtacc ccaaagagaa cagggcttgc tggaggccag    3300
tgccaagggc ggagtcgtgc tcgcagcaga cttgaattaa ccccatgtag gccggcgagc    3360
agttgcccgc gtgaaaacac caccctcttc tcctggctga aagatcaaa gctcttttt    3420 taccctcttt tcagcaaagg acctatttgt tttcaggcag gaggatgtta aacttgcagc    3480
ctctgacaca cggtggaacc tgcagtgctt ggagaaacgg cacgcacacg tgaaaacatc    3540
atgcctactc caaagccttc ttgttgctgg caggagggaa gcttgagact ttccacgca    3600 tagtcgtgac ccgcgtggcc gtttctgctc tcagcaacat tctctagtgt tccggcttca    3660
agcagcgctt gtcaggtttg aagctagcca ctattctgag aacgtcagaa aagcatggac    3720
catctcttgc ttggtgttgc cgttgtgca gtagcagcta ctacgtacct gcacgagttc     3780
cagggcagaa gtggcaatgt cccatgaagg cgtggcaccc acggggggg gggggggagt    3840 gtgccacggg cgtccacttc tgcagcagaa ggcatgtgcc tacagcacaa gcttgtaaaa    3900
aaatacttga acagaatatg ctgtacagaa ctaggggtta acaccgcata tgaagatgct    3960
aaaacatttg tataaatact ctgtatacaa gcatggagtc actcccgtag aaagggctca    4020
tccgtgaggc tatgaaaaac tgctgtcagc atgcccaaag agaaactact tccacagtag    4080
gaacagaaaa aaggactgtg ctgtgtctaa acacgtggtg catcagagac atagttacag    4140
ttcctactga ctgccccagc cacgacctgg gagtgctgag gacctgggag tgctcagcga    4200
gctgcaggag gtcagccctg tgagaaaata catttctaaa caatactttt gattgggatt    4260
tcagcaccgt atagacagat gttccttctg ggggcctggc aagcagccat ctcccagtgg    4320
gtctgacggg gaagaggggt acctggagcc cctcccagac agacggtaat cccaccctg    4380 ttctcacact cttcctggca tccgcatctg ctggcacaca ccccgtcac ctgccacttc     4440
```

```
cgcgtcccgt cgtggtgagt ggctgatagg cgctggatgc aaacaaggca tgagatggac    4500
gtacctggag acccagctcc agtactggtt ctggtctgcg gggtgaacga gggggcagag    4560
gaaggcggag agagtgcgtc ccagtccact taagctctgt ccccggaagt ggcatctaat    4620
ctggcatttc gatatttaat ttgggaggtg ggagcacata cttcccaggg ctctgggtaa    4680
tgaccaccct ggccttcttt cgaaacatgg gtgcgatttt aggggctcc ggaactgggg     4740 tctcttcggt ttcttcatta tcttcgtgat ggagatcata ggaaatgttt ccatattctc    4800
gtagaaatgg gaagatttca agcagaaact gacagaaatc tttgcggata ccaaaccacc    4860
ctgaaaaata agaatttttt atttcacaca cgaggctcaa ctgaccttcc tgttaacttt    4920
ctttccgtaa caagaagttt cactcctaca atgtcataac atactttatc cagactcctg    4980
agtcacaaag cctgaacagg gcttgagtac ccaaaatggg gaagaagtgc aaatgctagc    5040
tctgtggtgc ttggagtggg gttcccggac cggcagggac agcgtccacg ggcctagtt     5100 agggatgcca ttctcgggcc ccagcccaga cctccagaaa ctgagtcggg ctagggtggg    5160
ctccagcggt ccccttttcc tggccctttt gggattctgc tggatgccca aatttgagaa    5220
ctactgctcc agtgagtctc aaaatatctg tggtgcgcag actacggtgt cttccgctaa    5280
tcttctccag ccaggataaa ctcatggatg acagtgccac ccaagaacaa gatttctgtc    5340
accctctgga atccgtgagg gcggtagtca tgcacgggtt ggccaggagg gggcctgaac    5400
tcatggagcc accttaaagc cactttccca gtcccactac tcctctctgt aggctactgg    5460
agtgtcagct cggtgcaagc cctccctgct cccgggtgcg gggtagggg cagaggcaca     5520 aacagcaagc acagcccggg ctgctgggct gcagtgaggc cctgccccca aacccactgg    5580 cttttccgaag ggcaatgctc tgggcttccg tgccatggag cccacagcct tgccaggaag   5640
gcaccctctg cagagatcgt tttggaagtg tctgcctcag caagcaggtg gaggggaata    5700
gagtgttagc aaggcaagac aggcaagact cgggtgatgg cagcaaggat atggggagg     5760 cagagcggcc aacagggacc taggatgaat cccaggtttg ggtgggagat gtggattttc    5820
catcaaaccc tcccgggcct gggaagaatc tgtcttgatc cccatttttgc agaggaggga   5880 acgggatctc tgagaggttg cctgccgtgt ctggttctac ctcaaatggc agcgtgcact    5940
gcgagaaaag tcccggtgca ggccagcaga acaccagagt tacggcatgc ccttccctta   6000
gaaggtccca gaatttcctc agccctcact ttcccacaca agcttctaaa ttggggccct    6060
cggggactca tcccttccta gacttctatc cgccaccccc cacccctgg tccccccca     6120 gacacacacc aaggacttct gaaatgctga gtacatacag tggtttcctc ccttctgtcc    6180
aaatgtggtt gccatcagcg tgatcaacga gagccaaagg gggacaaaga tcggatgca    6240 ggagaaggcg ttgtggccat ccagtttgtg aaccagcaga atctaaagaa agagacatag    6300
tcccggttga tgccagcacc gaaaatgggc agaggcggaa gccagacttc attaggcagt    6360
tcctccccac caccccaccc ccgcgtgagc tcccacaaga gggaacatca gcaccgccag    6420
aaaaaggcag gaaaccacct atccctgggg aaagctcgaa atgagctttt atgtccctct    6480
tcagagctcg gcaatagcct atccacttga aaagttccca gtgccagcag tttatggca    6540 aactcctccg ggtgtttgtt ctaaggagtc aacagctccc attctagaat tctccacgtg    6600
actccaatac acaaatctga catcccactc tgctttcccc agagtggaaa ctggagccat    6660
acagaggcac catggctaaa aaggtgcact cttctccctg ccagcccac gtgctgcccc     6720 caagagaaag gaaggatgct ctcctttcac cgaagctccc tctcggagat ggctgtgttc    6780
```

-continued

| | |
|---|---|
| tctcccctct cctggagtgg gctcactgtg agctcgaggg acagaggctg cctttctagg | 6840 |
| ggtgcagaat cctgtcaggg gaagcgcaag cttcaggggc tgaagaggct tcccgtggaa | 6900 |
| cgcttacctc aaatgtaaga aggggcacga cgatggtcat ccagctcagg gccatggtta | 6960 |
| tgtgtgtcct gcgctgtccg caatcacatc catagagcgc aagaacaaga cggaccacac | 7020 |
| aatgtagtag aggaccacca ggcacagaaa ggacatgaga atccacagcg ggacacacac | 7080 |
| aacctgggggg tgggtgagag aacagcaaga gaagtctctt tagagcttcc aacctggcct | 7140 |
| ctgatggaag gcatctttag caccttgctg tgtctgtcca gttaaggcgg tccttcctgt | 7200 |
| gagccgaata aggaccgttc catctcccag gactgctggg agcatcgctc aggacagaaa | 7260 |
| aggtatggta tgttcactat ggggcctgct gccaccaggg gacacacacg ctcagtgagt | 7320 |
| catcagtccc tcttcctttg ggtgacagac agccctgcac ctggctccgc agcctctact | 7380 |
| cttccagagg cccactctcc cacactctct caggctcctc taggttctgc tgccatcaca | 7440 |
| gcttcccgga aaatgggaca caactgtcac cctgtgcaca cacacaagat ctcaccccaa | 7500 |
| cagactctct tcacaggcaa cattcccaca acctgctggg ggtactttgg caacacaaat | 7560 |
| gggaatgggc tccccagaaa gtctggctgc ctgggctcct aaggatccct aacctcaccc | 7620 |
| ctaccaagtt agtgaacttg gcgggttgat gctggataca ggttgatgct ggatacgtag | 7680 |
| cgctgccggg tgacc | 7695 |

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 14

| | |
|---|---|
| gggcgaattg ggcccgacgt cgcatgctcc cggccgccat ggcggccgcg ggaattcgat | 60 |
| atcactagtg aattcgcggc cggcgattgg gcccgacgtc gcatgctccc ggccgccatg | 120 |
| gcggccgcgg gaattcgatt ccttaattaa gtcgactggg acccaaactt ggagtcgtt | 180 |
| gacagatgtg acaggtgaag cctgggatga catcgccaaa aatgcaacgt ctcactcatt | 240 |
| gtcactactc ccagggctca gtcgtcactg gggaaaatct ccagaaggta gcgcgggcca | 300 |
| aggtgacagg tgtctgccaa gatctgcccg ccagactccc gggcggcgcg ctccctccct | 360 |
| gcaggccttc agcccgtcag catccccttc ctcggggccc tgctcactcc cagcctccat | 420 |
| cccctgcca tctcctccgc cggtcgcgtg cggacacaag gatgggacc tcccagcgag | 480 |
| gagcgctctg ggcggggctc cggacgcatg cgcggccctc gtacgaagc ccggaaggag | 540 |
| gggcagggggg cggtggctca ggtttctccg ggcggcggcg gcggcggcgg cggcgacggc | 600 |
| gacggcgacg gcagcgggga cggcagcagt agcgggagca gcagcgtgga cgcggctggc | 660 |
| gctggcgcca tgaacccgct gtaaggcgca ggctgtgcag cacggggtgc ggggaggag | 720 |
| gaggaggacg ccgcggtgaa gttctccgcc atgaacctga ggggcctctt ccaggacttc | 780 |
| aacccgaggt gaggcggcgt cgttggcgcc cccgggagtc cgcgctgcgg gctcgggcgc | 840 |
| gggctggtgt tcggctccgg ggaggcacgg cgggcgagat gctgcagccc gaggacccgg | 900 |
| gcgcctgccc gagcctccct gcgggtgcaa gcggtcccca ggcaaaacag tcggcctcgg | 960 |
| cgcccgcccg cttcctcctc ccgtgccgg tgctttcagc ccctgccgg ccacggccgg | 1020 |
| aagggcccgg ccgcgagccc cgtcctgccc caagggaacc ccattctttt ctgcttgctg | 1080 |

```
tccctcattg gtgtcccaac ttcttcgtct cggttccatc ctcttctgcg ccgctgcggg   1140
ccctccattc tccgcgtcag ggccgtctca ctcgacccaa caccccctacc cccacccag   1200 ctgtttcctc cagttcctcg cagtccttgg ggttttcctt gggtttatgc ccatccctct   1260
cttgtttgct tctttgttga acggatacct gaaacactgt tgaatccttg gagtcagtgt   1320
cggggtatgg caataccta tataatgcat ttctgggtga gcctgatcat tttccatact   1380
cattttctca tcagtcttca ctacaagttt atttgcagga agtagatatt gctgtccttc   1440
ttttccagat ggggaacacc cagtggacag tgtggagaaa acactggcta agcactcaag   1500
cgcctgtcct tgcacttgcc cgactgtttt gtaactgttc tttaccccag gctgtgagct   1560
ccctgaagct gagaccatct cctgctcatc tcagtgtccc cagcgcctcc cacccaccgt   1620
atctggcaca tagtaggcac atataaaatg tttgtggaac taaactgagc ccaaagactt   1680
ggattggaga cgaggccata tgtaactggg tgattctctg cccttctttg gcccttctgt   1740
aaaatgagga gttggcctaa ctgatctctt aaatgcacta ctctccgaaa ggagtatccg   1800
tttcccttat ttgccagttg ggaagacgtg ctcagtaaat atttgtgtgc tgtaacctat   1860
gttaggtgct ttagatgctg gcggtctcag catgggtga agaagggctt gtacacttaa    1920
gatgccttac agtactgtgc agtgctgtac tgcggggcc aactctgggg acctatgcct    1980
tggctgcttg ttgaggatga aaggaagttt taggggagta tttgtatgtt gagggtgcag   2040
tctccctagg gatggtgaca ttttaacttg tgagtcattg tgactttgta tgtgccctta   2100
ttccactttg agttcatgtt ctggttagga gtgccagtgt ctctaacacg gtgcagacat   2160
tatcattgtt ggcttcgaag gcatagagga ggtaacagaa ctaactgcag tcccttcctc   2220
tgctgcatca gggggttaag attggtctgc agggtagtag ggttggtgct gtggctggac   2280
aagccctgta tgtcttctat ttggagatgg tgataagaaa gttaagtaaa aactgaattg   2340
ttttgtgccc ttgggcaact cacttatcta ttgtttttatc tgtagaatga gtataatctc   2400
tcagtggggt agggaggcca attaaggatt gattacaaag tgccttacaa atagaaagct   2460
acagtgactt gtttgcaagg tgacagagaa ttcagaagcc tcagaaaact gccttaagtg   2520
atcaaacagg ctaacggagt tgccaaagca aaatagtgct gcactgatac tacctttaac   2580
cgttttttcc tttagccctt ttccccccaa aaaaattagt atatgaaatt acagtgaaat   2640
acctggtatc taagcagatt tatagtaatt ctcaacatat tcatcaatct cttaattcta   2700
cctgcattaa aatgtatttc tacctgaaaa gtttaaaggt cttttatact gtgccatttt   2760
cctgattcat tgttgccaga ggtagtgagt tccttaattt tacagatatt tcaagaggac   2820
attggccagg tattattggt aaatcagatt tgttttttta gctggtagtg tttcacctct   2880
cctgagcact cctagttttt gacagtgtgc tttagtctcc ttccatgctg aggaaggcct   2940
tctctatagg agaaagaaaa ctgaggggtg tacacaggaa gttaccttat gctggggact   3000
caaaccttga tgctactgct ttgctccctg cctctatttt tgaaccaatt caacatctcc   3060
ctcctacccc aggaccttgt cacacactgt tctctttacc aggaatgttt ccctctcttt   3120
tcctctcctc cagacctagt gaactcctat ttatcctcac ttggcacttg ctaagggaag   3180
cattcctgac ttccctgacc agatttactg ctccctgttt ctacagttcc tgtagtattt   3240
actactcctc catcatagtg catatttgta cccttgtgtc tgtctggatg cttatttgat   3300
taatacctgc ctcccccact aaactttaag ctccatgggg tcaaggccgt gactgtgtca   3360
gtatcgtagc ctgcatactt ggaatagtac ctggctcaat aaatatttgt ggagtaaata   3420
actgaataac tctccagagc ctataagata aatctagagc tgctgctttc aatcactgct   3480
```

```
ttcctggtgg tctgtggcct ggttctcttt cttctcacac tcttcccacc ttcagagtgc    3540
agccattgct ttggagagat gggagagaac atggcactaa ggcagaatat ggctatattt    3600
actttgaaga gcatgtcttt gtcatagaaa tagtcactgt catggtttgg tgggtcccaa    3660
ggcatgggtc atggctccag atccccttc cagccttttg gatcttggta agtctgaacc    3720
cactgctgcg ttggcaaggc tctggaaact atagtgacag agaatgattc acaagtgtca    3780
acactcagat gtacagggct gccagctgac ccactctacc tatttccatc tggcactgaa    3840
ctggttgatc atgaacttct tttcataatt gcttttagt tatgcaggtt aagacatgcc     3900
gaaacagatg taccggaccc acaaacaagt ccttccttga atgcctgagg cttcctaaca    3960
gtgaaagagc cctgttctta gagtaggcaa actgattctg aggcattgta ggtggtaggg    4020
atctggtagt aggtagcatt aggtgggctc ccggcactca ccatggagcc ttgaaatttt    4080
ctgctacttt gggggagttg ctggttcaga gaaggcccctt ccaccctggt agccatgtgg    4140
cactggaagg ctgtgaaaac tctgctgggc cttcttagtc atctgttgtg agctcctgat    4200
gggagtgtgg tgtatccctc aggtgtgcta gactggaaca aaggctgaga gtgttgctc    4260 tgggggttcc aacttgtggg catggggtac tgatgagatc agtagtgttt ggagacttct    4320
gtatgctcca tcttcagaag acattctgga gtccatataa gttatcttgt ctcttgtttg    4380
aagcaggaaa aaggaatgcg attgctggta atatagttca ctaaagtcag ctacctggcc    4440
tctaacagtt atttgcaaag tatattataa cattgattcc tcaaacatct agattcctat    4500
ctcgtgccaa gtgatgtact aggtgctcta agtacaaaaa taaaggaata tagtcctcct    4560
ctcaatgcgt aagcctagtg gaagaagcag aaatgaaagg gaaataagaa ttcaatagag    4620
tatgaggcat tacagtgaaa gaaaccaaat gtcttagaaa tacaaatggc agagctacta    4680
attctgtctc gagcaggcag ggaagagtct atagtggaaa tgacttttga gctagatttt    4740
gaattgagct agtcttttga gccagacttt tgagctagaa ttgtagggtt gtcatcagac    4800
cagagagtag gaagggtacc ttgtgaggaa gagagagaga gatcagattg ttactgtgtc    4860
tatgtagaaa aggaagacat aagaaactcc attttgatct gtactaagaa aaattgtttc    4920
tgctttgaga tgctgttaac ctgtaacttt agtcccaacc ctgtgctcac agaaacctgt    4980
gctgtaatga atcaaggttt aatggattta gggctgtgca ggatgtacct tgttaacaat    5040
atgtttgcag gcagtatgct tggtaaaagt catcgccatt ctccattctc gattaaccag    5100
ggacacagtg cactgcggaa ggccgcaggg acatctgccc aagaaagcct gggtattgtc    5160
caaggtttcc ccccactgag acagcctgag atatggcctt gtgggaaagg aaagacctta    5220 ccaccccca gcccgacacc cgtaaagtgt ctgtgctgag gaggagtagt gaaagagcgg    5280
ggcctctttg cagttgagat aagaggaagg cttctgtctc ctgctcatcc ctgggaatgg    5340
aatgtctctg tgtaaagctg accattccca ttcgttctat tctgagatag gagaaaacca    5400
ccctgtggct ggaggcgaag tatgctggca gcaatactgc tctgttactc tttgctacac    5460
tgagttgttt gggtaaagag aaacataaat ctagcctgcg tgcacatcca ggcacagtac    5520 cttccttga acttattcat gatacagatt cctttgctca cgtttccctg ctgaccttct    5580
ccccacctgt tgccctgcta cactcccctc gctaagatag taaaataat gatcagtaaa    5640 tactgaggta actcagaggc tagcgctggt gcgggtcctc cgtatgctga gtgccggtcc    5700
cctgggccca ctgttctttc tctatacttt gtttctgtgt cttatttctt ttctcagtct    5760
cgtcccacct gacgagaaat acccacaggt gtggaggggc tggccccttt cagtatctca    5820
```

-continued

| | | | | |
|---|---|---|---|---|
| gaagggacaa | agtacacaaa | ggcatggggt | catgatagtg | cctggtatgt tcaggtagtg | 5880 |
| aagaggtcca | tgtggtatga | gcactgcaga | tgatatgtgt | cgtatgaatt aaaaatacat | 5940 |
| agttactgca | aatagttttt | acaggttatt | gttttaaga | aagcagtatc taatgcacga | 6000 |
| gtgtactgtc | agtactgtca | atgaactact | taccactcaa | gtgactgctt acgcgtcgaa | 6060 |
| tcactagtga | attcgcggcc | gcctgcaggt | cgaccatatg | ggagagctcc caacgcgttg | 6120 |
| gatgcatagc | ttgagtattc | tatagtgtca | cctaaatagc | ttggcgtaat catggtcata | 6180 |
| gctgtttcct | gtgtgaaatt | gttatccgct | cacaattcca | cacaacatac gagccggaag | 6240 |
| cataaagtgt | aaagcctggg | gtgcctaatg | agtgagctaa | ctcacattaa ttgcgttgcg | 6300 |
| ctcactgccc | gctttccagt | cgggaaacct | gtcgtgccag | ctgcattaat gaatcggcca | 6360 |
| acgcgcgggg | agaggcggtt | tgcgtattgg | gcgctcttcc | gcttcctcgc tcactgactc | 6420 |
| gctgcgctcg | gtcgttcggc | tgcggcgagc | ggtatcagct | cactcaaagg cggtaatacg | 6480 |
| gttatccaca | gaatcagggg | ataacgcagg | aaagaacatg | tgagcaaaag gccagcaaaa | 6540 |
| ggccaggaac | cgtaaaaagg | ccgcgttgct | ggcgtttttc | cataggctcc gcccccctga | 6600 |
| cgagcatcac | aaaaatcgac | gctcaagtca | gaggtggcga | aacccgacag gactataaag | 6660 |
| ataccaggcg | tttccccctg | gaagctccct | cgtgcgctct | cctgttccga ccctgccgct | 6720 |
| taccggatac | ctgtccgcct | ttctcccttc | gggaagcgtg | gcgctttctc atagctcacg | 6780 |
| ctgtaggtat | ctcagttcgg | tgtaggtcgt | tcgctccaag | ctgggctgtg tgcacgaacc | 6840 |
| ccccgttcag | cccgaccgct | gcgccttatc | cggtaactat | cgtcttgagt ccaacccggt | 6900 |
| aagacacgac | ttatcgccac | tggcagcagc | cactggtaac | aggattagca gagcgaggta | 6960 |
| tgtaggcggt | gctacagagt | tcttgaagtg | gtggcctaac | tacggctaca ctagaagaac | 7020 |
| agtatttggt | atctgcgctc | tgctgaagcc | agttaccttc | ggaaaaagag ttggtagctc | 7080 |
| ttgatccggc | aaacaaacca | ccgctggtag | cggtggtttt | tttgtttgca agcagcagat | 7140 |
| tacgcgcaga | aaaaaaggat | ctcaagaaga | tcctttgatc | ttttctacgg ggtctgacgc | 7200 |
| tcagtggaac | gaaaactcac | gttaagggat | tttggtcatg | agattatcaa aaaggatctt | 7260 |
| cacctagatc | cttttaaatt | aaaaatgaag | ttttaaatca | atctaaagta tatatgagta | 7320 |
| aacttggtct | gacagttacc | aatgcttaat | cagtgaggca | cctatctcag cgatctgtct | 7380 |
| atttcgttca | tccatagttg | cctgactccc | cgtcgtgtag | ataactacga tacgggaggg | 7440 |
| cttaccatct | ggccccagtg | ctgcaatgat | accgcgagac | ccacgctcac cggctccaga | 7500 |
| tttatcagca | ataaaccagc | cagccggaag | ggccgagcgc | agaagtggtc ctgcaacttt | 7560 |
| atccgcctcc | atccagtcta | ttaattgttg | ccgggaagct | agagtaagta gttcgccagt | 7620 |
| taatagtttg | cgcaacgttg | ttgccattgc | tacaggcatc | gtggtgtcac gctcgtcgtt | 7680 |
| tggtatggct | tcattcagct | ccggttccca | acgatcaagg | cgagttacat gatcccccat | 7740 |
| gttgtgcaaa | aaagcggtta | gctccttcgg | tcctccgatc | gttgtcagaa gtaagttggc | 7800 |
| cgcagtgtta | tcactcatgg | ttatggcagc | actgcataat | tctcttactg tcatgccatc | 7860 |
| cgtaagatgc | ttttctgtga | ctggtgagta | ctcaaccaag | tcattctgag aatagtgtat | 7920 |
| gcggcgaccg | agttgctctt | gcccggcgtc | aatacgggat | aataccgcgc cacatagcag | 7980 |
| aactttaaaa | gtgctcatca | ttggaaaacg | ttcttcgggg | cgaaaactct caaggatctt | 8040 |
| accgctgttg | agatccagtt | cgatgtaacc | cactcgtgca | cccaactgat cttcagcatc | 8100 |
| ttttactttc | accagcgttt | ctgggtgagc | aaaaacagga | aggcaaaatg ccgcaaaaaa | 8160 |
| gggaataagg | gcgacacgga | aatgttgaat | actcatactc | ttcctttttc aatattattg | 8220 |

| | |
|---|---|
| aagcatttat cagggttatt gtctcatgag cggatacata tttgaatgta tttagaaaaa | 8280 |
| taaacaaata ggggttccgc gcacatttcc ccgaaaagtg ccacctgatg cggtgtgaaa | 8340 |
| taccgcacag atgcgtaagg agaaaatacc gcatcaggaa attgtaagcg ttaatatttt | 8400 |
| gttaaaattc gcgttaaatt tttgttaaat cagctcattt tttaaccaat aggccgaaat | 8460 |
| cggcaaaatc ccttataaat caaaagaata gaccgagata gggttgagtg ttgttccagt | 8520 |
| ttggaacaag agtccactat taaagaacgt ggactccaac gtcaaagggc gaaaaaccgt | 8580 |
| ctatcagggc gatggcccac tacgtgaacc atcaccctaa tcaagttttt tggggtcgag | 8640 |
| gtgccgtaaa gcactaaatc ggaaccctaa agggagcccc cgatttagag cttgacgggg | 8700 |
| aaagccggcg aacgtggcga aaggaaggg gaagaaagcg aaaggagcgg gcgctagggc | 8760 |
| gctggcaagt gtagcggtca cgctgcgcgt aaccaccaca cccgccgcgc ttaatgcgcc | 8820 |
| gctacagggc gcgtccattc gccattcagg ctgcgcaact gttgggaagg gcgatcggtg | 8880 |
| cgggcctctt cgctattacg ccagctggcg aaagggggat gtgctgcaag gcgattaagt | 8940 |
| tgggtaacgc cagggttttc ccagtcacga cgttgtaaaa cgacggccag tgaattgtaa | 9000 |
| tacgactcac tata | 9014 |

<210> SEQ ID NO 15
<211> LENGTH: 5954
<212> TYPE: DNA
<213> ORGANISM: Homo sapiens

<400> SEQUENCE: 15

| | |
|---|---|
| ggccgcggga attcgattcc ttaattaagt cgactgggac ccaaactttg gagtcgttga | 60 |
| cagatgtgac aggtgaagcc tgggatgaca tcgccaaaaa tgcaacgtct cactcattgt | 120 |
| cactactccc agggctcagt cgtcactggg gaaaatctcc agaaggtagc gcgggccaag | 180 |
| gtgacaggtg tctgccaaga tctgcccgcc agactcccgg gcggcgcgct ccctccctgc | 240 |
| aggccttcag cccgtcagca tccccttcct cggggccctg ctcactccca gcctccatcc | 300 |
| ccctgccatc tcctccgccg gtcgcgtgcg gacacaagga tggggacctc ccagcgagga | 360 |
| gcgctctggg cggggctccg gacgcatgcg cggccctcgt acggaagccc ggaaggaggg | 420 |
| gcaggggggcg gtggctcagg tttctccggg cggcggcggc ggcggcgcg gcgacggcga | 480 |
| cggcgacggc agcggggacg gcagcagtag cgggagcagc agcgtggacg cggctggcgc | 540 |
| tggcgccatg aacccgctgt aaggcgcagg ctgtgcagca cggggtgcgg gggaggagga | 600 |
| ggaggacgcc gcggtgaagt tctccgccat gaacctgagg ggcctcttcc aggacttcaa | 660 |
| cccgaggtga ggcggcgtcg ttggcgcccc cgggagtccg cgctgcgggc tcggcgcgg | 720 |
| gctggtgttc ggctccgggg aggcacggcg ggcgagatgc tgcagcccga ggacccgggc | 780 |
| gcctgcccga gctccctgc gggtgcaagc ggtcccagg caaaacagtc ggcctcggcg | 840 |
| cccgcccgct tcctcctccc gtgcccggtg ctttcagccc ctgcccggcc acggccggaa | 900 |
| gggcccggcc gcgagccccg tcctgcccca agggaacccc attcttttct gcttgctgtc | 960 |
| cctcattggt gtcccaactt cttcgtctcg gttccatcct cttctgcgcc gctgcgggcc | 1020 |
| ctccattctc cgcgtcaggg ccgtctcact cgacccaaca cccctacccc caccccagct | 1080 |
| gtttcctcca gttcctcgca gtccttgggg ttttccttgg gtttatgccc atccctctct | 1140 |
| tgtttgcttc tttgttgaac ggatacctga aacactgttg aatccttgga gtcagtgtcg | 1200 |
| gggtatggca ataccttata taatgcattt ctgggtgagc ctgatcattt tccatactca | 1260 |

-continued

```
ttttctcatc agtcttcact acaagtttat ttgcaggaag tagatattgc tgtccttctt    1320
ttccagatgg ggaacaccca gtggacagtg tggagaaaac actggctaag cactcaagcg    1380
cctgtccttg cacttgcccg actgttttgt aactgttctt taccccaggc tgtgagctcc    1440
ctgaagctga gaccatctcc tgctcatctc agtgtcccca gcgcctccca cccaccgtat    1500
ctggcacata gtaggcacat ataaaatgtt tgtggaacta aactgagccc aaagacttgg    1560
attggagacg aggccatatg taactgggtg attctctgcc cttctttggc ccttctgtaa    1620
aatgaggagt tggcctaact gatctcttaa atgcactact ctccgaaagg agtatccgtt    1680
tcccttattt gccagttggg aagacgtgct cagtaaatat ttgtgtgctg taacctatgt    1740
taggtgcttt agatgctggc ggtctcagca tggggtgaag aagggcttgt acacttaaga    1800
tgccttacag tactgtgcag tgctgtactg cgggggccaa ctctggggac ctatgccttg    1860
gctgcttgtt gaggatgaaa ggaagtttta ggggagtatt tgtatgttga gggtgcagtc    1920
tccctaggga tggtgacatt ttaacttgtg agtcattgtg actttgtatg tgcccttatt    1980
ccactttgag ttcatgttct ggttaggagt gccagtgtct ctaacacggt gcagacatta    2040
tcattgttgg cttcgaaggc atagaggagg taacagaact aactgcagtc ccttcctctg    2100
ctgcatcagg gggttaagat tggtctgcag ggtagtaggg ttggtgctgt ggctggacaa    2160
gccctgtatg tcttctattt ggagatggtg ataagaaagt taagtaaaaa ctgaattgtt    2220
ttgtgccctt gggcaactca cttatctatt gttttatctg tagaatgagt ataatctctc    2280
agtggggtag ggaggccaat taaggattga ttacaaagtg ccttacaaat agaaagctac    2340
agtgacttgt ttgcaaggtg acagagaatt cagaagcctc aagaaactgc cttaagtgat    2400
caaacaggct aacggagttg ccaaagcaaa atagtgctgc actgatacta cctttaaccg    2460
ttttttcctt tagcccttttt cccccaaaa aaattagtat atgaaattac agtgaaatac    2520
ctggtatcta agcagattta tagtaattct caacatattc atcaatctct taattctacc    2580
tgcattaaaa tgtatttcta cctgaaaagt ttaaaggtct tttatactgt gccatttcc    2640
tgattcattg ttgccagagg tagtgagttc cttaatttta cagatatttc aagaggacat    2700
tggccaggta ttattggtaa atcagatttg ttttttttagc tggtagtgtt tcacctctcc    2760
tgagcactcc tagtttttga cagtgtgctt tagtctcctt ccatgctgag gaaggccttc    2820
tctataggag aaagaaaact gaggggtgta cacaggaagt taccttatgc tggggactca    2880
aaccttgatg ctactgcttt gctccctgcc tctatttttg aaccaattca acatctccct    2940
cctaccccag gaccttgtca cacactgttc tctttaccag gaatgtttcc ctctcttttc    3000
ctctcctcca gacctagtga actcctattt atcctcactt ggcacttgct aagggaagca    3060
ttcctgactt ccctgaccag atttactgct ccctgtttct acagttcctg tagtatttac    3120
tactcctcca tcatagtgca tatttgtacc cttgtgtctg tctggatgct tatttgatta    3180
ataccctgcct cccccactaa actttaagct ccatggggtc aaggccgtga ctgtgtcagt    3240
atcgtagcct gcatacttgg aatagtacct ggctcaataa atatttgtgg agtaaataac    3300
tgaataactc tccagagcct ataagataaa tctagagctg ctgctttcaa tcactgcttt    3360
cctggtggtc tgtggcctgg ttctctttct tctcacactc ttcccacctt cagagtgcag    3420
ccattgcttt ggagagatgg gagagaacat ggcactaagg cagaatatgg ctatatttac    3480
tttgaagagc atgtctttgt catagaaata gtcactgtca tggtttggtg ggtcccaagg    3540
catgggtcat ggctccagat cccctttcca gccttttgga tcttggtaag tctgaaccca    3600
ctgctgcgtt ggcaaggctc tggaaactat agtgacagag aatgattcac aagtgtcaac    3660
```

```
actcagatgt acagggctgc cagctgaccc actctaccta tttccatctg gcactgaact    3720
ggttgatcat gaacttcttt tcataattgc tttttagtta tgcaggttaa gacatgccga    3780
aacagatgta ccggacccac aaacaagtcc ttccttgaat gcctgaggct tcctaacagt    3840
gaaagagccc tgttcttaga gtaggcaaac tgattctgag gcattgtagg tggtagggat    3900
ctggtagtag gtagcattag gtgggctccc ggcactcacc atggagcctt gaaattttct    3960
gctactttgg gggagttgct ggttcagaga aggcccttcc accctggtag ccatgtggca    4020
ctggaaggct gtgaaaactc tgctgggcct tcttagtcat ctgttgtgag ctcctgatgg    4080
gagtgtggtg tatccctcag gtgtgctaga ctggaacaaa ggctgagaag tgttgctctg    4140
ggggttccaa cttgtgggca tggggtactg atgagatcag tagtgtttgg agacttctgt    4200
atgctccatc ttcagaagac attctggagt ccatataagt tatcttgtct cttgtttgaa    4260
gcaggaaaaa ggaatgcgat tgctggtaat atagttcact aaagtcagct acctggcctc    4320
taacagttat ttgcaaagta tattataaca ttgattcctc aaacatctag attcctatct    4380
cgtgccaagt gatgtactag gtgctctaag tacaaaaata aaggaatata gtcctcctct    4440
caatgcgtaa gcctagtgga agaagcagaa atgaaaggga aataagaatt caatagagta    4500
tgaggcatta cagtgaaaga aaccaaatgt cttagaagta caaatggcag agctactaat    4560
tctgtctcga gcaggcaggg aagagtctat agtggaaatg acttttgagc tagattttga    4620
attgagctag tcttttgagc cagacttttg agctagaatt gtagggttgt catcagacca    4680
gagagtagga agggtacctt gtgaggaaga gagagagaga tcagattgtt actgtgtcta    4740
tgtagaaaag gaagacataa gaaactccat tttgatctgt actaagaaaa attgtttctg    4800
ctttgagatg ctgttaacct gtaactttag tcccaaccct gtgctcacag aaacctgtgc    4860
tgtaatgaat caaggtttaa tggatttagg gctgtgcagg atgtaccttg ttaacaatat    4920
gtttgcaggc agtatgcttg gtaaaagtca tcgccattct ccattctcga ttaaccaggg    4980
acacagtgca ctgcggaagg ccgcagggac atctgcccaa gaaagcctgg gtattgtcca    5040
aggtttcccc ccactgagac agcctgagat atggccttgt gggaaaggaa agaccttacc    5100
accccccagc ccgacacccg taaagtgtct gtgctgagga ggagtagtga aagagcgggg    5160
cctctttgca gttgagataa gaggaaggct tctgtctcct gctcatccct gggaatggaa    5220
tgtctctgtg taaagctgac cattcccatt cgttctattc tgagatagga gaaaccacc    5280
ctgtggctgg aggcgaagta tgctggcagc aatactgctc tgttactctt tgctacactg    5340
agttgtttgg gtaaagagaa acataaatct agcctgcgtg cacatccagg cacagtacct    5400
ttccttgaac ttattcatga tacagattcc tttgctcacg tttccctgct gaccttctcc    5460
ccacctgttg ccctgctaca ctcccctcgc taagatagta aaataatga tcagtaaata    5520
ctgaggtaac tcagaggcta gcgctggtgc gggtcctccg tatgctgagt gccggtcccc    5580
tgggcccact gttctttctc tatactttgt ttctgtgtct tatttctttt ctcagtctcg    5640
tcccacctga cgagaaatac ccacaggtgt ggaggggctg gccccttca gtatctcaga    5700
agggacaaag tacacaaagg catggggtca tgatagtgcc tggtatgttc aggtagtgaa    5760
gaggtccatg tggtatgagc actgcagatg atatgtgtcg tatgaattaa aaatacatag    5820
ttactgcaaa tagttttttac aggttattgt ttttaagaaa gcagtatcta atgcacgagt    5880
gtactgtcag tactgtcaat gaactactta ccactcaagt gactgcttac gcgtcgaatc    5940
actagtgaat tcgc                                                     5954
```

-continued

<210> SEQ ID NO 16
<211> LENGTH: 30756
<212> TYPE: DNA
<213> ORGANISM: Homo sapiens
<220> FEATURE:
<221> NAME/KEY: modified_base
<222> LOCATION: (5934)
<223> OTHER INFORMATION: a, c, g, t, unknown or other

<400> SEQUENCE: 16

```
gtacggaagc ccggaaggag gggcaggggg cggtggctca ggtttctccg ggcggcggcg        60
gcggcggcgg cggcgacggc gacggcgacg gcagcgggga cggcagcagt agcgggagca       120
gcagcgtgga cgcggctggc gctggcgcca tgaacccgct gtaaggcgca ggctgtgcag       180
cacggggtgc gggggaggag gaggaggacg ccgcggtgaa gttctccgcc atgaacctga       240
ggggcctctt ccaggacttc aacccgaggt gaggcggcgt cgttggcgcc cccgggagtc       300
cgcgctgcgg gctcgggcgc gggctggtgt tcggctccgg ggaggcacgg cgggcgagat       360
gctgcagccc gaggacccgg gcgcctgccc gagcctccct gcgggtgcaa gcggtcccca       420
ggcaaaacag tcggcctcgg cgcccgcccg cttcctcctc ccgtgcccgg tgctttcagc       480
ccctgcccgg ccacggccgg aagggcccgg ccgcgagccc cgtcctgccc caagggaacc       540
ccattctttt ctgcttgctg tccctcattg gtgtcccaac ttcttcgtct cggttccatc       600
ctcttctgcg ccgctgcggg ccctccattc tccgcgtcag ggccgtctca ctcgacccaa       660
cacccctacc cccaccccag ctgtttcctc cagttcctcg cagtccttgg ggttttcctt       720
gggtttatgc ccatccctct cttgtttgct tctttgttga acggatacct gaaacactgt       780
tgaatccttg gagtcagtgt cggggtatgg caatacctta tataatgcat ttctgggtga       840
gcctgatcat tttccatact cattttctca tcagtcttca ctacaagttt atttgcagga       900
agtagatatt gctgtccttc ttttccagat ggggaacacc cagtggacag tgtggagaaa       960
acactggcta agcactcaag cgcctgtcct tgcacttgcc cgactgtttt gtaactgttc      1020
tttaccccag gctgtgagct ccctgaagct gagaccatct cctgctcatc tcagtgtccc      1080
cagcgcctcc cacccaccgt atctggcaca tagtaggcac atataaaatg tttgtggaac      1140
taaactgagc ccaaagactt ggattggaga cgaggccata tgtaactggg tgattctctg      1200
cccttctttg gcccttctgt aaaatgagga gttggcctaa ctgatctctt aaatgcacta      1260
ctctccgaaa ggagtatccg tttcccttat ttgccagttg ggaagacgtg ctcagtaaat      1320
atttgtgtgc tgtaacctat gttaggtgct ttagatgctg cgcgtctcag catggggtga      1380
agaagggctt gtacacttaa gatgccttac agtactgtgc agtgctgtac tgcgggggcc      1440
aactctgggg acctatgcct tggctgcttg ttgaggatga aggaagtttt aggggagta       1500
tttgtatgtt gagggtgcag tctccctagg gatggtgaca ttttaacttg tgagtcattg      1560
tgactttgta tgtgccctta ttccactttg agttcatgtt ctggttagga gtgccagtgt      1620
ctctaacacg gtgcagacat tatcattgtt ggcttcgaag gcatagagga ggtaacagaa      1680
ctaactgcag tccttcctc tgctgcatca ggggttaag attggtctgc agggtagtag        1740
ggttggtgct gtggctggac aagccctgta tgtcttctat ttggagatgg tgataagaaa      1800
gttaagtaaa aactgaattg ttttgtgccc ttgggcaact cacttatcta ttgtttatc       1860
tgtagaatga gtataatctc tcagtggggt agggaggcca attaaggatt gattacaaag      1920
tgccttacaa atagaaagct acagtgactt gtttgcaagg tgacagagaa ttcagaagcc      1980
tcaagaaact gccttaagtg atcaaacagg ctaacggagt tgccaaagca aaatagtgct      2040
```

```
gcactgatac tacctttaac cgttttttcc tttagccctt ttcccccaa aaaaattagt    2100 atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccatttt cctgattcat tgttgccaga ggtagtgagt tccttaattt    2280
tacagatatt tcaagaggac attggccagg tattattggt aaatcagatt tgtttttta    2340 gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctctttacc    2580
aggaatgttt ccctctcttt tcctctcctc cagaccagt gaactcctat ttatcctcac    2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atcccctttc cagccttttg    3180
gatcttggta agtctgaacc cactgctgcg ttggcaaggc tctggaaact atagtgacag    3240
agaatgattc acaagtgtca acactcagat gtacagggct gccagctgac ccactctacc    3300
tatttccatc tggcactgaa ctggttgatc atgaacttct tttcataatt gcttttagt    3360 tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt ggggagttg ctggttcaga gaaggccctt    3600
ccaccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catgggtac tgatgagatc    3780 agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
taaaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200
tgacttttga gctagatttt gaattgagct agtcttttga gccagacttt tgagctagaa    4260
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
```

```
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagaccctta ccaccccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagaa aaacataaat ctagcctgcg   4980
tgcacatcca ggcacagtac ctttccttga acttattcat gatacagatt cctttgctca   5040
cgtttccctg ctgaccttct ccccacctgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggaggggc   5280 tggcccctttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gtttttaaga   5460
aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca acgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg acccccgccc attgacgtca   5760
ataatgacgt atgttcccat agtaacgcca tagggacttt ccattgacg tcaatgggtg   5820 gagtatttac ggtaaactgc ccacttggca gtacatcaag tgtatcatat gccaagtacg   5880 ccccccctatt gacgtcaatg acggtaaatg gcccgcctgg cattatgccc agtncatgac   5940
cttatgggac tttcctactt ggcagacatc tacgtattag tcatcgctat taccatggtg   6000
atgcggtttt ggcagtacat caatgggcgt ggatagcggt ttgactcacg ggattttcc   6060 aagtctccac cccattgacg tcaatgggag tttgttttgg caccaaaatc aacgggactt   6120
tccaaaatgt cgtaacaact ccgccccatt gacgcaaatg gcggtaggc gtgtacggtg   6180 ggaggtctat ataagcagag ctctctggct aactagagaa cccctgctta ctggcttatc   6240
gagatatctg cagaattcat ctgtcgactg ctaccggcag cgcgcagcgg caagaagtgt   6300
ctgggctggg acgacagga gaggctgtcg ccatcggcgt cctgtgcccc tctgctccgg   6360
cacggccctg tcgcagtgcc cgcgcttttcc ccggcgcctg cacgcggcgc gcctgggtaa   6420
catgcttggg gtcctggtcc ttggcgcgct ggccctggcc ggcctggggt tccccgcacc   6480
cgcagagccg cagccgggtg gcagccagtg cgtcgagcac gactgcttcg cgctctaccc   6540
gggccccgcg accttcctca atgccagtca gatctgcgac ggactgcggg ccacctaat   6600 gacagtgcgc tcctcggtgg ctgccgatgt catttccttg ctactgaacg gcgacggcgg   6660
cgttggccgc cggcgcctct ggatcggcct gcagctgcca cccggctgcg gcgacccccaa   6720 gcgcctcggg cccctgcgcg gcttccagtg ggttacggga gacaacaaca ccagctatag   6780
```

```
caggtgggca cggctcgacc tcaatggggc tcccctctgc ggcccgttgt gcgtcgctgt   6840
ctccgctgct gaggccactg tgcccagcga gccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcacccgt tcgcggcccg    7020
cggagcggac ttccaggcgc tgccggtggg cagctccgcc gcggtggctc ccctcggctt   7080
acagctaatg tgcaccgcgc cgcccggagc ggtccagggg cactgggcca gggaggcgcc   7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca cagggtggct cgagtgccca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccgagggc ttcgcgccca ttccccacga   7620
gccgcacagg tgccagatgt tttgcaacca gactgcctgt ccagccgact gcgaccccaa   7680
cacccaggct agctgtgagt gccctgaagg ctacatcctg gacgacggtt tcatctgcac   7740
ggacatcgac gagtgcgaaa acggcggctt ctgctccggg gtgtgccaca acctccccgg   7800
taccttcgag tgcatctgcg ggcccgactc ggcccttgcc cgccacattg gcaccgactg   7860
tgactccggc aagtggacg tggcgacag cggctctggc gagccccgc ccagcccgac     7920
gcccggctcc accttgactc ctccggccgt ggggctcgtg cattcgggct tgctcatagg   7980
catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac cccagctttt gctaccaaag   8220
caccttagct ggcattacag ctggagaaga ccctccccgc acccccaag ctgttttctt    8280
ctattccatg gctaactggc gaggggtga ttagagggag gagaatgagc ctcggcctct    8340
tccgtgacgt cactggacca ctgggcaatg atggcaattt gtaacgaag acacagactg    8400
cgatttgtcc caggtcctca ctaccggcg caggagggtg agcgttattg gtcggcagcc    8460
ttctgggcag accttgacct cgtgggctag ggatgactaa aatatttatt tttttaagt    8520
atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt ttttttttcct agccctctca cattatgaa gcaagcccca cttattcccc    8700
attcttccta gttttctcct cccaggaact gggccaactc acctgagtca ccctacctgt    8760
gcctgacccct acttcttttg ctcttagctg tctgctcaga cagaacccct acatgaaaca   8820
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caaagaggta tttatcttta   9000
cttttaaaca gtgagcctga attttgttgc tgttttgatt tgtactgaaa aatggtaatt   9060
gttgctaatc ttcttatgca atttccttt ttgttattat tacttatttt tgacagtgtt    9120
```

```
gaaaatgttc agaaggttgc tctagattga gagaagagac aaacacctcc caggagacag   9180
ttcaagaaag cttcaaactg catgattcat gccaattagc aattgactgt cactgttcct   9240
tgtcactggt agaccaaaat aaaaccagct ctactggtct tgtggaattg ggagcttggg   9300
aatggatcct ggaggatgcc caattagggc ctagccttaa tcaggtcctc agagaatttc   9360
taccatttca gagaggcctt ttggaatgtg gccctgaac aagaattgga agctgccctg    9420
cccatgggag ctggttagaa atgcagaatc ctaggctcca ccccatccag ttcatgagaa   9480
tctatattta acaagatctg caggggtgt gtctgctcag taatttgagg acaaccattc    9540
cagactgctt ccaattttct ggaatacatg aaatatagat cagttataag tagcaggcca   9600
agtcaggccc ttattttcaa gaaactgagg aattttcttt gtgtagcttt gctctttggt   9660
agaaaaggct aggtacacag ctctagacac tgccacacag ggtctgcaag gtctttggtt   9720
cagctaagct aggaatgaaa tcctgcttca gtgtatggaa ataaatgtat catagaaatg   9780
taacttttgt aagacaaagg ttttcctctt ctatttgta aactcaaaat atttgtacat    9840
agttatttat ttattggaga taatctagaa cacaggcaaa atccttgctt atgacatcac   9900
ttgtacaaaa taaacaaata acaatgtgaa aaaaaaaaa aaaaaaaaa aaaaaaaaa      9960
aaaaaaagg tagcagtcga cagatgaatt ccaccacact ggactagtgg atccgagctc   10020
ggtaccaagc ttaagtttgg gctgcaggaa ttctgatggc tctcaaaatt cctgcctcct  10080
ttagggataa aagactttaa gacttttttaa caaaaaagaa aagaaaaaa aaaattcctg  10140
cctcctggtg tacacacaca gaagggttcc ctcccctttga atgtgaccag gatctgtgaa  10200
aataacggga tagccgctcc tgtgattagg ttatgtggta gactagagca agattctcct  10260
gctggttttg aagaagtcag ctgccatgtt gtgagactgt catgggctag ggcatgagcc  10320
tttaaatatc tgggagcaac ccctggccag cagccagtga gaaaacgggc cctcagtcct  10380
acaatcacaa ggaactaaat tctgccaaca acctgaagga actttgaaga ggatcatgag  10440
tcccttgatt cagcttgatg agcccctgag cagaggatac agctaacttg tactagggaa  10500
gtataaaaaa catgcatggg aatgatatat atcaacttta aggataattg tcatacttct  10560
gggaatgaag ggaaagaaat ggggctttag ttgtattatg atctttaatt tctcaaaaaa  10620
aataagatca gaagcaaata tggcaaaatg ttaatacttt tgtgggtacg taggtattca  10680
gcataccctt ttttctgagt tcaaaatatt ttataattaa aatgaaatgc aggccaggca  10740
cagtggctca tgcctataat accagcactt tgcgaggccg aggtgggagg atggcttgag  10800
gccagaccag cctggccaac atggcaaaac cccatctcta cttaaaaaaa aaaaaactat  10860
atatatatat atgtgtgtgt gtgtgtatat atatatatgt atatatattt atatatgtgt  10920
gtatatatat atatgtatat atatttatat atgtgtgtgt atatatatat atacacacac  10980
acacatatat acatacatac atacacacac acacacacac aattagccag gcatggtggc  11040
gcacacctgt agtcccagct acttgggagg ctgagacatg agaattgctt gaacctggga  11100
ggcagagtag ttagtgagct gagatcatac cactgcactc cagcctggtg acagagtgag  11160
actctgtctt aaaaaaaata aaattaaaa ttaaatgcaa aaggtccaag tgaattgaag   11220
aggaaagggg tatcaaggaa ggttttgtgg aggtgacgtt tgagctgggt cttaaatgac  11280
ttaaacatgg gataagaagg gagggaataa ggacatttca ggtacgagaa ataaggagca  11340
aacagtggaa acaacctaac gtctgtcaac cagtgaatgg ataacaaaaa tgtaattcag  11400
atggtatcca acttacgatg gttcaacatg agatttttct gactttagga tagatttatc  11460
aaagtagtaa atccattttc aacttatgat attttcaact tcagatgggt ttatcaggac  11520
```

```
acagttgagg aacacctgtc tatccataca atttggcaat aaaaaggaaa tgagtgcaga   11580
tatactccac aacatgaatg aaccttgaaa acattaagtg agagaagcca gatacaaaag   11640
gccacatatt gtatgattct atttatacaa aatgtccaga ataggcaaat cttatagaca   11700
gcaagtaggt agatgatcag tttgctaggt gctgggggaa ggggaaatgg ggagtgatgg   11760
ctaaggggat tgggtttctt tgtgggcaa tgaaaatgtt ttaaaattga gcgtgataat    11820
gattgcacaa tgctgcatat atatataatc tatagattat atatatataa agagaggctg   11880
ttagacagtg ataagtgata tatatatata tatacataga gagagagaga gagagagaga   11940
gaggctgtta gtgataagtg atcaggaaaa taaaagtatt gaggaggaat acgaagttga   12000
cggtgtgaaa acatgagatt ttatatagga tggccaggga aggccttaat gagaaagtga   12060
cttatgagta aaaacaaggg atcctaaacc ttagcatgca tcagaatcac tcggaaactt   12120
gttaaagcat agcttgctgg gcctcatcac agatattttg attcggtagg ttcttgtctg   12180
atattaatac ttttggtcta gggaaccaca ttttgagaac cactgagcta aaggaagtaa   12240
aggtttccct tagtttacta gctggtaaca ctggcccagg aggcctttct ggaaaaggtc   12300
ccagtcccca aaggaagctg gggactcgcg ttcacatcgt caaggtttac caagttgtgg   12360
cgggcctttc cgtcttggaa aaagcctcaa aatggcagat tagggtgtcc atggccggcg   12420
gaaagggtct ttgaagttgc agaccaggag ggaagaagat tctgggcctc ccccatgcag   12480
tgtcagctgg caacagaatg caccccggct gggttggagg ccctgggtac tggctcttcc   12540
acaccagggg cccacctacc aagggcagca ggagcatctg cacctcctgc gccaggcgcc   12600
cttcagtgct tccacttgag cacctctcca gacaccagct agggtgacag tggtacaaat   12660
accagactcc cctggcctgc tcacctcaca gggtaatgtg ctgtggagtc aggggacac    12720 agcaaccacc agatgacatg gctggccccg gggaggacga cacgcagata cggctacttg   12780
gcacctgtga tattttacac actcgagagg ggcccgcacc atcctcagcc ctctccccac   12840
attcactctt agttcatgtc acctccaccc agagggggac acaggcccac agcgatggcc   12900
ccacaccctg cctgaggtcg cccacttccc aggaggcagt cctgggactt ccacccgacc   12960
aggccccaga gcccaccgac ttaacccctc cagaggcttg tcgttcatta ccttattcaa   13020
gatggagacc agccttttg cggagaaaat gcgggtgaag gtcctgaaag tgcattgacg    13080 ccgtttttcgg aagccataca agtttagctg gcggaagaag ctctttatcg aagttgtggc   13140
aaacactttg tgtgcgacgt ccctttttgag aatctccttt tcaaagagtt tttgattgat   13200
cactctacaa gccccactgt catcccacca gatggacgaa aactggttgc tgctgaccag   13260
tctccacagt ttctgtggaa agggggagga gaggagatta tcttctccct ggggcgggac   13320
gtcaccgtca gggtgcggcc ttctgaacga agcttcctcg gccagaggtt ggaaagcgat   13380
ttcttctgtc agcagcctca agttagggct cccagtggac cccgggtcgt cccaggcagg   13440
ggaaggatct gctgggtgaa ggtaggtctc tgactgcaac tggggaggga aaggcaccct   13500
ttccaagcca tgatcctgtc ctctcgaatt tctttcttca cagcgagcca tactcaatga   13560
tcgcttgtcc tccatctggc aaacttgcta gtgcagtgtg gccagcagca ccccttggca   13620
gtcatgtaac cagcccccatg acatcataaa ggggctctga ctgccggggg gtggcatctc   13680 caccccccagc aagttgtgta ataaagggcc aaggcagaca agtagctgcc catctgcatg   13740
tgcacattct ggtcctcaca gtcatttcaa tgggaaagat gacactagtg cacaagagtg   13800
ccgaggggcc ctgccacacc gtagatgcag acctggagcg gtccccttgt cctagagctc   13860
```

```
ctgagccagg cacaactaca gcaaagccct ggctcaggaa ggtcagagct caccgtctga  13920
gtcatgggcc cacagacccc agcacatgac tgacactcgg aagcacagaa caaagggtag  13980
gacggtgccc atgggtcagg ctgtagccac gccacccttt ccaccctgtc ctagccagag  14040
gcagcaatgt gctccataca gatcctccta acacacccac actgtcggtc cccagcacgc  14100
agatgcccga cagcccctta ggcaaatggc ttagctgact gccccaccac acgccgtcgc  14160
catgcagtcc agtggggagt cggaggcagc ctccttcctg cctctcctcg gcctgcacgt  14220
gtccccccac caggcagaga cccttctaca ccccgggtgt ctgcggtcac atcgcggtgg  14280
ggcatgcagc tgttggcctt cgagcatgtt ttgtttcct tggccagtgt ctccagagaa  14340
acgcacgtgg gtttgtgtcc agcggtccat ctctgcaaca gttgttcctt gggattgga  14400 tgctaggagt tcacgggaga ggtgtccatc caaagcagtg tctgtgtcac acactgtccc  14460
cacacacagg gccacctctg cacagactcc cccgactcga ttctgggcac agagctcagt  14520
gaccttccag agactgccac gaaccggtga tgcctccacg cttgagacat cctgaccgca  14580
gggcccaagg cgcactggct caggggtga cagtgagggg tctgcaaaca gactgctgat  14640
gctcaacccg gccgctgccg agctgtgtga cttgggcacg tcacttaacc tctctcggcc  14700
tctgtctcct cccggggata agagtagtag cacctgcttc ccggggctgt gaggatccag  14760
tgggacgtat aggaactagc gaggcaccgg cagttgggtc agagctactg ttgtcacttc  14820
acaaggcatt ttcttcaaca gcaagtcgga aatctcatga gcctaaggca gaatccacct  14880
gtggcctctg gttacaaccc acaggactga aaatccttcc agccacagca actggtgaat  14940
ttcctggtca attgccacaa gtcatgagct gaaccccact tgagtttcag ttcaggcaga  15000
actctagaga cgactagggc aagctagaca gcgactgcag agccttttgt tgcagcgtga  15060
gcagtcctca gctgttgaca tcactgggga gcaaacgagg accaggagcg gtgaaaggac  15120
agtgtctgct gcagattgtc gtagcaccca aggaacactc cagaaagcct cctaagcagt  15180
aacaagtgtg gcaaggtgta gcccagccaa cagtggcatc tgcgaggcgt ccctccttc  15240 ctcccactac cccgtatacc ctgggacctg tgcactgaag gactcattct aaaggctgtg  15300
cccctgcagc cgccagcctc actcactggc tgcctgtgcc agctagagat ttctttcctc  15360
tgaggctggc tgagaggacc actccagttt cctggcccat ccagcaaaga agatacacat  15420
catgcacgtg taaaatgagg aaccggttta ttgaacagct taaggagagc aaaaatagtg  15480
gctttagcta catttttac acactgagca ggaaagtcta aaccatcccg ttcccctgta  15540
ccccaaagag aacagggctt gctggaggcc agtgccaagg gcggagtcgt gctcgcagca  15600
gacttgaatt aaccccatgt aggccggcga gcagttgccc gcgtgaaaac accaccctct  15660
tctcctggct gagaagatca aagctctttt tttaccctct tttcagcaaa ggacctattt  15720
gttttcaggc aggaggatgt taaacttgca gcctctgaca cacggtggaa cctgcagtgc  15780
ttggagaaac ggcacgcaca cgtgaaaaca tcatgcctac tccaaagcct tcttgttgct  15840
ggcaggaggg aagcttgaga ctttcccacg catagtcgtg acccgcgtgg ccgtttctgc  15900
tctcagcaac attctctagt gttccggctt caagcagcgc ttgtcaggtt tgaagctagc  15960
cactattctg agaacgtcag aaaagcatgg accatctctt gcttggtgtt gccgttgtgg  16020
cagtagcagc tactacgtac ctgcacgagt tccagggcag aagtggcaat gtcccatgaa  16080
ggcgtggcac cccacggggg gggggggga gtgtgccacg ggcgtccact tctgcagcag  16140
aaggcatgtg cctacagcac aagcttgtaa aaaaatactt gaacagaata tgctgtacag  16200 aactagggt taacaccgca tatgaagatg ctaaaacatt tgtataaata ctctgtatac  16260
```

```
aagcatggag tcactcccgt agaaagggct catccgtgag gctatgaaaa actgctgtca   16320
gcatgcccaa agagaaacta cttccacagt aggaacagaa aaaaggactg tgctgtgtct   16380
aaacacgtgg tgcatcagag acatagttac agttcctact gactgcccca gccacgacct   16440
gggagtgctg aggacctggg agtgctcagc gagctgcagg aggtcagccc tgtggagaaa   16500
tacatttcta aacaatactt ttgattggga tttcagcacc gtatagacag atgttccttc   16560
tgggggcctg gcaagcagcc atctcccagt gggtctgacg gggaagaggg gtacctggag   16620
cccctcccag acagacggta atcccacccc tgttctcaca ctcttcctgg catccgcatc   16680
tgctggcaca caccccgtc acctgccact tccgcgtccc gtcgtggtga gtggctgata    16740
ggcgctggat gcaaacaagg catgagatgg acgtacctgg agacccagct ccagtactgg   16800
ttctggtctg cggggtgaac gaggggggcag aggaaggcgg agagagtgcg tcccagtcca  16860
cttaagctct gtccccggaa gtggcatcta atctggcatt tcgatattta atttgggagg   16920
tgggagcaca tacttcccag ggctctgggt aatgaccacc ctggccttct ttcgaaacat   16980
gggtgcgatt ttagggggct ccggaactgg ggtctcttcg gtttcttcat tatcttcgtg   17040
atggagatca taggaaatgt ttccatattc tcgtagaaat gggaagattt caagcagaaa   17100
ctgacagaaa tctttgcgga taccaaacca ccctgaaaaa taagaatttt ttatttcaca   17160
cacgaggctc aactgacctt cctgttaact ttctttccgt aacaagaagt ttcactccta   17220
caatgtcata acatacttta tccagactcc tgagtcacaa agcctgaaca gggcttgagt   17280
acccaaaatg gggaagaagt gcaaatgcta gctctgtggt gcttggagtg gggttcccgg   17340
accggcaggg acagcgtcca cggggcctag ttagggatgc cattctcggg ccccagccca   17400
gacctccaga aactgagtcg ggctagggtg ggctccagcg gtccccttt cctggccctt    17460 ttgggattct gctggatgcc caaatttgag aactactgct ccagtgagtc tcaaaatatc   17520
tgtggtgcgc agactacggt gtcttccgct aatcttctcc agccaggata aactcatgga   17580
tgacagtgcc acccaagaac aagatttctg tcaccctctg gaatccgtga gggcggtagt   17640
catgcacggg ttggccagga gggggcctga actcatggag ccaccttaaa gccactttcc   17700
cagtcccact actcctctct gtaggctact ggagtgtcag ctcggtgcaa gccctccctg   17760
ctcccgggtg cggggtaggg ggcagaggca caaacagcaa gcacagcccg ggctgctggg   17820
ctgcagtgag gccctgcccc caaacccact ggctttccga agggcaatgc tctgggcttc   17880
cgtgccatgg agcccacagc cttgccagga aggcaccctc tgcagagatc gttttggaag   17940
tgtctgcctc agcaagcagg tggagggggaa tagagtgtta gcaaggcaag acaggcaaga  18000
ctcgggtgat ggcagcaagg atatggggga ggcagagcgg ccaacaggga cctaggatga   18060
atcccaggtt tgggtgggag atgtggattt tccatcaaac cctcccgggc ctgggaagaa   18120
tctgtcttga tccccatttt gcagaggagg aacgggatc tctgagaggt tgcctgccgt    18180
gtctggttct acctcaaatg gcagcgtgca ctgcgagaaa agtcccggtg caggccagca   18240
gaacaccaga gttacggcat gcccttccct tagaaggtcc cagaatttcc tcagccctca   18300
cttccccaca caagcttcta aattggggcc ctcggggact catcccttcc tagacttcta   18360
tccgccaccc cccacccccct ggtccccccc cagacacaca ccaaggactt ctgaaatgct  18420
gagtacatac agtggtttcc tcccttctgt ccaaatgtgg ttgccatcag cgtgatcaac   18480
gagagccaaa gggggacaaa gatcgggatg caggagaagg cgttgtggcc atccagtttg   18540
tgaaccagca gaatctaaag aaagagacat agtcccggtt gatgccagca ccgaaaatgg   18600
```

```
gcagaggcgg aagccagact tcattaggca gttcctcccc accacccCac ccccgcgtga   18660
gctcccacaa gagggaacat cagcaccgcc agaaaaaggc aggaaaccac ctatccctgg   18720
ggaaagctcg aaatgagctt ttatgtccct cttcagagct cggcaatagc ctatccactt   18780
gaaaagttcc cagtgccagc agttttatgg caaactcctc cgggtgtttg ttctaaggag   18840
tcaacagctc ccattctaga attctccacg tgactccaat acacaaatct gacatcccac   18900
tctgctttcc ccagagtgga aactggagcc atacagaggc accatggcta aaaaggtgca   18960
ctcttctccc tgccagcccc acgtgctgcc cccaagagaa aggaaggatg ctctcctttc   19020
accgaagctc cctctcggag atggctgtgt tctctcccct ctcctggagt gggctcactg   19080
tgagctcgag ggacagaggc tgcctttcta ggggtgcaga atcctgtcag gggaagcgca   19140
agcttcaggg gctgaagagg cttcccgtgg aacgcttacc tcaaatgtaa aaggggcac    19200 gacgatggtc atccagctca gggccatggt tatgtgtgtc ctgcgctgtc cgcaatcaca   19260
tccatagagc gcaagaacaa gacggaccac acaatgtagt agaggaccac caggcacaga   19320
aaggacatga gaatccacag cgggacacac acaacctggg ggtgggtgag agaacagcaa   19380
gagaagtctc tttagagctt ccaacctggc ctctgatgga aggcatcttt agcaccttgc   19440
tgtgtctgtc cagttaaggc ggtccttcct gtgagccgaa taaggaccgt tccatctccc   19500
aggactgctg ggagcatcgc tcaggacaga aaaggtatgg tatgttcact atggggcctg   19560
ctgccaccag gggacacaca cgctcagtga gtcatcagtc cctcttcctt tgggtgacag   19620
acagccctgc acctggctcc gcagcctcta ctcttccaga ggcccactct cccacactct   19680
ctcaggctcc tctaggttct gctgccatca cagcttcccg ggaaatggga cacaactgtc   19740
accctgtgca cacacacaag atctcacccc aacagactct cttcacaggc aacattccca   19800
caacctgctg ggggtacttt ggcaacacaa atgggaatgg gctccccaga aagtctggct   19860
gcctgggctc ctaaggatcc ctaacctcac ccctaccaag ttagtgaact tggcgggttg   19920
atgctggata caggttgatg ctggatacgt agcgctgccg ggtcgtgacc cctaaggaat   19980
tatccaaact cttgttttta gatgctttat tatatcaaac tctccttaa acaagtggcc    20040 catctgctgg gatttggaag cctgtaatac tgaaattttc atcataatgg aaattttaaa   20100
aacagaattt gacccacctg tttttaaaac actttcatta cttaacaaga ggtctaatct   20160
tgggcaagtc ttgaaatttc tctggcctta gtttcccatg tgttaaatga aacttgaagc   20220
agttggtctc ttatagtctc ctgactctaa cattctaaga attatatttg tacaataact   20280
caaaaatcac ataatttaat ttaccatatg gactccaaaa tatattttct cattaggcta   20340
aacttgatct gcatttttctg gatgtgtcca tattcttgga ctacactaaa acatgatacc   20400
aatgcttcct ctcaccataa accctcactt cgctttctac atttaagaat tttatagctg   20460
gaagagtcct taacagaaaa taccatctaa taattacccc tcaaaatcga gaaagtccta   20520
tctgttctta tgctagttat aagaatgagg cagcatttca cataatggtt ataaacactg   20580
ccacaagaag attcatgatg tgttgtttat ctgtagctct catcatactc tgtcatataa   20640
ctatagcatt aagattttaa tgttctatat attcttctaa gacagtgttt accagagtaa   20700
ggcacaaaag atccactggt ttgcaagaaa gattagaact tttaaatttt ttacctcacc   20760
ttgtttaatc tatattttttg tatgtatttt gtaacatata tattattatt accataaatc   20820
atatataatt taaatgcat atattagggg taaatgctca ggaaactttt tataaattgg    20880
gcatgcaaat acaagtttga agactcactg ttctaggtat taaaagtaaa gttataacca   20940
agtaaagctt ccaccttttc atgtctcaaa gcagtttatt gttggaggta agatctctta   21000
```

```
gaagcctaaa caggtccaag tacagaatga agtaaggcta gcccataact tgtggcaagc   21060
aattcatact atttctctca tgctgagctc tcctcagtga agcagctact atagacaact   21120
gcagcctatt ggtagcctat tttacaggca ggaaaaaaat tacttttat tcaaagtgga    21180 actcaggaca tggggagaaa atgaatacaa aaaatagggt caatccaaag gcacacagca   21240
aatgagtaac acagttatgt ttttttccca tttgtatgag gtcccagtaa attctaagta   21300
aactgcaaat ttaataatac actaaaaaag ccatgcaatt gttcaaatga atcccagcat   21360
ggtacaagga gtacagacac tagagtctaa aaaacaaaag aatgccatta ttgagttttt   21420
gaattatatc aagtagttac atctctactt aataaatgag aaaaacgagg ataagaggcc   21480
atttgataaa atgaaaatag ccaagaagtg gtattagaga cttgaataca ggtattcggg   21540
tccaaagttc atctgctcaa atactaactg gggaaaagag ggaaaaatat ttatatacat   21600
atatatctgc acacaaaaat accccccaaaa gacaaaatga ggccaggcag ggtggctcac   21660
acccgtaatc ccggtacttt gggaggctga ggcaggtgga tacctgagat caggagttgg   21720
agatcagcct ggtcaacatg gtgaaaccct gtctctacta aagataaaaa aattagccag   21780
gcatggtggc gtgcgcctgt aatcccagct acttgggagt ctgaggcagg agaatcactt   21840
gaactgggaa ggggaggttg cagtgagcca agatcgtact actgcactcc agcctgggca   21900
gcagagtgag actccatcac aaaaataaat aaataaataa aatacaatga aacagaaagt   21960
tcaaataatc ccataatctt accaccaaga aataactttc actcgttata cttattgatt   22020
tttccataat aaatgtactt tactgtgact atcatgaaaa gaaagttatt ttagaaacag   22080
agaactgttt cagatcaaat ctatgtagta gaacagagcc attaggtggg aaagacgaga   22140
tcaaactaaa tctcagaagg cctaaaaggc taggtccatt ccagcactaa aaactgacca   22200
gacaagtaat ggcttcaaca gcttctaaat atggacaaag catgctgaaa gggaaggaca   22260
ggtctaacag tggtatatga aatgaacagg aggggcaaag ctcatttctc ctctgaagtt   22320
ttccaaagat gctgaggagg acattagttt gacatgaccc tgatatggga caagataatt   22380
tcacagaagt tttacatgtt aaagttttct tatagatact cattcaagta agcaatgaac   22440
actaaaatct aaagaaagaa aagagcttta gagtcaggtc tgtattcaaa ttcaagctct   22500
accacttact ggttctgtga ctttgggcaa gtcttttaac cttattaagt cttaatttcc   22560
tgatttgtaa aatggggata tcgtctccct cacaggattg ttgtgaaact tttatgagat   22620
taatgccttt atatttggca tagtgtaagt aaacaataac tggcagcttc aaaaaaaaaa   22680
agcagtagca ttccatcatt tattattggt tactctcaaa aagtttttca atgtactaga   22740
agataaatat tcaaatacct taatatctcc attattttca ggtaaacagc atgctcctga   22800
acaaccaatg ggtcaacaaa taattaaaaa gggaaatcta aaaacatctt gatattaaac   22860
tacatggaag cacaatatac caaaaccaat ggttcacact aggagaattt taaggtacaa   22920
gaaaactctt tgagatttct taaaataata gtatgtctga atttattgag tgatttacca   22980
gaaactgttg taagagctct acttgcatta tagcacttaa tcctcttaac tctatggctg   23040
ctattatcaa cctcacccta atcacatatg ggacacagag aggttaagta acttgcccaa   23100
ggtcagagtt aggaagtact aagccatgct ttgaatcagt tgtcaggctc cggaactcac   23160
actttcagcc actacataat actgctttgc tatctttag gaaactatgt gagtctacct   23220
cacatagact cacataggtt tgtttttttt tttttttaa aggctatctt ttccccccatc   23280 aatgtttttt gaaggatccc aaattagagt cccacagagg cagacagcag tacttgacaa   23340
```

```
tatggacatt taaggttaat gttggattct actgtcttt tactacatga cctagggaac    23400
gataattaac ctagactgct tccaagggtt aaataaccca tttagttata ctatgtaaat    23460
tatctcttag tgattgattg aaagcacact gttactaatt gactcggtat gaagtgcttt    23520
tttttcttcc ctttcaagat ataccttt ccagttaaag ttgagagatc atctccacca    23580
attactttta tgtccctgt tgactggtca ttctagttaa aaaaaaaaaa aactatatat    23640
atatatatct acacacacat atgtatatgt atatccttat gtacacacac aaacttcaaa    23700
ttaaatgaga actagaagat ttgagaagtt agctagctaa tatccatagc attatgatat    23760
tctaaatgat atgaattata agaattaggt ttcctgaaat gaatgactag aaaactttca    23820
agtagagatt agtaaaaatt aaaaagtcct aatcggccat tactgatttg atgttttaa    23880 gagtcctaaa aaatgggtta catccatttt taagtgggta gtattataac agccacccat    23940
cttcaatcac agtgatttct gaattgtgag ggaagttatt agcatgacag gtgtctggtt    24000
ctggccctgt acgattccca tgagtcaagc aaattgtaag ggctggtcta tatcacaccc    24060
aaccccaagg atatgtccct caaaagtcta gcccaggccc cgtcatcttc agcatcatct    24120
gggaaaccag gtctgattag tagtccttta aggaatacct cttaggctcc cattttactg    24180
ctatcacaga atccaataaa acccttacag gagattcaat gggaaatgct caacacccac    24240
tgtagttggt ggtgacaatg accataattt ggctgtgctg gattcaggac agaaaatttg    24300
ggtgaaagag caggtgaaca aaagagcttc gacttgccct agcagagagc aagccatacc    24360
ataccacaaa gccacagcaa ttacaacggt gcagtaccag cacagtaaat gaacaaagta    24420
gagcccagaa acagacccag aactatatga ggatttagta tacaataaag atggtatttc    24480
gagtcagtag ggaaaagatg aattattcaa taaatgatgt ttggccaact agtaacccat    24540
ttgggaaaaa ataaaagtat ggtccctacc tcacagcata cacaaaaata aattccagac    24600
ggattaaaat ctaaatgtaa aaaataaagc cataagtgga ctggaagaaa atagagaatt    24660
ttttttaaca tccgtagaaa gggtaaaaac ccaggcatga catgaaccaa aactgaagag    24720
gttctgtaac aaataccccc ttttatatat tgggctccaa caataagaac ccataggaaa    24780
atggagaatg aacacaaata gacaatttat agaagagaag gttataaggt gtaaaattat    24840
atctatctga gaaacaaaca ctaaaacaat gtgattctac tgttctccca cccatactgg    24900
caaaacttaa gcctgataat atgctgaggg gaaataagca ctcttgttgg tgagagtatt    24960
aattggcata gcttctttg aaaatgacat agcaatacct gttaaaattg caaacatgca    25020
tgtcacttaa tccagtaatc ccacttctgg gaatcaatgc tacaaaaaca ctgacaagta    25080
tacaaagata cattcaagag tgttcactgg gccgggtgcg gtggcttcat gcctgtaatc    25140
ccagggaggc agaggcaaga cgatcgcttg accccaggag ttcaaggcca gcccgagaaa    25200
cacagcaaga ccctgtctct cttttttta tttaaaaaat aaatgttcac tgtatcagtt    25260
gttcacaaaa acaaaccaac atgtccatta acagggaacc atttaaatta atcaagttca    25320
tctacacaat gtaataccat gcaactatta aaagcacct gataatccaa agcacactga    25380
gacagaataa tgctattaaa aacaccaagt agtggaacac tgtgttgcct atgacaccat    25440
ttttattcaa catttaaaca aatttgtaac agcaattaca tgagtagtga caatggcgtt    25500
tatgagactt tcacttta tgtgcttcta ttttgttat gcttctatat atacatccat    25560
ttattatgga gtgttacttt caaaaatcac aaatgggcca gtattatttg gtgttgcaag    25620
gtgagcatat gacttctgat atcaaccttt gcatattact tctcaattta gggaaattac    25680
agacatccct tattctaact aacttaaaac ccagcatttc aaacatacag aattgatggg    25740
```

```
gaaaaaaaag aaagaagaaa gaaagaaaag gcaacaagct tcagatgaca gtgactcaca    25800
tcaaattatt tataaaatct gttaaatagt gccatcttct ggagatacct ggtattacag    25860
tccaactcca gttgatgtct ttacagagac aagaggaata aaggaaaaaa tattcaagaa    25920
ctgaaaagta tggagtcatg gaaaaattgc tgtgatccaa aggctacggt gataggacaa    25980
gaaacaagag aactccaagc agtaagacac tgctgttcta ttagcatcca aacctccata    26040
ctcctgtttg ccccaaggct tttttaaaaa atagagacag gatctcacta ttttgctcag    26100
gctggtcttg aactcctgga ctcaagctat cctcctgcct cggcctccta aagtgccgag    26160
attacaggct tgagtcacca tacctggcta tttatttttt cttaactctc ttgcctggcc    26220
tatagccacc atggaagcta ataaagaata ttaatttaag agtaatggta tagttcacta    26280
cattggaata caggtataag tgcctacatt gtacatgaat ggcatacatg gatcaattac    26340
cccacctggg tggccaaagg aactgcgcga acctccctcc ttggctgtct ggaacaagct    26400
tcccactaga tccctttact gagtgcctcc ctcatcttta attatggtta agtctaggat    26460
aacaggactg gcaaaggtga ggggaaagct tcctccagag ttgctctacc ctctcctcta    26520
ccgtcctatc tcctcactcc tctcagccaa ggagtccaat ctgtcctgaa ctcagagcgt    26580
cactgtcaac tacataaaat tgccagagaa gctctttggg actacaaaca catcccctta    26640
atgtctttat ttctattttg tctacctctt cagtctaggt gaaaaaatag gaaggataat    26700
agggaagaac tttgtttatg cctacttatc cgccctagg aattttgaaa acctctaggt    26760
agcaataaga actgcagcat ggtatagaaa aagaggagga aagctgtata gaaatgcata    26820
ataaatgggc aggaaaagaa ctgcttggaa caaacaggga ggttgaacta taaggagaga    26880
aagcagagag gctaatcaac aaggctgggt tcccaagagg gcatgatgag actattacta    26940
aggtaggaat tactaagggc tccatgtccc cttagtggct tagtactatg tagcttgctt    27000
tctgcagtga acttcagacc cttcttttag gatcctagaa tggactttt tttttttatcg    27060 gaaaacagtc attctctcaa cattcaagca ggccccaagt ctaccacact caatcacatt    27120
ttctcttcat atcataatct ctcaaccatt ctctgtcctt ttaactgttt ttctataccc    27180
tgatcaaatg ccaacaaaag tgagaatgtt agaatcatgt attttagag gtagactgta    27240 tctcagataa aaaaaaggg cagatattcc attttccaaa atatgtatgc agaaaaaata    27300
agtatgaaag gacatatgct caggtaacaa gttaatttgt ttacttgtat tttatgaatt    27360
ccctaaaacc tacgtcaccc gccccgttcc cacgccccgc gccacgtcac aaactccacc    27420
ccctcattat catattggct tcaatccaaa ataaggtata ttattgatga tgttaattaa    27480
catgcatgga tccatatgcg gtgtgaaata ccgcacagat gcgtaaggag aaaataccgc    27540
atcaggcgct cttccgcttc ctcgctcact gactcgctgc gctcggtcgt tcggctgcgg    27600
cgagcggtat cagctcactc aaaggcggta atacggttat ccacagaatc aggggataac    27660
gcaggaaaga acatgtgagc aaaaggccag caaaaggcca ggaaccgtaa aaaggccgcg    27720
ttgctggcgt ttttccatag gctccgcccc cctgacgagc atcacaaaaa tcgacgctca    27780
agtcagaggt ggcgaaaccc gacaggacta taaagatacc aggcgtttcc ccctggaagc    27840
tccctcgtgc gctctcctgt tccgaccctg ccgcttaccg gatacctgtc cgcctttctc    27900
ccttcgggaa gcgtggcgct ttctcatagc tcacgctgta ggtatctcag ttcggtgtag    27960
gtcgttcgct ccaagctggg ctgtgtgcac gaaccccccg ttcagcccga ccgctgcgcc    28020
ttatccggta actatcgtct tgagtccaac ccggtaagac acgacttatc gccactggca    28080
```

```
gcagccactg gtaacaggat tagcagagcg aggtatgtag gcggtgctac agagttcttg   28140
aagtggtggc ctaactacgg ctacactaga aggacagtat ttggtatctg cgctctgctg   28200
aagccagtta ccttcggaaa aagagttggt agctcttgat ccggcaaaca aaccaccgct   28260
ggtagcggtg gttttttttgt ttgcaagcag cagattacgc gcagaaaaaa aggatctcaa   28320
gaagatcctt tgatcttttc tacggggtct gacgctcagt ggaacgaaaa ctcacgttaa   28380
gggattttgg tcatgagatt atcaaaaagg atcttcacct agatcctttt aaattaaaaa   28440
tgaagtttta aatcaatcta agtatatat gagtaaactt ggtctgacag ttaccaatgc   28500
ttaatcagtg aggcacctat ctcagcgatc tgtctatttc gttcatccat agttgcctga   28560
ctccccgtcg tgtagataac tacgatacgg gagggcttac catctggccc cagtgctgca   28620
atgataccgc gagacccacg ctcaccggct ccagatttat cagcaataaa ccagccagcc   28680
ggaagggccg agcgcagaag tggtcctgca actttatccg cctccatcca gtctattaat   28740
tgttgccggg aagctagagt aagtagttcg ccagttaata gtttgcgcaa cgttgttgcc   28800
attgctgcag ccatgagatt atcaaaaagg atcttcacct agatcctttt cacgtagaaa   28860
gccagtccgc agaaacggtg ctgaccccgg atgaatgtca gctactgggc tatctggaca   28920
agggaaaacg caagcgcaaa gagaaagcag gtagcttgca gtgggcttac atggcgatag   28980
ctagactggg cggttttatg gacagcaagc gaaccggaat tgccagctgg ggcgccctct   29040
ggtaaggttg ggaagccctg caaagtaaac tggatggctt tcttgccgcc aaggatctga   29100
tggcgcaggg atcaagctc tgatcaagag acaggatgag gatcgtttcg catgattgaa   29160
caagatggat tgcacgcagg ttctccggcc gcttgggtgg agaggctatt cggctatgac   29220
tgggcacaac agacaatcgg ctgctctgat gccgccgtgt tccggctgtc agcgcagggg   29280
cgcccggttc ttttttgtcaa gaccgacctg tccggtgccc tgaatgaact gcaagacgag   29340
gcagcgcggt tatcgtggct ggccacgacg ggcgttcctt gcgcagctgt gctcgacgtt   29400
gtcactgaag cgggaaggga ctggctgcta ttgggcgaag tgccggggca ggatctcctg   29460
tcatctcacc ttgctcctgc cgagaaagta tccatcatgg ctgatgcaat gcggcggctg   29520
catacgcttg atccggctac ctgcccattc gaccaccaag cgaaacatcg catcgagcga   29580
gcacgtactc ggatggaagc cggtcttgtc gatcaggatg atctggacga agagcatcag   29640
gggctcgcgc cagccgaact gttcgccagg ctcaaggcga gcatgcccga cggcgaggat   29700
ctcgtcgtga cccatggcga tgcctgcttg ccgaatatca tggtggaaaa tggccgcttt   29760
tctggattca tcgactgtgg ccggctgggt gtggcggacc gctatcagga catagcgttg   29820
gctacccgtg atattgctga agagcttggc ggcgaatggg ctgaccgctt cctcgtgctt   29880
tacggtatcg ccgctcccga ttcgcagcgc atcgccttct atcgccttct tgacgagttc   29940
ttctgaattt tgttaaaatt tttgttaaat cagctcattt tttaaccaat aggccgaaat   30000
cggcaaaatc ccttataaat caaaagaata gaccgagata gggttgagtg ttgttccagt   30060
ttggaacaag agtccactat taaagaacgt ggactccaac gtcaaagggc gaaaaaccgt   30120
ctatcagggc gatggcccac tacgtgaacc atcaccctaa tcaagttttt tggggtcgag   30180
gtgccgtaaa gcactaaatc ggaaccctaa agggagcccc cgatttagag cttgacgggg   30240
aaagccggcg aacgtggcga gaaaggaagg gaagaaagcg aaaggagcgg cgctagggc   30300
gctggcaagt gtagcggtca cgctgcgcgt aaccaccaca cccgccgcgc ttaatgcgcc   30360
gctacagggc gcgtccattc gccattcagg atcgaattaa ttcttaatta acatcatcaa   30420
taatataccct tattttggat tgaagccaat atgataatga ggggtggag tttgtgacgt   30480
```

```
ggcgcggggc gtgggaacgg ggcgggtgac gtagtagtgt ggcggaagtg tgatgttgca    30540
agtgtggcgg aacacatgta agcgacggat gtggcaaaag tgacgttttt ggtgtgcgcc    30600
ggtgtacaca ggaagtgaca attttcgcgc ggttttaggc ggatgttgta gtaaatttgg    30660
gcgtaaccga gtaagatttg gccattttcg cgggaaaact gaataagagg aagtgaaatc    30720
tgaataattt tgtgttactc atagcgcgta atactg                              30756
```